United States Patent
Apgar et al.

(10) Patent No.: US 11,597,770 B2
(45) Date of Patent: Mar. 7, 2023

(54) ANTI-E-SELECTIN ANTIBODIES, COMPOSITIONS AND METHODS OF USE

(71) Applicant: Pfizer Inc., New York, NY (US)

(72) Inventors: James Reasoner Apgar, Newton, MA (US); Sheryl Rubio Bowley, Norfolk, MA (US); Joanne Elizabeth-Ayriss Elwell, Salisbury (GB); Laura Lin, Weston, MA (US); Jatin Narula, Cambridge, MA (US); Chuenlei Parng, Lexington, MA (US); Debra Denene Pittman, Windham, NH (US); Swapnil Rakhe, Acton, MA (US); Chihyi Vincent Yu, Arlington, MA (US)

(73) Assignee: Pfizer Inc., New York, NY (US)

( * ) Notice: Subject to any disclaimer, the term of this patent is extended or adjusted under 35 U.S.C. 154(b) by 40 days.

(21) Appl. No.: 17/154,588

(22) Filed: Jan. 21, 2021

(65) Prior Publication Data

US 2021/0246213 A1    Aug. 12, 2021

Related U.S. Application Data

(60) Provisional application No. 63/121,467, filed on Dec. 4, 2020, provisional application No. 63/104,213, filed on Oct. 22, 2020, provisional application No. 62/965,688, filed on Jan. 24, 2020.

(51) Int. Cl.
*C07K 16/28* (2006.01)
*A61K 39/00* (2006.01)

(52) U.S. Cl.
CPC .... *C07K 16/2854* (2013.01); *A61K 2039/505* (2013.01); *C07K 2317/51* (2013.01); *C07K 2317/515* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,081,034 A | 1/1992 | Bevilacqua et al. |
| 5,632,991 A | 5/1997 | Gimbrone, Jr. |
| 5,756,095 A | 5/1998 | Jutila |
| 5,843,441 A | 12/1998 | Gundel et al. |
| 6,204,007 B1 | 3/2001 | Owens et al. |
| 6,406,693 B1 | 6/2002 | Thorpe et al. |
| 6,407,214 B1 | 6/2002 | Owens et al. |
| 6,670,321 B1 | 12/2003 | Adamis |
| 7,691,380 B2 | 4/2010 | Thorpe et al. |
| 10,450,375 B2 | 10/2019 | Frenette et al. |
| 2004/0191303 A1 | 9/2004 | Stahn et al. |
| 2005/0244404 A1 | 11/2005 | Sumitran-Holgersson et al. |
| 2014/0308271 A1* | 10/2014 | Attinger ............. A61K 47/6849 |
| | | 435/417 |
| 2015/0196663 A1* | 7/2015 | Shusta ................. A61K 9/0085 |
| | | 435/254.11 |
| 2015/0266947 A1* | 9/2015 | Sierks .................. C07K 16/005 |
| | | 435/6.12 |
| 2016/0331775 A1 | 11/2016 | Myers, Jr. et al. |
| 2017/0355756 A1* | 12/2017 | Julien ..................... A61P 25/00 |

FOREIGN PATENT DOCUMENTS

| | | |
|---|---|---|
| AU | 663332 B2 | 10/1992 |
| AU | 748561 B2 | 6/2002 |
| AU | 782952 B2 | 9/2006 |
| EP | 0505749 A2 | 9/1992 |
| EP | 0595794 B1 | 8/1996 |
| EP | 0534944 B1 | 9/1996 |
| EP | 0458911 B1 | 1/1998 |
| EP | 0807683 B1 | 9/2005 |
| WO | 9005539 A1 | 5/1990 |
| WO | 9005786 A1 | 5/1990 |
| WO | 199013300 A1 | 11/1990 |
| WO | 9209293 A1 | 6/1992 |
| WO | 9212729 A1 | 8/1992 |
| WO | 9302702 A1 | 2/1993 |
| WO | 9313798 A1 | 7/1993 |
| WO | 9317715 A1 | 9/1993 |
| WO | 9324614 A1 | 12/1993 |
| WO | 9526403 A1 | 10/1995 |
| WO | 9534320 A2 | 12/1995 |
| WO | 9534324 A1 | 12/1995 |
| WO | 9640942 A1 | 12/1996 |
| WO | 9929345 A1 | 6/1999 |
| WO | 9943353 A2 | 9/1999 |
| WO | 9943839 A1 | 9/1999 |
| WO | 0002584 A2 | 1/2000 |
| WO | 0038714 A1 | 7/2000 |
| WO | 0191792 A2 | 12/2001 |
| WO | 03098212 A2 | 11/2003 |
| WO | 2006083322 A2 | 8/2006 |
| WO | 2007146188 A2 | 12/2007 |

(Continued)

OTHER PUBLICATIONS

Kussie "A Single Engineered Amino Acid Substitution Changes Antibody Fine Specificity" J immunol 152(1):146-52 (Year: 1994).*
Chen "Enhancement and destruction of antibody function by somatic mutation: unequal occurrence is controlled by V gene combinatorial associations" EMBO 14(12):2784-2794 (Year: 1995).*
Ashley-Koch et al., "Sickle hemoglobin (HbS) allele and sickle cell disease: a HuGE review" Am. J. Epidemiol. 2000; 151:839-845.
Aslan & Freeman, "Redox-dependent impairment of vascular function in sickle cell disease" Free Radical Biology & Medicine 43 (2007) 1469-1483, 2007.

(Continued)

*Primary Examiner* — Adam Weidner

(57) ABSTRACT

The invention provides antibodies, and antigen-binding fragments thereof, that specifically bind to E-selectin. The invention includes uses, and associated methods of using the antibodies, and antigen-binding fragments thereof.

24 Claims, 20 Drawing Sheets

Specification includes a Sequence Listing.

(56) References Cited

FOREIGN PATENT DOCUMENTS

| WO | 2008011094 A2 | | 1/2008 |
|---|---|---|---|
| WO | 2008068048 A2 | | 6/2008 |
| WO | WO 2008068048 | * | 6/2008 |
| WO | 2010054393 A1 | | 5/2010 |
| WO | 2013126595 A1 | | 8/2013 |
| WO | 2017151708 A1 | | 9/2017 |
| WO | WO2020109994 A1 | | 6/2020 |
| WO | 202148983 A1 | | 7/2021 |

OTHER PUBLICATIONS

Ataga et al., "Crizanlizumab for the prevention of pain crises in sickle cell disease" New Engl. J. Med. 2017; 376(5):429-439.
Ballas & Lusardi, "Hospital readmission for adult acute sickle cell painful episodes: frequency, etiology, and prognostic significance" Am. J. Hematol. 2005; 79:17-25.
Ballas, "Pain Management of Sickle Cell Disease" Hematol. Oncol. Clin. North Am. 2005; 19(5):785-802.
Callaghan et al., "Elipsis: A Longitudinal Study of Electronic Patient-Reported Outcomes, Actigraphy and Biomarkers to Identify and Assess at-Home Vaso-Occlusive Crises in Adults and Adolescents with Sickle Cell Disease" Blood 2017; 130:973.
Charache et al., "Effect of hydroxyurea on the frequency of painful crises in sickle cell anemia" New Engl. J. Med. 1995; 332:1317-1322.
Chase et al., "E-Selectin Ligands as Mechanosensitive Receptors on Neutrophils in Health and Disease" Ann. Biomed. Eng. 2012; 40(4):849-885.
Darbari et al., "Severe painful vaso-occlusive crises and mortality in a contemporary adult sickle cell anemia cohort study" PloS One 2013; 8(11):e79923.
Ernst & Magnani, "From carbohydrate leads to glycomimetic drugs" Nat. Rev. Drug Discov. 2009; 8(8):661-77.
Fabry & Nagel, "The effect of deoxygenation on red cell density: significance for the pathophysiology of sickle cell anemia" Blood 1982; 60(6)1370-77.
Frenette & Atweh "Sickle cell disease: old discoveries, new concepts, and future promise" J. Clin. Invest. 2007; 117:850-858.
Gardner et al., "Survival in adults with sickle cell disease in a high-income setting" Blood 2016; 128(10)1436-38.
Hidalgo et al., "Complete Identification of E-Selectin Ligands on Neutrophils Reveals Distinct Functions of PSGL-1, ESL-1, and CD44" Immunity 2007; 26(4):477-489.
Hidalgo et al., "Heterotypic interactions enabled by polarized neutrophil microdomains mediate thromboinflammatory injury" Nat. Med. 2009; 15:384-391.
Kanas et al., "Selectins and Their Ligands: Current Concepts and Controversies" Blood 1996; 88:3259-3287.
Kato et al. "Levels of soluble endothelium-derived adhesion molecules in patients with sickle cell disease are associated with pulmonary hypertension, organ dysfunction, and mortality." British J. Haem. 2005; 130:943-953.
Labow et al., "Characterization of E-selectin-deficient mice: Demonstration of overlapping function of the endothelial selectins" Immunity 1994; 1:709-720.
Leeuwenberg et al., "E-selectin and intercellular adhesion molecule-1 are released by activated human endothelial cells in vitro" Immunology 1992; 77(4):543-549.
Manwani & Frenette, "Vaso-occlusion in sickle cell disease: pathophysiology and novel targeted therapies" Blood 2013; 122(24):3892-8.
McEver RP, Zhu C., "Rolling cell adhesion." Annu Rev Cell Dev Biol. 2010;26:363-96.
Morikis et al., "Selectin catch-bonds mechanotransduce integrin activation and neutrophil arrest on inflamed endothelium under shear flow" Blood 2017; 130(19):2101-10.
Piel et al., "Sickle Cell Disease" New Engl. J. Med. 2017; 376:1561-1573.
Platt et al., "Pain in Sickle Cell Disease: Rates and Risk Factors" New Engl. J. Med. 1991; 325(1);11-6.
Platt et al., "Mortality in Sickle Cell Disease—Life Expectancy and Risk Factors for Early Death" New Engl. J. Med. 1994; 330(23);1639-44.
Pruenster et al., "Extracellular MRP8/14 is a regulator of β2 integrin-dependent neutrophil slow rolling and adhesion" Nat. Commun. 2015; 6:6915.
Quinn, "l-Glutamine for sickle cell anemia: more questions than answers" Blood 2018; 132:689-693.
Rees et al., "Sickle-cell disease" Lancet 2010; 376:2018-31.
Roldán et al., "Soluble E-selectin in cardiovascular disease and its risk factors" Thromb. Haemost. 2003; 90:1007-1020.
Smith et al., "Daily Assessment of Pain in Adults with Sickle Cell Disease" Ann. Intern. Med. 2008; 148:94-101.
Steinberg, "Management of Sickle Cell" New Engl. J. Med. 1999; 340:1021-1030.
Stuart & Nagel, "Sickle-cell disease" Lancet 2004; 364(9942):1343-60.
Tedder et al., "The selectins: vascular adhesion molecules" FASEB J. 1995; 9:866-873.
Turhan et al., "Primary role for adherent leukocytes in sickle cell vascular occlusion: A new paradigm" Proc. Natl. Acad. Sci. 2002; 99(5):3047-51.
Yawn et al., "Management of sickle cell disease: summary of the 2014 evidence-based report by expert panel members" JAMA 2014; 312:1033-48.
Zhang et al., "Neutrophils, platelets, and inflammatory pathways at the nexus of sickle cell disease pathophysiology" Blood 2016:127:801-809.
Benjamin et al., "A blocking monoclonal antibody to endothelial-leukocyte adhesion molecule-1 (ELAM1)" Biochem. Biophys. Res. Comm. 1990; 171(1):348-353.
Bevilacqua et al., "Endothelial leukocyte adhesion molecule 1: an inducible receptor for neutrophils related to complement regulatory proteins" Science 1989; 243:1160-1165.
Chang et al., "GMI-1070, a novel pan-selecting antagonist, reverses acute vascular occlusions in sickle cell mice" Blood 2010; 116(10):1770-1786.
Chen, "Enhancement and destruction of antibody function by somatic mutation: unequal occurrence is controlled by V gene combinatorial associations" EMBO J. 1995; 14(12):2784-2794.
Collins et al., "Structure and chromosomal location of the gene for endothelial-leukocyte adhesion molecule 1" J. Biol. Chem. 1991; 266:2466-2473.
Gregory et al., "The DNA sequence and biological annotation of human chromosome 1" Nature 2006; 441:315-321.
Hession et al., "Endothelial leukocyte adhesion molecule 1: direct expression and functional interactions" Proc. Natl. Acad. Sci. USA 1990;87:1673-1677.
Kirschweger, "Crucell: Biopharmaceuticals—As human as they get." Mol. Therapy 2003; 7(1):5-6.
Kussie, "Single Engineered Amino Acid Substitution Changes Antibody Fine Specificity" J. Immunol. 1994; 152(1):146-152.
Liu et al., "High-throughput screening for developability during early-stage antibody discovery using self-interaction nanoparticle spectroscopy" mAbs 2014; 6:483-92.
Okpala, "Leukocyte adhesion and the pathophysiology of sickle cell disease" Curr. Opinion Hematol. 2006; 13(1):40-44.
Owens et al., "The in vivo and in vitro characterisation of an engineered human antibody to E-selectin" Immunotechnology 1997; 3(2):107-116.
Repo et al., "Binding of human peripheral blood polymorphonuclear leukocytes to E-selecting (CD62E) does not promote their activation" J. Immunol. 1997; 159(2):943-951.
Schafer et al., "Prediction of well-conserved HIV-1 ligands using a matrix-based algorithm, EpiMatrix" Vaccine 1998; 16(19):1880-84.
Vita et al., "The immune epitope database (IEDB) 3.0" Nucleic Acids Res. 2015; 28(43):D405-12.
Wang et al., "Peptide binding predictions for HLA DR, DP and DQ molecules" BMC Bioinformatics 2010; 11:568.

(56) References Cited

OTHER PUBLICATIONS

Wang et al., "A Systematic Assessment of MHC Class II Peptide Binding Predictions and Evaluation of a Consensus Approach" PLoS Comput. Biol. 2008; 4(4), e1000048.

* cited by examiner

\>Antibody 0841_VH (SEQ ID NO:25)

EVQLVESGGGLVQPGGSLRLSCAASGYNIRSSYMHWVRQAPGKGL
EWVARIDPANGNTIYAEKFKIRFTISADNAKNSAYLQMNSLRAEDTA
VYYCAMDLYSTSEYWGQGTLVTVSS

\>Antibody 0841_VL (SEQ ID NO:21)

DIQMTQSPSSLSASVGDRVTITCKTSQNINRYLNWYQQKPGKAPKL
LIYNANSLQTGVPSRFSGSGSGTDFTLTISSLQPEDFATYFCLQDNSW
PLTFGQGTKVEIK

FIG. 4

ANTI-E-SELECTIN ANTIBODIES, COMPOSITIONS AND METHODS OF USE

CROSS-REFERENCE TO RELATED APPLICATIONS

This application claims priority to U.S. Provisional Patent Application No. 62/965,688, filed Jan. 24, 2020, U.S. Provisional Patent Application No. 63/104,213 filed Oct. 22, 2020, and U.S. Provisional Patent Application No. 63/121,467 filed Dec. 4, 2020, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 6, 2021, is named PC072498A_Sequence_Listing_ST25.txt and is 1,048,576 bytes in size.

FIELD OF THE INVENTION

The present invention related to antibodies, and antigen-binding fragments thereof, that specifically bind E-selectin, and compositions, methods and uses thereof, including use of antibodies of the disclosure to treat Sickle Cell disease (SCD) including treatment and prevention of vaso-occlusive crisis (VOC) associated with SCD.

BACKGROUND

Sickle cell disease (SCD) is a severe, rare genetic disorder affecting over 100,000 people in the United States (US) alone (Center for Disease Control and Prevention). It is a chronic condition with substantial morbidity and mortality in a population with high unmet medical need. Individuals with SCD suffer from progressive organ damage and markedly shortened life expectancy, with a median survival of approximately 56 years (Gardner et al., Blood 2016; 128 (10)1436-38).

SCD is characterized by the presence of an abnormal form of hemoglobin (Hb)—sickle hemoglobin (HbS). A single nucleotide substitution in the β-globin gene (HBB) results in a one amino acid substitution (valine for glutamic acid) at residue 6 (HBS allele). Individuals homozygous for HBS have the most common and most severe form of sickle cell disease (SCD-SS). Variant forms of SCD arise when an individual has one copy of HBS and one copy of a mutation in another HBB gene. Individuals with 1 copy of the HBS allele and 1 copy of the hemoglobin C allele (HBC) have SC disease (SCD-SC). When an individual has 1 copy of HBS and one copy of a β-thalassemia allele the severity of the SCD is dependent on the severity of the β-thalassemia allele with Hbβ$^c$thalassemia deletion (SCD-Sβ$^o$-thal) often more severe than Hbβ$^+$-thalassemia allele (SCD-Sβ+-thal), or another interacting HB variant (SCD-SVariant) (Frenett & Atweh J. Clin. Invest. 2007; 117:850-858).

The primary event in the molecular pathogenesis of SCD is the tendency of HbS to polymerize under conditions of low oxygen tension causing red blood cells (RBCs) to become rigid and sickle shaped (Fabry & Nagel Blood 1982; 60(6)1370-77). Hypoxia in the microcapillary venous bed leads to inflammation of the endothelium and adherence of neutrophils, and a decrease in neutrophil rolling and flow velocity. These cell aggregates become trapped in the vasculature through interactions with endothelial cells. The adhesive interactions of the sickled RBC, leukocytes, and endothelial cells obstruct the vasculature leading to vaso-occlusion (Zhang et al., Blood 2016:127:801-809; Okpala, 2006; Frenette & Atweh, J. Clin. Invest. 2007; 117:850-858). Dysregulated nitric oxide homeostasis contributes to vascular dysfunction in SCD (Asian & Freeman, 2007). Blood cell aggregates lead to episodes of vascular obstruction, organ infarction and ischemia which manifest clinically as episodes of severe pain. Anemia is consequent upon a shortened red cell life span due to hemolysis and vascular occlusion that is precipitated by interactions between the vascular endothelium and sickled RBCs, leukocytes and platelets (Rees et al., Lancet 2010; 376:2018-31).

Vaso-occlusive crisis (VOC) is the most common clinical manifestation of SCD and is the major cause of morbidity in SCD with an interruption of daily functioning (Ballas & Lusardi, Am. J. Hematol. 2005; 79:17-25; Piel et al., New Engl. J. Med. 2017; 376:1561-1573; Darbari et al., PloS One 2013; 8(11):e79923). VOC is initiated by interaction between sickled RBCs and vascular endothelium in post-capillary venules, where oxygen tension is at its lowest (Manwani & Frenette, Blood 2013; 122(24):3892-8). This leads to endothelial damage that triggers an inflammatory response and causes leukocytes, platelets and additional RBCs to be recruited to the site of inflammation (Zhang et al., Blood 2016; 127(7):801). These cellular aggregates lead to vascular obstruction (Turhan et al., Proc. Natl. Acad. Sci. 2002; 99(5):3047-51) and slowing of blood flow in post-capillary venules which causes local tissue hypoxia, and further tissue inflammation. This results in more deoxygenation and sickling of RBCs, and propagation of the occlusion, sometimes called secondary recruitment of sickled cells and occluded vessels (Stuart & Nagel, Lancet 2004; 364(9942):1343-60).

VOC can manifest in patients with SCD as early as 6 months of age, although they are considerably less common in young infants than in older children or adults (Benjamin et al., Amer. Pain Soc. 1994; vol. 1, 94pp). Approximately 60% of patients with homozygous SCD have at least 1 severe VOC episode per year, but a proportion of patients have many more episodes (Platt et al., N. Engl. J. Med. 1991; 325(1); 11-6). In this same study 5.2% of patients with SCD genotype had 3-10 severe VOC episodes per year and a small proportion (>1%) of patients had 10 or more episodes per year.

Pain is the clinical manifestation of initial and ongoing vascular occlusion and ischemia (Ballas, Hematol. Oncol. Clin. North Am. 2005; 19(5):785-802), which may be particularly severe for patients with the SCD-SS genotype, who have also been observed to suffer from higher mortality than other genotypes (Platt et al., N. Engl. J. Med. 1994; 330(23); 1639-44).

Recruitment of leukocytes to areas of vascular endothelial damage involves the selectin family of adhesion molecules: E-selectin (also known as CD62E); P-selectin (also known as CD62P); and L-selectin (also known as CD62L), all of which are all regulated as part of an inflammatory response (Ernst & Magnani Nat. Rev. Drug Discov. 2009; 8(8):661-77; Morikis et al., Blood 2017; 130(19):2101-10). While similar in structure, each selectin exhibits a different distribution, ligand binding kinetics and diversity in both pathological and physiological functions.

The selectin family of adhesion molecules and their ligands are part of a proinflammatory response in SCD promoted by alteration in the sickled red blood cells and the activated endothelial cells. The selectins also play a critical role in regulating the initial contact of cell-cell adhesion, leukocyte rolling on the endothelium and integrin activation and transmigration of cells. Adhesion of leukocytes to inflamed endothelium and circulating cellular aggregates are a hallmark event in SCD.

The selectin family of carbohydrate binding proteins share a similar structure, with each having an N-terminal carbohydrate-recognition domain characteristic of $Ca^{2+}$-dependent (C type) lectins, followed by an epidermal growth factor (EGF)-like domain, a series of short consensus repeats with homology to complement regulatory domains, a transmembrane domain, and a short cytoplasmic tail (McEver & Zhu, 2010). The selectins and their ligands mediate the recruitment of platelets and leukocytes from the blood to the vascular endothelium contributing to creation of a chronic pro-inflammatory environment.

The pathophysiology of SCD is complex and heterogeneous. Symptoms include pain crises, chronic anemia, acute chest syndrome, stroke, splenic sequestration, vaso-occlusive acute pain events or crises, renal dysfunction, and susceptibility to bacterial infections (Ashley-Koch et al., Am. J. Epidemiol. 2000; 151:839-845; Steinberg, New Engl. J. Med. 1999; 340:1021-1030; Piel et al., New Engl. J. Med. 2017; 376:1561-1573). Acute end organ complications associated with SCD can include acute chest syndrome, acute stroke priapism, hepatobiliary complications, splenic sequestration and acute renal failure. Chronic complications from the cumulative insult of SCD include avascular necrosis, pulmonary hypertension, renal complications, ophthalmologic complications, leg ulcers and recurrent priapism (Yawn et al., JAMA 2014; 312:1033-48).

Hydroxyurea is approved for prophylactic therapy of SCD. Mechanistically, hydroxyurea increases fetal hemoglobin (HbF) concentrations and reduces the number of pain crises (Charache et al., New Engl. J. Med. 1995; 332:1317-1322). Although hydroxyurea is considered the standard of care in the prevention of VOC, it has a failure rate of ~30-35% and is ineffective in treating symptoms during an acute VOC. ENDARI (L-glutamine) was recently approved for prophylactic SCD treatment, however, the mechanism of action is uncertain and clinical benefit is modest (Quinn, Blood 2018; 132:689-693). Current treatments for acute VOC episodes are largely supportive with opioid analgesics, hydration, oxygen, and transfusion. In addition, most patients treat a VOC at home and do not seek direct medical intervention (Smith et al., Ann. Intern. Med. 2008; 148:94-101; Callaghan et al., Blood 2017; 130:973).

There remains a significant need for the prophylaxis and treatment of SCD and, in particular, to address the underlying pathophysiology (e.g., reduction of inflammation and cellular aggregation) of recurring and debilitating VOC in patients. The present invention provides novel therapeutic antibodies that specifically bind to E-selectin and are capable of neutralizing E-selectin functional activity. These antibodies may be used advantageously to prevent, or reduce the occurrence of, VOC when utilized as a prophylactic treatment for SCD, and to treat acute VOC in patients with SCD by decreasing the duration (e.g., a reduction in the time to resolve a VOC), intensity and/or severity of the VOC.

SUMMARY

The invention provides antibodies, and antigen-binding fragments thereof, that specifically bind to E-selectin, as well as uses, and associated methods. Those skilled in the art will recognize or be able to ascertain using no more than routine experimentation, many equivalents to the specific embodiments of the invention described herein. Such equivalents are intended to be encompassed by the following embodiments (E).

E1. An isolated antibody or antigen-binding fragment thereof that specifically binds to E-selectin (e.g., human and/or cynomolgus monkey E-selectin).

E2. The antibody, or antigen-binding fragment thereof, of E1, comprising the HCDR-1, HCDR-2, and HCDR-3 sequences selected from the group consisting of SEQ ID NO: 8, 23, 52, 63, 77, 92, 111, 125, 9, 24, 29, 38, 41, 44, 53, 64, 78, 93, 112, 126, 10, 54, 65, 79, 94, 113 and 127.

E3. The antibody, or antigen-binding fragment thereof, of any one of E1-E2, comprising the LCDR-1, LCDR-2, and LCDR-3 sequences selected from the group consisting of SEQ ID NO: 2, 18, 47, 68, 82, 97, 106, 9, 24, 29, 38, 41, 44, 53, 64, 78, 93, 112, 12610, 54, 65, 79, 94, 113 and 127.

E4. The antibody, or antigen binding fragment thereof, of any one of E1-E3 comprising one or more of (a)-(f)
  (a) LCDR-1 amino acid sequence selected from the group consisting of the sequence of SEQ ID NO:2, 18, 47, 68, 82, 97 and 106;
  (b) a LCDR-2 amino acid sequence selected from the group consisting of the sequence of SEQ ID NO:3, 19, 48, 69, 83, 98, 107 and 120;
  (c) a LCDR-3 amino acid sequence selected from the group consisting of the sequence of SEQ ID NO:4, 20, 49, 70, 84, 99, 108 and 121;
  (d) a HCDR-1 amino acid sequence selected from the group consisting of the sequence of SEQ ID NO:8, 23, 52, 63, 77, 92, 111 and 125;
  (e) a HCDR-2 amino acid sequence selected from the group consisting of the sequence of SEQ ID NO:9, 24, 29, 38, 41, 44, 53, 64, 78, 93, 112 and 126; and
  (f) a HCDR-3 amino acid sequence selected from the group consisting of the sequence of SEQ ID NO:10, 54, 65, 79, 94, 113 and 127.

E5. The antibody, or antigen binding fragment thereof, of any one of E1-E4 comprising one or more of the following:
  a LCDR-1 comprising the amino acid sequence of SEQ ID NO:2,
  a LCDR-2 comprising the amino acid sequence of SEQ ID NO:3,
  a LCDR-3 comprising the amino acid sequence of SEQ ID NO:4,
  a HCDR-1 comprising the amino acid sequence of SEQ ID NO:8,
  a HCDR-2 comprising the amino acid sequence of SEQ ID NO:9, and
  a HCDR-3 comprising the amino acid sequence of SEQ ID NO:10.

E6. The antibody, or antigen-binding fragment thereof, of any one of E1-E5, comprising the HCDR-1 (any one of SEQ ID NO:8, 23, 52, 63, 77, 92, 111 and 125), HCDR-2 (any one of SEQ ID NO:9, 24, 29, 38, 41, 44, 53, 64, 78, 93, 112 and 126), and HCDR-3 (any one of SEQ ID NO:10, 54, 65, 79, 94, 113 and 127) sequences of at least one sequence selected from the group consisting of SEQ ID NO:11, 25, 30, 35, 39, 42, 45, 55, 60, 66, 75, 80, 90, 95, 104, 114, 118, and 128.

E7. The antibody, or antigen-binding fragment thereof, of any one of E1-E6, comprising the LCDR-1 (any one of SEQ ID NO:2, 18, 47, 68, 82, 97 and 106), LCDR-2 (any one of SEQ ID NO:3, 19, 48, 69, 83, 98, 107 and 120), and LCDR-3 (any one of SEQ ID NO:4, 20, 49, 70, 84, 99, 108 and 121) sequences of at last one sequence selected from the group consisting of SEQ ID NO:5, 21, 27, 32, 50, 57, 71, 73, 85, 87, 100, 102, 109, 116, and 122.

E8. The antibody, or antigen-binding fragment thereof, of any one of E1-E7, comprising the HCDR-1 (any one of SEQ ID NO:8, 23, 52, 63, 77, 92, 111 and 125), HCDR-2 (any one of SEQ ID NO:9, 24, 29, 38, 41, 44, 53, 64, 78, 93, 112 and 126), and HCDR-3 (any one of SEQ ID NO:10, 54, 65, 79, 94, 113 and 127) sequences of at least one sequence selected from the group consisting of SEQ ID NO:7, 13, 22, 28, 34, 37, 40, 43, 51, 59, 62, 74, 76, 89, 91, 103, 110, 117 and 124.

E9. The antibody, or antigen-binding fragment thereof, of any one of E1-E8, comprising the LCDR-1 (any one of SEQ ID NO:2, 18, 47, 68, 82, 97 and 106), LCDR-2 (any one of SEQ ID NO:3, 19, 48, 69, 83, 98, 107 and 120), and LCDR-3 (any one of SEQ ID NO:4, 20, 49, 70, 84, 99, 108 and 121) sequences of at least one sequence selected from the group consisting of SEQ ID NO:1, 17, 26, 31, 46, 56, 67, 72, 81, 86, 96, 101, 105, 115 and 119.

E10. The antibody, or antigen-binding fragment thereof, of any one of E1-E9, comprising the HCDR-1 (SEQ ID NO:8), HCDR-2 (SEQ ID NO:9), and HCDR-3 (SEQ ID NO:10) sequences of SEQ ID NO:11.

E11. The antibody, or antigen-binding fragment thereof, of any one of E1-E10, comprising the LCDR-1 (SEQ ID NO:2), LCDR-2 (SEQ ID NO:3), and LCDR-3 (SEQ ID NO:4) sequence of SEQ ID NO:5.

E12. The antibody, or antigen-binding fragment thereof, or any one of E1-E11, comprising the HCDR-1 (SEQ ID NO:8), HCDR-2 (SEQ ID NO:9), and HCDR-3 (SEQ ID NO:10) sequence of SEQ ID NO:7 or 13.

E13. The antibody, or antigen-binding fragment thereof, or any one of E1-E12, comprising the LCDR-1 (SEQ ID NO:2), LCDR-2 (SEQ ID NO:3), and LCDR-3 (SEQ ID NO:4) sequences of SEQ ID NO:1.

E14. The antibody, or antigen-binding fragment thereof, of anyone of E1-E13, comprising a LCDR-1 comprising the amino acid sequence of SEQ ID NO:2, a LCDR-2 comprising the amino acid sequence of SEQ ID NO:3, a LCDR-3 comprising the amino acid sequence of SEQ ID NO:4, a HCDR-1 comprising the amino acid sequence of SEQ ID NO:8, a HCDR-2 comprising the amino acid sequence of SEQ ID NO:9, and a HCDR-3 comprising the amino acid sequence of SEQ ID NO:10.

E15. The antibody, or antigen-binding fragment thereof, of any one of E1-E4, comprising a LCDR-1 comprising the amino acid sequence of SEQ ID NO:2, a LCDR-2 comprising the amino acid sequence of SEQ ID NO:3, a LCDR-3 comprising the amino acid sequence of SEQ ID NO:4

E16. The antibody, or antigen-binding fragment thereof, of anyone of E1-E15, comprising a HCDR-1 comprising the amino acid sequence of SEQ ID NO:8, a HCDR-2 comprising the amino acid sequence of SEQ ID NO:9, and a HCDR-3 comprising the amino acid sequence of SEQ ID NO:10.

E17. The antibody, or antigen-binding fragment thereof, of any one of E1-E16, comprising a VL framework sequence derived from a human germline VL sequence selected from the group consisting of IGKV1-12*01, IGKV1-13*02, IGKV1-33*01, IGKV1-39*01, IGKV1-5*01, IGKV3-11*01, IGKV3-15*01, IGKV3-20*01, IGKV3D-20*02, and IGKV4-1*01.

E18. The antibody, or antigen-binding fragment thereof, of anyone of E1-E17, comprising a VH framework sequence derived from a human germline VH sequence selected from the group consisting of IGHV1-2*02, IGHV1-3*01, IGHV1-46*01, IGHV1-69*01, IGHV1-69*02, IGHV1-8*01, IGHV3-7*01, IGHV3-13*01, IGHV3-23*01, IGHV3-23*04, IGHV3-30*01, IGHV3-30*18, IGHV5-10-1*01, IGHV5-10-1*04, and IGHV5-51*01.

E19. The antibody, or antigen-binding fragment thereof, of anyone of E1-E18, comprising an IGHV1-39*01 VL framework sequence.

E20. The antibody, or antigen-binding fragment thereof, of any one of E1-E19, comprising an IGHV3-07*01 VH framework sequence.

E21. The antibody, or antigen-binding fragment thereof, of any one of E1-E20, comprising a VL framework sequence and a VH framework sequence, and wherein the VL framework sequence is at least 72% identical to the human germline sequence from which it was derived.

E22. The antibody, or antigen-binding fragment thereof, of any one of E1-E21, comprising a VL framework sequence and a VH framework sequence, and wherein the VL framework sequence is at least 72%, 74%, 75%, 77%, 90%, 91%, 92%, 93%, 94%, 95%, 96%, 97%, 98%, or 99% identical to the human germline sequence from which it was derived.

E23. The antibody, or antigen-binding fragment thereof, of anyone of E1-E22, comprising a VL framework sequence and a VH framework sequence, and wherein the VH framework sequence is at least 53% identical to the human germline sequence from which it was derived.

E24. The antibody, or antigen-binding fragment thereof, of any one of E1-E23, comprising a VL framework sequence and a VH framework sequence, and wherein the VH framework sequence is at least 53%, 58%, 60%, 63%, 71%, 72%, 90%, 91%, 92%, 93%, 94%, 95%, 96%, 97%, 98%, or 99% identical to the human germline sequence from which it was derived.

E25. The antibody, or antigen-binding fragment thereof, of any one of E1-E24, comprising a VH domain comprising an amino acid sequence at least 90% identical to SEQ ID NO:1.

E26. The antibody, or antigen-binding fragment thereof, of any one of E1-E25, comprising a VH domain comprising an amino acid sequence at least 91%, 92%, 93%, 94%, 95%, 96%, 97%, 98%, or 99% identical to SEQ ID NO:11.

E27. The antibody, or antigen-binding fragment thereof, of any one of E1-E26, comprising a VH domain comprising, or consisting of, the amino acid sequence of SEQ ID NO:11.

E28. The antibody, or antigen-binding fragment thereof, of any one of E1-E27, comprising a VL domain comprising an amino acid sequence at least 90% identical to SEQ ID NO:5.

E29. The antibody, or antigen-binding fragment thereof, of any one of E1-E28, comprising a VL domain comprising an amino acid sequence at least 91%, 92%, 93%, 94%, 95%, 96%, 97%, 98%, or 99%, identical to SEQ ID NO:5.

E30. The antibody, or antigen-binding fragment thereof, of any one of E1-E29, comprising, or consisting of, a VL domain comprising the amino acid sequence of SEQ ID NO:5.

E31. The antibody, or antigen-binding fragment thereof, of any one of E1-E30, comprising a VH domain comprising, or consisting of, the amino acid sequence of SEQ ID NO:11 and a VL domain comprising, or consisting of, the amino acid sequence of SEQ ID NO:5.

E32. The antibody, or antigen-binding fragment thereof, of any one of E1-E31, comprising an Fc domain.

E33. The antibody, or antigen-binding fragment thereof, of E32, wherein the Fc domain is the Fc domain of an IgA (for example $IgA_1$ or $IgA_2$), IgD, IgE, IgM, or IgG (for example $IgG_1$, $IgG_2$, $IgG_3$, or $IgG_4$).

E34. The antibody, or antigen-binding fragment thereof, of E33 wherein the Fc domain is the Fc domain of an IgG.

E35. The antibody, or antigen-binding fragment thereof, of E34, wherein the IgG is selected from the group consisting of $IgG_1$, $IgG_2$, $IgG_3$, and $IgG_4$.

E36. The antibody, or antigen-binding fragment thereof, of E35 wherein the IgG is IgG$_1$.

E37. The antibody, or antigen-binding fragment thereof, of any one of E1-E36, comprising a heavy chain comprising an amino acid sequence at least 90% identical to SEQ ID NO:7 or SEQ ID NO:13.

E38. The antibody, or antigen-binding fragment thereof, of any one of E1-E37, comprising a heavy chain comprising an amino acid sequence at least 91%, 92%, 93%, 94%, 95%, 96%, 97%, 98%, or 99%, identical to SEQ ID NO:7 or SEQ ID NO:13.

E39. The antibody, or antigen-binding fragment thereof, of anyone of E1-E38, comprising a heavy chain comprising, or consisting of, the amino acid sequence of SEQ ID NO:7 or SEQ ID NO:13.

E40. The antibody, or antigen-binding fragment thereof, of any one of E1-E39, comprising a heavy chain comprising an amino acid sequence at least 90%, 91%, 92%, 93%, 94%, 95%, 96%, 97%, 98%, or 99%, identical to any one of SEQ ID NO:22, 28, 34, 37, 40, 43, 51, 59, 62, 74, 76, 89, 91, 103, 110, 117 and 124.

E41. The antibody, or antigen-binding fragment thereof, of anyone of E1-E40, comprising a LC comprising an amino acid sequence at least 90% identical to SEQ ID NO:1.

E42. The antibody, or antigen-binding fragment thereof, of any one of E1-E41, comprising a LC comprising an amino acid sequence at least 91%, 92%, 93%, 94%, 95%, 96%, 97%, 98%, or 99%, identical to SEQ ID NO:

E43. The antibody, or antigen-binding fragment thereof, of anyone of E1-E42, comprising a LC comprising, or consisting of, the amino acid sequence of SEQ ID NO:1.

E44. An antibody, or antigen-binding fragment thereof, of any one of E1-E43, comprising a heavy chain comprising the amino acid sequence of SEQ ID NO:7 or SEQ ID NO:13 and a light chain comprising the amino acid sequence of SEQ ID NO:1.

E45. The antibody, or antigen-binding fragment thereof, of any one of E1-E45, comprising a light chain comprising an amino acid sequence at least 90%, 91%, 92%, 93%, 94%, 95%, 96%, 97%, 98%, or 99%, identical to any one of SEQ ID NO:17, 26, 31, 1, 46, 56, 67, 72, 81, 86, 96, 101, 105, 115 and 119.

E46. The antibody, or antigen-binding fragment thereof, of any one of E1-E45, comprising the HCDR-1, HCDR-2 and HCDR-3 encoded by the insert of the plasmid deposited at the ATCC and having ATCC Accession No. PTA-126529.

E47. The antibody, or antigen-binding fragment thereof, of anyone of E1-E46, comprising the LCDR-1, LCDR-2 and LCDR-3 encoded by the insert of the plasmid deposited at the ATCC and having ATCC Accession No. PTA-126530.

E48. The antibody, or antigen-binding fragment thereof, of anyone of E1-E47, comprising a VH domain encoded by the insert in the plasmid deposited at the ATCC and having ATCC Accession No. PTA-126529.

E49. The antibody, or antigen-binding fragment thereof, of any one of E1-E48, comprising a VL domain encoded by the insert in the plasmid deposited at the ATCC and having ATCC Accession No. PTA-126530.

E50. The antibody, or antigen-binding fragment thereof, of any one of E1-E49, comprising the HC amino acid sequence encoded by the insert in the plasmid deposited at the ATCC and having ATCC Accession No. PTA-126529 and the LC amino acid sequence encoded by the insert in the plasmid deposited at the ATCC and having ATCC Accession No. PTA-126530.

E51. The antibody, or antigen-binding fragment thereof, of any one of E1-E50, wherein the antibody or antigen-binding fragment is an Fc fusion protein, a monobody, a maxibody, a bifunctional antibody, an scFab, an scFv, a peptibody.

E52. The antibody, or antigen-binding fragment thereof, of anyone of E1-E52, wherein the antibody, or antigen binding fragment thereof, binds human E-selectin with a $K_D$ about or less than a value selected from the group consisting of about 800 nM, 700 nM, 600 nM, 500 nM, 400 nM, 300 nM, 200 nM, 175 nM, 150 nM, 125 nM, 100 nM, 90 nM, 80 nM, 70 nM, 60 nM, 50 nM, 40 nM, 30 nM, 20 nM, 10 nM, 5 nM, 2 nM, 1 nM, 900 pM, 800 pM, 700 pM, 600 pM and 500 pM.

E53. The antibody, or antigen-binding fragment thereof, of anyone of E1-E52, wherein the antibody, or antigen binding fragment thereof, binds cynomolgus monkey E-selectin with a $K_D$ about or less than a value selected from the group consisting of about 800 nM, 700 nM, 600 nM, 500 nM, 400 nM, 300 nM, 200 nM, 175 nM, 150 nM, 125 nM, 100 nM, 90 nM, 80 nM, 70 nM, 60 nM, 50 nM, 40 nM, 30 nM, 20 nM, 10 nM, 5 nM, 2 nM, 1 nM, 900 pM, 800 pM, 700 pM, 600 pM and 500 pM.

E54. The antibody, or antigen-binding fragment thereof, of anyone of E1-E53, wherein the antibody, or antigen binding fragment thereof, binds human E-selectin with a $K_D$ of about 10 nM to about 200 nM.

E55. The antibody, or antigen-binding fragment thereof, of anyone of E1-E54, wherein the antibody, or antigen binding fragment thereof, binds human E-selectin with a $K_D$ of about 68.4+/−3.18 nM.

E56. The antibody, or antigen-binding fragment thereof, of anyone of E1-E55, wherein the antibody, or antigen binding fragment thereof, binds cynomolgus monkey E-selectin with a $K_D$ of about 10 nM to about 200 nM.

E57. The antibody, or antigen-binding fragment thereof, of anyone of E1-E56, wherein the antibody, or antigen binding fragment thereof, binds cynomolgus monkey E-selectin with a $K_D$ of about 64.9+/−1.13 nM.

E58. The antibody, or antigen-binding fragment thereof, of any one of E1-E57, wherein the anti-E-selectin antibody binds human E-selectin with a $K_D$ selected from the group consisting of about 92.85 nM, about 70.3 nM, about 65.2 nM, about 61.8 nM, about 60.5 nM, about 68.0 nM, about 21.6 nM, about 324 nM, about 54.4 nM, about 628.5 nM and 2940 nM.

E59. The antibody, or antigen-binding fragment thereof, of anyone of E1-E58, wherein the anti-E-selectin antibody binds cynomolgus monkey E-selectin with a $K_D$ selected from the group of about 138.5 nM, about 78.3 nM, about 76.5 nM, about 81.5 nM, about 67.8 nM, about 45.8 nM, about 243.5 nM, about 45.4 nM, about 492 nM and 3145 nM.

E60. The antibody, or antigen-binding fragment thereof, of any one of E1-E59, wherein the mean half-life in cynomolgus monkeys is at least about 14.4 days (345 hours) following IV administration at a dose of 10 mg/kg.

E61. The antibody, or antigen-binding fragment thereof, of any one of E1-E60, wherein the mean half-life in cynomolgus monkeys is at least about 12 days (287 hours) following IV administration at a dose of 3 mg/kg.

E62. The antibody, or antigen-binding fragment thereof, of any one of E1-E61, wherein the mean half-life in cynomolgus monkeys is about 21.5 days (518 hours) following SC administration at a dose of 3 mg/kg.

E63. The antibody, or antigen-binding fragment thereof, of anyone of E1-E62, wherein the antibody, or antigen-binding fragment thereof, does not induce anti-drug antibodies.

E64. The antibody, or antigen-binding fragment thereof, of any one of E1-E63, wherein the predicted immunogenic potential of the antibody, as indicated by the t-regitope (T-Reg) adjusted score, is less than about −30.

E65. The antibody, or antigen-binding fragment thereof, of any one of E1-E64, wherein the predicted immunogenic potential of the antibody, as indicated by the t-regitope (T-Reg) adjusted score, is less than about −45 and there are 0 non-germline T cell epitopes.

E66. The antibody, or antigen-binding fragment thereof, of any one of E1-E65, wherein the predicted immunogenic potential of the antibody, as indicated by the T-Reg adjusted score, is less than the T-Reg adjusted score selected from the group consisting of about −24, −26, −27, −30, −32, −33, −34, −35, −36, −37, −38, −39, −40, −41, −42, −43, −44, −45, −46, −47 and −48.

E67. The antibody, or antigen-binding fragment thereof, of anyone of E1-E66, wherein the predicted immunogenic potential of the antibody, as indicated by T-Reg adjusted score, is about −45 or −46.

E68. The anti-E-selectin antibody, or antigen-binding fragment thereof, of any one of E1-E67, wherein the antibody, or antigen-binding fragment thereof is at low risk for polyreactivity, as measured by, for example an AC-SINS assay, a DNA binding assay and/or an insulin binding assay.

E69. The antibody, or antigen-binding fragment thereof, of anyone of E1-E68, wherein the antibody or antigen-binding fragment has a viscosity selected from the group consisting of about 7.97+/−1.83 cP at a concentration of about 23 mg/mL, about 12.38+/−5.28 cP at a concentration of about 48 mg/mL, about 4.26+/−0.6 cP at a concentration of about 90 mg/mL, about 5.58+/−0.99 cP at a concentration of about 102 mg/mL, about 8.44+/−1.54 cP at a concentration of about 121 mg/mL, about 9.78+/−2.32 cP at a concentration of about 140 mg/mL, about 17.47+/−3.24 cP at a concentration of about 158 mg/mL and about 37.99+/−7.03 cP at a concentration of about 188 mg/mL, when measured at 25° C. by, for example, dynamic light scattering (DLS).

E70. The antibody, or antigen-binding fragment thereof, of any one of E1-E69, wherein the antibody or antigen-binding fragment has a viscosity of about 15 cP to 40 cP at a concentration of about 150 mg/mL to about 190 mg/mL when measured at 25° C. by, for example DLS.

E71. The antibody, or antigen-binding fragment thereof, of any one of E1-E70, wherein the antibody or antigen-binding fragment has a viscosity of 33.4 cP at 185.7 mg/mL when measured at 25° C. by, for example an Anton Parr method.

E72. The antibody, or antigen-binding fragment thereof, of any one of E1-E71, wherein the antibody, or antigen-binding fragment thereof, binds to at least one of three epitopes of human E-selectin as determined by, for example a competition assay using, for example an Octet biosensor.

E73. The antibody, or antigen-binding fragment thereof, of E72, wherein at least 2 of the epitopes are overlapping.

E74. The antibody, or antigen-binding fragment thereof, of anyone of E1-E73, wherein the antibody, or antigen-binding fragment thereof, interacts with at least one amino acid residue of human E-selectin selected from the group consisting of T7, E8, A9, M10, T11, P46, S47, Y48, N82, N83, Q85, E88, E92, Y94, R97, N105, E107, R108, S110, K111, K112, K113, and a combination thereof.

E75. The antibody, or antigen-binding fragment thereof, of anyone of E1-E74, wherein the antibody, or antigen-binding fragment thereof, interacts with at least one amino acid residue of human E-selectin within 3.8 Å selected from the group consisting of T7, E8, A9, T11, P46, S47, Y48, N82, N83, Q85, E92, Y94, N105, E107, R108, S110, K111, K112 and a combination thereof.

E76. The antibody, or antigen-binding fragment thereof, of anyone of E1-E75, wherein the antibody, or antigen-binding fragment thereof, interacts with at least one amino acid residue of human E-selectin with a buried surface area (Å$^2$) of >5 Å$^2$ selected from the group consisting of T7, E8, A9, T11, P46, S47, Y48, N82, N83, Q85, E88, E92, Y94, R97, E107, R108, S110, K111, K112, K113 and a combination thereof.

E77. The antibody, or antigen-binding fragment thereof, of anyone of E1-E76, wherein the antibody, or antigen-binding fragment thereof interacts with at least one amino acid residue of human E-selectin via a hydrogen bond selected from the group consisting of E8, S47, N82, N83, E88, E92, Y94, N105, E107, R108, S110, K112, and a combination thereof.

E78. The antibody, or antigen-binding fragment thereof, of any one of E1-E77, wherein the antibody, or antigen-binding fragment thereof interacts with at least one amino acid residue of human E-selectin via a salt bridge selected from the group consisting of K111, K112, and a combination thereof.

E79. The antibody, or antigen-binding fragment thereof, of any one of E1-E78, wherein the antibody, or antigen-binding fragment thereof interacts with at least one amino acid residue of human E-selectin via a water-mediated hydrogen bond selected from the group consisting of R97, K112, and a combination thereof.

E80. The antibody, or antigen-binding fragment thereof, of anyone of E1-E79, wherein the antibody, or antigen-binding fragment thereof, interacts with at least one amino acid residue of human E-selectin which also interacts within 3.8 A of an sLex amino acid residue selected from the group consisting of Y48, N82, N83, E92, Y94, R97, N105, E107 and a combination thereof.

E81. The antibody, or antigen-binding fragment thereof, of anyone of E1-E80, wherein the percentage of HMMS and/or the percentage LMMS is less than 5% following storage at 40° C. for 4 weeks in a solution selected from the group consisting of 20 mM Tris at pH 7.5, 20 mM histidine at pH 5.8 and 20 mM glutamic acid at pH 4.5, and wherein optionally, the analysis is performed by aSEC.

E82. The antibody, or antigen-binding fragment thereof, of any one of E1-E81, wherein the percentage of HMMS is less than 5% following storage at 4° C. or 25° C. for up to 6 weeks in a solution selected from the group consisting of 20 mM Tris, 8.5% sucrose at pH 7.5, 20 mM histidine, 8.5% sucrose, 0.005% EDTA at pH 5.8 and 20 mM glutamic acid, 8.5% trehalose at pH 4.5; wherein the antibody is at a concentration of about 150 mg/ml; and wherein optionally, the analysis is performed by aSEC.

E83. The antibody, or antigen-binding fragment thereof, of any one of E1-E82, wherein the antibody, or antigen-binding fragment thereof, has a thermal stability with a melting temperature ($T_m1$), or the temperature at which the $C_H2$ of the antibody is 50% unfolded, of about 65° C. or greater, as measured by Differential Scanning Calorimetry.

E84. The antibody, or antigen-binding fragment thereof, of anyone of E1-E83, wherein the antibody, or antigen-binding fragment thereof, has a thermal stability with a melting temperature ($T_m1$), or the temperature at which the $C_H2$ of the antibody is 50% unfolded, between 65° C. and 72° C., as measured by Differential Scanning Calorimetry.

E85. The antibody, or antigen-binding fragment thereof, of any one of E1-E84, wherein the antibody, or antigen-binding fragment thereof, has a thermal stability with a melting temperature ($T_m1$), or the temperature at which the $C_H2$ of the antibody is 50% unfolded, of about 71.7° C., as measured by Differential Scanning Calorimetry.

E86. The antibody, or antigen-binding fragment thereof, of anyone of E1-E85, wherein the antibody, or antigen-binding fragment thereof, has a thermal stability with a melting temperature ($T_m2$), or the temperature at which the Fab of the antibody is 50% unfolded, of about 74° C. or greater, as measured by Differential Scanning Calorimetry.

E87. The antibody, or antigen-binding fragment thereof, of any one of E1-E86, wherein the antibody, or antigen-binding fragment thereof, has a thermal stability with a melting temperature ($T_m2$), or the temperature at which the Fab of the antibody is 50% unfolded, between 74° C. and 78° C., as measured by Differential Scanning Calorimetry.

E88. The antibody, or antigen-binding fragment thereof, of any one of E1-E87, wherein the antibody, or antigen-binding fragment thereof, has a thermal stability with a melting temperature ($T_m2$), or the temperature at which the Fab of the antibody is 50% unfolded, of about 78.2° C., as measured by Differential Scanning Calorimetry.

E89. The antibody, or antigen-binding fragment thereof, of any one of E1-E88, wherein the antibody, or antigen-binding fragment thereof, has a thermal stability with a melting temperature ($T_m3$), or the temperature at which the $C_H3$ of the antibody is 50% unfolded, of about 82° C. or greater, as measured by Differential Scanning Calorimetry.

E90. The antibody, or antigen-binding fragment thereof, of any one of E1-E89, wherein the antibody, or antigen-binding fragment thereof, has a thermal stability with a melting temperature ($T_m3$), or the temperature at which the $C_H3$ of the antibody is 50% unfolded, between 82° C. and 86° C., as measured by Differential Scanning Calorimetry.

E91. The antibody, or antigen-binding fragment thereof, of any one of E1-E90 wherein the antibody, or antigen-binding fragment thereof, has a thermal stability with a melting temperature ($T_m3$), or the temperature at which the $C_H3$ of the antibody is 50% unfolded, of about 84.3° C., as measured by Differential Scanning Calorimetry.

E92. The antibody, or antigen-binding fragment thereof, of any one of E1-E91, wherein the antibody, or antigen-binding fragment thereof, has a binding affinity, expressed as $EC_{50}$, for cell-surface expressed human E-selectin, that is less than or equal to 50 nM, for example, less than or equal to 48 nM, 45 nM, 40 nM, 20 nM, 10 nM, 5 nM, 4 nM, 3 nM, 2 nM, 1 nM, 0.75 nM, 0.5 nM, 0.25 nM or 0.1 nM as measured, for example, by FACS.

E93. The antibody, or antigen-binding fragment thereof, of anyone of E1-E92, wherein the antibody, or antigen-binding fragment thereof, has a binding affinity, expressed as $EC_{50}$, for cell-surface expressed human E-selectin that is about 0.66 nM, as measured, for example, by FACS.

E94. The antibody, or antigen-binding fragment thereof, of any one of E1-E93, wherein the antibody, or antigen-binding fragment thereof, has a binding affinity, expressed as $EC_{50}$, for cell-surface expressed cynomolgus E-selectin that is less than or equal to 50 nM, for example, less than or equal to 48 nM, 45 nM, 40 nM, 20 nM, 10 nM, 5 nM, 4 nM, 3 nM, 2 nM, 1 nM, 0.75 nM, 0.5 nM, 0.25 nM or 0.1 nM as measured, for example, by FACS.

E95. The antibody, or antigen-binding fragment thereof, of any one of E1-E94, wherein the antibody, or antigen-binding fragment thereof, has a binding affinity, expressed as $EC_{50}$, for cell-surface expressed human P-selectin that is greater than or equal to 350 nM, for example, greater than or equal to 400 nM, 450 nM, 500 nM, 550 nM, 600 nM, 650 nM or more, as measured, for example, by FACS.

E96. The antibody, or antigen-binding fragment thereof, of any one of E1-E95, wherein the antibody, or antigen-binding fragment thereof, has weak or no binding to soluble rat, mouse or rabbit E-selectin or to soluble human L- or P-selectin.

E97. The antibody, or antigen-binding fragment thereof, of anyone of E1-E96, wherein the antibody, or antigen-binding fragment thereof, has weak or no binding to cell-surface expressed human P-selectin.

E98. The antibody, or antigen-binding fragment thereof, of anyone of E1-E97, wherein the antibody, or antigen-binding fragment thereof, demonstrates no binding to rat, mouse or rabbit E-selectin or to soluble human L- or P-selectin up to 405 nM as measured, for example by SPR.

E99. The antibody, or antigen-binding fragment thereof, of any one of E1-E98, wherein the antibody, or antigen-binding fragment thereof, demonstrates weak-nonsaturable binding to soluble mouse or rat E-selectin that is about >100× lower than binding to human or rat E-selectin as measured, for example, by direct binding ELISA.

E100. The antibody, or antigen-binding fragment thereof, of any one of E1-E99, wherein the antibody, or antigen-binding fragment thereof, demonstrates weak-nonsaturable binding to soluble mouse or rat E-selectin up to 133.3 nM as measured, for example, by direct binding ELISA.

E101. The antibody, or antigen-binding fragment thereof, of any one of E1-E100, wherein the antibody, or antigen-binding fragment thereof, binds to soluble human E-selectin with an $EC_{50}$ of less than or equal to 2 nM, for example, less than or equal to 0.010 nM, 0.015 nM, 0.020 nM, 0.025 nM, 0.030 nM, 0.035 nM, 0.040 nm, 0.045 nM, 0.05 nM, 0.055 nM, 0.06 nM, 0.065 nM, 0.070 nM, 0.075 nM, 0.080 nM, 0.085 nM, 0.090 nM, 0.10 nM, 0.12 nM, 0.15 nM, 0.2 nM, 0.5 nM, 0.9 nM, 0.95 nM, 1.0 nM 1.5 nM, 18 nM or 1.9 nM.

E102. The antibody, or antigen-binding fragment thereof, of any one of E1-E101, wherein the antibody, or antigen-binding fragment thereof, binds to soluble human E-selectin with an $EC_{50}$ of about 0.085 nM to about 0.12 nM as measured, for example, by direct binding ELISA.

E103. The antibody, or antigen-binding fragment thereof, of any one of E1-E102, wherein the antibody, or antigen-binding fragment thereof, binds to soluble cynomolgus E-selectin with an $EC_{50}$ of less than or equal to 1 nM, for example, less than or equal to 0.010 nM, 0.015 nM, 0.020 nM, 0.025 nM, 0.030 nM, 0.035 nM, 0.040 nm, 0.045 nM, 0.05 nM, 0.055 nM, 0.06 nM, 0.065 nM, 0.070 nM, 0.075 nM, 0.080 nM, 0.085 nM, 0.090 nM, 0.10 nM, 0.12 nM, 0.15 nM, 0.2 nM, 0.5 nM, 0.9 nM or 0.95 nM.

E104. The antibody, or antigen-binding fragment thereof, of any one of E1-E103, wherein the antibody, or antigen-binding fragment thereof, binds to soluble cynomolgus E-selectin with an $EC_{50}$ of 0.071 nM to 0.093 nM as measured, for example, by direct binding ELISA.

E105. The antibody, or antigen-binding fragment thereof, of any one of E1-E104, wherein the antibody, or antigen-binding fragment thereof, binds free soluble human E-selectin in human serum with an $IC_{50}$ of about 1 nM to about 3 nM, and preferably with an $IC_{50}$ of about 1.2 nM.

E106. The antibody, or antigen-binding fragment thereof, of any one of E1-E105, wherein the antibody, or antigen-binding fragment thereof, neutralizes binding of a sialyl-Lewis A ligand to soluble human E-selectin with an $IC_{50}$ of less than or equal to 100 nM, for example, less than or equal to 95 nM, 90 nM, 80 nM, 70 nM, 60 nM, 50 nM, 40 nM, 20 nM, 10 nM, 5 nM, 4 nM, 3 nM, 2 nM or 1 nM as measured, for example, by competition ELISA under static conditions.

E107. The antibody, or antigen-binding fragment thereof, of any one of E1-E106, wherein the antibody, or antigen-binding fragment thereof, neutralizes binding of a sialyl-Lewis A ligand to soluble human E-selectin with an $IC_{50}$ of about 2.87 nM to about 3.01 nM as measured, for example, by competition ELISA under static conditions.

E108. The antibody, or antigen-binding fragment thereof, of any one of E1-107, wherein the antibody, or antigen-binding fragment thereof, neutralizes binding of a sialyl-Lewis A ligand to soluble cynomolgus E-selectin with an $IC_{50}$ of less than or equal to 100 nM, for example, less than or equal to 95 nM, 90 nM, 80 nM, 70 nM, 60 nM, 50 nM, 40 nM, 20 nM, 10 nM, 5 nM, 4 nM, 3 nM, 2 nM or 1 nM as measured, for example, by competition ELISA under static conditions.

E109. The antibody, or antigen-binding fragment thereof, of any one of E1-E108, wherein the antibody, or antigen-binding fragment thereof, neutralizes binding of a sialyl-Lewis A ligand to soluble cynomolgus E-selectin with an $IC_{50}$ of about 2.39 nM to about 2.91 nM as measured, for example, by competition ELISA under static conditions.

E110. The antibody, or antigen-binding fragment thereof, of any one of E1-E109, wherein the antibody, or antigen-binding fragment thereof, neutralizes binding of a sialyl-Lewis A ligand to cell-surface expressed human E-selectin with an $IC_{50}$ of less than or equal to 100 nM, for example, less than or equal to 95 nM, 90 nM, 80 nM, 70 nM, 60 nM, 50 nM, 40 nM, 20 nM, 10 nM, 5 nM, 4 nM, 3 nM, 2 nM or 1 nM as measured, for example, by competition ELISA under static conditions.

E111. The antibody, or antigen-binding fragment thereof, of any one of E1-E110, wherein the antibody, or antigen-binding fragment thereof, neutralizes binding of a sialyl-Lewis A ligand to cell-surface expressed human E-selectin with an $IC_{50}$ of about 1.88 nM to about 2.89 nM as measured, for example, by competition ELISA under static conditions.

E112. The antibody, or antigen-binding fragment thereof, of any one of E1-E111, wherein the antibody, or antigen-binding fragment thereof, neutralizes binding of a sialyl-Lewis A ligand to cell-surface expressed cynomolgus E-selectin with an $IC_{50}$ of less than or equal to 100 nM, for example, less than or equal to 95 nM, 90 nM, 80 nM, 70 nM, 60 nM, 50 nM, 40 nM, 20 nM, 10 nM, 5 nM, 4 nM, 3 nM, 2 nM or 1 nM as measured, for example, by competition ELISA under static conditions.

E113. The antibody, or antigen-binding fragment thereof, of any one of E1-E112, wherein the antibody, or antigen-binding fragment thereof, neutralizes binding of a sialyl-Lewis A ligand to cell-surface expressed cynomolgus E-selectin with an $IC_{50}$ of about 1.47 nM to about 2.65 nM as measured, for example, by competition ELISA under static conditions.

E114. The antibody, or antigen-binding fragment thereof, of any one of E1-E113, wherein the antibody, or antigen-binding fragment thereof, inhibits adhesion of cells expressing an E-selectin ligand (e.g., E selectin ligand, PSGL-1 and other sialyl Lewis ligands) to cell-surface expressed human E-selectin with an $IC_{50}$ of less than or equal to 100 nM, for example, less than or equal to 95 nM, 90 nM, 80 nM, 70 nM, 60 nM, 50 nM, 40 nM, 20 nM, 10 nM, 5 nM, 4 nM, 3 nM, 2 nM or 1 nM as measured, for example, under static conditions.

E115. The antibody, or antigen-binding fragment thereof, of any one of E1-E114, wherein the antibody, or antigen-binding fragment thereof, inhibits adhesion of cells expressing an E-selectin ligand (e.g., E selectin ligand, PSGL-1 and other sialyl Lewis ligands) to cell-surface expressed human E-selectin with an $IC_{50}$ of about 3.36 nM to about 4.7 nM as measured, for example, under static conditions.

E116. The antibody, or antigen-binding fragment thereof according to E1-E115, wherein the antibody, or antigen-binding fragment thereof, inhibits adhesion of cells expressing an E-selectin ligand (e.g., E selectin ligand, PSGL-1 and other sialyl Lewis ligands) to cell-surface expressed cynomolgus E-selectin with an $IC_{50}$ of about 3.84 nM as measured, for example, under static conditions.

E117. The antibody, or antigen-binding fragment thereof, of any one of E1-E116, wherein the antibody, or antigen-binding fragment thereof, inhibits adhesion of cells expressing an E-selectin ligand (e.g., E selectin ligand, PSGL-1 and other sialyl Lewis ligands) to cell-surface expressed human E-selectin with an $IC_{50}$ of less than or equal to 100 nM, for example, less than or equal to 95 nM, 90 nM, 80 nM, 70 nM, 60 nM, 50 nM, 40 nM, 30 nM, 20 nM, 10 nM, 5 nM or 2 nM as measured, for example, under physiological flow conditions.

E118. The antibody, or antigen-binding fragment thereof, of any one of E1-E117, wherein the antibody, or antigen-binding fragment thereof, inhibits adhesion of cells expressing an E-selectin ligand (e.g., E selectin ligand, PSGL-1 and other sialyl Lewis ligands) to cell-surface expressed human E-selectin with an $IC_{50}$ of about 4.25 nM to about 4.56 nM as measured, for example, under physiological flow conditions.

E119. The antibody, or antigen-binding fragment thereof, of any one of E1-E118, wherein the antibody, or antigen-binding fragment thereof, inhibits adhesion of cells expressing an E-selectin ligand (e.g., E selectin ligand, PSGL-1 and other sialyl Lewis ligands) to cell-surface expressed cynomolgus E-selectin with an $IC_{50}$ of about 4.32 nM to about 4.35 nM as measured, for example, under physiological flow conditions.

E120. The antibody, or antigen-binding fragment thereof, of any one of E1-E119, wherein the antibody, or antigen-binding fragment thereof, inhibits adhesion of cells expressing an E-selectin ligand (e.g., E selectin ligand, PSGL-1 and other sialyl Lewis ligands) to soluble human E-selectin with an $IC_{50}$ of less than or equal to 300 nM, for example, less than or equal to 290 nM, 280 nM, 270 nM, 260 nM, 250 nM, 150 nM, 100 nM, 90 nM, 100 nM, 90 nM, 80 nM, 70 nM, 60 nM, 50 nM, 40 nM, 20 nM, 20 nM, 5 nM, 2 nM, or 1 nM as measured, for example, under physiologic flow conditions.

E121. The antibody, or antigen-binding fragment thereof, of any one of E1-E120, wherein the antibody, or antigen-binding fragment thereof, inhibits adhesion of cells expressing an E-selectin ligand (e.g., E selectin ligand, PSGL-1 and other sialyl Lewis ligands) to soluble human E-selectin with an $IC_{50}$ of about 13.28 nM to about 15.94 nM as measured, for example, under physiologic flow conditions.

E122. The antibody, or antigen-binding fragment thereof, of any one of E1-E121, wherein the antibody, or antigen-binding fragment thereof, inhibits adhesion of activated human neutrophils (e.g., TNF-α activated) to cell-surface expressed cynomolgus E-selectin with an $IC_{50}$ of about 9.45 nM to about 16.33 nM as measured, for example, under physiologic flow conditions.

E123. The antibody, or antigen-binding fragment thereof, of any one of E1-E122, wherein the antibody, or antigen-binding fragment thereof, inhibits adhesion of activated human neutrophils (e.g., TNF-α activated) to cell-surface expressed human E-selectin with an $IC_{50}$ of about 2.87 nM to about 4.65 nM as measured, for example, under physiologic flow conditions.

E124. The antibody, or antigen-binding fragment thereof, of any one of E1-E123, wherein the antibody, or antigen-binding fragment thereof, inhibits adhesion of blood cells from SCD patients to soluble human E-selectin with an $IC_{50}$ of about 6.17 nM to about 18.66 nM as measured, for example, under physiologic flow conditions.

E125. The antibody, or antigen-binding fragment thereof, of any one of E1-E124, wherein the antibody, or antigen-binding fragment thereof, inhibits adhesion of blood cells from SCD patients to soluble human E-selectin with an $IC_{50}$ of about 12.4 nM as measured, for example, under physiologic flow conditions.

E126. An isolated nucleic acid molecule comprising a nucleic acid sequence encoding the antibody, or antigen binding fragment thereof, of any one of E1-E125.

E127. An isolated nucleic acid molecule comprising at least one nucleic acid sequence encoding the antibody, or antigen binding fragment thereof, of any one of E1-E125.

E128. An isolated nucleic acid molecule encoding a VL, VH, or both, of an antibody, or an antigen-binding fragment thereof, that specifically binds human E-selectin, wherein said nucleic acid molecule comprises the nucleic acid sequence of SEQ ID NO:136, the nucleic acid sequence of SEQ ID NO:137, or both.

E129. An isolated nucleic acid molecule comprising, or consisting of, the nucleic acid sequence of SEQ ID NO:136, the nucleic acid sequence of SEQ ID NO:137, or both.

E130. An isolated nucleic acid molecule comprising, or consisting of, the nucleic acid sequence as set forth as SEQ ID NO:136.

E131. An isolated nucleic acid molecule comprising, or consisting of, the nucleic acid sequence as set forth as SEQ ID NO:137.

E132. An isolated nucleic acid molecule encoding the VH of an antibody, or antigen-binding fragment thereof, that specifically binds human E-selectin, comprising at least one nucleic acid sequence selected from the group consisting of SEQ ID NO:136, 144, 146, 148, 150, 151, 152, 153, 155, 157, 159, 161, 163, 165, 167, 169, 171 and 173.

E133. An isolated nucleic acid molecule encoding the VH of an antibody, or antigen-binding fragment thereof, that specifically binds human E-selectin, comprising a nucleic acid at least 90%, 91%, 92%, 93%, 94%, 95%, 96%, 97%, 98% or 99% identical to a nucleic acid sequence selected from the group consisting of SEQ ID NO:136, 144, 146, 148, 150, 151, 152, 153, 155, 157, 159, 161, 163, 165, 167, 169, 171 and 173.

E134. An isolated nucleic acid molecule encoding the VL of an antibody, or antigen-binding fragment thereof, that specifically binds human E-selectin, comprising at least one nucleic acid sequence selected from the group consisting of SEQ ID NO:137, 145, 147, 149, 154, 156, 158, 160, 162, 164, 166, 168, 170, 172 and 174.

E135. An isolated nucleic acid molecule encoding the VL of an antibody, or antigen-binding fragment thereof, that specifically binds human E-selectin, comprising a nucleic acid at least 90%, 91%, 92%, 93%, 94%, 95%, 96%, 97%, 98% or 99% identical to a nucleic acid sequence selected from the group consisting of SEQ ID NO: 137, 145, 147, 149, 154, 156, 158, 160, 162, 164, 166, 168, 170, 172 and 174.

E136. An isolated nucleic acid molecule encoding a light chain, heavy chain, or both, of an antibody, or an antigen-binding fragment thereof, that specifically binds human E-selectin, wherein said nucleic acid molecule comprises the nucleic acid sequence of SEQ ID NO:206 or 138; the nucleic acid sequence of SEQ ID NO:139; or both.

E137. An isolated nucleic acid molecule comprising, or consisting of, the nucleic acid sequence of SEQ ID NO:206 or 138; the nucleic acid sequence of SEQ ID NO:139; or both.

E138. An isolated nucleic acid molecule comprising, or consisting of, the nucleic acid sequence of SEQ ID NO:206 or 138.

E139. An isolated nucleic acid molecule comprising, or consisting of, the nucleic acid sequence of SEQ ID NO:139.

E140. An isolated nucleic acid molecule encoding an antibody, or an antigen-binding fragment thereof, that specifically binds human E-selectin, wherein said nucleic acid molecule comprises the nucleic acid sequence of the insert of the plasmid deposited with the ATCC and having the Accession Number PTA-126529.

E141. An isolated nucleic acid molecule encoding an antibody, or an antigen-binding fragment thereof, that specifically binds human E-selectin, wherein said nucleic acid molecule comprises the nucleic acid sequence of the insert of the plasmid deposited with the ATCC and having the Accession Number PTA-126530.

E142. An isolated nucleic acid molecule encoding an antibody, or an antigen-binding fragment thereof, that specifically binds human E-selectin, wherein said nucleic acid comprises the nucleic acid sequence of the insert of the plasmid deposited with the ATCC and having the Accession Number PTA-126529 and the nucleic acid sequence of the insert of the plasmid deposited with the ATCC and having the Accession Number PTA-126530.

E143. An isolated nucleic acid molecule comprising the nucleic acid sequence of the insert of the plasmid deposited with the ATCC and having the Accession Number PTA-126529.

E144. An isolated nucleic acid molecule comprising the nucleic acid sequence of the insert of the plasmid deposited with the ATCC and having the Accession Number PTA-126530.

E145. An isolated nucleic acid molecule comprising the nucleic acid sequence of the insert of the plasmid deposited with the ATCC and having the Accession Number PTA-126529, and the nucleic acid sequence of the insert of the plasmid deposited with the ATCC and having the Accession Number PTA-126530.

E146. A vector comprising the nucleic acid molecule of any one of E126-E145.

E147. A host cell comprising the nucleic acid molecule of any one of E126-E145, or the vector of E146.

E148. The host cell of E147, wherein said cell is a mammalian cell.

E149. The host cell of E147 or E148, wherein said host cell is a CHO cell, a HEK-293 cell, an NS0 cell, a PER.C6® cell (an immortalized primary human embryonic retinal cell), or an Sp2.0 cell.

E150. A method of making an antibody or antigen-binding fragment thereof, comprising culturing the host cell of any one of E147-E149, under a condition wherein said antibody or antigen-binding fragment is expressed by said host cell.

E151. The method of E150, further comprising isolating said antibody or antigen-binding fragment thereof.

E152. A pharmaceutical composition comprising an antibody or antigen-binding fragment thereof of any one of E1-E125 and E221, and a pharmaceutically acceptable carrier or excipient.

E153. The pharmaceutical composition of E152, wherein the composition comprises 1.12 mg/mL L-histidine, 2.67 mg/mL L-histidine hydrochloride monohydrate, 85 mg/mL sucrose, 0.05 mg/mL edetate disodium dihydrate, 0.2 mg/mL polysorbate 80 at pH 5.8.

E154. The pharmaceutical composition of E152 or E153, wherein the composition comprises 20 mM histidine, 8.5% sucrose, and 0.02% polysorbate 80, 0.005% EDTA at pH 5.8.

E155. The pharmaceutical composition of any one of E152-E154, wherein the composition comprises about 25 mg/mL, 50 mg/mL, 75 mg/mL, 100 mg/mL, 125 mg/mL, 150 mg/ml antibody, or antigen binding fragment thereof.

E156. The pharmaceutical composition of E155, wherein the composition comprises about 100 mg/mL antibody, or antigen binding fragment thereof.

E157. The pharmaceutical composition of any one of E152-E156, wherein the dose is a 1 mL dose.

E158. The pharmaceutical composition of E152-E157, wherein the composition is suitable for SC and/or IV administration.

E159. The pharmaceutical composition of any one of E152-E158 comprising an antibody, or antigen-binding fragment thereof, comprising i) HCDR-1 (SEQ ID NO:8), HCDR-2 (SEQ ID NO:9), and HCDR-3 (SEQ ID NO:10) sequence of SEQ ID NO:11 and LCDR-1 (SEQ ID NO:2), LCDR-2 (SEQ ID NO:3), and LCDR-3 (SEQ ID NO:4) sequence of SEQ ID NO:5; ii) a VH domain comprising the amino acid sequence of SEQ ID NO:11 and a VL domain comprising the amino acid sequence of SEQ ID NO:5; or iii) a HC comprising the amino acid sequence of SEQ ID NO:7 or 13 and a LC comprising the amino acid sequence of SEQ ID NO:1.

E160. The pharmaceutical composition of anyone of E152-E159 comprising an additional therapeutically active compound selected from the group consisting of L-glutamine (e.g., ENDARI), an anti-P-selectin antibody (e.g., crizanlizumab (ADAKVEO)), a compound that modulates HbS so as to maintain it in its R state (i.e., oxygenated), for example, a 2-aminoquinoline and those described in WO 2020/109994 (incorporated herein by reference), a compound that modulates oxygen affinity of HbS (e.g., voxelotor (OXBRYTA)), a compound that targets HbS polymerization by modulating generation of 2,3-disphosphoglyceric acid, a compound that targets HbS polymerization by inducing expression of fetal hemoglobin (e.g., hydroxyurea, e.g., DROXIA, HYDREA), a compound that targets dysfunctional cellular adhesion, vascular dysfunction and/or inflammation (e.g., a phosphodiesterase-9 inhibitor), a compound that increases levels of nitric oxide in the blood (e.g., a soluble guanylate cyclase stimulator, e.g., IW-1701, riociguat (ADEMPAS)), intravenous IG, a compound that targets hypercoagulability (e.g., riociguat (ADEMPAS), apixaban (ELIQUIS), rivaroxaban (XARELTO)), a compound that blocks NMDA receptor binding (e.g., memantine (NAMENDA)) and a combination thereof.

E161. The pharmaceutical composition of anyone of E152-E159 comprising an additional therapeutically active compound selected from the group consisting of penicillin prophylaxis to prevent pneumococcal infection, hydroxyurea (e.g., DROXIA, HYDREA), L-glutamine (e.g., ENDARI), crizanlizumab (ADAKVEO), voxelotor (OXBRYTA), apixaban (ELIQUIS), rivaroxaban (XARELTO), a non-steroidal anti-inflammatory drug, an analgesic generally, an opioid analgesic, IW-1701, riociguat (ADEMPAS), ticagrelor (BRILINTA), memantine (NAMENDA) and a combination thereof.

E162. A method of reducing or inhibiting E-selectin activity, comprising administering to a subject in need thereof a therapeutically effective amount of the antibody, or antigen-binding fragment thereof, of any one of E1-E125, E221, or the pharmaceutical composition of any one of E152-E161, and comparing the activity of E-selectin before administration with the level of E-selectin activity after administration of the antibody, thereby reducing the activity of E-selectin.

E163. The method of E162, wherein reducing or inhibiting E-selectin activity treats a disease, disorder or condition which is improved, ameliorated, inhibited or prevented by removal, inhibition or reduction of E-selectin activity.

E164. The method of any one of E162-E163, wherein the activity of E-selectin is selected from the group consisting of:
(a) leukocyte tethering to endothelial cells;
(b) activation of stable adhesion to endothelial cells;
(c) slow rolling of leukocytes to arrest;
(d) efficient trans-endothelial migration of leukocytes;
(e) affinity and avidity of CD18 integrins;
(f) trafficking of leukocytes to sites of acute inflammation;
(g) increase in cytosolic calcium;
(h) increase in tyrosine phosphorylation that activates p38 MAP kinase and Syk kinase;
(i) recruitment of platelets and leukocytes from the blood to the vascular endothelium; and
(j) creation of a pro-inflammatory environment.

E165. A method of reducing the level of free E-selectin in a subject in need thereof, the method comprising administering to a subject a therapeutically effective amount of the antibody, or antigen-binding fragment thereof, of any one of E1-E125, or the pharmaceutical composition of any one of E152-E161.

E166. A method of treating and/or preventing a disease, disorder and/or condition associated with, or mediated by, E-selectin expression and/or E-selectin binding to a ligand, comprising administering to a subject in need thereof a therapeutically effective amount of the antibody, or antigen-binding fragment thereof, of any one of E1-E125, or the pharmaceutical composition of any one of E152-E161.

E167. The method of E166, wherein the disease, disorder and/or condition is at least one selected from the group consisting of SCD, vaso-occlusive crisis (VOC), pain, organ infarction, ischemia, stroke, end organ dysfunction, acute chest and vascular obstruction, skin diseases (e.g., psoriasis), inflammatory diseases (e.g., rheumatoid arthritis) and complications of diabetes.

E168. The method of any one of E167, wherein the VOC is associated with SCD.

E169. The method of any one of E166-E168, comprising a prophylactic treatment for SCD by preventing or reducing the occurrence of a VOC.

E170. The method of any one of E167-E169, comprising an acute treatment for SCD by decreasing the duration (e.g., reduction in the time to resolve a VOC) and intensity of a VOC.

E171. The method of any one of E166-E170, wherein the treatment is a prophylactic treatment.

E172. The method of any one of E166-E171, that treats, prevents and/or ameliorates at least one sign and/or symptom of SCD, for example, those affecting the cardiothoracic system (e.g., chronic restrictive lung disease, left ventricular diastolic disease, pulmonary hypertension, acute chest syndrome, dysrhythmias, sudden death, vaso-occlusive crisis), the nervous system (e.g., hemorrhagic stroke, venous sinus thrombosis, silent cerebral infarction of the brain, chronic pain, acute ischemic stroke of the brain, proliferative retinopathy, orbital infarction, cognitive impairment) the reticuloendothelial system (e.g., splenic sequestration, functional hyposplenism, anemia, hemolysis), the musculoskeletal system (e.g., avascular necrosis, skin ulcerations), the urogenital system (e.g., papillary necrosis, proteinuria, renal failure, hematuria, nocturnal enuresis, priapism) and the gastrointestinal system (e.g., cholelithiasis, cholangiopathy, hepatopathy, mesenteric vaso-occlusion).

E173. The method of any one of E166-E172, wherein the subject is a human.

E174 The method of anyone of E166-E173, wherein the subject is a patient with SCD.

E175. The method of any one of E166-E174, wherein the subject has a HBSS, HBSC, HBS/β°thal, HBS/β⁺thal or HBS-variant genotype.

E176. The method of any one of E166-E175, wherein the antibody or antigen-binding fragment thereof, or pharmaceutical composition, is administered subcutaneously.

E177. The method of any one of E166-E176, wherein the antibody or antigen-binding fragment thereof, or pharmaceutical composition, is administered intravenously.

E178. The method of anyone of E166-E177, wherein the antibody or antigen-binding fragment thereof, or pharmaceutical composition, is administered about twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, once every three months, once every four months, once every five months, once every six months, once every seven months, once every eight months, once every nine months, once every ten months, once every eleven months or once every twelve months.

E179. The method of anyone of E166-E177, wherein the antibody or antigen-binding fragment thereof, or pharmaceutical composition, is administered once a month.

E180. The method of anyone of E166-E179, wherein the antibody, or antigen-binding fragment thereof, or pharmaceutical composition, is administered once a week.

E181. The method of any one of E66-E180, wherein the therapeutically effective amount comprises a dose of about 1 mg to about 800 mg of the anti-E-selectin antibody, or antigen binding fragment thereof.

E182. The method of E181, wherein the dose is an initial fixed dose.

E183. The method of any one of E181-E182, wherein the dose is about 1 mg to about 10 mg, about 10 mg to about 20 mg, about 20 mg to about 30 mg, about 30 mg to about 40 mg, about 40 mg to about 50 mg, about 50 mg to about 60 mg, about 60 mg to about 70 mg, about 70 mg to about 80 mg, about 80 mg to about 90 mg, about 90 mg to about 100 mg, about 100 mg to about 150 mg, about 150 mg to about 200 mg, about 200 mg to about 300 mg, about 300 mg to about 400 mg, about 400 mg to about 500 mg, about 500 mg to about 600 mg, about 600 mg to about 700 mg or about 700 mg to about 800 mg of the anti-E-selectin antibody, or antigen binding fragment thereof.

E184. The method of any one of E181-E183, wherein the dose is about 15 mg, 40 mg, 100 mg, 150 mg, 300 mg, 500 mg or 600 mg of an anti-E-selectin antibody, or antigen binding fragment thereof.

E185. The method of any one of E181-E184, wherein the dose is about 150 mg of the anti-E-selectin antibody, or antigen binding fragment thereof.

E186. The method of any one of E81-E185, comprising administering the dose once a week, once every 2 weeks, once a month, once every two months, or a combination thereof.

E187. The method of any one of E162-E186, wherein the antibody is antibody 1444 and the antigen-binding fragment is a fragment of antibody 1444.

E188. The method of any one of E162-E187, wherein the administration is subcutaneous or intravenous administration.

E189. The method of any one of E162-E188 comprising administering an antibody, or antigen-binding fragment thereof, comprising i) HCDR-1 (SEQ ID NO:8), HCDR-2 (SEQ ID NO:9), and HCDR-3 (SEQ ID NO:10) sequences of SEQ ID NO:11 and LCDR-1 (SEQ ID NO:2), LCDR-2 (SEQ ID NO:3), and LCDR-3 (SEQ ID NO:4) sequences of SEQ ID NO:5, ii) a VH domain comprising the amino acid sequence of SEQ ID NO:11 and a VL domain comprising the amino acid sequence of SEQ ID NO:5; or iii) a HC comprising the amino acid sequence of SEQ ID NO:7 or 13 and a LC comprising the amino acid sequence of SEQ ID NO:1.

E190. The method of any one of E162-E188 comprising administering a pharmaceutical composition comprising an antibody, or antigen-binding fragment thereof, comprising i) HCDR-1 (SEQ ID NO:8), HCDR-2 (SEQ ID NO:9), and HCDR-3 (SEQ ID NO:10) sequences of SEQ ID NO:11 and LCDR-1 (SEQ ID NO:2), LCDR-2 (SEQ ID NO:3), and LCDR-3 (SEQ ID NO:4) sequences of SEQ ID NO:5, ii) a VH domain comprising the amino acid sequence of SEQ ID NO:11 and a VL domain comprising the amino acid sequence of SEQ ID NO:5; or iii) a HC comprising the amino acid sequence of SEQ ID NO:7 or 13 and a LC comprising the amino acid sequence of SEQ ID NO:1.

E191. The method of any one of E162-E190, wherein the subject is a patient with SCD.

E192. A method of treating SCD, comprising administering to a subject in need thereof a therapeutically effective amount of an anti-E-selectin antibody, or antigen-binding fragment thereof, comprising i) HCDR-1 (SEQ ID NO:8), HCDR-2 (SEQ ID NO:9), and HCDR-3 (SEQ ID NO:10) sequences of SEQ ID NO:11 and LCDR-1 (SEQ ID NO:2), LCDR-2 (SEQ ID NO:3), and LCDR-3 (SEQ ID NO:4) sequences of SEQ ID NO:5, ii) a VH domain comprising the amino acid sequence of SEQ ID NO:11 and a VL domain comprising the amino acid sequence of SEQ ID NO:5; or iii) a HC comprising the amino acid sequence of SEQ ID NO:7 or 13 and a LC comprising the amino acid sequence of SEQ ID NO:1, and a pharmaceutically acceptable carrier or excipient.

E193. The method of E192, wherein treating SCD includes treating at least one symptom of SCD including VOC.

E194. The method of any one of E192-E193, wherein the subject is a patient with SCD.

E195. The method of any one of E192-E194, comprising administering the antibody or antigen-binding fragment thereof, subcutaneously and/or intravenously.

E196. The method of any one of E192-E195, wherein said antibody or antigen-binding fragment thereof, is administered about twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, once every three months, once every four months, once every five months, once every six months, once every seven months, once every eight months, once every nine months, once every ten months, once every eleven months or once every twelve months.

E197. The method of anyone of E192-E196, wherein the antibody or antigen-binding fragment thereof, or pharmaceutical composition, is administered once a week, once every 2 weeks, once every 3 weeks, once a month, or a combination thereof.

E198. The method of anyone of E192-E197, wherein the antibody or antigen-binding fragment thereof is administered at a dose between about 1 mg to about 800 mg.

E199. The method of any one of E192-198, wherein said antibody or antigen-binding fragment thereof, or pharmaceutical composition, is administered at a dose selected from the group consisting of about 15 mg, about 40 mg, about 100 mg, about 150 mg, about 300 mg, about 500 mg, and about 600 mg.

E200. The method of any one of E192-E199, wherein the antibody, or antigen-binding fragment thereof is administered in combination with a therapeutically effective amount of one or more additional therapeutically active compounds or treatment modalities effective in treating and/or preventing at least one sign and/or symptom of SCD.

E201. The method of any one of E192-E200, wherein the amount of the anti-E-selectin antibody, or antigen-binding fragment thereof, and the amount of the therapeutically active compound or treatment modality effective in treating and/or preventing at least one sign and/or symptom of SCD, are administered in amounts that together achieve synergistic effects in the treatment and/or prevention of at least one sign and/or symptom of SCD.

E202. The method of any one of E192-E201, wherein the amount of the anti-E-selectin antibody, or antigen-binding fragment thereof, and/or the amount of the therapeutically active compound or treatment modality effective in treating and/or preventing at least one sign and/or symptom of SCD, are each administered at a dosage that is lower than would be administered if not in combination.

E203. The method of any one of E192-E202, wherein the additional therapeutically active compound is selected from the group consisting of penicillin prophylaxis to prevent pneumococcal infection, hydroxyurea (e.g., DROXIA, HYDREA), L-glutamine (e.g., ENDARI), crizanlizumab (ADAKVEO), voxelotor (OXBRYTA), apixaban (ELIQUIS), rivaroxaban (XARELTO), a non-steroidal anti-inflammatory drug, an analgesic generally, an opioid analgesic, IW-1701, riociguat (ADEMPAS), ticagrelor (BRILINTA), memantine (NAMENDA) and a combination thereof.

E204. The method of any one of E192-E203, wherein the additional therapeutically active compound is selected from the group consisting of L-glutamine (e.g., ENDARI), an anti-P-selectin antibody (e.g., crizanlizumab (ADAKVEO)), a compound that modulates HbS so as to maintain it in its R state (i.e., oxygenated), for example, a 2-aminoquinoline and those described in WO 2020/109994 (incorporated herein by reference), a compound that modulates oxygen affinity of HbS (e.g., voxelotor (OXBRYTA)), a compound that targets HbS polymerization by modulating generation of 2,3-disphosphoglyceric acid, a compound that targets HbS polymerization by inducing expression of fetal hemoglobin (HbF) (e.g., hydroxyurea, e.g., DROXIA, HYDREA), a compound that targets dysfunctional cellular adhesion, vascular dysfunction and/or inflammation (e.g., phosphodiesterase-9 inhibitors), a compound that increases levels of nitric oxide in the blood (e.g., soluble guanylate cyclase stimulators, e.g., IW-1701, riociguat (ADEMPAS)), intravenous IG, a compound that targets hypercoagulability (e.g., riociguat (ADEMPAS), apixaban (ELIQUIS), rivaroxaban (XARELTO)), a compound that blocks NMDA receptor binding (e.g., memantine (NAMENDA)) and a combination thereof.

E205. The method of any one of E192-204, wherein the therapeutically active treatment modality useful for the treatment and/or prevention of at least one sign and/or symptom of SCD is selected from the group consisting of supplemental oxygen, blood transfusion, optionally with iron chelation, bone marrow transplant, gene therapy (e.g., LentiGlobin®), a gene editing therapy by CRISPR (e.g., CTX001) or a zinc finger technique and a combination thereof.

E206. The method of any one of E200-E205 wherein the anti-E-selectin antibody, or antigen-binding fragment thereof and the therapeutically active compound or treatment modality which is effective in treating and/or preventing at least one sign and or symptom of SCD, are co-administered.

E207. The method of any one of E200-E206, wherein the combination therapies are administered according to the same dosing regimen (e.g., both therapies are administered daily) or according to different dosing regimens (e.g., one therapy is administered daily, the other therapy is administered weekly).

E208. The method of any one of E200-E207, wherein the combination therapies are administered to a subject by the same or different routes of administration.

E209. Use of the pharmaceutical composition of any one of E152-E161 in the manufacture of a medicament for treating a disease, disorder of condition mediated by E-selectin (e.g., SCD).

E210. Use of an antibody, or antigen-binding fragment thereof, of anyone of E1-E125 or E221 in the manufacture of a medicament for treating and/or preventing a disease, disorder or condition associated with, or mediated by, E-selectin expression and/or E-selectin binding to a ligand.

E211. Use of a pharmaceutical composition of any one of E152-E161 in the manufacture of a medicament for treating and/or preventing a disease, disorder or condition associated with, or mediated by, E-selectin expression and/or E-selectin binding to a ligand.

E212. An antibody, or antigen-binding fragment thereof, of any one of E1-E125 or E221, or the pharmaceutical composition of E152-E161, for use as a medicament.

E213. An antibody, or antigen binding fragment thereof, of any one of E1-E125 or E221, or the pharmaceutical composition of any one of E152-E161, for use in the treatment and/or prevention of at least one sign and/or symptom of SCD.

E214. The antibody, or antigen binding fragment thereof, or the pharmaceutical composition, for use of E213, wherein the symptom of SCD is VOC.

E215. The antibody, or antigen binding fragment thereof, or the pharmaceutical composition, for use of any one of E213-214, wherein the treatment and/or prevention further comprises an additional therapeutic agent, such as, but not limited to at least one other therapeutically active compound or treatment modality which is effective in treating and/or preventing at least one sign and/or symptom of SCD.

E216. The antibody, or antigen binding fragment thereof, or the pharmaceutical composition, for use of E215, wherein the additional therapeutic agent is an agent that is standard of care for the prevention and/or treatment of at least one sign and/or symptom of SCD (e.g., L-glutamine, hydroxyurea, a blood transfusion and any other therapy known in the art).

E217. The antibody, or antigen binding fragment thereof, or the pharmaceutical composition, for use of E215-216, wherein the treatment and/or prevention comprises i) a synergistic, therapeutically effective amount of the anti-E- selectin antibody or antigen-binding fragment thereof, and ii) a synergistic, therapeutically effective amount of the additional therapeutic agent.

E218. The antibody, or antigen binding fragment thereof, or the pharmaceutical composition, for use of E215 or E216, wherein the treatment and/or prevention comprises i) a synergistic, therapeutically effective amount of the anti-E-selectin antibody, or antigen-binding fragment thereof, and ii) a synergistic, therapeutically effective amount of the treatment modality.

E219. The pharmaceutical composition of any one of E152-E161, wherein the appropriate amount of each compound, as used in the combination for administration to a patient with SCD is determined by taking into account at least one factor selected from the group consisting of age, weight, general health, the compound administered, the route of administration, the nature and advancement of the treatment of SCD, and the presence of other medications.

E220. A pharmaceutical composition of any one of E152-E161, formulated for use as a medicament for treating a disease, disorder of condition mediated by E-selectin (e.g., SCD).

E221. An isolated monoclonal antibody that specifically binds E-selectin, wherein the antibody is antibody 0039, 0164, 0158, 0159, 0170, 0180, 0841, 1282 1284, 1444 or 1448.

BRIEF DESCRIPTION OF THE SEVERAL VIEWS OF THE DRAWINGS

FIG. 4 depicts predicted non-germline T-cell epitopes for the VH and VL regions of humanized antibody 0841. Amino acid residues predicted by Epivax/ISPRI or IEDB to encompass T-cell epitopes not found in human germlines are underlined.

FIG. 6 depicts exemplary neutralization of sialyl Lewis X ligand adhesion to CHO cells expressing cynomolgus monkey E-selectin. Antibodies tested included anti-E-selectin antibodies 164 (also known as 0164), 1282, 1284, 1444, 1448 and an IgG isotype control.

FIG. 10A depicts results for antibody 1282; FIG. 10B depicts results for antibody 1284; FIG. 10C depicts results for antibody 1444; FIG. 10D depicts results for antibody 1448.

DETAILED DESCRIPTION

Figure 1:
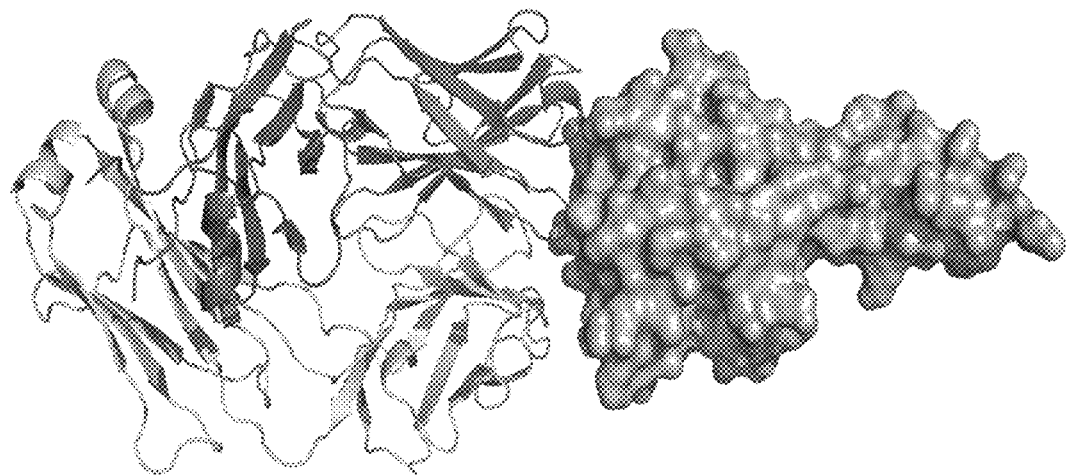
FIG. 1 depicts an exemplary crystal structure of Fab of anti-E-selectin antibody 0164 co-crystallized with truncated human E-selectin. E-selectin is shown as a gray surface (molecule on the right). The 0164 Fab (molecule on the left) is shown as ribbons with the VL in light gray and the VH in dark gray.

The present disclosure provides antibodies, and antigen-binding fragments thereof, that specifically bind to E-selectin and reduce or inhibit E-selectin activity, including but not limited to, the ability of E-selectin to interact (e.g., bind) with ligands comprising carbohydrate structures with a sialyl Lewis (sLex) determinant on glycoproteins or glycolipids. The disclosure also provides processes for making, preparing, or producing anti-E-selectin antibodies. Antibodies of the disclosure are useful in the diagnosis, prophylaxis, and/or treatment of disorders or conditions mediated by, or associated with, E-selectin activity (e.g., binding), including, but not limited to, SCD, vaso-occlusive crisis, pain, organ infarction, ischemia, stroke and vascular obstruction. The disclosure further encompasses expression of antibodies, and preparation and manufacture of compositions comprising antibodies of the disclosure, or antigen-binding fragments thereof, such as medicaments for the use of the antibodies.

Polynucleotides encoding antibodies that bind E-selectin, or antigen-binding fragments thereof, are provided. Polynucleotides encoding antibody heavy chains or light chains, or both are also provided. Host cells that express anti-E-selectin antibodies are provided. Methods of treatment using antibodies to E-selectin are provided. Such methods include, but are not limited to, methods of treating and/or preventing diseases associated with or mediated by E-selectin expression and/or E-selectin binding to sLex ligands, including, but not limited to, SCD, vaso-occlusive crisis, pain, organ infarction, ischemia, stroke, end organ dysfunction, acute chest and vascular obstruction.

Without wishing to be bound by any particular theory, the selectin family of adhesion molecules (e.g., E-selectin) and their ligands play a critical role in regulating the initial contact of cell-cell adhesion, leukocyte rolling on the endothelium, integrin activation and transmigration of cells, all part of a pro-inflammatory response in SCD which manifests clinically as episodes of severe pain or vaso-occlusive crisis (including, e.g., vascular obstruction, organ infarction and ischemia). Thus, antibodies, and antigen-binding fragments thereof, of the disclosure enable selective antagonism of E-selectin activity and binding in the vascular system, thus reducing vaso-occlusion in a subject. In some embodiments disclosed in the Examples herein, antibodies, and antigen-binding fragments thereof, against E-selectin have been shown to inhibit, neutralize or reduce binding of E-selectin to its ligands when the E-selectin is in solution or expressed on cells (e.g., Chinese hamster ovary (CHO) cells, neutrophils and/or blood cells from patients with SCD) and its ligand(s) are in solution or expressed on cells (e.g., HL-60 cells, human umbilical vein endothelial cells (HU-VEC), cynomolgus monkey lung microvascular endothelial cells (CLMEC)).

An anti-E-selectin antibody, or antigen-binding fragment thereof, including a humanized antibody, can be used, alone or in combination with a second therapy, in the prevention, treatment, and/or amelioration of at least one sign and/or symptom of SCD including vaso-occlusive crisis, pain, organ infarction, ischemia, stroke and vascular obstruction.

The section headings used herein are for organizational purposes only and are not to be construed as limiting the subject matter described.

All references cited herein, including patent applications, patent publications, UniProtKB accession numbers are herein incorporated by reference, as if each individual reference were specifically and individually indicated to be incorporated by reference in its entirety.

The techniques and procedures described or referenced herein are generally well understood and commonly employed using conventional methodology by those skilled in the art, such as, for example, the widely utilized methodologies described in Sambrook et al, Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds); Gene Transfer Vectors for Mammalian Cells (J. M. Miller and M. P. Calos, eds., 1987); PCR: The Polymerase Chain Reaction, (Mullis et al, eds., 1994); Current Protocols in Immunology (J. E. Coligan et al, eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999)); The Antibodies (M. Zanetti and J. D. Capra, eds., Harwood Academic Publishers, 1995); and updated versions thereof.

The present disclosure may be understood more readily by reference to the following detailed description of exemplary embodiments of the invention and the Examples included therein.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Definitions

Unless otherwise defined, all technical and scientific terms used herein have the same meaning as commonly understood by one of ordinary skill in the art to which this invention belongs. In case of conflict, the present specification, including definitions, will control.

Further, unless otherwise required by context or expressly indicated, singular terms shall include pluralities and plural terms shall include the singular.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10.

As used herein, the singular form "a", "an", and "the" includes plural references unless indicated otherwise.

As used herein, the term "and/or" refers to and encompasses any and all possible combinations of one or more of the associated listed items, as well as the lack of combinations when interpreted in the alternative, "or".

As used herein, the term "about," or "approximately" refers to a measurable value such as an amount of the biological activity, length of a polynucleotide or polypeptide sequence, content of G and C nucleotides, codon adaptation index, number of CpG dinucleotides, dose, time, temperature, and the like, and is meant to encompass variations of 25%, 20%, 19%, 18%, 17%, 16%, 15%, 14%, 13%, 12%, 11%, 10%, 9%, 8%, 7%, 6%, 5%, 4%, 3%, 2% 1%, 0.5% or even 0.1%, in either direction (greater than or less than) of the specified amount unless otherwise stated, otherwise evident from the context, or except where such number would exceed 100% of a possible value.

As used herein, the term "ameliorate" means a detectable or measurable improvement in a subject's disease, disorder or condition, (e.g., SCD) or symptom thereof (e.g., vaso-occlusive crisis), or an underlying cellular response. A detectable or measurable improvement includes a subjective or objective decrease, reduction, inhibition, suppression, limit or control in the occurrence, frequency, severity, progression or duration of, complication caused by or associated with, improvement in a symptom of, or a reversal of the disease, disorder or condition.

As used herein "another" may mean at least a second or more. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular.

As used herein, the term "associated with" refers to with one another, if the presence, level and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example, by means of hydrogen bonds, van der Waals interaction, hydrophobic interactions, magnetism, and a combination thereof.

As used herein, the term "coding sequence" refers to a sequence which encodes a particular protein or "encoding nucleic acid," denotes a nucleic acid sequence which is transcribed (in the case of DNA) and translated (in the case of mRNA) into a polypeptide in vitro or in vivo when placed under the control of (operably linked to) appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences.

Throughout this specification and claims, the word "comprise," or variations such as "comprises" or "comprising," and the words "having/including" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting. It is understood that wherever embodiments are described herein with the language "comprising," otherwise analogous embodiments described in terms of "consisting of" and/or "consisting essentially of" are also provided.

As used herein, the term "conservative substitution" refers to replacement of one amino acid by a biologically, chemically or structurally similar residue. Biologically similar means that the substitution does not destroy a biological activity. Structurally similar means that the amino acids have side chains with similar length, such as alanine, glycine and serine or a similar size. Chemical similarity means that the residues have the same charge or are both hydrophilic or hydrophobic. Particular examples include the substitution of a hydrophobic residue, such as isoleucine, valine, leucine or methionine with another, or the substitution of one polar residue for another, such as the substitution of arginine for lysine, glutamic acid for aspartic acid or glutamine for asparagine, serine for threonine, and the like. Particular examples of conservative substitutions include the substitution of a hydrophobic residue such as isoleucine, valine, leucine or methionine for one another, the substitution of a polar residue for another, such as the substitution of arginine for lysine, glutamic acid for aspartic acid, or glutamine for asparagine, and the like. Conservative amino acid substitutions typically include, for example, substitutions within the following groups: glycine, alanine, valine, isoleucine, leucine; aspartic acid, glutamic acid; asparagine, glutamine; serine, threonine; lysine, arginine; and phenylalanine, tyrosine. A "conservative substitution" also includes the use of a substituted amino acid in place of an unsubstituted parent amino acid.

As used herein, the term "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, the term an "effective dosage" or "effective amount" of drug, compound, or pharmaceutical composition is an amount sufficient to affect any one or more beneficial or desired results. In more specific aspects, an effective amount prevents, alleviates and/or ameliorates at least one sign and/or symptom of a disease, e.g., SCD. For prophylactic use, beneficial or desired results include eliminating or reducing the risk, lessening the severity, or delaying the outset of the disease, including biochemical, histological and/or a behavioral symptom of the disease, its complications and intermediate pathological phenotypes presenting during development of the disease. For therapeutic use, beneficial or desired results include clinical results such as reducing at least one sign and/or symptom of an E-selectin-mediated disease, disorder or condition, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, the term "functional" refers to a biological molecule in a form in which it exhibits a property and/or activity by which it is characterized. A biological molecule may have two functions (i.e., bifunctional) or many functions (i.e., multifunctional).

As used herein, the term "glycosylation pattern" means the pattern of carbohydrate units that are covalently attached to a protein (e.g., the glycoform) as well as to the site(s) to which the glycoform(s) are covalently attached to the peptide backbone of a protein, more specifically to an immunoglobulin protein.

As used herein, the term "homologous" or "homology" refer to two or more reference entities (e.g., nucleotide or polypeptide sequences) that share at least partial identity over a given region or fragment. For example, when an amino acid position in two peptides is occupied by identical amino acids, the peptides are homologous at that position. Notably, a homologous peptide will retain activity or function associated with the unmodified or reference peptide and the modified peptide will generally have an amino acid sequence "substantially homologous" with the amino acid sequence of the unmodified sequence. When referring to a polypeptide, nucleic acid or fragment thereof, "substantial homology" or "substantial similarity," means that when optimally aligned with appropriate insertions or deletions with another polypeptide, nucleic acid (or its complementary strand) or fragment thereof, there is sequence identity in at least about 95% to 99% of the sequence. The extent of homology (identity) between two sequences can be ascertained using computer program or mathematical algorithm. Such algorithms that calculate percent sequence homology (or identity) generally account for sequence gaps and mismatches over the comparison region or area. Exemplary programs and algorithms are provided below.

As used herein, the terms "host cell," "host cell line," and "host cell culture" are used interchangeable and mean an individual cell or cell culture that can be or has been a recipient for vector(s) for incorporation of polynucleotide inserts. Host cells include "transformants," "transformed cells," and "transduced cells," which include the primary transformed or transduced cell and progeny derived therefrom without regard to the number of passages. Host cell progeny may not necessarily be completely identical (in morphology or in genomic DNA complement) to the original parent cell due to natural, accidental, or deliberate mutation. A host cell includes cells transfected and/or transformed in vivo with a polynucleotide of this invention (e.g., a polynucleotide encoding an amino acid sequence of an anti-E-selectin antibody).

As used herein, the term "identity" or "identical to" refers to the overall relatedness between polymeric molecules, e.g., between nucleic acid molecules (e.g., DNA molecules and/or RNA molecules) and/or between polypeptide molecules. "Identity" measures the percent of identical matches between two or more sequences with gap alignments addressed by a particular mathematical model of computer programs (i.e. "algorithms").

In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, 98% or 99% identical.

Calculation of the percent identity of two nucleic acid or polypeptide sequences, for example, can be performed by aligning the two sequences for optimal comparison purposes (e.g., gaps can be introduced in one or both of a first and a second sequence for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. The comparison of sequences and determination of percent identity between two sequences can be accomplished using a mathematical algorithm.

To determine percent identity, sequences can be aligned using the methods and computer programs, including BLAST, available over the world wide web at ncbi.nlm.nih.gov/BLAST/. Other alignment programs include MegAlign® program in the Lasergene® suite of bioinformatics software (DNASTAR®, Inc., Madison, Wis.). Another alignment algorithm is FASTA, available in the Genetics Computing Group (GCG) package, from Madison, Wis., USA. Other techniques for alignment are described in Methods in Enzymology, vol. 266: Computer Methods for Macromolecular Sequence Analysis (1996), ed. Doolittle, Academic Press, Inc. Of particular interest are alignment programs that permit gaps in the sequence. Smith-Waterman is one type of algorithm that permits gaps in sequence alignments. See Meth. Mol. Biol. 70:173-187 (1997). Also, the GAP program using the Needleman and Wunsch alignment method can be utilized to align sequences. See J. Mol. Biol. 48: 443-453 (1970).

Also, of interest is the BestFit program using the local homology algorithm of Smith and Waterman (1981, Advances in Applied Mathematics 2: 482-489) to determine sequence identity. The gap generation penalty will generally range from 1 to 5, usually 2 to 4 and in some embodiments will be 3. The gap extension penalty will generally range from about 0.01 to 0.20 and in some instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters: Mismatch Penalty: 1.00; Gap Penalty: 1.00; Gap Size Penalty: 0.33; and Joining Penalty: 30.0.

As used herein, the terms "increase," "improve," "decrease" or "reduce" indicate values that are relative to a baseline measurement, such as a measurement in the same individual prior to initiation of treatment described herein, or a measurement in a control individual (or multiple control individuals) in the absence of the treatment described herein. In some embodiments, a "control individual" is an individual afflicted with the same form of disease or injury as an individual being treated. In some embodiments, a "control individual" is an individual that is not afflicted with the same form of disease or injury as an individual being treated.

As used herein, the term "isolated molecule" (where the molecule is, for example, a polypeptide, a polynucleotide, or an antibody or antigen-binding fragment thereof) means a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

As used herein, the terms "leader peptide" or "leader sequence" or "leader signal sequence" or "signal sequence", (used interchangeably herein) mean any nucleic acid sequence, or amino acid sequence encoded thereby, that may be present on the 5' end of a nucleic acid molecule and/or at or near the N-terminus of a polypeptide, that when present may mediate the transport of the polypeptide to an organelle of destination, including, but not limited to, the secretion of the polypeptide from a cell. Such leader sequences include, but are not limited to, nucleic acid sequences comprising, e.g., ATGGAATGGAGCTGGGTCTTTCTCTTCTTCCTGTCAGTAACTACAGGTGTCCACTCC (SEQ ID NO: 140) and ATGGGATGGAGCTGTATCATCCTCTTCTTGGTGGCAACAGCTACAGGCGTGCACTCC (SEQ ID NO:41), and amino acid sequences encoded thereby, such as, but not limited to, MGWSCIILFLVATATGVHS (SEQ ID NO:129) and MEWSWVFLFFLSVTTGVHS (SEQ ID NO:130) or other leader sequences such as MGWSCIILFLVATATGAHS (SEQ ID NO:131). The invention encompasses these and any other leader signals (nucleic and amino acid sequences) known in the art or to be identified which can result in the transport of a polypeptide to the desired organelle, e.g., the endoplasmic reticulum, and/or secreted from the cell. Generally, the signal peptide is removed from and/or is not present in the mature polypeptide.

As used herein, the term "residue" means a position in a protein and its associated amino acid identity. For example, asparagine 297 (also referred to as Asn297, also referred to as N297) is a residue in a human antibody IgG1.

The term "similarity" is a related concept, but in contrast to "identity," refers to a measure of similarity which includes both identical matches and conservative substitution matches. Since conservative substitutions apply to polypeptides and not nucleic acid molecules, similarity only applies to polypeptide sequence comparisons. If two polypeptide sequences have, for example, 10 out of 20 identical amino acids, and the remainder are all nonconservative substitutions, then the percent identity and similarity would both be 50%. If in the same example, there are 5 more positions where there are conservative substitutions, then the percent identity remains 50%, but the percent similarity would be 75% (15 out of 20). Therefore, in cases where there are conservative substitutions, the degree of similarity between two polypeptide sequences will be higher than the percent identity between those two sequences.

As used herein, the term "subject" means a mammal, more preferably, a human. Mammals also include, but are not limited to, farm animals (e.g., cows, pigs, horses, chickens, etc.), pets, primates, horses, dogs, cats, mice and rats. In some embodiments, a subject is a patient. In some embodiments, a subject is at risk for a disease, disorder or condition mediated by or associated with E-selectin binding to its ligand. In some embodiments, a subject is a patient who has a disease, disorder or condition as described herein, e.g., SCD. In some embodiments, a subject (e.g., a patient) has SCD, a variant of SCD or SC disease. In some embodiments, a subject (e.g., a patient) has a HBSS, HBSC, HBS/β°thal, HBS/β+thal, HBS/HPHP, HBSE or HBS-variant genotype.

As used herein, the term "substantially pure" means an object species is the predominant species present (i.e., on a molar basis it is more abundant than any other individual species in the composition), and preferably a substantially purified fraction is a composition wherein the object species (e.g., a glycoprotein, including an antibody or receptor) comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species. In certain embodiments, a substantially pure material is at least 50% pure (i.e., free from contaminants), more preferably, at least 90% pure, more preferably, at least 95% pure, yet more preferably, at least 98% pure, and most preferably, at least 99% pure.

Polypeptide or antibody "fragments" or "portions" according to the invention may be made by truncation, e.g. by removal of one or more amino acids from the N and/or C-terminal ends of a polypeptide. One, 2, 3, 4, 5, up to 10, up to 20, up to 30, up to 40 or more amino acids may be removed from the N and/or C terminus in this way. Fragments may also be generated by one or more internal deletions.

As used herein, the terms "nucleic acid sequence" and "nucleotide sequence," refer interchangeably to any molecule composed of or comprising monomeric nucleotides. A nucleic acid may be an oligonucleotide or a polynucleotide. A nucleotide sequence may be a DNA or RNA (e.g., genomic DNA, cDNA, antisense DNA, mRNA, tRNA, rRNA, etc.). A nucleotide sequence may be chemically modified or artificial. Nucleotide sequences include peptide nucleic acids (PNA), mopholinos and locked nucleic acids (LNA), as well as glycol nucleic acids (GNA) and threose nucleic acids (TNA). Each of these sequences is distinguished from naturally occurring DNA or RNA by changes to the backbone of the molecule. Also, phosphorothioate nucleotides may be used. Other deoxynucleotide analogs include methylphosphonates, phosphoramidates, phosphorodithioates, N3'-P5'-phosphoramidates, and oligoribonucleotide phosphorothioates and their 2'-0-allyl analogs and 2'-0-methylribonucleotide methylphosphonates which may be used in a nucleotide sequence of the disclosure.

As used here, the term "nucleic acid construct," refers to a non-naturally occurring nucleic acid molecule resulting from the use of recombinant DNA technology (e.g., a recombinant nucleic acid). A nucleic acid construct is a nucleic acid molecule, either single or double stranded, which has been modified to contain segments of nucleic acid sequences, which are combined and arranged in a manner not found in nature. A nucleic acid construct may be a "vector" (e.g., a plasmid), that is, a nucleic acid molecule designed to deliver exogenously created DNA into a host cell.

As used herein, the term "operably linked" refers to a linkage of polynucleotide (or polypeptide) elements in a functional relationship. A nucleic acid is operably linked when it is placed into a functional relationship with another nucleic acid sequence. For instance, a promoter or other transcription regulatory sequence (e.g., an enhancer) is operably linked to a coding sequence if it affects the transcription of the coding sequence. In some embodiments, operably linked means that the nucleic acid sequences being linked are contiguous. In some embodiments, operably linked does not mean that the nucleic acid sequences are contiguously linked, rather intervening sequences are between those nucleic acid sequences that are linked.

As used herein, the term "polynucleotide" (also referred to herein as a "nucleic acid molecule") refers to a sequence of nucleotides connected by phosphodiester linkages. Polynucleotides are presented herein in the direction from the 5' to the 3' direction. A polynucleotide of the present disclosure can be a deoxyribonucleic acid (DNA) molecule or ribonucleic acid (RNA) molecule and refers to all forms of a nucleic acid such as, double stranded molecules, single stranded molecules, small or short hairpin RNA (shRNA), micro RNA, small or short interfering RNA (siRNA), trans-splicing RNA, antisense RNA. Where a polynucleotide is a DNA molecule, that molecule can be a gene, a cDNA, an antisense molecule or a fragment of any of the foregoing molecules. Nucleotide bases are indicated herein by a single letter code: adenine (A), guanine (G), thymine (T), cytosine (C), inosine (I) and uracil (U). A polynucleotide of the present disclosure can be prepared using standard techniques well known to one of skill in the art.

As used herein, the terms "polypeptide," "protein" and "peptide" encoded by a polynucleotide (nucleic acid sequence or nucleotide sequence) refer to full-length native sequences, as with naturally occurring proteins, as well as functional subsequences, modified forms or sequence variants so long as the subsequence, modified form or variant retains some degree of functionality of the native full-length protein. In methods and uses of the disclosure, such polypeptides, proteins and peptides encoded by the polynucleotide sequences can be but are not required to be identical to the endogenous protein that is defective, or whose expression is insufficient, or deficient in a subject treated with gene therapy.

As used herein, the term "prevent" or "prevention" refers to delay of onset, and/or reduction in frequency and/or severity of at least one sign and/or symptom (e.g., vasoocclusive crisis, pain) of a particular disease, disorder or condition (e.g., SCD). In some embodiments, prevention is assessed on a population basis such that an agent is considered to "prevent" a particular disease, disorder or condition if a statistically significant decrease in the development, frequency and/or intensity of one or more symptoms of the disease, disorder or condition is observed in a population susceptible to the disease, disorder or condition. Prevention may be considered complete when onset of disease, disorder or condition has been delayed for a predefined period of time.

As used herein, the term "recombinant," refers to a vector, polynucleotide, polypeptide or cell that is the product of various combinations of cloning, restriction or ligation steps (e.g. relating to a polynucleotide or polypeptide comprised therein), and/or other procedures that result in a construct that is distinct from a product found in nature.

As used herein, the terms "treat" or "treatment" means to administer a therapy that partially or completely alleviates, ameliorates, relieves, inhibits, delays onset of, reduces severity of, and/or reduces incidence of one or more symptoms, features and causes of a particular disease, disorder and/or condition (e.g., SCD). For purposes of this invention, beneficial or desired clinical results include, but are not limited to, one or more of the following: improved survival rate (reduced mortality), reduction in the amount of tissue fibrosis, decreased extent of damage from the disease, decreased duration of the disease, and/or reduction in the number, extent, or duration of a symptom related to the disease. The term includes the administration of a compound or agent of the present invention to prevent or delay the onset of a symptom, complication, or biochemical indicia of a disease, alleviating a symptom or arresting or inhibiting further development of a disease, condition, or disorder. Treatment may be prophylactic (to prevent or delay the onset of the disease, or to prevent the manifestation of a clinical or subclinical symptom thereof) or therapeutic suppression or alleviation of a symptom after the manifestation of the disease. In some embodiments, the disease, condition or disorder is SCD.

Antibodies

An "antibody" or "Ab" is an immunoglobulin molecule capable of recognizing and binding to a specific target or antigen (Ag), such as a carbohydrate, polynucleotide, lipid, polypeptide, etc., through at least one antigen recognition site, located in the variable region of the immunoglobulin molecule. As used herein, the term "antibody" can encompass any type of antibody, including but not limited to monoclonal antibodies, polyclonal antibodies, antigen-binding fragments (or portion), of intact antibodies that retain the ability to specifically bind to a given antigen (e.g., E-selectin), and any other modified configuration of the immunoglobulin molecule that comprises an antigen recognition site.

An antibody includes an antibody of any class, such as IgG, IgA, or IgM (or subclass thereof), and the antibody need not be of any particular class. Depending on the antibody amino acid sequence of the constant region of its heavy chains (HC), immunoglobulins can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$ and $IgA_2$. In some embodiments, an anti-E-selectin antibody of the present disclosure is and IgG1 antibody. The heavy chain constant regions that correspond to the different classes of immunoglobulins are called alpha, delta, epsilon, gamma, and mu, respectively. The subunit structures and three-dimensional configurations of different classes of immunoglobulins are well known.

Antibodies may be derived from any mammal, including, but not limited to, humans, monkeys, pigs, horses, rabbits, dogs, cats, mice, rats (e.g., a Sprague Dawley rat) etc., or other animals such as birds (e.g. chickens), fish (e.g., sharks) and camelids (e.g., llamas).

The term "antigen" refers to the molecular entity used for immunization of an immunocompetent vertebrate to produce the antibody that recognizes the antigen or to screen an expression library (e.g., phage, yeast or ribosome display library, among others). Herein, antigen is termed more broadly and is generally intended to include target molecules that are specifically recognized by the antibody, thus including fragments or mimics of the molecule used in an immunization process for raising the antibody or in library screening for selecting the antibody. Thus, for antibodies of the invention binding to E-selectin, full-length E-selectin from mammalian species (e.g., human, monkey (including cynomolgus monkey), mouse, rabbit and rat), including monomers and multimers, such as dimers, trimers, etc. thereof, truncated and other variants of E-selectin (e.g., extracellular domain), as well as soluble E-selectin and cell-surface expressed E-selectin, are referred to herein as an antigen.

An "antigen-binding fragment" of an antibody refers to a one or more fragments of a full-length antibody that retains the ability to specifically bind to an antigen (preferably with substantially the same binding affinity). It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature 1989; 341:544-546), which consists of a VH domain; and (vi) an isolated complementarity determining region (CDR), disulfide-linked Fvs (dsFv), and anti-idiotypic (anti-Id) antibodies and intrabodies. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see e.g., Bird et al., Science 1988; 242:423-426 and Huston et al., Proc. Natl. Acad. Sci. 1988 USA 85:5879-5883. Other forms of single chain antibodies, such as diabodies are also encompassed. Such single chain antibodies are also intended to be encompassed within the term "antigen-binding fragment" of an antibody. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites (see e.g., Holliger et al, Proc. Natl. Acad. Sci. USA 1993; 90:6444-6448; Poljak et al., Structure 1994; 2:1121-1123).

An antibody "variable domain" refers to the variable region of the antibody light chain (VL) or the variable region of the antibody heavy chain (VH), either alone or in combination. As known in the art, the variable regions of the heavy and light chains each consist of four framework regions (FR) connected by three "complementarity determining regions" (CDRs) and contribute to the formation of the antigen-binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonical class as the subject variable region (Chothia and Lesk, J. Mol. Biol. 1987; 196(4): 901-917).

Residues in a variable domain are typically numbered according Kabat, which provides a numbering system used for heavy chain variable domains or light chain variable domains of the compilation of antibodies. See, Kabat et al., 1991, Sequences of Proteins of Immunological Interest, 5th Ed. Public Health Service, National Institutes of Health, Bethesda, Md. Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, according to Kabat) after heavy chain FR residue 82. The Kabat numbering of residues may be determined for a given antibody by alignment at regions of homology of the sequence of the antibody with a "standard" Kabat numbered sequence. Various algorithms for assigning Kabat numbering are available. For example, the algorithm implemented in the version 2.3.3 release of Abysis (www.abysis.org) can be used to assign Kabat numbering to variable regions LCDR-1, LCDR-2, LCDR-3, HCDR-2, and HCDR-3, and the AbM definition can then be used for HCDR-1.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition, the contact definition, and the conformational definition.

"Complementarity Determining Regions" (CDRs) can be identified according to the definitions of Kabat, Chothia, the accumulation of both Kabat and Chothia, AbM, contact, North, and/or conformational definitions or any method of CDR determination well known in the art. See, e.g., Kabat et al., 1991, Sequences of Proteins of Immunological Interest, 5th ed. (hypervariable regions); Chothia et al., Nature 1989; 342:877-883 (structural loop structures). The identity of the amino acid residues in a particular antibody that make up a CDR can be determined using methods well known in the art. The AbM definition of CDRs is a compromise between Kabat and Chothia and uses Oxford Molecular AbM antibody modeling software (Accelrys®).

The "contact" definition of CDRs is based on observed antigen contacts, set forth in MacCallum et al., J. Mol. Biol. 1996; 262:732-745. The "conformational" definition of CDRs is based on residues that make enthalpic contributions to antigen binding (see, e.g., Makabe et al., J. Biol. Chem., 2008; 283:1156-1166). North has identified canonical CDR conformations using a different preferred set of CDR definitions (North et al., J. Mol. Biol. 2011; 406: 228-256). In another approach, referred to herein as the "conformational definition" of CDRs, the positions of the CDRs may be identified as the residues that make enthalpic contributions to antigen binding (Makabe et al., J. Biol. Chem. 2008, 283:1156-1166). Still other CDR boundary definitions may not strictly follow one of the above approaches but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs (or other residue of the antibody) may be defined in accordance with any of Kabat, Chothia, North, extended, AbM, contact, and/or conformational definitions.

"Contact residue" as used herein with respect to an antibody or the antigen specifically bound thereby, refers to an amino acid residue present on an antibody/antigen comprising at least one heavy atom (i.e., not hydrogen) that is within 4 Å or less of a heavy atom of an amino acid residue present on the cognate antibody/antigen.

"Framework" (FR) residues are antibody variable domain residues other than the CDR residues. A VH or VL domain framework comprises four framework sub-regions, FR1, FR2, FR3 and FR4, interspersed with CDRs in the following structure: FR1-CDR1-FR2-CDR2-FR3-CDR3-FR4.

As known in the art, a "constant region" of an antibody refers to the constant region of the antibody light chain or the constant region of the antibody heavy chain, either alone or in combination.

The terms "IgG Fc region," "Fc region," "Fc domain" and "Fc," as interchangeably used herein, refer to the portion of an immunoglobulin (Ig) molecule that correlates to a crystallizable fragment obtained by papain digestion of an Ig molecule. As used herein, the terms relate to the constant region of an antibody excluding the first constant region immunoglobulin domain and further relates to portions of that region. Thus, Fc refers to the last two constant region immunoglobulin domains of IgA, IgD, and IgG, and the last three constant region immunoglobulin domains of IgE and IgM, and the flexible hinge N-terminal to these domains, or portions thereof. For IgA and IgM, Fc may include the J chain.

For IgG, Fc comprises immunoglobulin domains Cγ2 and Cγ3 (C gamma 2 and C gamma 3) and the hinge between Cγ1 (C gamma 1) and Cγ2 (C gamma 2). Although the boundaries of the Fc region may vary, the human IgG heavy chain Fc region is usually defined to comprise residues C226 or P230 to its carboxyl-terminus, wherein the numbering is according to the EU index of Edelman et al., Proc. Natl. Acad. Sci. USA 1969; 63(1):78-85 and as described in Kabat et al., 1991. Typically, the Fc domain comprises from about amino acid residue 236 to about 447 of the human IgG1 constant domain. An exemplary human wild type IgG1 Fc domain amino acid sequence is set forth in SEQ ID NO: 16 and SEQ ID NO: 15 (including an optional terminal lysine (K) residue). Fc polypeptide may refer to this region in isolation, or this region in the context of an antibody, or an antigen-binding fragment thereof, or Fc fusion protein.

The heavy chain constant domain comprises the Fc region and further comprises the CH1 domain and hinge as well as the CH2 and CH3 (and, optionally, CH4 of IgA and IgE) domains of the IgG heavy chain.

A "functional Fc region" possesses at least one effector function of a native sequence Fc region. Exemplary "effector functions" include C1q binding; complement dependent cytotoxicity (CDC); Fc receptor binding; antibody-dependent cell-mediated cytotoxicity (ADCC); phagocytosis; down-regulation of cell surface receptors (e.g., B cell receptor), B cell activation, etc. Such effector functions generally require the Fc region to be combined with a binding domain (e.g., an antibody variable domain or antigen-binding fragment thereof) and can be assessed using various assays known in the art for evaluating such antibody effector functions.

As used herein, "Fc receptor" or "FcR" describes a receptor that binds to the Fc region of an antibody. In some embodiments, an Fc□R is a native human FcR. In some embodiments, an FcR is one which binds an IgG antibody (a gamma receptor) and includes receptors of the Fc⌣RI, Fc⌣RII, and Fc⌣RIII subclasses, including allelic variants and alternatively spliced forms of those receptors. Fc□RII receptors include Fc□RIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see, e.g., Daeron, Annu. Rev. Immunol. 1997; 15:203-234). FcRs are reviewed, for example, in Ravetch and Kinet, Annu. Rev. Immunol 1991; 9:457-92; Capel et al., Immunomethods 1994; 4:25-34; and de Haas et al., J. Lab. Clin. Med. 1995; 126:330-41. Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., J. Immunol. 1976; 117:587 and Kim et al., J. Immunol. 1994; 24:249) and regulation of homeostasis of immunoglobulins. Methods of measuring binding to FcRn are known (see, e.g., Ghetie and Ward., Immunol. Today 1997; 18(12):592-598; Ghetie et al., Nature Biotechnology, 1997; 15(7):637-640; Hinton et al., J. Biol. Chem. 2004; 279(8):6213-6216; WO 2004/92219).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, macrophages, cytotoxic T cells, and neutrophils. The effector cells may be isolated from a native source, e.g., from blood.

As used herein, "antibody-dependent cell-mediated cytotoxicity" or "ADCC" refers to a form of cytotoxicity in which secreted Ig bound onto Fc receptors (FcRs) present on certain cytotoxic cells (e.g., NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. To assess ADCC activity of a molecule of interest, an in vitro ADCC assay, such as that described in U.S. Pat. Nos. 5,500,362, 5,821,337 or 6,737,056, may be performed. Useful effector cells for such assays include PBMC and NK cells. Alternatively, or additionally, ADCC activity of the molecule of interest may be assessed in vivo, e.g., in an animal model such as that disclosed in Clynes et al., Proc. Natl. Acad. Sci. (USA) 1998; 95:652-656. Additional antibodies with altered Fc region amino acid sequences and increased or decreased ADCC activity are described, e.g., in U.S. Pat. Nos. 7,923,538, and 7,994,290.

An antibody having an "enhanced ADCC activity" refers to an antibody that is more effective at mediating ADCC in vitro or in vivo compared to the parent antibody, wherein the antibody and the parent antibody differ in at least one structural aspect, and when the amounts of such antibody and parent antibody used in the assay are essentially the same. In some embodiments, the antibody and the parent antibody have the same amino acid sequence, but the antibody is afucosylated while the parent antibody is fucosylated. In some embodiments, ADCC activity will be determined using the in vitro ADCC assay as herein disclosed, but other assays or methods for determining ADCC activity, e.g. in an animal model etc., are contemplated. In some embodiments, an antibody with enhanced ADCC activity has enhanced affinity for Fc gamma RIIIA.

An antibody with "altered" FcR binding affinity or ADCC activity is one which has either enhanced or diminished FcR binding activity and/or ADCC activity compared to a parent antibody, wherein the antibody and the parent antibody differ in at least one structural aspect. An antibody that "displays increased binding" to an FcR binds at least one FcR with better affinity than the parent antibody. An antibody that "displays decreased binding" to an FcR, binds at least one FcR with lower affinity than a parent antibody. Such antibodies that display decreased binding to an FcR may possess little or no appreciable binding to an FcR, e.g., 0-20 percent binding to the FcR compared to a native sequence IgG Fc region.

"Enhanced affinity for FcγRIIIA" refers to an antibody that has greater affinity for FcγRIIIA than a parent antibody, wherein the antibody and the parent antibody differ in at least one structural aspect.

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass), which are bound to their cognate antigen. To assess complement activation, a CDC assay, e.g., as described in Gazzano-Santoro et al., J. Immunol. Methods 1996; 202:163, may be performed. Antibodies with altered Fc region amino acid sequences and increased or decreased Clq binding capability are described, e.g., in U.S. Pat. Nos. 6,194,551, 7,923,538, 7,994,290 and WO 1999/51642.

A heavy chain constant domain comprises a Fc region and further comprises the CH1 domain and hinge as well as the CH2 and CH3 (and, optionally, CH4 of IgA and IgE) domains of the IgG heavy chain.

In some embodiments, where an anti-E-selectin antibody comprises a C-terminal lysine (K) amino acid residue on a heavy chain polypeptide (e.g., human IgG1 heavy chain comprises a terminal lysine), one skilled in the art would understand that the lysine residue may be clipped resulting in an antibody with a heavy chain lacking the C-terminal lysine residue. Additionally, the antibody heavy chain may be produced using a nucleic acid that does not encode the lysine. Thus, in some embodiments, an anti-E-selectin antibody comprises a heavy chain where the terminal lysine otherwise present is not present.

In certain embodiments, the antibody, or antigen-binding fragment thereof, described herein comprises an Fc domain. The Fc domain can be derived from IgA (e.g., $IgA_1$ or $IgA_2$), IgD, IgE, IgM, or IgG (e.g., $IgG_1$, $IgG_2$, $IgG_3$, or $IgG_4$). In some embodiments, an anti-E-selectin antibody is and IgG antibody. In some embodiments, an anti-E-selectin antibody (e.g., antibody 1444) is an $IgG_1$ antibody.

An "Fc fusion" protein is a protein wherein one or more polypeptides are operably linked to an Fc polypeptide. An Fc fusion combines the Fc region of an immunoglobulin with a fusion partner.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

An "epitope" refers to the area or region of an antigen to which an antibody specifically binds, e.g., an area or region comprising residues that interact with the antibody, as determined by any method well known in the art, for example, by conventional immunoassays or as described in Example 9 and 10 of the present disclosure. There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an anti-E-selectin antibody binds. Epitope mapping is commercially available from various sources, for example, Pepscan Systems (Edelhertweg 15, 8219 PH Lelystad, The Netherlands). Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to E-selectin, e.g., the antibodies compete for binding to the antigen.

In addition, the epitope to which the anti-E-selectin antibody binds can be determined in a systematic screening by using overlapping peptides derived from the E-selectin (e.g., a human E-selectin sequence) and determining binding by the antibody. According to the gene fragment expression assays, the open reading frame encoding E-selectin can be fragmented either randomly or by specific genetic constructions and the reactivity of the expressed fragments of E-selectin with the antibody to be tested is determined. The gene fragments may, for example, be produced by PCR and then transcribed and translated into protein in vitro, in the presence of radioactive amino acids. The binding of the antibody to the radioactively labeled E-selectin fragments is then determined by immunoprecipitation and gel electrophoresis.

Certain epitopes can also be identified by using large libraries of random peptide sequences displayed on the surface of phage particles (phage libraries) or yeast (yeast display). Alternatively, a defined library of overlapping peptide fragments can be tested for binding to the test antibody in simple binding assays. In an additional example, mutagenesis of an antigen, domain swapping experiments and alanine scanning mutagenesis can be performed to identify residues required, sufficient, and/or necessary for epitope binding.

At its most detailed level, the epitope for the interaction between the antigen and the antibody can be defined by the spatial coordinates defining the atomic contacts present in the antigen-antibody interaction, as well as information about their relative contributions to the binding thermodynamics. At a less detailed level, the epitope can be characterized by the spatial coordinates defining the atomic contacts between the antigen and antibody. At a further less detailed level the epitope can be characterized by the amino acid residues that it comprises as defined by a specific criterion, e.g., by distance between atoms (e.g., heavy, i.e., non-hydrogen atoms) in the antibody and the antigen. At a further less detailed level the epitope can be characterized through function, e.g., by competition binding with other antibodies. The epitope can also be defined more generically as comprising amino acid residues for which substitution by another amino acid will alter the characteristics of the interaction between the antibody and antigen (e.g. using alanine scanning).

From the fact that descriptions and definitions of epitopes, dependent on the epitope mapping method used, are obtained at different levels of detail, it follows that comparison of epitopes for different antibodies on the same antigen can similarly be conducted at different levels of detail.

Epitopes described at the amino acid level, e.g., determined from an X-ray crystallography, Nuclear Magnetic Resonance (NMR) spectroscopy, hydrogen/deuterium exchange Mass Spectrometry (H/D-MS), are said to be identical if they contain the same set of amino acid residues. Epitopes are said to overlap if at least one amino acid is shared by the epitopes. Epitopes are said to be separate (unique) if no amino acid residue is shared by the epitopes.

Yet another method which can be used to characterize an anti-E-selectin antibody is to use competition assays (e.g., as described in Example 9 of the present disclosure) with other antibodies known to bind to the same antigen, to determine if an anti-E-selectin antibody binds to the same epitope as other antibodies. Competition assays are well known to those of skill in the art Epitopes characterized by competition binding are said to be overlapping if the binding of the corresponding antibodies are mutually exclusive, i.e., binding of one antibody excludes simultaneous or consecutive binding of the other antibody. The epitopes are said to be separate (unique) if the antigen is able to accommodate binding of both corresponding antibodies simultaneously.

Epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds.

The binding affinity of an antibody can be expressed as $K_D$ value, which refers to the dissociation rate of a particular antigen-antibody interaction. $K_D$ is the ratio of the rate of dissociation, also called the "off-rate ($k_{off}$)," or "$k_d$" to the association rate, also called the "on-rate ($k_{on}$)" or "$k_a$." Thus, $K_D$ equals $k_{off}/k_{on}$ (or $k_d/k_a$) and is expressed as a molar concentration (M), and the smaller the $K_D$, the stronger the affinity of binding. $K_D$ values for antibodies can be determined using methods well established in the art. One exemplary method for measuring $K_D$ is surface plasmon resonance (SPR), typically using a biosensor system such as a BIACORE® system. BIAcore kinetic analysis comprises analyzing the binding and dissociation of an antigen from chips with immobilized molecules (e.g. molecules comprising epitope binding domains), on their surface. Another method for determining the $K_D$ of an antibody is by using Bio-Layer Interferometry, typically using OCTET technology (Octet QKe system, ForteBio). Alternatively, or in addition, a KinExA (Kinetic Exclusion Assay) assay, available from Sapidyne Instruments (Boise, Id.) can also be used.

An antibody that "preferentially binds" or "specifically binds" (used interchangeably herein) to an epitope is a term well understood in the art, and methods to determine such specific or preferential binding are also well known in the art. A molecule (e.g., a protein, a nucleic acid, an antibody, and the like) is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an E-selectin epitope is an antibody that binds a particular epitope with greater affinity, avidity, more readily, and/or with greater duration than it binds to other E-selectin epitopes or non-E-selectin epitopes, including P-selectin and/or L-selectin epitopes. Thus, under designated assay conditions, the specified binding moiety (e.g., an antibody or an antigen-binding fragment thereof or a receptor or a ligand binding fragment thereof) binds preferentially to a particular target molecule and does not bind in a significant amount to other components present in a test sample. Generally, but not necessarily, reference to binding means preferential binding.

A variety of assay formats may be used to select an antibody or peptide that specifically binds a molecule of interest. For example, solid-phase ELISA immunoassay (including a competition binding ELIA), AlphaLISA® immunoassay (Perkin-Elmer), immunoprecipitation, BIAcore™ (GE Healthcare, Piscataway, N.J.), fluorescence-activated cell sorting (FACS), Octet™ (FortéBio, Inc., Menlo Park, Calif.) and Western blot analysis are among many assays that may be used to identify an antibody that specifically reacts with an antigen or a receptor, or ligand binding fragment thereof, that specifically binds with a cognate ligand or binding partner. Typically, a specific or selective reaction will be at least twice background signal or noise and more typically more than 10 times background, more than 50 times background, more than 1000 times background or more. An antibody is said to "specifically bind" an antigen when the equilibrium dissociation constant ($K_D$) is $\leq 1$ µM, $\leq 100$ nM, $\leq 10$ nM, $\leq 1$ nM or $\leq 100$ pM. In some embodiments, an anti-E-selectin antibody binds E-selectin (e.g., human E-selectin) with a $K_D$ of <70 nM (e.g., 68.4+/−3.18 nM). In some embodiments, an anti-E-selectin antibody binds E-selectin (e.g., cynomolgus monkey E-selectin) with a $K_D$ of <68 nM (e.g., 64.9+/−1.13 nM).

In some embodiments, an anti-E-selectin antibody binds human E-selectin with a $K_D$ selected from the group consisting of about 92.85 nM, about 70.3 nM, about 65.2 nM, about 61.8 nM, about 60.5 nM, about 68.0 nM, about 21.6 nM, about 324 nM, about 54.4 nM, about 628.5 nM and 2940 nM. In some embodiments, an anti-E-selectin antibody binds cynomolgus monkey E-selectin with a $K_D$ selected from the group of about 138.5 nM, about 78.3 nM, about 76.5 nM, about 81.5 nM, about 67.8 nM, about 45.8 nM, about 243.5 nM, about 45.4 nM, about 492 nM and 3145 nM.

The term "compete," as used herein with regard to an antibody, means that binding of a first antibody, or an antigen-binding fragment thereof, to an antigen reduces the subsequent binding of the same antigen by a second antibody or an antigen-binding fragment thereof. The alternative, where the binding of the second antibody to an antigen is also detectably decreased in the presence of the first antibody, can, but need not be the case. That is, a first antibody can inhibit the binding of a second antibody to an antigen without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or fragment thereof), the skilled artisan would appreciate, based upon the teachings provided herein, that such competing and/or cross-competing antibodies are encompassed and can be useful for the methods disclosed herein.

Standard competition assays may be used to determine whether two antibodies compete with each other. One suitable assay for antibody competition involves the use of the Biacore technology, which can measure the extent of interactions using surface plasmon resonance (SPR) technology, typically using a biosensor system (such as a BIACORE system). For example, SPR can be used in an in vitro competitive binding inhibition assay to determine the ability of one antibody to inhibit the binding of a second antibody. Another assay for measuring antibody competition uses an ELISA-based approach.

Furthermore, a high throughput process for "binning" antibodies based upon their competition is described in International Patent Application No. WO2003/48731. Competition is present if one antibody (or fragment) reduces the binding of another antibody (or fragment) to E-selectin. For example, a sequential binding competition assay may be used, with different antibodies being added sequentially. The first antibody may be added to reach binding that is close to saturation. Then, the second antibody is added. If the binding of second antibody to E-selectin is not detected, or is significantly reduced (e.g., at least about 10%, at least about 20%, at least about 30%, at least about 40%, at least about 50%, at least about 60%, at least about 70%, at least about 80%, or at least about 90% reduction) as compared to a parallel assay in the absence of the first antibody (which value can be set as 100%), the two antibodies are considered as competing with each other.

The definition of the term "paratope" is derived from the above definition of "epitope" by reversing the perspective. Thus, the term "paratope" refers to the area or region on the antibody which specifically binds an antigen, i.e., the amino acid residues on the antibody which make contact with the antigen (E-selectin, or a fragment thereof) as "contact" is defined elsewhere herein. The paratope for a given antibody/antigen pair may be identified by routine methods. For example, the antibody and target molecule may be combined, and the antibody/antigen complex may be crystallized. The crystal structure of the complex may be determined and used to identify specific sites of interaction between the antibody and its target.

In some embodiments, an antibody is a "variant antibody". A variant antibody may comprise 1, 2, 3, 4, 5, up to 10, up to 20, up to 30 or more amino acid substitutions and/or deletions and/or insertions from the specific sequences and fragments disclosed herein, and in particular in Table 2. "Deletion" variants may comprise the deletion of individual amino acids, deletion of small groups of amino acids such as 1, 2, 3, 4 or 5 amino acids, or deletion of larger amino acid regions, such as the deletion of specific amino acid domains or other features. "Insertion" variants may comprise the insertion of individual amino acids, insertion of small groups of amino acids such as 1, 2, 3, 4 or 5 amino acids, or insertion of larger amino acid regions, such as the insertion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophillic amino acid, another hydrophobic amino acid, another polar amino acid, another aromatic amino acid or another aliphatic amino acid.

Substitution variants have at least one amino acid residue in the antibody molecule removed and different residue inserted in its place. The sites of greatest interest for substitutional mutagenesis include the hypervariable regions, but framework alterations are also contemplated. Conservative substitutions are shown in Table 1. If such substitutions result in a change in biological activity, then more substantial changes, denominated "exemplary substitutions" shown below, or as further described below in reference to amino acid classes, may be introduced and the products screened.

TABLE 1

Amino Acids and Substitutions

| Original Residue | Conservative Substitutions | Exemplary Substitutions |
|---|---|---|
| alanine Ala (A) | Val | Val; Leu; Ile |
| arginine Arg (R) | Lys | Lys; Gln; Asn |
| asparagine Asn (N) | Gln | Gln; His; Asp, Lys; Arg |
| aspartic Asp (D) | Glu | Glu; Asn |
| cysteine Cys (C) | Ser | Ser; Ala |
| glutamine Gln (Q) | Asn | Asn; Glu |
| glutamic Glu (E) | Asp | Asp; Gln |
| glycine Gly (G) | Ala | Ala |
| histidine His (H) | Arg | Asn; Gln; Lys; Arg |
| isoleucine Ile (I) | Leu | Leu; Val; Met; Ala; Phe; Norleucine |
| leucine Leu (L) | Ile | Norleucine; Ile; Val; Met; Ala; Phe |
| lysine Lys (K) | Arg | Arg; Gln; Asn |
| methionine Met (M) | Leu | Leu; Phe; Ile |
| phenylalanine Phe (F) | Tyr | Leu; Val; Ile; Ala; Tyr |
| proline Pro (P) | Ala | Ala |
| serine Ser (S) | Thr | Thr |
| threonine Thr (T) | Ser | Ser |
| tryptophan Trp (W) | Tyr | Tyr; Phe |
| tyrosine Tyr (Y) | Phe | Trp; Phe; Thr; Ser |
| valine Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a beta-sheet or helical conformation, (b) the charge or hydrophobicity of the molecule at the target site, or (c) the bulk of the side chain. Naturally occurring residues are divided into groups based on common side-chain properties:
   i. Non-polar: Norleucine, Met, Ala, Val, Leu, Ile;
   ii. Polar without charge: Cys, Ser, Thr, Asn, Gln;
   iii. Acidic (negatively charged): Asp, Glu;
   iv. Basic (positively charged): Lys, Arg;
   v. Residues that influence chain orientation: Gly, Pro; and
   vi. Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

In a process known as "germlining," certain amino acids in the VH and VL sequences can be mutated to match those found naturally in germline VH and VL sequences. In particular, the amino acid sequences of the framework regions in the VH and VL sequences can be mutated to match the germline sequences to reduce the risk of immunogenicity when the antibody is administered. As used herein, the term "germline" refers to the nucleotide sequences and amino acid sequences of the antibody genes and gene segments as they are passed from parents to offspring via the germ cells. This germline sequence is distinguished from the nucleotide sequences encoding antibodies in mature B cells which have been altered by recombination and hypermutation events during the course of B cell maturation. An antibody that "utilizes" a particular germline has a nucleotide or amino acid sequence that most closely aligns with that germline nucleotide sequence or with the amino acid sequence that it specifies. Such antibodies frequently are mutated compared with the germline sequence. Germline DNA sequences for human VH and VL genes are known in the art (see e.g., the "Vbase" human germline sequence database; see also Kabat, E. A., et al., 1991, Sequences of Proteins of Immunological Interest, Fifth Edition, U.S. Department of Health and Human Services, NIH Publication No. 91-3242; Tomlinson et al., J. Mol. Biol. 1992; 227:776-798; and Cox et al., Eur. J. Immunol. 1994; 24:827-836).

Antibodies to E-Selectin

The disclosure provides antibodies, and antigen-binding fragments thereof, that bind to E-selectin. E-selectin is also known as CD62 antigen-like family member E (CD62E), endothelial-leukocyte adhesion molecule 1 (ELAM-1) or leukocyte-endothelial cell adhesion molecule 2 (LECAM2).

As used herein, the term "E-selectin" includes variants, isoforms, homologs, orthologs and paralogs of human E-selectin. In some embodiments, an antibody, or antigen-binding fragment thereof, disclosed herein cross-reacts with E-selectin from species other than human, such as E-selectin of cynomolgus monkey, as well as different forms of E-selectin. In some embodiments, an antibody, or antigen binding fragment thereof, may be completely specific for human E-selectin and may not exhibit species cross-reactivity (e.g., does not bind mouse E-selectin) or other types of cross-reactivity (e.g., does not bind P-selectin and/or L-selectin). As used herein the term E-selectin refers to naturally occurring human E-selectin unless contextually dictated otherwise. Therefore, an "E-selectin antibody, or antigen-binding fragment thereof," "anti-E-selectin antibody, or antigen-binding fragment thereof" or other similar designation means any antibody, or antigen-binding fragment thereof, (as defined herein) that specifically and/or preferentially associates, binds or reacts with E-selectin, an isoform, fragment or derivative thereof. The full length, mature form of human E-selectin, as represented by UniProtKB/Swiss-Prot accession number P16581 (amino acids 22-610) is herein provided as SEQ ID NO:132. The full length, mature form of mouse E-selectin, as represented by UniProtKB/Swiss-Prot accession number O00690 (amino acids 22-612) is herein provided as SEQ ID NO:134. The full length, mature form of cynomolgus E-selectin, as represented by UniProtKB/Swiss-Prot accession number G8F370 (amino acids 22-610) is herein provided as SEQ ID NO:201.

E-selectin is expressed on endothelial cells, L-selectin is constitutively expressed on leukocyte microvilli, and P-selectin is stored in the $\alpha$-granules of platelets and Weibel-Palade bodies of endothelial cells (Tedder et al., FASEB J. 1995; 9:866-873; Kanas et al., Blood 1996; 88:3259-3287). They all bind to carbohydrate structures with a sialyl Lewis (sLex) determinant on glycoproteins or glycolipids (Chase et al., Ann. Biomed. Eng. 2012; 40(4):849-885). P- and L-selectins also require sulfation on the ligand for optimal binding, while E-selectin binding to ligands is more permissive requiring only sialyl Lewis determinants. The P-selectin glycoprotein ligand-1 (PSGL-1) is expressed on leukocytes and binds to all of the selectins. E-selectin also interacts with ligands including L-selectin ligand, CD44 and E-selectin ligand-1 (ESL-1) (Chase et al., Ann. Biomed. Eng. 2012; 40(4):849-885; Hidalgo et al., Immunity 2007; 26(4):477-489).

Expression of E-selectin by endothelial cells requires new protein synthesis in response to hypoxia or an inflammatory stimulus. E-selectin is critical for neutrophil adherence to the endothelium and generation of waves of activating signals on the endothelium that produce a polarized expression of activated $\alpha M\beta 2$ integrin (Hidalgo et al., Nat. Med. 2009; 15:384-391; Pruenster et al., Nat. Commun. 2015; 6:6915; Manwani, & Frenette, Blood 2014; 122:3892-3898). E-selectin-deficient mice do not exhibit an obvious phenotype distinguishable from wild-type mice (Labow et al., Immunity 1994; 1:709-720).

In addition to endothelial cell E-selectin, soluble E-selectin (sE-selectin) is found in circulation. The mechanism for sE-selectin release into the circulation may be enzymatic cleavage or result from shedding of damaged or activated endothelial cells; however, the precise mechanism is not known (Roldán et al., Thromb. Haemost 2003; 90:1007-1020). The concentration of sE-selectin appears to correlate with its expression on the surface of endothelial cells, thus plasma sE-selectin concentration might be a marker of endothelial cell damage or activation (Leeuwenberg et al., Immunology 1992; 77(4):543-549; Roldán et al., Thromb. Haemost. 2003; 90:1007-1020). Increased levels of circulating soluble E-selectin levels have been found in a number of disease states including hypertension, diabetes and hyperlipidemia (Roldán et al., Thromb. Haemost. 2003; 90:1007-1020). Kato et al. studied 160 SCD patients and 41 control subjects and found that soluble E-selectin was significantly elevated in the plasma of SCD patients as compared to controls (median 74.6. 41.5 ng/mL, p<0.001) (British J. Haem. 2005; 130:943-953). Mild and moderate levels of pulmonary hypertension were significantly associated with the linear concentration of sE-selectin and had an increased relative risk for early mortality in SCD patients (RR of 4.2; 95% CI 2.0,8.9) (Kato et al.).

Preferably, antibodies, and antigen binding fragments thereof, of the present disclosure bind to E-selectin but do not bind, or bind at a lower affinity, to other selectins (e.g., P-selectin, L-selectin). In some embodiments, antibodies, or antigen-binding fragments thereof, of the present disclosure specifically bind E-selectin, and more preferably, specifically bind human and/or cynomolgus monkey E-selectin. The disclosure also provides for compositions comprising such antibodies, and antigen-binding fragments thereof, as well as uses for such antibodies, including therapeutic and pharmaceutical uses.

An anti-E-selectin antibody, preferably, a high affinity antibody (e.g., a specific antibody), may be effective in the vascular system and multiple tissue compartments, where E-selectin is expressed on the surface of endothelial cells, or found in a soluble form, and is thought to interact with target cells (e.g., neutrophils, monocytes, eosinophils, memory-effector T-like lymphocytes, natural killer cells, myeloid cells) expressing E-selectin ligands. Antibodies, and antigen-binding fragments thereof, of the disclosure have the potential to inhibit binding of E-selectin to ligands including, for example, glycoproteins or glycolipids with a sialyl Lewis (sLex) determinant (e.g., α2,3 sialylated and α1,3 or α1,4 fucosylated tetrasaccharide sialyl Lewis x), sialyl Lewis A determinant, E-selectin ligand-1 (ESL-1), L-selectin, CD44, P-selectin glycoprotein ligand-1 (PSGL-1), lysosomal-associated membrane protein 1 (LAMP1), lysosomal-associated membrane protein 2 (LAMP2), death receptor-3 (DR3) and αMβ2 integrin (CD11b/CD18; Mac-1) (Chase et al., Annals Biomed. Engin. 2012; 40(4): 849-859). Without wishing to be bound by any particular theory, blockade of the E-selectin cellular ligand interaction inhibits leukocyte (e.g., neutrophil) adherence to the endothelium preventing cellular aggregates from blocking blood flow and leading to VOC.

A neutralizing or "blocking" antibody refers to an antibody whose binding to E-selectin (i) interferes with, limits, or inhibits the interaction between E-selectin, or an E-selectin fragment, and a E-selectin ligand, such as a sLex determinant; and/or (ii) results in inhibition of at least one biological function of E-selectin binding. Assays to determine neutralization by an antibody of the disclosure are described elsewhere herein and are well-known in the art.

"Biological function" or "biological activity" of E-selectin is meant to include leukocyte tethering, slow rolling and activation of stable adhesion of leukocytes to endothelial cells, selective and efficient extravasation signaling at sites of inflammation. "Biological function" or "biological activity" of E-selectin includes mediating an increase in: affinity and avidity of CD18 integrins to support PMN deceleration and trafficking to sites of acute inflammation, cytosolic calcium, tyrosine phosphorylation to activate p38 MAP kinase and Syk kinase, among others now known in the art or later identified. The biological function or biological activity of E-selectin can, but need not be, mediated by the interaction between E-selectin and its ligands.

The disclosure includes an antibody, or antigen-binding fragment thereof, that can modulate a biological activity of E-selectin. That is, the invention includes an isolated antibody, or antigen-binding fragment thereof, that specifically binds E-selectin and modulates at least one detectable E-selectin activity such that the antibody: (a) decreases leukocyte tethering to endothelial cells; (b) decreases activation of stable adhesion to endothelial cells; (c) reduces slow rolling of leukocytes to arrest; (d) reduces efficient trans-endothelial migration of leukocytes; (e) decreases affinity and avidity of CD18 integrins; (f) reduces trafficking of leukocytes to sites of acute inflammation; (g) decreases cytosolic calcium; (h) decreases tyrosine phosphorylation that activates p38 MAP kinase and Syk kinase; (i) reduces recruitment of platelets and leukocytes from the blood to the vascular endothelium; and/or (j) does not create a pro-inflammatory environment.

The biological activity of E-selectin can be assessed in an in vitro static neutralization binding assays using E-selectin (e.g., soluble E-selectin or CHO cells expressing E-selectin) and a ligand (e.g., soluble sialyl Lewis ligand or cell surface expressed ligand (e.g., on HL-60 cells)). Binding of E-selectin can also be assessed using soluble or cell surface expressed proteins in physiological flow assays know in the art and set forth in the Examples section of the present disclosure. The ability of neutralizing antibodies to prevent E-selectin binding can also be assessed by incubating cells expressing E-selectin (e.g., human, cynomolgus monkey) with a soluble (sialyl Lewis antigen) or cell surface expressed (e.g., on HL-60 cells, HUVEC, CLMEC) E-selectin ligand in the absence or presence of increasing concentrations of the anti-E-selectin antibody, or antigen-binding fragment thereof.

In some embodiments, an anti-E-selectin antibody of the disclosure encompasses an antibody that competes for binding to human E-selectin with, and/or binds the same epitope as, an antibody, or antigen-binding fragment thereof, having the amino acid sequence of a heavy chain variable region set forth as SEQ ID NO:11 and the amino acid sequence of a light chain variable region set forth as SEQ ID NO:5.

In some embodiments, an anti-E-selectin antibody, or antigen-binding fragment thereof, of the disclosure encompasses an antibody, or antigen-binding fragment thereof, that inhibits or reduces binding of E-selectin to at least one E-selectin ligand (e.g., glycoproteins or glycolipids with a sialyl Lewis (sLex) determinant (e.g., α2,3 sialylated and α1,3 or α1,4 fucosylated tetrasaccharide sialyl Lewis x), sialyl Lewis A determinant, ESL-1, L-selectin, CD44, PSGL-1, LAMP1, LAMP2, DR3 and αMβ2 integrin (CD11b/CD18; Mac-1)).

In some embodiments, the disclosure encompasses an antibody, or antigen-binding fragment thereof, that competes with an antibody, or antigen-binding fragment thereof, having the amino acid sequence of a heavy chain variable region set forth as SEQ ID NO:11 and the amino acid sequence of a light chain variable region set forth as SEQ ID NO:5, in inhibiting the binding of E-selectin with a ligand.

In some embodiments, an antibody, or antigen-binding fragment thereof of the disclosure, includes an IgG1 heavy chain constant region, for example an anti-E-selectin heavy chain set forth as SEQ ID NO:7, or SEQ ID NO:13 (without C-terminal lysine). In some embodiments, an antibody, or antigen-binding fragment thereof, includes a kappa light chain constant region, for example an anti-E-selectin light chain set forth as SEQ ID NO:1.

Anti-E-selectin antibodies of the present disclosure can encompass monoclonal antibodies, polyclonal antibodies, antibody fragments (e.g., Fab, Fab', F(ab')$_2$, Fv, Fc, etc.), chimeric antibodies, bispecific antibodies, heteroconjugate antibodies, single chain (ScFv), mutants thereof, fusion proteins comprising an antibody fragment (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some embodiments, an anti-E-selectin antibody is a monoclonal antibody. In some embodiments, an anti-E- selectin antibody is a human or humanized antibody. In some embodiments, an anti-E-selectin antibody is a chimeric antibody.

Table 2 provides amino acid and nucleotide sequences for the chimeric and humanized anti-E-selectin antibodies as described herein. Generally, unless specifically indicated, anti-E-selectin antibodies of the disclosure can include any combination of one or more CDRs. In some embodiments, anti-E-selectin antibodies of the disclosure can include any combination of one or more VH and/or VL sequences as set forth in Table 2, with particular antibodies defined by SEQ ID NO: in Table 3. The CDRs of the anti-E-selectin VHs and VLs were defined using the Kabat definition with the extended H1. For HCDR-1, the last residue includes any insert before the H36 position (i.e. H35a, H35b, H35c, etc.). The CDRs were defined as follows: HCDR-1 (H26 to H35c), HCDR-2 (H50 to H65), HCDR-3 (H95 to H102), LCDR-1 (L24 to L34), LCDR-2 (L50 to L56), and LCDR-3 (L89 to L87).

In some embodiments, an anti-E-selectin antibody, or antigen-binding fragment thereof, comprises a HC, LC, VL domain, and/or VH domain comprising an amino acid sequence at least 80%, 85%, 90%, 91%, 925, 93%, 94%, 95%, 96%, 97%, 98% or 99% identical to an amino acid sequence of Table 2. In some embodiments, an anti-E-selectin antibody, or antigen-binding fragment thereof, comprises a HC, LC, VL domain, and/or VH domain encoded by a nucleic acid sequence at least 80%, 85%, 90%, 91%, 925, 93%, 94%, 95%, 96%, 97%, 98% or 99% identical to a nucleic acid sequence of Table 2.

Table 2. Sequences of E-selectin peptides, anti-E-selectin antibodies and fragments thereof.

| SEQ | Description | Sequence |
| --- | --- | --- |
| 1 | 1444_optimized_L (LC) | DIQMTQSPSS LSASVGDRVT ITCKTSQNIE RYLNWYQQKP GKAPKLLIYA ASSLQSGVPS RFSGSGSGTD FTLTISSLQP EDFATYFCLQ DNAWPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 2 | 1444_optimized_L CDR_L1 | KTSQNIERYL N |
| 3 | 1444_optimized_L CDR_L2 | AASSLQS |
| 4 | 1444_optimized_L CDR_L3 | LQDNAWPLT |
| 5 | 1444_optimized_L FV_L(VL) | DIQMTQSPSS LSASVGDRVT ITCKTSQNIE RYLNWYQQKP GKAPKLLIYA ASSLQSGVPS RFSGSGSGTD FTLTISSLQP EDFATYFCLQ DNAWPLTFGQ GTKVEIK |
| 6 | 1444_optimized_L FW_L4 | FGQGTKVEIK |
| 7 | 1444_optimized_H (HC) (with C-terminal lysine(K)) | EVQLVESGGG LVQPGGSLRL SCAASGYAIR SAYMHWVRQA PGKGLEWVAR IDPANGNTIY VDSVTGRFTI SADNAKNSAY LQMNSLRAED TAVYYCAMDL YSTSEYWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APEAAGAPSV FLFPPKPKDT LMTSRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDTAVE WESNGQPENN YKTTPPVLDS DGSFFLYSKL TVDKSRWQQG NVFSCSVMHE ALHNHYTQKS LSLSPGK |
| 8 | 1444_optimized_H CDR_H1 | GYAIRSAYMH |
| 9 | 1444_optimized_H CDR_H2 | RIDPANGNTI YVDSVTG |
| 10 | 1444_optimized_H CDR_H3 | DLYSTSEY |
| 11 | 1444_optimized_H FV_H ( FV) | EVQLVESGGG LVQPGGSLRL SCAASGYAIR SAYMHWVRQA PGKGLEWVAR IDPANGNTIY VDSVTGRFTI SADNAKNSAY LQMNSLRAED TAVYYCAMDL YSTSEYWGQG TLVTVSS |
| 12 | 1444_optimized_H FW_H4 | WGQGTLVTVS S |

| SEQ | Description | Sequence |
|---|---|---|
| 13 | 1444_optimized_H (HC) (without C-terminal lysine(K)) | EVQLVESGGG LVQPGGSLRL SCAASGYAIR SAYMHWVRQA PGKGLEWVAR IDPANGNTIY VDSVTGRFTI SADNAKNSAY LQMNSLRAED TAVYYCAMDL YSTSEYWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APEAAGAPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPG |
| 14 | 1444_optimized_L CL | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |
| 15 | 1444_optimized_H CH (with C-terminal lysine (K)) | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 16 | 1444_optimized_H CH (without C-terminal lysine (K)) | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 17 | 0841_humanized1_L | DIQMTQSPSS LSASVGDRVT ITCKTSQNIN RYLNWYQQKP GKAPKLLIYN ANSLQTGVPS RFSGSGSGTD FTLTISSLQP EDFATYFCLQ DNSWPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 18 | 0841_humanized1_L CDR_L1 | KTSQNINRYL N |
| 19 | 0841_humanized1_L CDR_L2 | NANSLQT |
| 20 | 0841_humanized1_L CDR_L3 | LQDNSWPLT |
| 21 | 0841_humanized1_L FV_L | DIQMTQSPSS LSASVGDRVT ITCKTSQNIN RYLNWYQQKP GKAPKLLIYN ANSLQTGVPS RFSGSGSGTD FTLTISSLQP EDFATYFCLQ DNSWPLTFGQ GTKVEIK |
| 22 | 0841_humanized1_H | EVQLVESGGG LVQPGGSLRL SCAASGYNIR SSYMHWVRQA PGKGLEWVAR IDPANGNTIY AEKFKIRFTI SADNAKNSAY LQMNSLRAED TAVYYCAMDL YSTSEYWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APEAAGAPSV |

-continued

| SEQ | Description | Sequence |
|---|---|---|
| | | FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPG |
| 23 | 0841_humanized1_H CDR_H1 | GYNIRSSYMH |
| 24 | 0841_humanized1_H CDR_H2 | RIDPANGNTI YAEKFKI |
| 25 | 0841_humanized1_H FV_H | EVQLVESGGG LVQPGGSLRL SCAASGYNIR SSYMHWVRQA PGKGLEWVAR IDPANGNTIY AEKFKIRFTI SADNAKNSAY LQMNSLRAED TAVYYCAMDL YSTSEYWGQG TLVTVSS |
| 26 | 0978_humanized2_L | DIQMTQSPSS LSASVGDRVT ITCKTSQNIN RYLNWYQQKP GKAPKLLIYA ASSLQSGVPS RFSGSGSGTD FTLTISSLQP EDFATYFCLQ DNSWPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 27 | 0978_humanized2_L FV_L | DIQMTQSPSS LSASVGDRVT ITCKTSQNIN RYLNWYQQKP GKAPKLLIYA ASSLQSGVPS RFSGSGSGTD FTLTISSLQP EDFATYFCLQ DNSWPLTFGQ GTKVEIK |
| 28 | 0978_humanized2_H | EVQLVESGGG LVQPGGSLRL SCAASGYNIR SSYMHWVRQA PGKGLEWVAR IDPANGNTIY VDSVKGRFTI SADNAKNSAY LQMNSLRAED TAVYYCAMDL YSTSEYWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APEAAGAPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPG |
| 29 | 0978_humanized2_H CDR_H2 | RIDPANGNTI YVDSVKG |
| 30 | 0978_humanized2_H FV_H | EVQLVESGGG LVQPGGSLRL SCAASGYNIR SSYMHWVRQA PGKGLEWVAR IDPANGNTIY VDSVKGRFTI SADNAKNSAY LQMNSLRAED TAVYYCAMDL YSTSEYWGQG TLVTVSS |
| 31 | 0164_chimera_L | DIQMTQSPSF LSASVGDRVT INCKTSQNIN RYLNWYQQKL GEAPKLLIYN ANSLQTGIPS RFSASGSGTD FTLTINSLQP EDVATYFCLQ DNSWPLTFGS GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 32 | 0164_chimera_L FV_L | DIQMTQSPSF LSASVGDRVT INCKTSQNIN RYLNWYQQKL GEAPKLLIYN ANSLQTGIPS RFSASGSGTD FTLTINSLQP EDVATYFCLQ DNSWPLTFGS GTKLEIK |
| 33 | 0164_chimera_L FW_L4 | FGSGTKLEIK |
| 34 | 0164_chimera_H | EVQLQQSGAE FGKPGTSVKL SCKVSGYNIR SSYMHWVNQR PGKGLEWIGR IDPANGNTIY AEKFKIKAIL TADSSSNTAY MQLSQLKSDD TAIYFCAMDL YSTSEYWGQG VMVTVSSAST |

| SEQ | Description | Sequence |
|---|---|---|
| | | KGPSVFPLAP SSKSTSGGTA ALGCLVKDYF<br>PEPVTVSWNS GALTSGVHTF PAVLQSSGLY<br>SLSSVVTVPS SSLGTQTYIC NVNHKPSNTK<br>VDKKVEPKSC DKTHTCPPCP APEAAGAPSV<br>FLFPPKPKDT LMISRTPEVT CVVVDVSHED<br>PEVKFNWYVD GVEVHNAKTK PREEQYNSTY<br>RVVSVLTVLH QDWLNGKEYK CKVSNKALPA<br>PIEKTISKAK GQPREPQVYT LPPSREEMTK<br>NQVSLTCLVK GFYPSDIAVE WESNGQPENN<br>YKTTPPVLDS DGSFFLYSKL TVDKSRWQQG<br>NVFSCSVMHE ALHNHYTQKS LSLSPGK |
| 35 | 0164_chimera_H FV_H | EVQLQQSGAE FGKPGTSVKL SCKVSGYNIR<br>SSYMHWVNQR PGKGLEWIGR IDPANGNTIY<br>AEKFKIKAIL TADSSSNTAY MQLSQLKSDD<br>TAIYFCAMDL YSTSEYWGQG VMVTVSS |
| 36 | 0164_chimera_H FW_H4 | WGQGVMVTVS S |
| 37 | 1448_optimized_H | EVQLVESGGG LVQPGGSLRL SCAASGYAIR<br>SAYMHWVRQA PGKGLEWVAR IDPANGNTIY<br>VDSVKERFTI SADNAKNSAY LQMNSLRAED<br>TAVYYCAMDL YSTSEYWGQG TLVTVSSAST<br>KGPSVFPLAP SSKSTSGGTA ALGCLVKDYF<br>PEPVTVSWNS GALTSGVHTF PAVLQSSGLY<br>SLSSVVTVPS SSLGTQTYIC NVNHKPSNTK<br>VDKKVEPKSC DKTHTCPPCP APEAAGAPSV<br>FLFPPKPKDT LMISRTPEVT CVVVDVSHED<br>PEVKFNWYVD GVEVHNAKTK PREEQYNSTY<br>RVVSVLTVLH QDWLNGKEYK CKVSNKALPA<br>PIEKTISKAK GQPREPQVYT LPPSREEMTK<br>NQVSLTCLVK GFYPSDIAVE WESNGQPENN<br>YKTTPPVLDS DGSFFLYSKL TVDKSRWQQG<br>NVFSCSVMHE ALHNHYTQKS LSLSPG |
| 38 | 1448_optimized_H CDR_H2 | RIDPANGNTI YVDSVKE |
| 39 | 1448_optimized_H FV_H | EVQLVESGGG LVQPGGSLRL SCAASGYAIR<br>SAYMHWVRQA PGKGLEWVAR IDPANGNTIY<br>VDSVKERFTI SADNAKNSAY LQMNSLRAED<br>TAVYYCAMDL YSTSEYWGQG TLVTVSS |
| 40 | 1284_optimized_H | EVQLVESGGG LVQPGGSLRL SCAASGYAIR<br>SAYMHWVRQA PGKGLEWVAR IDPANGNTIY<br>VESVEGRFTI SADNAKNSAY LQMNSLRAED<br>TAVYYCAMDL YSTSEYWGQG TLVTVSSAST<br>KGPSVFPLAP SSKSTSGGTA ALGCLVKDYF<br>PEPVTVSWNS GALTSGVHTF PAVLQSSGLY<br>SLSSVVTVPS SSLGTQTYIC NVNHKPSNTK<br>VDKKVEPKSC DKTHTCPPCP APEAAGAPSV<br>FLFPPKPKDT LMISRTPEVT CVVVDVSHED<br>PEVKFNWYVD GVEVHNAKTK PREEQYNSTY<br>RVVSVLTVLH QDWLNGKEYK CKVSNKALPA<br>PIEKTISKAK GQPREPQVYT LPPSREEMTK<br>NQVSLTCLVK GFYPSDIAVE WESNGQPENN<br>YKTTPPVLDS DGSFFLYSKL TVDKSRWQQG<br>NVFSCSVMHE ALHNHYTQKS LSLSPG |
| 41 | 1284_optimized_H CDR_H2 | RIDPANGNTI YVESVEG |
| 42 | 1284_optimized_H FV_H | EVQLVESGGG LVQPGGSLRL SCAASGYAIR<br>SAYMHWVRQA PGKGLEWVAR IDPANGNTIY<br>VESVEGRFTI SADNAKNSAY LQMNSLRAED<br>TAVYYCAMDL YSTSEYWGQG TLVTVSS |
| 43 | 1282_optimized_H | EVQLVESGGG LVQPGGSLRL SCAASGYAIR<br>SAYMHWVRQA PGKGLEWVAR IDPANGNTIY<br>VDSVEGRFTI SADNAKNSAY LQMNSLRAED<br>TAVYYCAMDL YSTSEYWGQG TLVTVSSAST<br>KGPSVFPLAP SSKSTSGGTA ALGCLVKDYF<br>PEPVTVSWNS GALTSGVHTF PAVLQSSGLY<br>SLSSVVTVPS SSLGTQTYIC NVNHKPSNTK<br>VDKKVEPKSC DKTHTCPPCP APEAAGAPSV<br>FLFPPKPKDT LMISRTPEVT CVVVDVSHED<br>PEVKFNWYVD GVEVHNAKTK PREEQYNSTY |

| SEQ | Description | Sequence |
|---|---|---|
| | | RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPG |
| 44 | 1282_optimized_H CDR_H2 | RIDPANGNTI YVDSVEG |
| 45 | 1282_optimized_H FV_H | EVQLVESGGG LVQPGGSLRL SCAASGYAIR SAYMHWVRQA PGKGLEWVAR IDPANGNTIY VDSVEGRFTI SADNAKNSAY LQMNSLRAED TAVYYCAMDL YSTSEYWGQG TLVTVSS |
| 46 | 0525_humanized_L | DIQMTQSPSS LSASVGDRVT ITCKASQTVG INVDWYQQKP GKAPKLLIYG ASNRHTGVPS RFSGSGSGTD FTLTISSLQP EDFATYCCLQ YGSIPHTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 47 | 0525_humanized_L CDR_L1 | KASQTVGINV D |
| 48 | 0525_humanized_L CDR_L2 | GASNRHT |
| 49 | 0525_humanized_L CDR_L3 | LQYGSIPHT |
| 50 | 0525_humanized_L FV_L | DIQMTQSPSS LSASVGDRVT ITCKASQTVG INVDWYQQKP GKAPKLLIYG ASNRHTGVPS RFSGSGSGTD FTLTISSLQP EDFATYCCLQ YGSIPHTFGQ GTKVEIK |
| 51 | 0525_humanized_H | EVQLVESGGG LVQPGGSLRL SCAASGFSLT GYYMQWVRQA PGKGLEWMGF IRSSGSTEYN SEFKSRFTIS RDNAKNSVYL QMNSLRAEDT AVYYCARCPY KYSSFVYVGV MDAWGQGTLV TVSSASTKGP SVFPLAPSSK STSGGTAALG CLVKDYFPEP VTVSWNSGAL TSGVHTFPAV LQSSGLYSLS SVVTVPSSSL GTQTYICNVN HKPSNTKVDK KVEPKSCDKT HTCPPCPAPE AAGAPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SREEMTKNQV SLTCLVKGFY PSDIAVEWES NGQPENNYKT TPPVLDSDGS FFLYSKLTVD KSRWQQGNVF SCSVMHEALH NHYTQKSLSL SPG |
| 52 | 0525_humanized_H CDR_H1 | GFSLTGYYMQ |
| 53 | 0525_humanized_H CDR_H2 | FIRSSGSTEY NSEFKS |
| 54 | 0525_humanized_H CDR_H3 | CPYKYSSFVY VGVMDA |
| 55 | 0525_humanized_H FV_H | EVQLVESGGG LVQPGGSLRL SCAASGFSLT GYYMQWVRQA PGKGLEWMGF IRSSGSTEYN SEFKSRFTIS RDNAKNSVYL QMNSLRAEDT AVYYCARCPY KYSSFVYVGV MDAWGQGTLV TVSS |
| 56 | 0039_chimera_L | EIVMTQSPTS MSTSIGERVT LNCKASQTVG INVDWYQQTP GQPPKLLIYG ASNRHTGVPD RFTGSGFGRD FTLTISNVEA EDLAVYCCLQ YGSIPHTFGP GTKLELKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |

| SEQ | Description | Sequence |
|---|---|---|
| 57 | 0039_chimera_L FV_L | EIVMTQSPTS MSTSIGERVT LNCKASQTVG INVDWYQQTP GQPPKLLIYG ASNRHTGVPD RFTGSGFGRD FTLTISNVEA EDLAVYCCLQ YGSIPHTFGP GTKLELK |
| 58 | 0039_chimera_L FW_L4 | FGPGTKLELK |
| 59 | 0039_chimera_H | QVQLKETGPG LVQPTQTLSI TCTVSGFSLT GYYMQWVRQT PGKGLEWMGF IRSSGSTEYN SEFKSRLSIS RDTSKNQVFL KMNSLKTEDT GVYYCARCPY KYSSFVYVGV MDAWGQGAPV TVSSASTKGP SVFPLAPSSK STSGGTAALG CLVKDYFPEP VTVSWNSGAL TSGVHTFPAV LQSSGLYSLS SVVTVPSSSL GTQTYICNVN HKPSNTKVDK KVEPKSCDKT HTCPPCPAPE AAGAPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SREEMTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 60 | 0039_chimera_H FV_H | QVQLKETGPG LVQPTQTLSI TCTVSGFSLT GYYMQWVRQT PGKGLEWMGF IRSSGSTEYN SEFKSRLSIS RDTSKNQVFL KMNSLKTEDT GVYYCARCPY KYSSFVYVGV MDAWGQGAPV TVSS |
| 61 | 0039_chimera_H FW_H4 | WGQGAPVTVS S |
| 62 | 0265_0254_humanized_H | EVQLVESGGG LVQPGGSLRL SCAVSGFSIS TYNVHWLRQA PGKGLEWMGM MWSGGSPDYN SALKSRFTIS RDTAKNSVYL QMNSLRAEDT AVYYCARWGG GFDYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THTCPPCPAP EAAGAPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSREEMTKNQ VSLTCLVKGF YPSDIAVEWE SNGQPENNYK TTPPVLDSDG SFFLYSKLTV DKSRWQQGNV FSCSVMHEAL HNHYTQKSLS LSPG |
| 63 | 0265_0254_humanized_H CDR_H1 | GFSISTYNVH |
| 64 | 0265_0254_humanized_H CDR_H2 | MMWSGGSPDY NSALKS |
| 65 | 0265_0254_humanized_H CDR_H3 | WGGGFDY |
| 66 | 0265_0254_humanized_H FV_H | EVQLVESGGG LVQPGGSLRL SCAVSGFSIS TYNVHWLRQA PGKGLEWMGM MWSGGSPDYN SALKSRFTIS RDTAKNSVYL QMNSLRAEDT AVYYCARWGG GFDYWGQGTL VTVSS |
| 67 | 0265_0254_humanized_L | DIQLTQSPSS LSASVGDRVT ITCRASHSIG TNLHWYQQKP GKAPKLLIYF TSQSISGVPS RFSGSGSGTD FTLTISSLQP EDFATYYCQQ TQSWPLTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 68 | 0265_0254_humanized_L CDR_L1 | RASHSIGTNL H |
| 69 | 0265_0254_humanized_L CDR_L2 | FTSQSIS |

| SEQ | Description | Sequence |
|---|---|---|
| 70 | 0265_0254_humanized_L CDR_L3 | QQTQSWPLT |
| 71 | 0265_0254_humanized_L FV_L | DIQLTQSPSS LSASVGDRVT ITCRASHSIG TNLHWYQQKP GKAPKLLIYF TSQSISGVPS RFSGSGSGTD FTLTISSLQP EDFATYYCQQ TQSWPLTFGQ GTKVEIK |
| 72 | 0158_chimera_L | DIVLTQSPTT LSVTPGETVS LSCRASHSIG TNLHWYQQKT NESPRLLIKF TSQSISGIPS RFSASGSGTD FTLNINNVEF DDVSSYFCQQ TQSWPLTFGS GTKLETKRTV AAPSVFTFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 73 | 0158_chimera_L FV_L | DIVLTQSPTT LSVTPGETVS LSCRASHSIG TNLHWYQQKT NESPRLLIKF TSQSISGIPS RFSASGSGTD FTLNINNVEF DDVSSYFCQQ TQSWPLTFGS GTKLEIK |
| 74 | 0158_chimera_H | QVQLKESGPG LVQPSETLSL TCTVSGFSIS TYNVHWLRQP PGKGLEWMGM MNSGGSPDYN SALKSRLSIS RDTSKNQVFL KMNSLQSEDT TTYYCARWGG GFDYWGQGVM VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THTCPPCPAP EAAGAPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSREEMTKNQ VSLTCLVKGF YPSDIAVEWE SNGQPENNYK TTPPVLDSDG SFFLYSKLTV DKSRWQQGNV FSCSVMHEAL HNHYTQKSLS LSPGK |
| 75 | 0158_chimera_H FV_H | QVQLKESGPG LVQPSETLSL TCTVSGFSIS TYNVHWLRQP PGKGLEWMGM MWSGGSPDYN SALKSRLSIS RDTSKNQVFL KMNSLQSEDT TTYYCARWGG GFDYWGQGVM VTVSS |
| 76 | 0929_0548_humanized_H | QVQLVQSGAE VKKPGASVKV SCKVSGYNIR STYMHWVRQA PGQGLEWMGR IDPANGNTIY AEKFKRRVTL TRDTSTSTAY MELSSLRSED TAVYYCAMEV RVSFEYWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APEAAGAPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PTEKTTSKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPG |
| 77 | 0929_0548_humanized_H CDR_H1 | GYNIRSTYMH |
| 78 | 0929_0548_humanized_H CDR_H2 | RIDPANGNTI YAEKFKR |
| 79 | 0929_0548_humanized_H CDR_H3 | EVRVSFEY |
| 80 | 0929_0548_humanized_H FV_H | QVQLVQSGAE VKKPGASVKV SCKVSGYNIR STYMHWVRQA PGQGLEWMGR IDPANGNTIY AEKFKRRVTL TRDTSTSTAY MELSSLRSED TAVYYCAMEV RVSFEYWGQG TLVTVSS |
| 81 | 0929_0548_humanized_L | DIQMTQSPSS LSASVGDRVT ITCKASQNIN KYLDWYQQKP GKAPKLLIYY TNNLHTGVPS RFSGSGSGTD FTFTISSLQP EDIATYYCLQ |

| SEQ | Description | Sequence |
|---|---|---|
| | | HDSGYTFGQG TKVEIKRTVA APSVFIFPPS DEQLKSGTAS VVCLLNNFYP REAKVQWKVD NALQSGNSQE SVTEQDSKDS TYSLSSTLTL SKADYEKHKV YACEVTHQGL SSPVTKSFNR GEC |
| 82 | 0929_0548_humanized_L CDR_L1 | KASQNINKYL D |
| 83 | 0929_0548_humanized_L CDR_L2 | YTNNLHT |
| 84 | 0929_0548_humanized_L CDR_L3 | LQHDSGYT |
| 85 | 0929_0548_humanized_L FV_L | DIQMTQSPSS LSASVGDRVT ITCKASQNIN KYLDWYQQKP GKAPKLLIYY TNNLHTGVPS RFSGSGSGTD FTFTISSLQP EDIATYYCLQ HDSGYTFGQG TKVEIK |
| 86 | 0159_chimera_L | DIQMTQSPSF LSASVGDRVT TNCKASQNTN KYLDWYQQKL GEGPKLLIYY TNNLHTGIPS RFSGSGSGTD FTLTISSLQP EDVATYFCLQ HDSGYTFGAG TKLELKRTVA APSVFIFPPS DEQLKSGTAS VVCLLNNFYP REAKVQWKVD NALQSGNSQE SVTEQDSKDS TYSLSSTLTL SKADYEKHKV YACEVTHQGL SSPVTKSFNR GEC |
| 87 | 0159_chimera_L FV_L | DIQMTQSPSF LSASVGDRVT INCKASQNIN KYLDWYQQKL GEGPKLLIYY TNNLHTGIPS RFSGSGSGTD FTLTISSLQP EDVATYFCLQ HDSGYTFGAG TKLELK |
| 88 | 0159_chimera_L FW_L4 | FGAGTKLELK |
| 89 | 0159_chimera_H | EVQLQQSGAE LGKPGTSVKL SCKVSGYNIR STYMHWVSQR PGKGLEWIGR IDPANGNTIY AEKFKRKATL TADTSSNTAY MQLSQLKSDD RAIYFCAMEV RVSFEYWGQG VMVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APEAAGAPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 90 | 0159_chimera_H FV_H | EVQLQQSGAE LGKPGTSVKL SCKVSGYNIR STYMHWVSQR PGKGLEWIGR IDPANGNTIY AEKFKRKATL TADTSSNTAY MQLSQLKSDD RAIYFCAMEV RVSFEYWGQG VMVTVSS |
| 91 | 0955_0300_humanized_H | QVQLVQSGAE VKKPGSSVKV SCKVSGYSIR STYMHWVRQA PGQGLEWMGR IDPANGNTIY AERFKNRVTL TADTSTSTAY MELSSLRSED TAVYYCAVEI LGIFDYWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APEAAGAPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPG |
| 92 | 0955_0300_humanized_H CDR_H1 | GYSIRSTYMH |

| SEQ | Description | Sequence |
|---|---|---|
| 93 | 0955_0300_humanized_H CDR_H2 | RIDPANGNTI YAERFKN |
| 94 | 0955_0300_humanized_H CDR_H3 | EILGIFDY |
| 95 | 0955_0300_humanized_H FV_H | QVQLVQSGAE VKKPGSSVKV SCKVSGYSIR STYMHWVRQA PGQGLEWMGR IDPANGNTIY AERFKNRVTL TADTSTSTAY MELSSLRSED TAVYYCAVEI LGIFDYWGQG TLVTVSS |
| 96 | 0955_0300_humanized_L | DIQMTQSPSS LSASVGDRVT ITCKASQNID KYLDWYQQKP GKAPKLLMYN TNSLHTGVPS RFSGSGSGTD FTLTISSLQP EDFATYFCLQ HNSGYTFGQG TKVEIKRTVA APSVFIFPPS DEQLKSGTAS VVCLLNNFYP REAKVQWKVD NALQSGNSQE SVTEQDSKDS TYSLSSTLTL SKADYEKHKV YACEVTHQGL SSPVTKSFNR GEC |
| 97 | 0955_0300_humanized_L CDR_L1 | KASQNIDKYL D |
| 98 | 0955_0300_humanized_L CDR_L2 | NTNSLHT |
| 99 | 0955_0300_humanized_L CDR_L3 | LQHNSGYT |
| 100 | 0955_0300_humanized_L FV_L | DIQMTQSPSS LSASVGDRVT ITCKASQNID KYLDWYQQKP GKAPKLLMYN TNSLHTGVPS RFSGSGSGTD FTLTISSLQP EDFATYFCLQ HNSGYTFGQG TKVEIK |
| 101 | 0170_chimera_L | DIQMTQSPSF LSASVGDRVT INCKASQNID KYLDWYQQKL GEAPKLLMYN TNSLHTGIPS RFSGSGSGTD FTLTISSLQP EDVATYFCLQ HNSGYTFGAG TKLELKRTVA APSVFIFPPS DEQLKSGTAS VVCLLNNFYP REAKVQWKVD NALQSGNSQE SVTEQDSKDS TYSLSSTLTL SKADYEKHKV YACEVTHQGL SSPVTKSFNR GEC |
| 102 | 0170_chimera_L FV_L | DIQMTQSPSF LSASVGDRVT INCKASQNID KYLDWYQQKL GEAPKLLMYN TNSLHTGIPS RFSGSGSGTD FTLTISSLQP EDVATYFCLQ HNSGYTFGAG TKLELK |
| 103 | 0170_chimera_H | EVQLQQSGAE LGKPGTSVKL SCKVSGYSIR STYMHWVNQR PGKGLEWVGR IDPANGNTIY AERFKNKATL TADTSSNTAY MQLSQLKSDD TAIYFCAVEI LGIFDYWGQG VMVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APEAAGAPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 104 | 0170_chimera_H FV_H | EVQLQQSGAE LGKPGTSVKL SCKVSGYSIR STYMHWVNQR PGKGLEWVGR IDPANGNTIY AERFKNKATL TADTSSNTAY MQLSQLKSDD TAIYFCAVEI LGIFDYWGQG VMVTVSS |

| SEQ | Description | Sequence |
|---|---|---|
| 105 | 0564_humanized_L | DIQMTQSPSS LSASVGDRVT ITCKASQHIN RYLNWYQQKP GKAPKLLIYD ANNLQTGVPS RFSGSGSGTD FTLTISSLQP EDFATYFCLQ HNSWPNTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 106 | 0564_humanized_L CDR_L1 | KASQHINRYL N |
| 107 | 0564_humanized_L CDR_L2 | DANNLQT |
| 108 | 0564_humanized_L CDR_L3 | LQHNSWPNT |
| 109 | 0564_humanized_L FV_L | DIQMTQSPSS LSASVGDRVT ITCKASQHIN RYLNWYQQKP GKAPKLLIYD ANNLQTGVPS RFSGSGSGTD FTLTISSLQP EDFATYFCLQ HNSWPNTFGQ GTKVEIK |
| 110 | 0564_humanized_H | EVQLVESGGG LVQPGGSLRL SCAVSGYKIR SSYMHWVRQA PGKGLEWIGR IDPANGNTIY GDKFKSRFTL SSDTAKNSAY LQMNSLRAED TAVYYCAIDI GTTFDYWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APEAAGAPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPG |
| 111 | 0564_humanized_H CDR_H1 | GYKIRSSYMH |
| 112 | 0564_humanized_H CDR_H2 | RIDPANGNTI YGDKFKS |
| 113 | 0564_humanized_H CDR_H3 | DIGTTFDY |
| 114 | 0564_humanized_H FV_H | EVQLVESGGG LVQPGGSLRL SCAVSGYKIR SSYMHWVRQA PGKGLEWIGR IDPANGNTIY GDKFKSRFTL SSDTAKNSAY LQMNSLRAED TAVYYCAIDI GTTFDYWGQG TLVTVSS |
| 115 | 0180_chimera_L | DIQMTQSPSF LSASVGDRVT INCKASQHIN RYLNWYQQKL GEAPKLLIYD ANNLQTGIPS RFSGSGSGTD FTLTISSLQP EDVATYFCLQ HNSWPNTFGA GTKLELKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 116 | 0180_chimera_L FV_L | DIQMTQSPSF LSASVGDRVT INCKASQHIN RYLNWYQQKL GEAPKLLIYD ANNLQTGIPS RFSGSGSGTD FTLTISSLQP EDVATYFCLQ HNSWPNTFGA GTKLELK |
| 117 | 0180_chimera_H | EVQLQQSGAE LGKPGTSVKL SCKVSGYKIR SSYMHWVNQR PGKGLEWIGR IDPANGNTIY GDKFKSKATL TSDTSSNTAY IQLSQLKSDD TAIYFCAIDI GTTFDYWGQG VMVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APEAAGAPSV FLFPPKPKDT LMISRTPEVT CVVVDVSHED |

-continued

| SEQ | Description | Sequence |
|---|---|---|
| | | PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 118 | 0180_chimera_H FV_H | EVQLQQSGAE LGKPGTSVKL SCKVSGYKIR SSYMHWVNQR PGKGLEWIGR IDPANGNTIY GDKFKSKATL TSDTSSNTAY IQLSQLKSDD TAIYFCAIDI GTTFDYWGQG VMVTVSS |
| 119 | 0027_chimera_L | DIQMTQSPSF LSASVGDRIT INCKTSQNIN RYLNWFQQKL GEPPKLLIYN ANSLQADIPS RFSGSGSGTD FTLTITSLQP EDVATYFCLQ HHFWPYTFGA GTKLELRRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 120 | 0027_chimera_L CDR_L2 | NANSLQA |
| 121 | 0027_chimera_L CDR_L3 | LQHHFWPYT |
| 122 | 0027_chimera_L FV_L | DIQMTQSPSF LSASVGDRIT INCKTSQNIN RYLNWFQQKL GEPPKLLIYN ANSLQADIPS RFSGSGSGTD FTLTITSLQP EDVATYFCLQ HHFWPYTFGA GTKLELR |
| 123 | 0027_chimera_L FW_L4 | FGAGTKLELR |
| 124 | 0027_chimera_H | EVHLHQSGPE LGRPGSSVKI SCKASGYTFT DYVMNWVRQS PGQGLEWIGW INPEDYSFDS GEKFLERATL TAATSSNTVY IQLSGLTSDD TATYFCVRGG LPGDWFAYWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSREEM TKNQVSLTCL VKGFYPSDIA VEWESNGQPE NNYKTTPPVL DSDGSFFLYS KLTVDKSRWQ QGNVFSCSVM HEALHNHYTQ KSLSLSPGK |
| 125 | 0027_chimera_H CDR_H1 | GYTFTDYVMN |
| 126 | 0027_chimera_H CDR_H2 | WINPEDYSFD SGEKFLE |
| 127 | 0027_chimera_H CDR_H3 | GGLPGDWFAY |
| 128 | 0027_chimera_H FV_H | EVHLHQSGPE LGRPGSSVKI SCKASGYTFT DYVMNWVRQS PGQGLEWIGW INPEDYSFDS GEKFLERATL TAATSSNTVY IQLSGLTSDD TATYFCVRGG LPGDWFAYWG QGTLVTVSS |
| 129 | 1444_L Leader Sequence | MGWSCIILFL VATATGVHS |
| 130 | 1444_H Leader Sequence | MEWSWVFLFF LSVTTGVHS |
| 131 | 0164_chimera_L Leader Sequence | MGWSCIILFL VATATGAHS |

| SEQ | Description | Sequence |
|---|---|---|
| 132 | Human E-selectin (amino acid residues 22-610 of UniProtKB sequence P16581) | WSYNTSTEAM TYDEASAYCQ QRYTHLVAIQ NKEEIEYLNS ILSYSPSYYW IGIRKVNNVW VWVGTQKPLT EEAKNWAPGE PNNRQKDEDC VEIYIKREKD VGMWNDERCS KKKLALCYTA ACTNTSCSGH GECVETINNY TCKCDPGFSG LKCEQIVNCT ALESPEHGSL VCSHPLGNFS YNSSCSISCD RGYLPSSMET MQCMSSGEWS APIPACNVVE CDAVTNPANG FVECFQNPGS FPWNTTCTFD CEEGFELMGA QSLQCTSSGN WDNEKPTCKA VTCRAVRQPQ NGSVRCSHSP AGEFTFKSSC NFTCEEGFML QGPAQVECTT QGQWTQQIPV CEAFQCTALS NPERGYMNCL PSASGSFRYG SSCEFSCEQG FVLKGSKRLQ CGPTGEWDNE KPTCEAVRCD AVHQPPKGLV RCAHSPIGEF TYKSSCAFSC EEGFELHGST QLECTSQGQW TEEVPSCQVV KCSSLAVPGK INMSCSGEPV FGTVCKFACP EGWTLNGSAA RTCGATGHWS GLLPTCEAPT ESNIPLVAGL SAAGLSLLTL APFLLWLRKC LRKAKKFVPA SSCQSLESDG SYQKPSYIL |
| 133 | Human E-selectin extracellular domain | WSYNTSTEAM TYDEASAYCQ QRYTHLVAIQ NKEEIEYLNS ILSYSPSYYW IGIRKVNNVW VWVGTQKPLT EEAKNWAPGE PNNRQKDEDC VEIYIKREKD VGMWNDERCS KKKLALCYTA ACTNTSCSGH GECVETINNY TCKCDPGFSG LKCEQIVNCT ALESPEHGSL VCSHPLGNFS YNSSCSISCD RGYLPSSMET MQCMSSGEWS APIPACNVVE CDAVTNPANG FVECFQNPGS FPWNTTCTFD CEEGFELMGA QSLQCTSSGN WDNEKPTCKA VTCRAVRQPQ NGSVRCSHSP AGEFTFKSSC NFTCEEGFML QGPAQVECTT QGQWTQQIPV CEAFQCTALS NPERGYMNCL PSASGSFRYG SSCEFSCEQG FVLKGSKRLQ CGPTGEWDNE KPTCEAVRCD AVHQPPKGLV RCAHSPIGEF TYKSSCAFSC EEGFELHGST QLECTSQGQW TEEVPSCQVV KCSSLAVPGK INMSCSGEPV FGTVCKFACP EGWTLNGSAA RTCGATGHWS GLLPTCEAPT ESNIP |
| 134 | Mouse E-selectin (amino acid residues 22-612 of UniProtKB sequence Q00690) | WYYNASSELM TYDEASAYCQ RDYTHLVAIQ NKEEINYLNS NLKHSPSYYW IGIRKVNNVW IWVGTGKPLT EEAQNWAPGE PNNKQRNEDC VEIYIQRTKD SGMWNDERCN KKKLALCYTA SCTNASCSGH GECIETINSY TCKCHPGFLG PNCEQAVTCK PQEHPDYGSL NCSHPFGPFS YNSSCSFGCK RGYLPSSMET TVRCTSSGEW SAPAPACHVV ECEALTHPAH GIRKCSSNPG SYPWNTTCTF DCVEGYRRVG AQNLQCTSSG IWDNETPSCK AVTCDAIPQP QNGFVSCSHS TAGELAFKSS CNFTCEQSFT LQGPAQVECS AQGQWTPQIP VCKAVQCEAL SAPQQGNMKC LPSASGPFQN GSSCEFSCEE GFELKGSRRL QCGPRGEWDS KKPTCSAVKC DDVPRPQNGV MECAHATTGE FTYKSSCAFQ CNEGFSLHGS AQLECTSQGK WTQEVPSCQV VQCPSLDVPG KMNMSCSGTA VFGTVCEFTC PDDWTLNGSA VLTCGATGRW SGMPPTCEAP VSPTRPLVVA LSAAGTSLLT SSSLLYLLMR YFRKKAKKFV PASSCQSLQS FENYHVPSYN V |
| 135 | Mouse E-selectin extracellular Domain | WYYNASSELM TYDEASAYCQ RDYTHLVAIQ NKEEINYLNS NLKHSPSYYW IGIRKVNNVW IWVGTGKPLT EEAQNWAPGE PNNKQRNEDC VEIYIQRTKD SGMWNDERCN KKKLALCYTA SCTNASCSGH GECIETINSY TCKCHPGFLG PNCEQAVTCK PQEHPDYGSL NCSHPFGPFS YNSSCSFGCK RGYLPSSMET TVRCTSSGEW SAPAPACHVV ECEALTHPAH GIRKCSSNPG SYPWNTTCTF DCVEGYRRVG AQNLQCTSSG IWDNETPSCK AVTCDAIPQP QNGFVSCSHS TAGELAFKSS CNFTCEQSFT LQGPAQVECS AQGQWTPQIP VCKAVQCEAL SAPQQGNMKC LPSASGPFQN GSSCEFSCEE GFELKGSRRL QCGPRGEWDS KKPTCSAVKC DDVPRPQNGV MECAHATTGE FTYKSSCAFQ CNEGFSLHGS |

-continued

| SEQ | Description | Sequence |
|---|---|---|
| | | AQLECTSQGK WTQEVPSCQV VQCPSLDVPG KMNMSCSGTA VFGTVCEFTC PDDWTLNGSA VLTCGATGRW SGMPPTCEAP VSPTRP |
| 136 | 1444_H FV_H | GAAGTGCAGC TTGTGGAATC CGGGGGCGGC TTGGTCCAAC CGGGTGGCAG CCTCCGTCTG TCGTGCGCGG CTTCGGGCTA TGCCATCCGT TCTGCCTACA TGCACTGGGT TCGCCAGGCG CCTGGGAAGG GCCTGGAATG GGTGGCCAGG ATTGATCCTG CAAACGGAAA TACTATATAT GTGGACTCCG TGACCGGCCG CTTTACAATC AGCGCCGACA ACGCTAAGAA TTCCGCCTAC CTGCAAATGA ATAGCCTGCG GGCAGAGGAT ACCGCGGTGT ACTATTGTGC CATGGATTTA TATTCCACGT CTGAATATTG GGGCCAAGGA ACCCTGGTAA CGGTGTCGTC G |
| 137 | 1444_L FV_L | GATATTCAGA TGACGCAGTC CCCATCTTCC CTTTCAGCAT CTGTGGGTGA CCGGGTTACA ATCACTTGTA AAACATCCCA GAACATTGAG CGTTATTTAA ATTGGTATCA GCAGAAACCG GGTAAAGCCC CGAAACTATT GATTTATGCC GCGTCCTCGC TGCAATCCGG CGTGCCGAGT CGTTTTAGCG GCTCCGGGAG CGGCACCGAT TTTACTCTTA CCATTTCGAG TCTGCAGCCG GAAGACTTTG CCACTTATTT CTGTCTCCAG GATAACGCCT GGCCATTAAC CTTCGGTCAG GGTACCAAAG TTGAAATTAA A |
| 138 | 1444_HC (with C-terminal lysine (K)) | GAAGTGCAGC TTGTGGAATC CGGGGGCGGC TTGGTCCAAC CGGGTGGCAG CCTCCGTCTG TCGTGCGCGG CTTCGGGCTA TGCCATCCGT TCTGCCTACA TGCACTGGGT TCGCCAGGCG CCTGGGAAGG GCCTGGAATG GGTGGCCAGG ATTGATCCTG CAAACGGAAA TACTATATAT GTGGACTCCG TGACCGGCCG CTTTACAATC AGCGCCGACA ACGCTAAGAA TTCCGCCTAC CTGCAAATGA ATAGCCTGCG GGCAGAGGAT ACCGCGGTGT ACTATTGTGC CATGGATTTA TATTCCACGT CTGAATATTG GGGCCAAGGA ACCCTGGTAA CGGTGTCGTC GGCGTCGACC AAGGGCCCAT CGGTCTTCCC CCTGGCACCC TCCTCCAAGA GCACCTCTGG GGGCACAGCG GCCCTGGGCT GCCTGGTCAA GGACTACTTC CCCGAACCGG TGACGGTGTC GTGGAACTCA GGCGCCCTGA CCAGCGGCGT GCACACCTTC CCGGCTGTCC TACAGTCCTC AGGACTCTAC TCCCTCAGCA GCGTGGTGAC CGTGCCCTCC AGCAGCTTGG GCACCCAGAC CTACATCTGC AACGTGAATC ACAAGCCCAG CAACACCAAG GTGGACAAGA AAGTTGAGCC CAAATCTTGT GACAAAACTC ACACATGCCC ACCGTGCCCA GCACCTGAAG CCGCTGGGGC ACCGTCAGTC TTCCTCTTCC CCCCAAAACC CAAGGACACC CTCATGATCT CCCGGACCCC TGAGGTCACA TGCGTGGTGG TGGACGTGAG CCACGAAGAC CCTGAGGTCA AGTTCAACTG GTACGTGGAC GGCGTGGAGG TGCATAATGC CAAGACAAAG CCGCGGGAGG AGCAGTACAA CAGCACGTAC CGTGTGGTCA GCGTCCTCAC CGTCCTGCAC CAGGACTGGC TGAATGGCAA GGAGTACAAG TGCAAGGTCT CCAACAAAGC CCTCCCAGCC CCCATCGAGA AAACCATCTC CAAAGCCAAA GGGCAGCCCC GAGAACCACA GGTGTACACC CTGCCCCCAT CCCGGGAGGA GATGACCAAG AACCAGGTCA GCCTGACCTG CCTGGTCAAA GGCTTCTATC CCAGCGACAT CGCCGTGGAG TGGGAGAGCA ATGGGCAGCC GGAGAACAAC TACAAGACCA CGCCTCCCGT GCTGGACTCC GACGGCTCCT TCTTCCTCTA TAGCAAGCTC ACCGTGGACA AGAGCAGGTG GCAGCAGGGG AACGTCTTCT CATGCTCCGT GATGCATGAG GCTCTGCACA ACCACTACAC GCAGAAGAGC CTCTCCCTGT CCCCGGGAAA A |

| SEQ | Description | Sequence |
|---|---|---|
| 139 | 1444_LC | GATATTCAGA TGACGCAGTC CCCATCTTCC CTTTCAGCAT CTGTGGGTGA CCGGGTTACA ATCACTTGTA AACATCCCA GAACATTGAG CGTTATTTAA ATTGGTATCA GCAGAAACCG GGTAAAGCCC CGAAACTATT GATTTATGCC GCGTCCTCGC TGCAATCCGG CGTGCCGAGT CGTTTTAGCG GCTCCGGGAG CGGCACCGAT TTTACTCTTA CCATTTCGAG TCTGCAGCCG GAAGACTTTG CCACTTATTT CTGTCTCCAG GATAACGCCT GGCCATTAAC CTTCGGTCAG GGTACCAAAG TTGAAATTAA ACGTACGGTG GCTGCACCAT CTGTCTTCAT CTTCCCGCCA TCTGATGAGC AGTTGAAATC TGGAACTGCC TCTGTTGTGT GCCTGCTGAA TAACTTCTAT CCCAGAGAGG CCAAAGTACA GTGGAAGGTG GATAACGCCC TCCAATCGGG TAACTCCCAG GAGAGTGTCA CAGAGCAGGA CAGCAAGGAC AGCACCTACA GCCTCAGCAG CACCCTGACG CTGAGCAAAG CAGACTACGA GAAACACAAA GTCTACGCCT GCGAAGTCAC CCATCAGGGC CTGAGCTCGC CCGTCACAAA GAGCTTCAAC AGGGGAGAGT GT |
| 140 | 1444_H Leader Sequence | ATGGAATGGA GCTGGGTCTT TCTCTTCTTC CTGTCAGTAA CTACAGGTGT CCACTCC |
| 141 | 1444_L Leader Sequence | ATGGGATGGA GCTGTATCAT CCTCTTCTTG GTGGCAACAG CTACAGGCGT GCACTCC |
| 142 | 1444_H CH (with C-terminal lysine (K)) | GCGTCGACCA AGGGCCCATC GGTCTTCCCC CTGGCACCCT CCTCCAAGAG CACCTCTGGG GGCACAGCGG CCCTGGGCTG CCTGGTCAAG GACTACTTCC CCGAACCGGT GACGGTGTCG TGGAACTCAG GCGCCCTGAC CAGCGGCGTG CACACCTTCC CGGCTGTCCT ACAGTCCTCA GGACTCTACT GCCTCAGCAG CGTGGTGACC GTGCCCTCCA GCAGCTTGGG CACCCAGACC TACATCTGCA ACGTGAATCA CAAGCCCAGC AACACCAAGG TGGACAAGAA AGTTGAGCCC AAATCTTGTG ACAAAACTCA CACATGCCCA CCGTGCCCAG CACCTGAAGC CGCTGGGGCA CCGTCAGTCT TCCTCTTCCC CCCAAAACCC AAGGACACCC TCATGATCTC CCGGACCCCT GAGGTCACAT GCGTGGTGGT GGACGTGAGC CACGAAGACC CTGAGGTCAA GTTCAACTGG TACGTGGACG GCGTGGAGGT GCATAATGCC AAGACAAAGC CGCGGGAGGA GCAGTACAAC AGGACGTAOC GTGTGGTCAG CGTCCTCACC GTCCTGCACC AGGACTGGCT GAATGGCAAG GAGTACAAGT GCAAGGTCTC CAACAAAGCC CTCCCAGCCC CCATCGAGAA AACCATCTCC AAAGCCAAAG GGCAGCCCCG AGAACCACAG GTGTACACCC TGCCCCCATC CCGGGAGGAG ATGACCAAGA ACCAGGTCAG CCTGACCTGC CTGGTCAAAG GCTTCTATCC CAGCGACATC GCCGTGGAGT GGGAGAGCAA TGGGCAGCCG GAGAACAACT ACAAGACCAC GCCTCCCGTG CTGGACTCCG ACGGCTCCTT CTTCCTCTAT AGCAAGCTCA CCGTGGACAA GAGCAGGTGG CAGCAGGGGA ACGTCTTCTC ATGCTCCGTG ATGCATGAGG CTCTGCACAA CCACTACACG CAGAAGAGCC TCTCCCTGTC CCCGGGAAAA |
| 143 | 1444_L CL | CGTACGGTGG CTGCACCATC TGTCTTCATC TTCCCGCCAT CTGATGAGCA GTTGAAATCT GGAACTGCCT CTGTTGTGTG CCTGCTGAAT AACTTCTATC CCAGAGAGGC CAAAGTACAG TGGAAGGTGG ATAACGCCCT CCAATCGGGT AACTCCCAGG AGAGTGTCAC AGAGCAGGAC AGCAAGGACA GCACCTACAG CCTCAGCAGC ACCCTGACGC TGAGCAAAGC AGACTACGAG AAACACAAAG TCTACGCCTG CGAAGTCACC CATCAGGGCC TGAGCTCGCC CGTCACAAAG AGCTTCAACA GGGGAGAGTG T |

| SEQ | Description | Sequence |
|---|---|---|
| 144 | 0841_humanized1_H FV_H | GAAGTGCAGC TTGTGGAATC CGGGGGCGGC TTGGTCCAAC CGGGTGGCAG CCTCCGTCTG TCGTGCGCGG CTTCGGGCTA TAACATCCGT TCTAGCTACA TGCACTGGGT TCGCCAGGCG CCTGGGAAGG GCCTGGAATG GGTGGCCAGG ATTGATCCTG CAAACGGAAA TACTATATAT GCTGAGAAGT TCAAAATCCG CTTTACAATC AGCGCCGACA ACGCTAAGAA TTCCGCCTAC CTGCAAATGA ATAGCCTGCG GGCAGAGGAT ACCGCGGTGT ACTATTGTGC CATGGATTTA TATTCCACGT CTGAATATTG GGGCCAAGGA ACCCTGGTAA CGGTGTCGTC G |
| 145 | 0841_humanized1_L FV_L | GATATTCAGA TGACGCAGTC CCCATCTTCC CTTTCAGCAT CTGTGGGTGA CCGGGTTACA ATCACTTGTA AAACATCCCA GAACATTAAC CGTTATTTAA ATTGGTATCA GCAGAAACCG GGTAAAGCCC CGAAACTATT GATTTATAAC GCGAACTCGC TGCAAACTGG CGTGCCGAGT CGTTTTAGCG GCTCCGGGAG CGGCACCGAT TTTACTCTTA CCATTTCGAG TCTGCAGCCG GAAGACTTTG CCACTTATTT CTGTCTCCAG GATAACTCCT GGCCATTAAC CTTCGGTCAG GGTACCAAAG TTGAAATTAA A |
| 146 | 0978_humanized2_H FV_H | GAAGTGCAGC TTGTGGAATC CGGGGGCGGC TTGGTCCAAC CGGGTGGCAG CCTCCGTCTG TCGTGCGCGG CTTCGGGCTA TAACATCCGT TCTAGCTACA TGCACTGGGT TCGCCAGGCG CCTGGGAAGG GCCTGGAATG GGTGGCCAGG ATTGATCCTG CAAACGGAAA TACTATATAT GTGGACTCCG TGAAAGGCCG CTTTACAATC AGCGCCGACA ACGCTAAGAA TTCCGCCTAC CTGCAAATGA ATAGCCTGCG GGCAGAGGAT ACCGCGGTGT ACTATTGTGC CATGGATTTA TATTCCACGT CTGAATATTG GGGCCAAGGA ACCCTGGTAA CGGTGTCGTC G |
| 147 | 0978_humanized2_L FV_L | GATATTCAGA TGACGCAGTC CCCATCTTCC CTTTCAGCAT CTGTGGGTGA CCGGGTTACA ATCACTTGTA AAACATCCCA GAACATTAAC CGTTATTTAA ATTGGTATCA GCAGAAACCG GGTAAAGCCC CGAAACTATT GATTTATGCC GCGTCCTCGC TGCAATCCGG CGTGCCGAGT CGTTTTAGCG GCTCCGGGAG CGGCACCGAT TTTACTCTTA CCATTTCGAG TCTGCAGCCG GAAGACTTTG CCACTTATTT CTGTCTCCAG GATAACTCCT GGCCATTAAC CTTCGGTCAG GGTACCAAAG TTGAAATTAA A |
| 148 | 0164_chimera_H FV_H | GAAGTCCAGC TGCAGCAGTC TGGGGCTGAG TTTGGGAAAC TGGGACCTC AGTCAAGTTG TCTTGCAAGG TTTCTGGGTA TAACATTAGG AGTTCATACA TGCACTGGGT GAATCAGAGG CCTGGAAAGG GCCTGGAATG GATAGGAAGG ATTGATCCTG CAAACGGAAA TACTATATAT GCTGAGAAGT TCAAAATCAA GGCCATTCTG ACTGCAGATT CATCGTCCAA CACAGCCTAC ATGCAACTCA GCCAACTGAA ATCTGACGAC ACAGCAATCT ATTTTTGTGC TATGGACCTC TACAGTACCT CTGAATACTG GGGCCAAGGA GTCATGGTCA CAGTCTCCTC A |
| 149 | 0164_chimera_L FV_L | GACATCCAGA TGACGCAGTC TCCTTCATTC CTGTCTGCAT CTGTGGGAGA CAGAGTCACT ATCAACTGCA AAACGAGTCA GAATATTAAC AGGTACTTAA ACTGGTACCA GCAAAAGCTT GGAGAAGCTC CCAAACTCCT GATATATAAT GCAAACAGTT TGCAAACGGG CATCCCATCA CGGTTCAGTG CCAGTGGATC CGGTACTGAT TTCACACTCA CCATCAACAG CCTGCAGCCT GAAGATGTTG CCACATATTT TTGCTTGCAG GATAATAGTT GGCCGCTCAC GTTCGGTTCT GGGACCAAGC TGGAGATCAA A |

-continued

| SEQ | Description | Sequence |
|---|---|---|
| 150 | 1448_optimized_H FV_H | GAAGTGCAGC TTGTGGAATC CGGGGGCGGC TTGGTCCAAC CGGGTGGCAG CCTCCGTCTG TCGTGCGCGG CTTCGGGCTA TGCCATCCGT TCTGCCTACA TGCACTGGGT TCGCCAGGCG CCTGGGAAGG GCCTGGAATG GGTGGCCAGG ATTGATCCTG CAAACGGAAA TACTATATAT GTGGACTCCG TGAAAGAGCG CTTTACAATC AGCGCCGACA ACGCTAAGAA TTCCGCCTAC CTGCAAATGA ATAGCCTGCG GGCAGAGGAT ACCGCGGTGT ACTATTGTGC CATGGATTTA TATTCCACGT CTGAATATTG GGGCCAAGGA ACCCTGGTAA CGGTGTCGTC G |
| 151 | 1284_optimized_H FV_H | GAAGTGCAGC TTGTGGAATC CGGGGGCGGC TTGGTCCAAC CGGGTGGCAG CCTCCGTCTG TCGTGCGCGG CTTCGGGCTA TGCCATCCGT TCTGCCTACA TGCACTGGGT TCGCCAGGCG CCTGGGAAGG GCCTGGAATG GGTGGCCAGG ATTGATCCTG CAAACGGAAA TACTATATAT GTGGAGTCCG TGGAGGGCCG CTTTACAATC AGCGCCGACA ACGCTAAGAA TTCCGCCTAC CTGCAAATGA ATAGCCTGCG GGCAGAGGAT ACCGCGGTGT ACTATTGTGC CATGGATTTA TATTCCACGT CTGAATATTG GGGCCAAGGA ACCCTGGTAA CGGTGTCGTC G |
| 152 | 1282_optimized_H FV_H | GAAGTGCAGC TTGTGGAATC CGGGGGCGGC TTGGTCCAAC CGGGTGGCAG CCTCCGTCTG TCGTGCGCGG CTTCGGGCTA TGCCATCCGT TCTGCCTACA TGCACTGGGT TCGCCAGGCG CCTGGGAAGG GCCTGGAATG GGTGGCCAGG ATTGATCCTG CAAACGGAAA TACTATATAT GTGGAGTCCG TGGAGGGCCG CTTTACAATC AGCGCCGACA ACGCTAAGAA TTCCGCCTAC CTGCAAATGA ATAGCCTGCG GGCAGAGGAT ACCGCGGTGT ACTATTGTGC CATGGATTTA TATTCCACGT CTGAATATTG GGGCCAAGGA ACCCTGGTAA CGGTGTCGTC G |
| 153 | 0525_humanized_H FV_H | GAGGTACAGT TGGTGGAATC TGGCGGCGGC CTGGTCCAGC CGGGCGGGTC TTTGCGCCTG AGTTGTGCAG CGAGTGGGTT TAGCCTGACG GGCTACTACA TGCAATGGGT CCGTCAGGCG CCGGGCAAAG GTCTGGAATG GATGGGTTTT ATACGGAGTA GTGGAAGCAC AGAGTATAAT TCAGAGTTCA ATCCCGTTT ACCATCTCT CGCGATAACG CGAAAAACAG CGTGTATCTG CAGATGAATA GCCTGCGCG CGAAGATACC GCCGTGTACT ACTGCGCGCG TTGCCCGTAT AAATATAGTT CATTTGTATA TGTGGGTGTC ATGGATGCGT GGGGCCAGGG TACACTGGTT ACCGTGAGCT CG |
| 154 | 0525_humanized_L FV_L | GATATCCAAA TGACGCAATC GCCTAGCAGC TTATCCGCGT CAGTTGGCGA TCGCGTGACC ATCACTTGCA AAGCGTCGCA AACCGTCGGA ATCAACGTGG ATTGGTACCA ACAGAAACCG GGCAAGGCGC CGAAACTGCT GATCTATGGA GCCAGCAATC GCCACACAGG AGTGCCGTCC CGTTTTAGCG GCAGCGGGAG CGGTACGGAT TTTACCCTGA CGATTTCTTC ACTCCAACCC GAAGACTTTG CAACCTATTG CTGCTTGCAA TATGGTTCAA TCCCGCATAC TTTCGGCCAG GGTACAAAAG TGGAAATTAA A |
| 155 | 0039_chimera_H FV_H | CAGGTGCAGC TGAAGGAGAC AGGACCTGGC CTGGTGCAAC CAACACAGAC CCTGTCCATC ACATGTACTG TTTCTGGGTT CTCATTAACC GGCTATTATA TGCAGTGGGT TCGCCAGACT CCAGGAAAGG GGCTAGAATG GATGGGATTT ATACGGAGTA GTGGAAGCAC AGAGTATAAT TCAGAGTTCA ATCCCGACT TAGCATCAGC AGGGACACCT CCAAGAACCA GTTTTCTTA AAAATGAACA GTCTGAAAAC AGAAGATACA GGCGTGTATT ACTGTGCCAG ATGCCCTTAT AAGTATAGCA GCTTTGTCTA CGTAGGGGTT |

-continued

| SEQ | Description | Sequence |
|---|---|---|
| | | ATGGATGCCT GGGGTCAAGG AGCTCCAGTC ACTGTCTCCT CA |
| 156 | 0039_chimera_L FV_L | GAAATTGTGA TGACCCAGTC TCCCACATCC ATGTCCACAT CAATAGGAGA GAGGGTCACC CTGAACTGCA AGGCCAGTCA GACTGTGGGT ATTAATGTTG ACTGGTACCA ACAGACACCA GGGCAGCCTC CTAAACTACT GATATATGGG GCATCCAACC GACACACTGG GGTCCCTGAT CGCTTCACAG GCAGTGGATT TGGGAGAGAT TTCACTCTCA CCATCAGCAA CGTGGAGGCT GAAGACCTAG CTGTTTATTG CTGTCTGCAA TATGGCTCCA TTCCTCACAC GTTTGGACCT GGGACCAAGC TGGAGCTGAA A |
| 157 | 0265_0254_humanized_H FV_H | GAAGTGCAGT TAGTGGAAAG TGGCGGTGGC CTGGTGCAAC CGGGAGGATC CTTAGGTTTA AGCTGCGCCG TGTCCGGGTT TAGTATCAGC ACCTATAATG TACACTGGCT GCGTCAAGCC CCGGGCAAAG GGTTAGAATG GATGGGAATG ATGTGGAGTG GTGGAAGCCC AGATTATAAT TCAGCTCTCA ATCCCGATT CACTATTAGT CGCGATACCG CAAAAAACTC CGTGTACCTT CAGATGAACT CTCTTCGCGC AGAGGATACG GCGGTTTACT ACTGTGCTCG CTGGGGCGGC GGGTTTGATT ACTGGGGCCA GGGAACGCTG GTAACGGTTT CCAGT |
| 158 | 0265_0254_humanized_L FV_L | GACATTCAAC TGACCCAGAG CCCGTCCAGC TTATCTGCGA GTGTTGGGGA CCGGGTCACG ATTACCTGCC GGGCTAGTCA GAGCATTGGG ACGAACTTGC ATTGGTACCA GCAGAAACCT GGCAAAGCTC CGAAACTGCT GATTTATTTT ACATCCCAAA GCATCAGCGG TGTCCCCTCC CGATTTTCCG GGTCCGGATC CGGTACCGAT TTTACTTTAA CGATCAGCAG TCTGCAGCCA GAGGATTTCG CCACCTACTA TTGTCAGCAA ACTCAGTCTT GGCCCCTGAC CTTTGGCCAA GGGACCAAGG TAGAAATCAA G |
| 159 | 0158_chimera_H FV_H | CAGGTGCAGC TGAAGGAGTC AGGACCTGGC CTGGTGCAGC CCTCAGAGAC CCTGTCCCTC ACCTGCACTG TCTCTGGGTT CTCAATAAGC ACCTATAACG TACACTGGCT TCGACAGCCT CCAGGAAAAG GTCTGGAGTG GATGGGAATG ATGTGGAGTG GTGGAAGCCC AGATTATAAT TCAGCTCTCA ATCCCGACT GAGCATCAGC AGGGACACCT CCAAGAACCA AGTTTTCTTA AAAATGAACA GTCTGCAAAG TGAAGACACA ACCACTTACT ACTGTGCCAG ATGGGGGGGG GGGTTTGATT ACTGGGGCCA AGGAGTCATG GTCACAGTCT CCTCA |
| 160 | 0158_chimera_L FV_L | GACATCGTGC TGACTCAGTC TCCAACCACC CTGTCTGTGA CTCCAGGAGA GACAGTCAGT CTCTCCTGCA GGGCTAGCCA TAGTATTGGC ACAAATCTAC ACTGGTATCA ACAAAAAACA AATGAGTCTC CAAGGCTTCT CATCAAGTTT ACTTCCCAGT CCATCTCTGG GATCCCCTCC AGGTTCAGTG CCAGTGGATC AGGGACAGAT TTTACTCTCA ACATCAACAA TGTGGAGTTT GATGATGTCT CAAGTTATTT TTGTCAACAG ACTCAAAGCT GGCCCCTCAC GTTCGGTTCT GGGACCAAGC TGGAGATCAA A |
| 161 | 0929_0548_humanized_H F_VH | CAAGTACAAC TGGTGCAGAG TGGGGCCGAA GTGAAAAAAC CCGGCGCTAG CGTGAAAGTC AGCTGTAAAG TGTCCGGTTA TAATATTAGA AGCACCTATA TGCATTGGGT GCGTCAAGCG CCGGGCCAGG GCTTAGAGTG GATGGGTAGG ATTGATCCTG CAAATGGAAA TACTATTTAT GCTGAGAAGT TCAAAGGAG AGTTACGCTG ACCCGCGACA CGTCCACCTC GACGGCCTAT ATGGAGCTGT CTTCTTTACG CTCAGAGGAC ACTGCAGTTT ACTATTGTGC CATGGAAGTT AGAGTTAGCT TCGAATATTG GGGTCAAGGC ACATTGGTCA CGGTCAGCAG T |

-continued

| SEQ | Description | Sequence |
|---|---|---|
| 162 | 0929_0548_humanized_L FV_L | GATATCCAGA TGACTCAATC TCCATCGAGC CTTTCGGCGT CAGTGGGTGA TCGTGTTACC ATCACTTGTA AGGCCTOCCA AAACATTAAT AAATATCTGG ACTGGTACCA GCAGAAACCG GGCAAAGCCC CAAAGTTACT GATCTACTAT ACAAATAACC TACACACAGG TGTTCCATCA CGCTTTTCAG GTAGCGGAAG CGGGACCGAC TTTACGTTTA CGATCTCCAG CTTGCAACCA GAAGACATTG CCACTTATTA TTGTCTCCAG CATGACAGTG CTATACCTT TGGACAGGGT ACTAAGGTGG AAATCAAG |
| 163 | 0159_chimera_H FV_H | GAAGTCCAGC TGCAGCAGTC TGGGGCTGAG CTAGGGAAAC CTGGGACCTC AGTCAAGTTG TCTTGCAAGG TTTCTGGCTA TAACATTAGG AGTACCTACA TGCACTGGGT GAGTCAGAGG CCTGGAAAGG GCCTGGAATG GATAGGAAGG ATTGATCCTG CAAATGGAAA TACTATTTAT GCTGAGAAGT TCAAAAGGAA GGCCACACTG ACTGCAGATA CATCGTCCAA CACAGCCTAC ATGCAACTCA GCCAACTGAA ATCTGACGAC AGAGCAATCT ATTTTTGTGC TATGGAAGTA CGGGTGTCCT TTGAGTACTG GGGCCAGGGA GTCATGGTCA CCGTCTCCTC A |
| 164 | 0159_chimera_L FV_L | GACATCCAGA TGACCCAGTC TCCTTCATTC CTGTCTGCAT CTGTGGGAGA CAGAGTCACT ATCAACTGCA AAGCAAGTCA GAATATTAAC AAGTACTTAG ACTGGTATCA GCAAAAGCTT GGTGAAGGTC CCAAACTCCT GATATATTAT ACAAACAATT TACATACAGG AATCCCATCA AGGTTCAGTG GCAGTGGGTC TGGTACTGAT TTCACACTTA CCATCAGCAG CCTGCAGCCT GAAGATGTTG CCACATATTT CTGCCTTCAG CATGACAGTG GGTACACGTT TGGAGCTGGG ACCAAGCTGG AACTGAAA |
| 165 | 0955_0300_humanized_H FV_H | CAAGTGCAGC TGGTACAGTC TGGTGCCGAG GTTAAAAAGC CGGGTAGTAG CGTGAAAGTA AGCTGCAAAG TGAGTGGTTA TAGCATTCGT TCAACCTATA TGCACTGGGT TCGTCAGGCG CCAGGCCAAG GTCTCGAGTG GATGGGAAGG ATTGATCCTG CAAATGGAAA TACAATATAT GCTGAGAGGT TCAAAAACCG CGTGACGCTG ACCGCAGATA CCAGCACTTC CACGGCGTAC ATGGAACTGT CCTCCCTGCG GTCCGAAGAT ACCGCAGTAT ATTATTGCGC CGTAGAAATC CTAGGCATTT TGATTATTG GGGCAGGGC ACACTGGTCA CCGTATCGAG C |
| 166 | 0955_0300_humanized_L FV_L | GATATACAAA TGACACAGAG TCCGAGTTCC CTATCAGCGA GCGTGGGAGA CAGGGTTACC ATAACGTGTA AAGCATCGCA GAATATTGAC AAATATCTCG ACTGGTATCA ACAGAAGCCG GGCAAAGCAC CAAAACTCCT TATGTATAAC ACCAACTCTT TACATACTGG CGTCCCAAGT CGTTTTTCGG GGTCTGGCAG CGGCACAGAT TTTACGCTCA CCATTAGTTC GCTGCAGCCA GAAGACTTTG CTACCTACTT CTGTCTGCAA CATAATAGCG GGTACACGTT CGGTCAGGGG ACTAAAGTTG AAATAAAA |
| 167 | 0170_chimera_H FV_H | GAAGTCCAGC TGCAGCAGTC CGGGGCTGAG CTTGGGAAAC CTGGGACCTC AGTCAAGTTG TCTTGCAAGG TTTCTGGCTA TAGTATTAGG AGTACCTACA TGCACTGGGT GAATCAGAGG CCTGGAAAGG GCCTGGAATG GGTAGGAAGG ATTGATCCTG CAAATGGAAA TACAATATAT GCTGAGAGGT TCAAAAACAA GGCCACACTG ACTGCAGATA CATCGTCCAA CACAGCCTAC ATGCAACTCA GCCAACTGAA ATCTGACGAC ACAGCAATCT ATTTTTGTGC TGTGGAGATC CTTGGGATCT TTGATTACTG GGGCCAAGGA GTCATGGTCA CAGTCTCCTC A |

| SEQ | Description | Sequence |
|---|---|---|
| 168 | 0170_chimera_L FV_L | GACATCCAGA TGACCCAGTC TCCTTCATTC CTGTCTGCAT CTGTGGGAGA CAGAGTCACT ATCAACTGCA AAGCAAGTCA GAATATTGAC AAGTACTTAG ACTGGTATCA GCAAAAGCTT GGTGAAGCTC CCAAACTCCT GATGTATAAT ACAAACAGTT TGCATACAGG AATTCCATCA AGGTTCAGTG CAGTGGATC TGGTACTGAT TTCACACTTA CCATCAGCAG CCTGCAGCCT GAAGATGTTG CCACATATTT CTGCCTTCAG CATAACAGTG GGTACACGTT TGGAGCTGGG ACCAAGCTGG AACTGAAA |
| 169 | 0564_humanized_H FV_H | GAGGTACAGC TGGTTGAATC GGGTGGTGGT CTGGTTCAGC CGGGTGGCTC ATTAAGACTG TCATGCGCCG TGTCTGGTTA TAAAATCCGC AGCAGTTATA TGCATTGGGT TCGTCAAGCT CCGGGTAAAG GTTTAGAATG GATCGGGAGG ATTGATCCTG CAAATGGAAA TACTATATAC GGTGACAAGT TCAAAAGTCG GTTTACTCTG TCATCCGATA CCGCGAAAAA CTCAGCCTAT CTGCAAATGA ATTCCCTGCG CGCGGAAGAC ACTGCTGTCT ATTATTGCGC AATTGATATC GGTACCACGT TTGATTATTG GGGCCAGGGT ACGTTGGTGA CGGTTAGCTC C |
| 170 | 0564_humanized_L FV_L | GACATCCAAA TGACCCAATC TCCGAGTTCT CTGTCTGCTT CCGTGGGCGA CCGAGTCACC ATAACCTGTA AGGCTTCGCA ACACATCAAC CGTTATTTGA ACTGGTATCA ACAGAAACCG GGGAAAGCGC CGAAATTGCT GATTTATGAT GCTAACAACC TGCAGACAGG CGTACCATCG CGATTTAGCG GCTCCGGAAG CGGGACGGAT TTTACTCTCA CCATCAGCTC TCTGCAGCCG GAAGACTTTG CAACCTATTT CTGTTTACAG CATAATTCCT GGCCGAATAC CTTTGGCCAG GGGACAAAGG TGGAAATCAA A |
| 171 | 0180_chimera_H FV_H | GAGGTCCAGC TGCAGCAGTC TGGGGCTGAG CTTGGGAAAC CTGGGACCTC AGTCAAGTTG TCTTGCAAGG TTTCTGGCTA TAAGATTAGG AGTTCCTACA TGCACTGGGT GAATCAGAGG CCTGGAAAGG GCCTGGAATG GATAGGAAGG ATTGATCCTG CAAATGGAAA TACTATATAC GGTGACAAGT TCAAAAGTAA GGCCACACTG ACTTCAGATA CATCGTCCAA CACAGCCTAC ATCCAACTCA GCCAACTGAA ATCTGACGAC ACAGCAATCT ATTTTTGTGC TATAGATATA GGTACAACCT TTGATTATTG GGGCCAAGGA GTCATGGTCA CAGTCTCCTC A |
| 172 | 0180_chimera_L FV_L | GACATCCAGA TGACCCAGTC TCCTTCATTC CTGTCTGCAT CTGTGGGAGA CAGAGTCACT ATCAACTGCA AAGCAAGTCA GCATATTAAT AGGTACTTAA ACTGGTACCA GCAAAAGCTT GGAGAAGCTC CCAAACTCCT GATATATGAT GCAAACAATT TGCAAACGGG CATCCCATCA CGGTTCAGTG CAGTGGATC TGGTACTGAT TTCACACTCA CCATCAGCAG CCTGCAGCCT GAAGATGTTG CCACATATTT CTGCTTGCAG CATAATAGTT GGCCGAACAC GTTTGGGGCT GGGACCAAGC TGGAATTGAA A |
| 173 | 0027_chimera_H FV_H | GAAGTCCACC TGCAGCAGTC TGGGGCTGAG CTTGGGAGGC CTGGGTCCTC AGTCAAGATT TCTTGCAAGG CTTCTGGCTA CACCTTTACA GATTAGGTTA TGAACTGGGT GAGGCAGAGT CCTGGACAGG GGCTGGAATG GATAGGATGG ATCAATCCTG AAGATTATAG TTTTGATTCT GGTGAGAAGT TCCTAGAGAG GGCCACACTG ACTGCAGCTA CGTCCTCCAA CACAGTCTAC ATCCAGCTTA GCGGCCTGAC ATCTGACGAC ACAGCCACCT ATTTTTGTGT TAGAGGGGGA CTACCCGGGG ATTGGTTTGC TTACTGGGGC CAAGGCACTC TGGTCACTGT CTCTTCA |

| SEQ | Description | Sequence |
|---|---|---|
| 174 | 0027_chimera_L FV_L | GACATCCAGA TGACCCAGTC TCCTTCATTC CTGTCTGCAT CTGTGGGAGA CAGAATCACT ATCAACTGCA AGACAAGTCA GAATATTAAC AGGTACTTAA ACTGGTTCCA GCAAAAGCTT GGAGAACCTC CCAAACTCCT GATATATAAT GCAAACAGTT TGCAAGCGGA CATTCCATCA CGGTTCAGTG GCAGTGGATC TGGTACTGAT TTCACACTCA CCATCACCAG CCTGCAGCCT GAAGATGTTG CCACATATTT CTGCTTGCAG CATCATTTCT GGCCGTACAC GTTTGGAGCT GGGACCAAGC TGGAACTGAG A |
| 175 | truncated cynomolgus monkey E-selectin (amino acid residues 22-556 of UniProtKB sequence G8F370) | WSYNTSTEAMTYDEASAYCQQRYTHLVAIQNKEE IEYLNSILSYSPSYYWIGIRKVNNVWVWVGTQKP LTEEAKNWAPGEPNNRQKDEDCVETYIKRDKDVG MWNDERCSKKKLALCYTAACTNTSCSGHGECVET TNNYTCKCDPGFSGLECEQIVNCTALESPEHGSL VCSHPLGNFSYSSSCSVSCDRGYLPSSVETTQCM SSGEWSVPTPACKVVECDAVTNPANGFVECFQNP GSFPWNTTCTFDCEEGFELMGAQSLQCTSSGNWD NEKPTCKAVTCRAIRQPQNGSVRCSHSPAGEFTF KSSCNFTCEEGEWLQGAAQVECTTQGQWTQQVPV CEAFQCTALSNPERGYMNCLPSASGSFRNGSSCE FSCEQGFVLKGSKRLQCGPTGEWDNEKPTCEAVR CDAVHQPQRGLVRCAHSPIGEFTYKSSCAFSCEE GFELHGSTQLECTSQGQWTEEVPSCQVVKCSSLA VLEKINMSCSGEPVFGTVCNFACPEGWRLNGSAA MTCGATGHWSGMLPTCEAPTESNTP |
| 176 | site of NG deamidation (underlined) in HC CDR2 | IDPA<u>NG</u>NTIYAEK |
| 177 | site of NR deamidation (underlined) in LC CDR1 | TSQNI<u>NR</u>YLNWYQQKPGK |
| 178 | H27 predicted non-germline T-cell epitope | YNIRSSYMH |
| 179 | H63 predicted non-germline T-cell epitope | FKIRFTISA |
| 180 | H65 predicted non-germline T-cell epitope | IRFTISADN |
| 181 | L29 predicted non-germline T-cell epitope | INRYLNWYQ |
| 182 | L46 predicted non-germline T-cell epitope | LLIYNANSL |
| 183 | L47 predicted non-germline T-cell epitope | LIYNANSLQ |
| 184 | L48 predicted non-germline T-cell epitope | IYNANSLQT |
| 185 | L49 predicted non-germline T-cell epitope | YNANSLQTG |
| 186 | DP-54 sequence of H59-H65 | YVDSVKG |
| 187 | H63 predicted T-cell epitope | VKGRFTISA |

| SEQ | Description | Sequence |
|---|---|---|
| 188 | H27 predicted T-cell epitope | YAIRSAYMH |
| 189 | H63 predicted T-cell epitope | VEGRFTISA |
| 190 | H63 predicted T-cell epitope | VTGRFTISA |
| 191 | H63 predicted T-cell epitope | VKERFTISA |
| 192 | L29 predicted T-cell epitope | IERYLNWYQ |
| 193 | tryptic peptide for E-selectin | CSSLAVLEK |
| 194 | 1444 HC CDR2 region | IDPANGNTIYVDSVTGR |
| 195 | 1444 LC CDR1 region | TSQNIERYLNWYQQKPGK |
| 196 | human E-selectin UniProtKB P16581 (leader sequence is underlined) | MIASQFLSALTLVLLIKESGAWSYNTSTEAMTYD EASAYCQQRYTHLVAIQNKEEIEYLNSILSYSPS YYWIGIRKVNNVWVWVGTQKPLTEEAKNWAPGEP NNRQKDEDCVEIYIKREKDVGMWNDERCSKKKLA LCYTAACTNTSCSGHGECVETINNYTCKCDPGFS GLKCEQIVNCTALESPEHGSLVCSHPLGNFSYNS SCSISCDRGYLPSSMETMQCMSSGEWSAPIPACN VVECDAVTNPANGFVECFQNPGSFPWNTTCTFDC EEGFELMGAQSLQCTSSGNWDNEKPTCKAVTCRA VRQPQNGSVRCSHSPAGEFTFKSSCNFTCEEGFM LQGPAQVECTTQGQWTQQIPVCEAFQCTALSNPE RGYMNCLPSASGSFRYGSSCEFSCEQGFVLKGSK RLQCGPTGEWDNEKPTCEAVRCDAVHQPPKGLVR CAHSPIGEFTYKSSCAFSCEEGFELHGSTQLECT SQGQWTEEVPSCQVVKCSSLAVPGKINMSCSGEP VFGTVCKFACPEGWTLNGSAARTCGATGHWSGLL PTCEAPTESNIPLVAGLSAAGLSLLTLAPFLLWL RKCLRKAKKFVPASSCQSLESDGSYQKPSYIL |
| 197 | truncated human E-selectin (amino acid residues 22-178 of UniProtKB sequence P16581) | WSYNTSTEAMTYDEASAYCQQRYTHLVAIQNKEE IEYLNSILSYSPSYYWIGIRKVNNVWVWVGTQKP LTEEAKNWAPGEPNNRQKDEDCVEIYIKREKDVG MWNDERCSKKKLALCYTAACTNTSCSGHGECVET INNYTCKCDPGFSGLKCEQIV |
| 198 | mouse E-selectin UniProtKB Q00690 (leader sequence is underlined) | MNASRFLSALVFVLLAGESTAWYYNASSELMTYD EASAYCQRDYTHLVAIQNKEEINYLNSNLKHSPS YYWIGIRKVNNVWIWVGTGKPLTEEAQNWAPGEP NNKQRNEDCVEIYIQRTKDSGMWNDERCNKKKLA LCYTASCTNASCSGHGECIETINSYTCKCHPGFL GPNCEQAVTCKPQEHPDYGSLNCSHPFGPFSYNS SCSFGCKRGYLPSSMETTVRCTSSGEWSAPAPAC HVVECEALTHPAHGIRKCSSNPGSYPWNTTCTFD CVEGYRRVGAQNLQCTSSGIWDNETPSCKAVTCD AIPQPQNGFVSCSHSTAGELAFKSSCNFTCEQSF TLQGPAQVECSAQGQWTPQIPVCKAVQCEALSAP QQGNMKCLPSASGPFQNGSSCEFSCEEGFELKGS RRLQCGPRGEWDSKKPTCSAVKCDDVPRPQNGVM ECAHATTGEFTYKSSCAFQCNEGFSLHGSAQLEC TSQGKWTQEVPSCQVVQCPSLDVPGKMNMSCSGT AVFGTVCEFTCPDDWTLNGSAVLTCGATGRWSGM PPTCEAPVSPTRPLVVALSAAGTSLLTSSSLLYL LMRYFRKKAKKFVPASSCQSLQSFENYHVPSYNV |
| 199 | truncated mouse E-selectin (amino acid residues 22-178 of UniProtKB sequence Q00690) | WYYNASSELMTYDEASAYCQRDYTHLVAIQNKEE INYLNSNLKHSPSYYWIGIRKVNNVWIWVGTGKP LTEEAQNWAPGEPNNKQRNEDCVEIYIQRTKDSG MWNDERCNKKKLALCYTASCTNASCSGHGECIET INSYTCKCHPGFLGPNCEQAV |

| SEQ | Description | Sequence |
|---|---|---|
| 200 | cynomolgus monkey E-selectin UniProtKB G8F370 (leader sequence is underlined) | <u>MIASQFLSAL TLVLLIKESG AWSYNTSTEA</u> MTYDEASAYC QQRYTHLVAI QNKEEIEYLN SILSYSPSYY WIGIRKVNNV WVWVGTQKPL TEEAKNWAPG EPNNRQKDED CVEIYIKRDK DVGMWNDERC SKKKLALCYT AACTNTSCSG HGECVETINN YTCKCDPGFS GLECEQIVNC TALESPEHGS LVCSHPLGNF SYSSSCSVSC DRGYLPSSVE TTQCMSSGEW SVPIPACKW ECDAVTNPAN GFVECFQNPG SFPWNTTCTF DCEEGFELMG AQSLQCTSSG NWDNEKPTCK AVTCRAIRQP QNGSVRCSHS PAGEETFKSS CNFTCEEGFM LQGAAQVECT TQGQWTQQVP VCEAFQCTAL SNPERGYMNC LPSASGSFRN GSSCEFSCEQ GFVLKGSKRL QCGPTGEWDN EKPTCEAVRC DAVHQPQRGL VRCAHSPIGE FTYKSSCAFS CEEGFELHGS TQLECTSQGQ WTEEVPSCQV VKCSSLAVLE KINMSCSGEP VFGTVCNFAC PEGWRLNGSA AMTCGATGHW SGMLPTCEAP TESNTPLVAG LSAAGLSLLT LAPFLLWLRK CFRKAKKFVP ASSCQSLESD GSYQKPSYIL |
| 201 | cynomolgus monkey E-selectin (amino acid residues 22-610 of UniProtKB sequence G8F370) | WSYNTSTEAMTYDEASAYCQQRYTHLVAIQNKEE IEYLNSILSYSPSYYWIGIRKVNNVWVWVGTQKP LTEEAKNWAPGEPNNRQKDEDCVEIYIKRDKDVG MWNDERCSKKKLALCYTAACTNTSCSGHGECVET INNYTCKCDPGFSGLECEQIVNCTALESPEHGSL VCSHPLGNFSYSSSCSVSCDRGYLPSSVETTQCM SSGEWSVPIPACKVVECDAVTNPANGFVECFQNP GSFPWNTTCTFDCEEGFELMGAQSLQCTSSGNWD NEKPTCKAVTCRAIRQPQNGSVRCSHSPAGEFTF KSSCNFTCEEGEWLQGAAQVECTTQGQWTQQVPV CEAFQCTALSNPERGYMNCLPSASGSFRNGSSCE FSCEQGFVLKGSKRLQCGPTGEWDNEKPTCEAVR CDAVHQPQRGLVRCAHSPIGEFTYKSSCAFSCEE GFELHGSTQLECTSQGQWTEEVPSCQVVKCSSLA VLEKINMSCSGEPVFGTVCNFACPEGWRLNGSAA MTCGATGHWSGMLPTCEAPTESNTPLVAGLSAAG LSLLTLAPFLLWLRKCFRKAKKFVPASSCQSLES DGSYQKPSYIL |
| 202 | IGHV3-07*01 (DP-54) heavy chain germline | EVQLVESGGGLVQPGGSLRLSCAASGFTFSSYWM SWVRQAPGKGLEWVANIKQDGSEKYYVDSVKGRF TISRDNAKNSLYLQMNSLRAEDTAVYYCAR |
| 203 | IGHJ4*01 | YFDYWGQGTLVTVSS |
| 204 | IGKV1-39*01 (DPK-9) light chain germline | DIQMTQSPSSLSASVGDRVTITCRASQSISSYLN WYQQKPGKAPKLLIYAASSLQSGVPSRFSGSGSG TDFTLTISSLQPEDFATYYCQQSYSTP |
| 205 | IGKJ1*01 | WTFGQGTKVEIK |
| 206 | 1444 HC nucleic acid sequence (without C-terminal lysine (K)) | GAAGTGCAGC TTGTGGAATC CGGGGGCGGC TTGGTCCAAC CGGGTGGCAG CCTCCGTCTG TCGTGCGCGG CTTCGGGCTA TGCCATCCGT TCTGCCTACA TGCACTGGGT TCGCCAGGCG CCTGGGAAGG GCCTGGAATG GGTGGCCAGG ATTGATCCTG CAAACGGAAA TACTATATAT GTGGACTCCG TGACCGGCCG CTTTACAATC AGCGCCGACA ACGCTAAGAA TTCCGCCTAC CTGCAAATGA ATAGCCTGCG GGCAGAGGAT ACCGCGGTGT ACTATTGTGC CATGGATTTA TATTCCACGT CTGAATATTG GGGCCAAGGA ACCCTGGTAA CGGTGTCGTC GGCGTCGACC AAGGGCCCAT CGGTCTTCCC CCTGGCACCC TCCTCCAAGA GCACCTCTGG GGGCACAGCG GCCCTGGGCT GCCTGGTCAA GGACTACTTC CCCGAACCGG TGACGGTGTC GTGGAACTCA GGCGCCCTGA CCAGCGGCGT GCACACCTTC CCGGCTGTCC TACAGTCCTC AGGACTCTAC TCCCTCAGCA GCGTGGTGAC CGTGCCCTCC AGCAGCTTGG GCACCCAGAC CTACATCTGC AACGTGAATC ACAAGCCCAG CAACACCAAG GTGGACAAGA AAGTTGAGCC CAAATCTTGT GACAAAACTC ACACATGCCC ACCGTGCCCA |

-continued

| SEQ Description | Sequence |
|---|---|
| | GCACCTGAAG CCGCTGGGGC ACCGTCAGTC |
| | TTCCTCTTCC CCCCAAAACC CAAGGACACC |
| | CTCATGATCT CCCGGACCCC TGAGGTCACA |
| | TGCGTGGTGG TGGAOGTGAG CCACGAAGAC |
| | CCTGAGGTCA AGTTCAACTG GTACGTGGAC |
| | GGCGTGGAGG TGCATAATGC CAAGACAAAG |
| | CCGCGGGAGG AGCAGTACAA CAGCACGTAC |
| | CGTGTGGTCA GCGTCCTCAC CGTCCTGCAC |
| | CAGGACTGGC TGAATGGCAA GGAGTACAAG |
| | TGCAAGGTCT CCAACAAAGC CCTCCCAGCC |
| | CCCATCGAGA AAACCATCTC CAAAGCCAAA |
| | GGGCAGCCCC GAGAACCACA GGTGTACACC |
| | CTGCCCCCAT CCCGGGAGGA GATGACCAAG |
| | AACCAGGTCA GCCTGACCTG CCTGGTCAAA |
| | GGCTTCTATC CCAGCGACAT CGCCGTGGAG |
| | TGGGAGAGCA ATGGGCAGCC GGAGAACAAC |
| | TACAAGACCA CGCCTCCCGT GCTGGACTCC |
| | GACGGCTCCT TCTTCCTCTA TAGCAAGCTC |
| | ACCGTGGACA AGAGCAGGTG GCAGCAGGGG |
| | AACGTCTTCT CATGCTCCGT GATGCATGAG |
| | GCTCTGCACA ACCACTACAC GCAGAAGAGC |
| | CTCTCCCTGT CCCCGGGA |

TABLE 3

Anti-E-selectin antibodies.

| Antibody | HCD R-1 | HCD R-2 | HCD R-3 | LCD R-1 | LCD R-2 | LCD R-3 | VH | VL | JH (FW_H4) | JK (FW_L4) | CL | CH | HC | LC | L Leader | H Leader | FV_H DNA | FV_L DNA |
|---|---|---|---|---|---|---|---|---|---|---|---|---|---|---|---|---|---|---|
| 1444 optimized | 8 | 9 | 10 | 2 | 3 | 4 | 11 | 5 | 12 | 6 | 14 | 15/16 | 7/13 | 1 | 129 | 130 | 136 | 137 |
| 0841 humanized | 23 | 24 | 10 | 18 | 19 | 20 | 25 | 21 | 12 | 6 | 14 | 16 | 22 | 17 | 129 | 129 | 144 | 145 |
| 0978 humanized | 23 | 29 | 10 | 18 | 3 | 20 | 30 | 27 | 12 | 6 | 14 | 16 | 28 | 26 | 129 | 129 | 146 | 147 |
| 0164 chimera | 23 | 24 | 10 | 18 | 19 | 20 | 35 | 32 | 36 | 33 | 14 | 15 | 34 | 31 | 131 | 131 | 148 | 149 |
| 1448 optimized | 8 | 38 | 10 | 2 | 3 | 4 | 39 | 5 | 12 | 6 | 14 | 16 | 37 | 1 | 129 | 129 | 150 | 137 |
| 1284 optimized | 8 | 41 | 10 | 2 | 3 | 4 | 42 | 5 | 12 | 6 | 14 | 16 | 40 | 1 | 129 | 129 | 151 | 137 |
| 1282 optimized | 8 | 44 | 10 | 2 | 3 | 4 | 45 | 5 | 12 | 6 | 14 | 16 | 43 | 1 | 129 | 129 | 152 | 137 |
| 0525 humanized | 52 | 53 | 54 | 47 | 48 | 49 | 55 | 50 | 12 | 6 | 14 | 16 | 51 | 46 | 129 | 129 | 153 | 154 |
| 0039 chimera | 52 | 53 | 54 | 47 | 48 | 49 | 60 | 57 | 61 | 58 | 14 | 15 | 59 | 56 | 131 | 131 | 155 | 156 |
| 0265_0254 humanized | 63 | 64 | 65 | 68 | 69 | 70 | 66 | 71 | 12 | 6 | 14 | 16 | 62 | 67 | 129 | 129 | 157 | 158 |
| 0158 chimera | 63 | 64 | 65 | 68 | 69 | 70 | 75 | 73 | 36 | 33 | 14 | 15 | 74 | 72 | 131 | 131 | 159 | 160 |
| 0929_0548 humanized | 77 | 78 | 79 | 82 | 83 | 84 | 80 | 85 | 12 | 6 | 14 | 16 | 76 | 81 | 129 | 129 | 161 | 162 |
| 0159 chimera | 77 | 78 | 79 | 82 | 83 | 84 | 90 | 87 | 36 | 88 | 14 | 15 | 89 | 86 | 131 | 131 | 163 | 164 |
| 0955_0300 humanized | 92 | 93 | 94 | 97 | 98 | 99 | 95 | 100 | 12 | 6 | 14 | 16 | 91 | 96 | 129 | 129 | 165 | 166 |
| 0170 chimera | 92 | 93 | 94 | 97 | 98 | 99 | 104 | 102 | 36 | 88 | 14 | 15 | 103 | 101 | 131 | 131 | 167 | 168 |
| 0564 humanized | 111 | 112 | 113 | 106 | 107 | 108 | 114 | 109 | 12 | 6 | 14 | 16 | 110 | 105 | 129 | 129 | 169 | 170 |
| 0180 chimera | 111 | 112 | 113 | 106 | 107 | 108 | 118 | 116 | 36 | 88 | 14 | 15 | 117 | 115 | 131 | 131 | 171 | 172 |
| 0027 chimera | 125 | 126 | 127 | 18 | 120 | 121 | 128 | 122 | 12 | 123 | 14 | 15 | 124 | 119 | 131 | 131 | 173 | 174 |

In some embodiments, an anti-E-selectin antibody, or antigen-binding fragment thereof, may comprise a VH domain comprising an amino acid sequence at least 90% identical to the amino acid sequence of SEQ ID NO:11. In some embodiments, an anti-E-selectin antibody, or antigen-binding fragment thereof, may comprise a VH domain comprising, or consisting of, an amino acid of SEQ ID NO:11.

In some embodiments, an anti-E-selectin antibody, or antigen-binding fragment thereof, may comprise a VH domain may comprise an amino acid sequence at least 90%, 91%, 92%, 93%, 94%, 95%, 96%, 97%, 98%, or 99%, identical to the amino acid sequence of any one of SEQ ID NOs: 11, 25, 30, 35, 39, 42, 45, 55, 60, 66, 75, 80, 90, 95, 104, 114, 118 and 128. In some embodiments, an anti-E-selectin antibody, or antigen-binding fragment thereof, may comprise a VH domain may comprise or consist of the amino acid sequence of any one of SEQ ID NOs: 11, 25, 30, 35, 39, 42, 45, 55, 60, 66, 75, 80, 90, 95, 104, 114, 118 and 128.

In some embodiments, an anti-E-selectin antibody, or antigen-binding fragment thereof, may comprise a VL domain comprising an amino acid sequence at least 90% identical to the amino acid sequence of SEQ ID NO:5. In some embodiments, an anti-E-selectin antibody, or antigen-binding fragment thereof, may comprise a VL domain comprising, or consisting of, an amino acid sequence at least 90% identical to the amino acid sequence of SEQ ID NO:5.

In some embodiments, an anti-E-selectin antibody, or antigen-binding fragment thereof, may comprise a VL domain may comprise an amino acid sequence at least 90%, 91%, 92%, 93%, 94%, 95%, 96%, 97%, 98%, or 99%, identical to the amino acid sequence of any one of SEQ ID NOs: 5, 21, 27, 32, 50, 57, 71, 73, 85, 87, 100, 102, 109, 116 and 122. In some embodiments, an anti-E-selectin antibody, or antigen-binding fragment thereof, may comprise a VL domain may comprise or consist of the amino acid sequence of any one of SEQ ID NOs: 5, 21, 27, 32, 50, 57, 71, 73, 85, 87, 100, 102, 109, 116 and 122.

In some embodiments, an anti-E-selectin antibody, or antigen-binding fragment thereof, may comprise a VL domain comprising an amino acid sequence of SEQ ID NO:5 and a VH domain comprising an amino acid sequence of SEQ ID NO:11. An anti-E-selectin antibody, or antigen-binding fragment thereof, may comprise a VL domain comprising an amino acid sequence of SEQ ID NO:5 and a VH domain comprising an amino acid sequence of any one of SEQ ID NO:39, 42 or 45. An anti-E-selectin antibody, or antigen-binding fragment thereof, may comprise a VL domain comprising an amino acid sequence of SEQ ID NO:21 and a VH domain comprising an amino acid sequence of SEQ ID NO:25. An anti-E-selectin antibody, or antigen-binding fragment thereof, may comprise a VL domain comprising an amino acid sequence of SEQ ID NO:27 and a VH domain comprising an amino acid sequence of SEQ ID NO:30. An anti-E-selectin antibody, or antigen-binding fragment thereof, may comprise a VL domain comprising an amino acid sequence of SEQ ID NO:32 and a VH domain comprising an amino acid sequence of SEQ ID NO:35. An anti-E-selectin antibody, or antigen-binding fragment thereof, may comprise a VL domain comprising an amino acid sequence of SEQ ID NO:50 and a VH domain comprising an amino acid sequence of SEQ ID NO:55. An anti-E-selectin antibody, or antigen-binding fragment thereof, may comprise a VL domain comprising an amino acid sequence of SEQ ID NO:57 and a VH domain comprising an amino acid sequence of SEQ ID NO:60. An anti-E-selectin antibody, or antigen-binding fragment thereof, may comprise a VL domain comprising an amino acid sequence of SEQ ID NO:71 and a VH domain comprising an amino acid sequence of SEQ ID NO:66. An anti-E-selectin antibody, or antigen-binding fragment thereof, may comprise a VL domain comprising an amino acid sequence of SEQ ID NO:73 and a VH domain comprising an amino acid sequence of SEQ ID NO:75. An anti-E-selectin antibody, or antigen-binding fragment thereof, may comprise a VL domain comprising an amino acid sequence of SEQ ID NO:85 and a VH domain comprising an amino acid sequence of SEQ ID NO:80. An anti-E-selectin antibody, or antigen-binding fragment thereof, may comprise a VL domain comprising an amino acid sequence of SEQ ID NO:87 and a VH domain comprising an amino acid sequence of SEQ ID NO:90. An anti-E-selectin antibody, or antigen-binding fragment thereof, may comprise a VL domain comprising an amino acid sequence of SEQ ID NO:100 and a VH domain comprising an amino acid sequence of SEQ ID NO:95. An anti-E-selectin antibody, or antigen-binding fragment thereof, may comprise a VL domain comprising an amino acid sequence of SEQ ID NO:102 and a VH domain comprising an amino acid sequence of SEQ ID NO:104. An anti-E-selectin antibody, or antigen-binding fragment thereof, may comprise a VL domain comprising an amino acid sequence of SEQ ID NO:109 and a VH domain comprising an amino acid sequence of SEQ ID NO:114. An anti-E-selectin antibody, or antigen-binding fragment thereof, may comprise a VL domain comprising an amino acid sequence of SEQ ID NO:116 and a VH domain comprising an amino acid sequence of SEQ ID NO:118. An anti-E-selectin antibody, or antigen-binding fragment thereof, may comprise a VL domain comprising an amino acid sequence of SEQ ID NO:122 and a VH domain comprising an amino acid sequence of SEQ ID NO:128.

An anti-E-selectin antibody, or antigen-binding fragment thereof, may comprise a VL domain comprising an amino acid sequence of any one of SEQ ID NOs:5, 21, 27, 32, 50, 57, 71, 73, 85, 87, 100, 102, 109, 116 and 122 and a VH domain comprising an amino acid sequence of any one of SEQ ID NOs:11, 25, 30, 35, 39, 42, 45, 55, 60, 66, 75, 80, 90, 95, 104, 114, 118 and 128.

In some embodiments, an anti-E-selectin antibody, or antigen-binding fragment thereof, comprises a LCDR-1 (any one of SEQ ID NO:2, 18, 47, 68, 82, 97 and 106), a LCDR-2 (any one of SEQ ID NO:3, 19, 48, 69, 83, 98, 107 and 120), and a LCDR-3 (any one of SEQ ID NO:4, 20, 49, 70, 84, 99, 108 and 121) as set forth in the amino acid sequence of at least one of SEQ ID NOs:5, 21, 27, 32, 50, 57, 71, 73, 85, 87, 100, 102, 109, 116 and 122.

In some embodiments, an anti-E-selectin antibody, or antigen-binding fragment thereof, further comprises a HCDR-1 (any one of SEQ ID NO:8, 23, 52, 63, 77, 92, 111 and 125), a HCDR-2 (any one of SEQ ID NO:9, 24, 29, 38, 41, 44, 53, 64, 78, 93, 112 and 126), and a HCDR-3 (any one of SEQ ID NO:10, 54, 65, 79, 94, 113 and 127) as set forth in the amino acid sequences of at least one of SEQ ID NOs:11, 25, 30, 35, 39, 42, 45, 55, 60, 66, 75, 80, 90, 95, 104, 114, 118 and 128.

In some embodiments, an anti-E-selectin antibody, or antigen-binding fragment thereof, comprises a LCDR-1 (SEQ ID NO:2), a LCDR-2 (SEQ ID NO:3), a LCDR-3 (SEQ ID NO:4) as set forth in the amino acid sequence of SEQ ID NO:5, and a HCDR-1 (SEQ ID NO:8), a HCDR-2 (SEQ ID NO:9), and a HCDR-3 (SEQ ID NO:10) as set forth in the amino acid sequence of SEQ ID NO:11.

In some embodiments, an anti-E-selectin antibody, or antigen-binding fragment thereof, comprises a LCDR-1 comprising an amino acid of SEQ ID NO:2, a LCDR-2 comprising an amino acid sequence of SEQ ID NO:3 and a LCDR-3 comprising an amino acid of SEQ ID NO:4. In some embodiments, an anti-E-selectin antibody, or antigen-binding fragment thereof, comprises a HCDR-1 comprising an amino acid of SEQ ID NO:8, a HCDR-2 comprising an amino acid sequence of SEQ ID NO:9 and a HCDR-3 comprising an amino acid of SEQ ID NO:10. In some embodiments, an anti-E-selectin antibody, or antigen-binding fragment thereof, comprises a HCDR-1 comprising an amino acid sequence of SEQ ID NO:8, a HCDR-2 comprising an amino acid sequence of any one of SEQ ID NO:38, 41 or 44 and a HCDR-3 comprising an amino acid sequence of SEQ ID NO:10.

In some embodiments, an anti-E-selectin antibody, or antigen-binding fragment thereof, comprises a LCDR-1 comprising an amino acid of any one of SEQ ID NO:2, 18, 47, 68, 82, 97 or 106, a LCDR-2 comprising an amino acid sequence of any one of SEQ ID NO:3, 19, 48, 69, 83, 98, 107 or 120 and a LCDR-3 comprising an amino acid of SEQ ID NO:4, 20, 49, 70, 84, 99, 108 or 121. In some embodiments, an anti-E-selectin antibody, or antigen-binding fragment thereof, comprises a HCDR-1 comprising an amino acid of SEQ ID NO:8, 23, 52, 63, 77, 92, 111 or 125, a HCDR-2 comprising an amino acid sequence of SEQ ID NO:9, 24, 29, 38, 41, 44, 53, 64, 78, 93, 112 or 126 and a HCDR-3 comprising an amino acid of SEQ ID NO:10, 54, 65, 79, 94, 113 or 127.

In some embodiments, an anti-E-selectin antibody, or antigen-binding fragment thereof, comprises a LCDR-1, a LCDR-2, and a LCDR-3 as set forth in the amino acid sequence encoded by the insert of the plasmid deposited with the ATCC having the Accession number PTA-126530.

In some embodiments, an anti-E-selectin antibody, or antigen-binding fragment thereof, comprises a HCDR-1, a HCDR-2, and a HCDR-3 as set forth in the amino acid sequence encoded by the insert of the plasmid deposited with the ATCC having Accession number PTA-126529.

In some embodiments, an anti-E-selectin antibody, or antigen-binding fragment thereof, comprises a LCDR-1, a LCDR-2, and a LCDR-3 amino acid sequence encoded by the insert of the plasmid deposited with the ATCC having the Accession number PTA-126530, and a HCDR-1, a HCDR-2, and a HCDR-3 amino acid sequence encoded by the insert of the plasmid deposited with the ATCC having Accession number PTA-126529.

In some embodiments, an anti-E-selectin antibody, or antigen-binding fragment thereof, comprises a light chain variable region comprising the amino acid sequence encoded by the insert of the plasmid deposited with the ATCC having the Accession number PTA-126530.

In some embodiments, an anti-E-selectin antibody, or antigen-binding fragment thereof, comprises a heavy chain variable region comprising the amino acid sequence encoded by the insert of the plasmid deposited with the ATCC having the Accession number PTA-126529.

In some embodiments, an anti-E-selectin antibody, or antigen-binding fragment thereof, comprises a light chain comprising the amino acid sequence encoded by the insert of the plasmid deposited with the ATCC having the Accession number PTA-126530.

In some embodiments, an anti-E-selectin antibody, or antigen-binding fragment thereof, comprises a heavy chain comprising the amino acid sequence encoded by the insert of the plasmid deposited with the ATCC having the Accession number PTA-126529.

In some embodiments, an anti-E-selectin antibody, or antigen-binding fragment thereof, may comprise a LC comprising an amino acid sequence at least 90% identical to the amino acid sequence of SEQ ID NO:1. In some embodiments, an anti-E-selectin antibody, or antigen-binding fragment thereof, comprises, or consist of, an amino acid sequence of SEQ ID NO:1

A LC may comprise an amino acid sequence at least 90, 91%, 92%, 93%, 94%, 95%, 96%, 97%, 98%, or 99%, identical to the amino acid sequence of any one of SEQ ID NO:1, 17, 26, 31, 46, 56, 67, 72, 81, 86, 96, 101, 105, 115, or 119. In some embodiments, an antibody LC may comprise an amino acid sequence comprising or consisting of any one of SEQ ID Nos: 1, 17, 26, 31, 46, 56, 67, 72, 81, 86, 96, 101, 105, 115, or 119.

In some embodiments, an anti-E-selectin antibody, or antigen-binding fragment thereof, may comprise a HC comprising an amino acid sequence at least 90% identical to the amino acid sequence of SEQ ID NO:7 or 13. In some embodiments, an anti-E-selectin antibody, or antigen-binding fragment thereof, may comprise a HC comprising, or consisting of, an amino acid sequence at least 90% identical to the amino acid sequence of SEQ ID NO:7 or 13.

In some embodiments, an anti-E-selectin antibody, or antigen-binding fragment thereof, may comprise a heavy chain comprising an amino acid sequence at least 90, 91%, 92%, 93%, 94%, 95%, 96%, 97%, 98%, or 99%, identical to the amino acid sequence of any one of SEQ ID NOs:7, 13, 22, 28, 34, 37, 40, 43, 51, 59, 62, 74, 76, 89, 91, 103, 110, 117 or 124. In some embodiments, an antibody HC may comprise an amino acid sequence comprising, or consisting of, any one of SEQ ID NOs:7, 13, 22, 28, 34, 37, 40, 43, 51, 59, 62, 74, 76, 89, 91, 103, 110, 117 or 124.

In some embodiments, an anti-E-selectin antibody, or antigen-binding fragment thereof, comprises a LC comprising, or consisting of the amino acid sequence of SEQ ID NO:1 and a HC comprising, or consisting of, the amino acid sequence of SEQ ID NO:7 or SEQ ID NO:13. In some embodiments, an anti-E-selectin antibody, or antigen-binding fragment thereof, lacks effector function (i.e., is effector null).

In some embodiments, an anti-E-selectin antibody, or antigen-binding fragment thereof, may comprise a heavy chain comprising a VH domain comprising the amino acid sequence of any one of SEQ ID NOs: 11, 25, 30, 35, 39, 42, 45, 55, 60, 66, 75, 80, 90, 95, 104, 114, 118 and 128 (e.g., SEQ ID NO: 11), and further comprising an IgG1 constant domain (e.g., an IgG1 constant domain comprising the amino acid sequence of SEQ ID NO:15 or SEQ ID NO:16).

In some embodiments, an anti-E-selectin antibody, or antigen-binding fragment thereof, comprises a heavy chain comprising a VH domain comprising the amino acid sequence of SEQ ID NO:1 and further comprises an IgG1 constant domain comprising the amino acid sequence of SEQ ID NO:15 or SEQ ID NO:16. In some embodiments, an antibody, or antigen-binding fragment thereof, comprises a VH domain consisting of the amino acid sequence of SEQ ID NO:1 and further comprises an IgG1 constant domain consisting of the amino acid sequence of SEQ ID NO:15 or SEQ ID NO:16. In some embodiments, an anti-E-selectin antibody lacks effector function(s).

In some embodiments, an anti-E-selectin antibody, or antigen-binding fragment thereof, has a light chain constant region chosen from, e.g., a (e.g., human) kappa light chain constant region (e.g., encoded by the amino acid sequence of SEQ ID NO:14) or a lambda light chain constant region.

In some embodiments, an anti-E-selectin antibody, or antigen-binding fragment thereof, comprises a light chain comprising a VL domain comprising the amino acid sequence of any one of SEQ ID NOs: 5, 21, 27, 32, 50, 57, 71, 73, 85, 87, 100, 102, 109, 116 and 122 (e.g., SEQ ID NO:5), and further comprises a kappa constant domain comprising the amino acid sequence of SEQ ID NO:14. In some embodiments, an anti-E-selectin antibody, or antigen-binding fragment thereof, comprises a light chain comprising a VL domain consisting of the amino acid sequence of SEQ ID NO:5 and further comprises a kappa constant domain consisting of the amino acid sequence of SEQ ID NO:14.

In some embodiments, the constant region of an anti-E-selectin antibody, or antigen-binding fragment thereof, can be altered, e.g., mutated, to modify the properties of the antibody (e.g., to increase or decrease one or more of: Fc receptor binding, antibody glycosylation, the number of cysteine residues, effector cell function, and/or complement function).

In some aspects, an antibody, or antigen-binding fragment, variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to the full length heavy chain (e.g., a HC of the amino acid sequence of SEQ ID NO:7 or 13) and/or the full length light chain. In a further aspect, a variant antibody shares at least 65%, at least 75%, at least 85%, at least 90%, at least 95%, at least 96%, at least 97%, at least 98%, or at least 99% sequence identity with the full length heavy chain, and wherein said antibody or antigen-binding fragment specifically binds E-selectin. In a further aspect, a variant antibody shares at least 65%, at least 75%, at least 85%, at least 90%, at least 95%, at least 96%, at least 97%, at least 98%, or at least 99% sequence identity with the full length light chain (e.g., a LC of the amino acid sequence of SEQ ID NO:1), and wherein said antibody or antigen-binding fragment specifically binds E-selectin.

Germline Substitutions

A wide variety of acceptor human germline sequences are available and the process for "humanizing" a non-human species antibody to use in humans is well-known in the art and also discussed elsewhere herein. Therefore, the skilled artisan would appreciate that the above CDR sequences from a mouse, rat, etc., can be placed in the context of human variable domain amino acid sequences. In doing so, changes to the acceptor human germline sequences are generally made to preserve antibody binding and other desirable characteristics of the original parent (i.e., donor) antibody. Both the CDRs and framework regions (FW may be engineered as follows.

In certain embodiments, a substitution is a human germline substitution in which a (donor) CDR residue is replaced with the corresponding human germline (acceptor) residue, to increase the human amino acid content and potentially reduce immunogenicity of the antibody as described in, e.g., U.S. Patent Application Publication No. 2017/0073395 and Townsend et al., Proc. Nat. Acad. Sci. USA 2015; 112(50): 15354-15359, both of which are herein incorporated by reference in their entirety.

An antibody, or antigen-binding fragment thereof, may comprise a VH framework comprising a human germline VH framework sequence. In some aspects, a VH framework from the following germlines may be used: IGHV1-2*02, IGHV1-3*01, IGHV1-46*01, IGHV1-69*01, IGHV1-69*02, IGHV1-8*01, IGHV3-7*01, IGHV3-13*01, IGHV3-23*01, IGHV3-23*04, IGHV3-30*01, IGHV3-30*18, IGHV5-10-1*01, IGHV5-10-1*04, or IGHV5-51*01 (germline names are based on IMGT germline definition). In some embodiments, an anti-E-selectin antibody, or antigen binding fragment thereof, uses the VH framework from germline IGHV3-7*01 (SEQ ID NO:202). In some embodiments, an anti-E-selectin antibody, or antigen-binding fragment thereof, uses the VH framework from germline IGHV3-7*01 (SEQ ID NO:202) for the CDR regions and IGHJ4*01 (SEQ ID NO:203) for the framework region.

Preferred human germline light chain frameworks are frameworks derived from VK or Vλ germlines. In some aspects, a VL framework from the following germlines may be used: IGKV1-12*01, IGKV1-13*02, IGKV1-33*01, IGKV1-39*01, IGKV1-5*01, IGKV3-11*01, IGKV3-15*01, IGKV3-20*01, IGKV3D-20*02, and IGKV4-1*01 (germline names are based on IMGT germline definition). In some embodiments, an anti-E-selectin antibody, or antigen-binding fragment thereof, uses the VL framework from germline IGHV1-39*01 (SEQ ID NO:204). In some embodiments, an anti-E-selectin antibody, or antigen-binding fragment thereof, uses the VL framework from germline IGHV1-39*01 (SEQ ID NO:204) for the CDR regions and IGKJ1*01 (SEQ ID NO:205) for the framework region.

Alternatively, or in addition, the framework sequence may be a human germline consensus framework sequence, such as the framework of human Vλ1 consensus sequence, VK1 consensus sequence, VK2 consensus sequence, VK3 consensus sequence, VH3 germline consensus sequence, VH1 germline consensus sequence, VH5 germline consensus sequence, or VH4 germline consensus sequence. Sequences of human germline frameworks are available from various public databases, such as V-base, IMGT, NCBI, or Abysis.

An anti-E-selectin antibody, or antigen-binding fragment thereof, may comprise a VL framework comprising a human germline VL framework sequence. A VL framework may comprise one or more amino acid substitutions, additions, or deletions, while still retaining functional and structural similarity with the germline from which it was derived. In some aspects, a VL framework is at least 90%, at least 91%, at least 92%, at least 93%, at least 94%, at least 95%, at least 96%, at least 97%, at least 98%, at least 99%, or 100% identical to a human germline VL framework sequence. In some embodiments, an antibody, or antigen binding fragment thereof, comprises a VL framework comprising 1, 2, 3, 4, 5, 6, 7, 8, 9, 10 amino acid substitutions, additions or deletions relative to the human germline VL framework sequence. In some embodiments, the 1, 2, 3, 4, 5, 6, 7, 8, 9, or 10 amino acid substitutions, additions or deletions are only in the framework regions. In some embodiments, the percent identity is based on similarity with VL domain excluding those portions herein defined as CDRs.

A human germine VL framework may be, for example, the framework of IGKV1-39*01. A human germline VL framework may be, for example, the framework of IGKV1-33*01. A human germline VL framework may be the framework of any one of human consensus sequence including: Vλ, Vλ1, Vλ3, VK, VK1, VK2 or VK3.

In some embodiments, a VL framework is IGK-39*01_IGKJ1*01. Other similar framework regions are also predicted to deliver advantageous antibodies of the invention comprising CDRs of SEQ ID NOs: 2-4, 18-20, 47-49, 68-70, 82-84, 97-99, 106-108, 120 and 121; and CDRs specified by the following VL amino acid sequences: SEQ ID NOs: 5, 21, 27, 32, 50, 57, 71, 73, 85, 87, 100, 102, 109, 116, 122, which may comprise 99%, 97%, 97%, 96%, 80%, 76%, 74% and 66%, identity respectively to the framework region of any one of IGKV1-12*01, IGKV1-13*02, IGKV1-33*01, IGKV1-39*01, IGKV1-5*01, IGKV3-11*01, IGKV3-15*01, IGKV3-2001, IGKV3D-20*02, and IGKV4-1*01. In some embodiments, the percent identity is based on similarity with VL excluding those portions herein defined as CDRs.

An anti-E-selectin antibody, or antigen-binding fragment thereof, may comprise a VH framework comprising a human germine VH framework sequence. A VH framework may comprise one or more amino acid substitutions, additions, or deletions, while still retaining functional and structural similarity with the germline from which it was derived. In some aspects, a VH framework is at least 90%, at least 91%, at least 92%, at least 93%, at least 94%, at least 95%, at least 96%, at least 97%, at least 98%, at least 99%, or 100% identical to a human germline VH framework sequence. In some embodiments, an antibody, or antigen binding fragment thereof, comprises a VH framework comprising 1, 2, 3, 4, 5, 6, 7, 8, 9, 10 amino acid substitutions, additions or deletions relative to the human germline VH framework sequence. In some embodiments, the 1, 2, 3, 4, 5, 6, 7, 8, 9, or 10 amino acid substitutions, additions or deletions are only in the framework regions. In some embodiments, the percent identify is based on similarity with VH domain excluding those portions herein defined as CDRs.

A human germline VH framework may be, for example, the framework of IGHV3-7*01. A human germline VH framework may be, for example, the framework of IGHV1-46*01. A human germline VH framework may be, for example, IGHV1-69*01. A human germline VH framework may be the framework of human VH germline consensus sequence. The human germline VH framework may be the framework of a human germline consensus sequence including: VH3, VH5, VH1 or VH4.

In some embodiments, a VH framework is IGHV3-7*01 Other similar framework regions are also predicted to deliver advantageous antibodies of the invention comprising CDRs of SEQ ID NOs:8-10, 23, 24, 29, 38, 41, 44, 52-54, 63-65, 77-79, 92-94, 111-113, 125-127, and CDRs specified by any of the following VH amino acid sequences: SEQ ID NOs:11, 25, 30, 35, 39, 42, 45, 55, 60, 66, 75, 80, 90, 95, 104, 114, 118, 128, including IGHV1-2*02, IGHV1-3*01, IGHV1-46*01, IGHV1-69*01, IGHV1-69*02, IGHV1-8*01, IGHV3-7*01, IGHV3-13*01, IGHV3-23*01, IGHV3-23*04, IGHV3-30*01, IGHV3-30*18, IGHV5-10-1*01, IGHV5-10-1*04, or IGHV5-51*01, which may comprise 92, 93, 94, 95, 96, 97, 98, 99% identity respectively to the FW region of DP-54 and one or fewer amino acid differences in common structural features (Kabat Numbering) In some aspects, the percent identity is based on similarity with VH domain excluding those portions herein defined as CDRs.

In certain embodiments, the antibody, or antigen-binding fragment thereof, described herein comprises (i) a VH domain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO:11, and/or (I) a VL domain comprising an amino acid sequence that is at least 50%, at least 60%, at least 66%, at least 70%, at least 75%, at least 76%, at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO:5. Any combination of these VL and VH sequences is also encompassed by the invention.

In certain embodiments, the antibody, or antigen-binding fragment thereof, described herein comprises (i) a HC comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO:7 or SEQ ID NO:13; and/or (I) a LC comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO:1. Any combination of these HC and LC sequences is also encompassed by the invention.

In certain embodiments, the antibody, or antigen-binding fragment thereof, described herein comprises an Fc domain. The Fc domain can be derived from IgA (e.g., $IgA_1$ or $IgA_2$), IgG, IgE, or IgG (e.g., $IgG_1$, $IgG_2$, $IgG_3$, or $IgG_4$). In some embodiments, an anti-E-selectin antibody is and IgG1 antibody.

Biological Activity of Anti-E-Selectin Antibodies

In addition to binding an epitope on E-selectin, an antibody, or antigen-binding fragment thereof, of the disclosure can mediate a biological activity. That is, the disclosure includes an isolated antibody, or antigen-binding fragment thereof, that specifically binds E-selectin and mediates at least one detectable activity selected from the following:
(i) binds specifically to human E-selectin
(ii) binds specifically to cynomolgus monkey E-selectin;
(iii) reduces, inhibits and/or neutralizes interaction (e.g., binding) between soluble E-selectin (e.g., human, cynomolgus) and an E-selectin ligand (e.g., sialyl-Lewis A and/or sialyl-Lewis X ligand);
(iv) reduces, inhibits and/or neutralizes interaction (e.g., binding) between cell surface expressed E-selectin (e.g., human, cynomolgus) and an E-selectin ligand (e.g., sialyl-Lewis A and/or sialyl-Lewis X ligand);
(v) reduces, inhibits and/or neutralizes interaction (e.g., adhesion) between cell surface expressed E-selectin (e.g., human, cynomolgus) and cell surface expressed E-selectin ligands (e.g., sialyl-Lewis A and/or sialyl-Lewis X ligand on, e.g., HL-60 cells);
(vi) reduces, inhibits and/or neutralizes interaction (e.g., adhesion) of soluble E-selectin to cells expressing E-selectin ligand (e.g., HL-60);
(vii) reduces, inhibits and/or neutralizes adhesion of cells expressing E-selectin ligand (e.g., HL-60) to cells expressing E-selectin under static and physiological flow conditions;
(vii) reduces, inhibits and/or neutralizes adhesion of activated human neutrophils to cells expressing E-selectin (e.g., human and cynomolgus) under physiological flow conditions;
(ix) binds to at least one amino acid residue selected from: T7, E8, A9, M10, T11, P46, S47, Y48, N82, N83, Q85, E88, E92, Y94, R97, N105, E107, R108, S110, K111, K112 and K113 of human E-selectin;
(x) has a viscosity of about 38+/−7 cP at a concentration of about 187 mg/mL at 25° C.;
(xi) has a half-life of about 21.5 days (518 hours) when administered SC at a dose of 3 mg/kg;
(xii) shows suitable formulation properties, including a high degree of thermal stability and minimal aggregation at high concentration; and
(xiii) may show reproducible expression and purity in large-scale manufacturing conditions.

In some embodiments, an anti-E-selectin antibody, or antigen-binding fragment thereof, has a binding affinity, expressed as $K_D$ for soluble human E-selectin that is less than or equal to 200 nM, for example, less than or equal to 195 nM, 190 nM, 180 nM, 160 nM, 140 nM, 120 nM, 110 nM, 100 nM, 90 nM, 80 nM, 75 nM, 50 nM. In some embodiments, an anti-E-selectin antibody, or antigen-binding fragment thereof, has a binding affinity, expressed as $K_D$ for soluble human E-selectin that is less than or equal to 200 nM as measured by SPR. In some embodiments, an anti-E-selectin antibody (e.g., antibody 1444), or an antigen-binding fragment thereof, has a binding affinity, expressed as $K_D$ for soluble human E-selectin that is about 61.8 to about 68.4+/−3.18 nM as measured, for example, by SPR.

In some embodiments, an anti-E-selectin antibody, or antigen-binding fragment thereof, has a binding affinity, expressed as $K_D$, for soluble cynomolgus E-selectin that is less than or equal to 200 nM, for example, less than or equal to 195 nM, 190 nM, 180 nM, 160 nM, 140 nM, 120 nM, 110 nM, 100 nM, 90 nM, 80 nM, 75 nM, 50 nM. In some embodiments, an anti-E-selectin antibody (e.g., antibody 1444), or an antigen-binding fragment thereof, has a binding affinity, expressed as $K_D$, for soluble cynomolgus E-selectin that is about 64.9+/−1.13 nM to about 81.5 nM as measured, for example, by SPR.

In some embodiments, an anti-E-selectin antibody, or antigen-binding fragment thereof, has a binding affinity, expressed as $EC_{50}$, for cell-surface expressed human E-selectin that is less than or equal to 50 nM, for example, less than or equal to 48 nM, 45 nM, 40 nM, 20 nM, 10 nM, 5 nM, 4 nM, 3 nM, 2 nM, 1 nM, 0.75 nM, 0.5 nM, 0.25 nM or 0.1 nM, as measured, for example, by FACS. In some embodiments, an anti-E-selectin antibody (e.g., antibody 1444), or an antigen-binding fragment thereof, has a binding affinity, expressed as $EC_{50}$, for cell-surface expressed human E-selectin that is about 0.66 nM, as measured, for example, by FACS.

In some embodiments, an anti-E-selectin antibody, or an antigen-binding fragment thereof, has a binding affinity, expressed as $EC_{50}$ for cell-surface expressed cynomolgus E-selectin that is less than or equal to 50 nM, for example, less than or equal to 48 nM, 45 nM, 40 nM, 20 nM, 10 nM, 5 nM, 4 nM, 3 nM, 2 nM, 1 nM, 0.75 nM, 0.5 nM, 0.25 nM or 0.1 nM as measured, for example, by FACS. In some embodiments, an anti-E-selectin antibody (e.g., antibody 1444), or an antigen-binding fragment thereof, has a binding affinity, expressed as $EC_{50}$, for cell-surface expressed cynomolgus E-selectin that is about 0.75 nM, as measured, for example, by FACS.

In some embodiments, an anti-E-selectin antibody, or antigen-binding fragment thereof, has a binding affinity, expressed as $EC_{50}$, for cell-surface expressed human P-selectin that is greater than or equal to 350 nM, for example, greater than or equal to 400 nM, 450 nM, 500 nM, 550 nM, 600 nM, 650 nM or more, as measured, for example, by FACS.

In some embodiments, an anti-E-selectin antibody, or antigen-binding fragment thereof, has weak or no binding to soluble rat, mouse or rabbit E-selectin or soluble human L- or P-selectin. In some embodiments, an anti-E-selectin antibody, or antigen-binding fragment thereof, demonstrates no binding to soluble rat, mouse or rabbit E-selectin or soluble human L- or P-selectin up to 405 nM as measured, for example, by SPR. In some embodiments, an anti-E-selectin antibody, or antigen-binding fragment thereof, demonstrates week-non-saturable binding (e.g., >100× lower) to soluble mouse or rat E-selectin up to 133.3 nM as measured, for example, by direct binding ELISA.

In some embodiments, an anti-E-selectin antibody, or antigen-binding fragment thereof, binds to soluble human E-selectin with an $EC_6$ of less than or equal to 2 nM, for example, less than or equal to 0.010 nM, 0.015 nM, 0.020 nM, 0.025 nM, 0.030 nM, 0.035 nM, 0.040 nm, 0.045 nM, 0.05 nM, 0.055 nM, 0.06 nM, 0.065 nM, 0.070 nM, 0.075 nM, 0.080 nM, 0.085 nM, 0.090 nM, 0.10 nM, 0.12 nM, 0.15 nM, 0.2 nM, 0.5 nM, 0.9 nM, 0.95 nM, 1 nM, 1.5 nM, 1.8 nM or 1.9 nM. In some embodiments, an anti-E-selectin antibody (e.g., antibody 1444), or an antigen-binding fragment thereof, binds to soluble human E-selectin with an $EC_{50}$ of about 0.085 nM to about 0.12 as measured, for example, by direct binding ELISA.

In some embodiments, an anti-E-selectin antibody, or antigen-binding fragment thereof, neutralizes binding of a sialyl-Lewis A ligand to soluble human E-selectin with an $EC_{50}$ of less than or equal to 2 nM, for example, less than or equal to 0.010 nM, 0.015 nM, 0.020 nM, 0.025 nM, 0.030 nM, 0.035 nM, 0.040 nm, 0.045 nM, 0.05 nM, 0.055 nM, 0.06 nM, 0.065 nM, 0.070 nM, 0.075 nM, 0.080 nM, 0.085 nM, 0.090 nM, 0.10 nM, 0.12 nM, 0.15 nM, 0.2 nM, 0.5 nM, 0.9 nM, 0.95 nM, 1 nM, 1.5 nM, 1.8 nM or 1.9 nM, as measure, for example, by a AlphaLisa homogenous competition assay.

In some embodiments, an anti-E-selectin antibody, or antigen-binding fragment thereof, binds to soluble cynomolgus E-selectin with an $EC_{50}$ of less than or equal to 1 nM, for example, less than or equal to 0.010 nM, 0.015 nM, 0.020 nM, 0.025 nM, 0.030 nM, 0.035 nM, 0.040 nm, 0.045 nM, 0.05 nM, 0.055 nM, 0.06 nM, 0.065 nM, 0.070 nM, 0.075 nM, 0.080 nM, 0.085 nM, 0.090 nM, 0.10 nM, 0.12 nM, 0.15 nM, 0.2 nM, 0.5 nM, 0.9 nM or 0.95 nM. In some embodiments, an anti-E-selectin antibody (e.g., antibody 1444), or an antigen-binding fragment thereof binds to soluble cynomolgus E-selectin with an $EC_{50}$ of 0.071 nM to 0.093 nM as measured, for example, by direct binding ELISA.

In some embodiments, an anti-E-selectin antibody, or antigen-binding fragment thereof, binds free soluble human E-selectin in human serum with an $IC_{50}$ of about 1 nM to about 3 nM, and preferably with an $IC_{50}$ of about 1.2 nM.

In some embodiments, an anti-E-selectin antibody, or antigen-binding fragment thereof, neutralizes binding of a sialyl-Lewis A ligand to soluble human E-selectin with an $IC_{50}$ of less than or equal to 100 nM, for example, less than or equal to 95 nM, 90 nM, 80 nM, 70 nM, 60 nM, 50 nM, 40 nM, 30 nM, 20 nM, 10 nM, 5 nM, 2 nM or 1 nM as measured, for example, by competition ELISA under static conditions. In some embodiments, an anti-E-selectin antibody (e.g., antibody 1444), or antigen-binding fragment thereof, neutralizes binding of a sialyl-Lewis A ligand to soluble human E-selectin with an $IC_{50}$ of about 2.87 nM to about 3.01 nM as measured, for example, by competition ELISA under static conditions.

In some embodiments, an anti-E-selectin antibody, or antigen-binding fragment thereof, neutralizes binding of a sialyl-Lewis A ligand to soluble cynomolgus E-selectin with an $IC_{50}$ of less than or equal to 100 nM, for example, less than or equal to 95 nM, 90 nM, 80 nM, 70 nM, 60 nM, 50 nM, 40 nM, 30 nM, 20 nM, 10 nM, 5 nM, 2 nM or 1 nM as measured, for example, by competition ELISA under static conditions. In some embodiments, an anti-E-selectin antibody (e.g., antibody 1444), or antigen-binding fragment thereof, neutralizes binding of a sialyl-Lewis A ligand to soluble cynomolgus E-selectin with an $IC_{50}$ of about 2.39 nM to about 2.91 nM as measured, for example, by competition ELISA under static conditions.

In some embodiments, an anti-E-selectin antibody, or antigen-binding fragment thereof, neutralizes binding of a sialyl-Lewis A ligand to cell-surface expressed human E-selectin with an $IC_{50}$ of less than or equal to 50 nM, for example, less than or equal to 48 nM, 45 nM, 40 nM, 20 nM, 10 nM, 5 nM, 4 nM, 3 nM, 2 nM or 1 nM as measured, for example, by competition ELISA under static conditions. In some embodiments, an anti-E-selectin antibody, or antigen-binding fragment thereof, neutralizes binding of a sialyl-Lewis A ligand to cell-surface expressed human E-selectin with an $IC_{50}$ of about 1.88 nM to about 2.89 nM as measured, for example, by competition ELISA under static conditions.

In some embodiments, an anti-E-selectin antibody, or antigen-binding fragment thereof, neutralizes binding of a sialyl-Lewis A ligand to cell-surface expressed cynomolgus E-selectin with an $IC_{50}$ of less than or equal to 100 nM, for example, less than or equal to 95 nM, 90 nM, 80 nM, 70 nM, 60 nM, 50 nM, 40 nM, 20 nM, 10 nM, 5 nM, 2 nM or 1 nM as measured, for example, by competition ELISA under static conditions. In some embodiments, an anti-E-selectin antibody, or antigen-binding fragment thereof, neutralizes binding of a sialyl-Lewis A ligand to cell-surface expressed cynomolgus E-selectin with an $IC_{50}$ of about 1.47 nM to about 2.65 nM as measured, for example, by competition ELISA under static conditions.

In some embodiments, an anti-E-selectin antibody, or antigen-binding fragment thereof, inhibits adhesion of cells expressing an E-selectin ligand (e.g., E selectin ligand, PSGL-1 and other sialyl Lewis ligands) to cell-surface expressed human E-selectin with an $IC_{50}$ of less than or equal to 100 nM, for example, less than or equal to 95 nM, 90 nM, 80 nM, 70 nM, 60 nM, 50 nM, 40 nM, 20 nM, 10 nM, 5 nM, 2 nM or 1 nM as measured, for example, under static conditions. In some embodiments, an anti-E-selectin antibody (e.g., antibody 1444), or antigen-binding fragment thereof, inhibits adhesion of cells expressing an E-selectin ligand (e.g., E selectin ligand, PSGL-1 and other sialyl Lewis ligands) to cell-surface expressed human E-selectin with an $IC_{50}$ of about 3.36 nM to about 4.7 nM as measured, for example, under static conditions.

In some embodiments, an anti-E-selectin antibody (e.g., antibody 1444), or antigen-binding fragment thereof, inhibits adhesion of cells expressing an E-selectin ligand (e.g., E selectin ligand, PSGL-1 and other sialyl Lewis ligands) to cell-surface expressed cynomolgus E-selectin with an $IC_{50}$ of about 3.84 nM as measured, for example, under static conditions.

In some embodiments, an anti-E-selectin antibody, or antigen-binding fragment thereof, inhibits adhesion of cells expressing an E-selectin ligand (e.g., E selectin ligand, PSGL-1 and other sialyl Lewis ligands) to cell-surface expressed human E-selectin with an IC of less than or equal to 100 nM, for example, less than or equal to 95 nM, 90 nM, 80 nM, 70 nM, 60 nM, 50 nM, 40 nM, 30 nM, 20 nM, 10 nM, 5 nM, 2 nM or 1 nM as measured, for example, under physiological flow conditions. In some embodiments, an anti-E-selectin antibody (e.g., antibody 1444), or antigen-binding fragment thereof, inhibits adhesion of cells expressing an E-selectin ligand (e.g., E selectin ligand, PSGL-1 and other sialyl Lewis ligands) to cell-surface expressed human E-selectin with an $IC_{50}$ of about 4.25 nM to about 4.56 nM as measured, for example, under physiological flow conditions.

In some embodiments, an anti-E-selectin antibody (e.g., antibody 1444), or antigen-binding fragment thereof, inhibits adhesion of cells expressing an E-selectin ligand (e.g., E selectin ligand, PSGL-1 and other sialyl Lewis ligands) to cell-surface expressed cynomolgus E-selectin with an $IC_{50}$ of about 4.32 nM to about 4.35 nM as measured, for example, under physiological flow conditions.

In some embodiments, an anti-E-selectin antibody, or antigen-binding fragment thereof, inhibits adhesion of cells expressing an E-selectin ligand (e.g., E selectin ligand, PSGL-1 and other sialyl Lewis ligands) to soluble human E-selectin with an $IC_{50}$ of less than or equal to 300 nM, for example, less than or equal to 290 nM, 280 nM, 270 nM, 260 nM, 250 nM, 150 nM, 100 nM, 90 nM, 100 nM, 90 nM, 80 nM, 70 nM, 60 nM, 50 nM, 40 nM, 20 nM, 20 nM, 5 nM, 2 nM, or 1 nM as measured, for example, under physiologic flow conditions. In some embodiments, an anti-E-selectin antibody (e.g., antibody 1444), or antigen-binding fragment thereof, inhibits adhesion of cells expressing an E-selectin ligand (e.g., E selectin ligand, PSGL-1 and other sialyl Lewis ligands) to soluble human E-selectin with an $IC_{50}$ of about 13.28 nM to about 15.94 nM as measured, for example, under physiologic flow conditions.

In some embodiments, anti-E-selectin antibody (e.g., antibody 1444), or antigen-binding fragment thereof, inhibits adhesion of activated human neutrophils to cell-surface expressed human, or cell surface expressed cynomolgus, E-selectin with an $IC_{50}$ of about 2.87 nM to about 4.65 nM or 9.45 nM to about 16.33 nM as measured, for example, under physiologic flow conditions. In some embodiments, neutrophils are activated by TNF-α.

In some embodiments, an anti-E-selectin antibody (e.g., antibody 1444), or antigen-binding fragment thereof, inhibits adhesion of blood cells from SCD patients to soluble human E-selectin with an $IC_{50}$ of about 6.17 nM to about 18.66 nM as measured, for example, under physiologic flow conditions. In some embodiments, an anti-E-selectin antibody (e.g., antibody 1444), or antigen-binding fragment thereof, inhibits adhesion of blood cells from SCD patients to soluble human E-selectin with an $IC_{50}$ of about 12.4 nM as measured, for example, under physiologic flow conditions.

In some embodiments, an anti-E-selectin antibody, or antigen-binding fragment thereof, binds to at least one of three epitopes of human E-selectin as determined by, for example a competition assay using, for example an Octet biosensor.

In some embodiments, an anti-E-selectin antibody, or antigen-binding fragment thereof, binds to at least one, at least 2, at least 3, at least 4, at least 5, at least 6, at least 7, at least 8, at least 9, at least 10, or more amino acid residues of human E-selectin selected from the group consisting of T7, E8, A9, M10, T11, P46, S47, Y48, N82, N83, Q85, E88, E92, Y94, R97, N105, E107, R108, S110, K111, K112, K113 and a combination thereof, optionally, according to the crystal structure.

In some embodiments, an anti-E-selectin antibody, or antigen-binding fragment thereof, interacts with amino acid residues T7, E8, A9, M10, T11, P46, S47, Y48, N82, N83, Q85, E88, E92, Y94, R97, N105, E107, R108, S110, K111, K112 and K113 of human E-selectin, optionally, according to the crystal structure.

In some embodiments, an anti-E-selectin antibody, or antigen-binding fragment thereof interacts with at least one, at least 2, at least 3, at least 4, at least 5, at least 6, at least 7, at least 8, at least 9, at least 10, or more amino acid residues of human E-selectin within 3.8 Å selected from the group consisting of T7, E8, A9, T11, P46, S47, Y48, N82, N83, Q85, E92, Y94, N105, E107, R108, S110, K111, K112 and a combination thereof, optionally, according to the crystal structure.

In some embodiments, an anti-E-selectin antibody, or antigen-binding fragment thereof interacts with amino acid residues T7, E8, A9, T11, P46, S47, Y48, N82, N83, Q85, E92, Y94, N105, E107, R108, S110, K111 and K112 of human E-selectin within 3.8 Å, optionally, according to the crystal structure.

In some embodiments, an anti-E-selectin antibody, or antigen-binding fragment thereof interacts with at least one, at least 2, at least 3, at least 4, at least 5, at least 6, at least 7, at least 8, at least 9, at least 10, or more amino acid residues of human E-selectin with a buried surface area ($Å^2$) of >5 $Å^2$ selected from the group consisting of T7, E8, A9, T11, P46, S47, Y48, N82, N83, Q85, E88, E92, Y94, R97, E107, R108, S110, K111, K112, K113 and a combination thereof, optionally, according to the crystal structure.

In some embodiments, an anti-E-selectin antibody, or antigen-binding fragment thereof interacts with amino acid residues T7, E8, A9, T11, P46, S47, Y48, N82, N83, Q85, E88, E92, Y94, R97, E107, R108, S110, K111, K112 and K113 of human E-selectin with a buried surface area ($Å^2$) of >5 $Å^2$, optionally, according to the crystal structure.

In some embodiments, an anti-E-selectin antibody, or antigen-binding fragment thereof interacts with at least one, at least 2, at least 3, at least 4, at least 5, at least 6, at least 7, at least 8, at least 9, at least 10 or more amino acid residues of human E-selectin via a hydrogen bond selected from the group consisting of E8, S47, N82, N83, E88, E92, Y94, N105, E107, R108, S110, K112, and a combination thereof, optionally, according to the crystal structure.

In some embodiments, an anti-E-selectin antibody, or antigen-binding fragment thereof interacts with amino acid residues E8, S47, N82, N83, E88, E92, Y94, N105, E107, R108, S110 and K112 of human E-selectin via a hydrogen bond, optionally, according to the crystal structure.

In some embodiments, an anti-E-selectin antibody, or antigen-binding fragment thereof, interacts with at least one amino acid residue of human E-selectin via a salt bridge selected from the group consisting of K111, K112, and a combination thereof, optionally, according to the crystal structure.

In some embodiments, an anti-E-selectin antibody, or antigen-binding fragment thereof, interacts with amino acid residues K111 and K112 of human E-selectin via a salt bridge, optionally, according to the crystal structure.

In some embodiments, an anti-E-selectin antibody, or antigen-binding fragment thereof, interacts with at least one amino acid residue of human E-selectin via a water-mediated hydrogen bond selected from the group consisting of R97, K112, and a combination thereof, optionally, according to the crystal structure.

In some embodiments, an anti-E-selectin antibody, or antigen-binding fragment thereof, interacts with amino acid residues R97 and K112 of human E-selectin via a water-mediated hydrogen bond, optionally, according to the crystal structure.

In some embodiments, an anti-E-selectin antibody, or antigen-binding fragment thereof, interacts with at least one, at least 2, at least 3, at least 4, at least 5, at least 6, at least 7, more amino acid residues of human E-selectin which also Interacts within 3.8 Å of an sLex amino acid residue contact selected from the group consisting of Y48, N82, N83, E92, Y94, R97, N105, E107 and a combination thereof, optionally, according to the crystal structure.

In some embodiments, an anti-E-selectin antibody, or antigen-binding fragment thereof, interacts with amino acid residues Y48, N82, N83, E92, Y94, R97, N105 and E107 of human E-selectin which also interact within 3.8 Å of an sLex amino acid residue contact, optionally, according to the crystal structure.

Binding, or interaction of, an anti-E-selectin antibody, or antigen-binding fragment thereof with at least one or more amino acid residues of human E-selectin may be determined according to methods know in the art, including analysis of a crystal structure of the bound molecules as described in the Examples herein.

In some embodiments, an anti-E-selectin antibody, or antigen-binding fragment thereof, is at low risk for polyreactivity, as measured by, for example an AC-SINS assay, a DNA binding assay and/or an insulin binding assay. In some embodiments, an anti-E-selectin antibody, or antigen-binding fragment thereof has a low immunogenicity risk, e.g., has a T-reg Adjusted score of about −44, −45, −46 or −47.

In some embodiments, an anti-E-selectin antibody, or antigen-binding fragment thereof, demonstrated at least one predicted human pharmacokinetic (PK) parameter, when administered IV, chosen from: (i) a systemic clearance of about 0.15 mLh/kg to about 0.39 mLh/kg; (ii) an apparent volume of distribution at steady state of 22 mL/kg to 36 mL/kg; (iii) a mean half-life of about 102 hours to about 345 hours. In some embodiments, an anti-E-selectin antibody, or antigen-binding fragment thereof, administered SC demonstrates a half-life of about 243 to about 518 hours.

In some embodiments, a mean half-life of an anti-E-selectin antibody, or antigen-binding fragment thereof, is at least about 102 hours (about 4.25 days) following IV administration at a dose of 0.3 mg/kg. In some embodiments, a mean ha-life of an anti-E-selectin antibody, or antigen-binding fragment thereof, is at least about 264 hours (about 11 days) following IV administration at a dose of 0.6 mg/kg. In some embodiments, a mean half-life of an anti-E-selectin antibody, or antigen-binding fragment thereof, is at least about 188 hours (about 7.8 days) following IV administration at a dose of 1.0 mg/kg. In some embodiments, a mean half-life of an anti-E-selectin antibody, or antigen-binding fragment thereof, is at least about 345 hours (about 14.4 days) following IV administration at a dose of 10 mg/kg.

In some embodiments, a mean half-life of an anti-E-selectin antibody, or antigen-binding fragment thereof, is at least about 243 hours (about 10 days) following SC administration at a dose of 1.0 mg/kg. In some embodiments, a mean half-life of an anti-E-selectin antibody, or antigen-binding fragment thereof, is at least about 518 hours (about 21.5 days) following SC administration at a dose of 3.0 mg/kg.

In some embodiments, an anti-E-selectin antibody, or antigen-binding fragment thereof, has a viscosity selected from the group consisting of about 7.97+/−1.83 cP at a concentration of about 23 mg/mL, about 12.38+/−5.28 cP at a concentration of about 48 mg/mL, about 4.26+/−0.6 cP at a concentration of about 90 mg/mL, about 5.58+/−0.99 cP at a concentration of about 102 mg/mL, about 8.44+/−1.54 cP at a concentration of about 121 mg/mL, about 9.78+/−2.32 cP at a concentration of about 140 mg/mL, about 17.47+/−3.24 cP at a concentration of about 158 mg/mL and about 37.99+/−7.03 cP at a concentration of about 188 mg/mL, when measured at 25° C. by, for example, dynamic light scattering (DLS).

In some embodiments, an anti-E-selectin antibody, or antigen-binding fragment thereof, has a viscosity of about 15 cP to 40 cP at a concentration of about 150 mg/mL to about 190 mg/mL when measured at 25° C. by, for example DLS.

In some embodiments, an anti-E-selectin antibody, or antigen-binding fragment thereof, has a viscosity of 33.4 cP at 185.7 mg/mL when measured at 25° C. by, for example an Anton Parr method.

Immunogenicity

Immunogenicity is a major barrier to the development and utilization of protein therapeutics, including antibodies and Fc fusion proteins. Several factors can contribute to protein immunogenicity, including but not limited to the protein sequence, the route and frequency of administration, and the patient population. Although immune responses are typically most severe for non-human proteins, such as murine antibodies, even therapeutics with mostly or entirely human sequence content may be immunogenic. Immunogenicity is a complex series of responses to a substance that is perceived as foreign and may include production of neutralizing and non-neutralizing antibodies, formation of immune complexes, complement activation, mast cell activation, inflammation, and anaphylaxis. Unwanted immune responses may reduce the efficacy of antibody and Fc fusion protein therapeutics by directly interfering with antigen recognition, altering interactions with effector molecules, or perturbing the serum half-life or tissue distribution of the therapeutic.

Protein therapeutics can be analyzed to predict the presence of potential immunogenic epitopes using commercially available services such as provided by Epivax, Inc. of Providence, R.I. Potential immunogenic epitopes may also be predicted using methods such as the IEDB Consensus method. In some embodiments, in silico algorithms can predict epitopes that bind to Class II MHC molecules. Analysis of a data set of the polypeptide with such algorithms provides predicted epitopes. Predicted epitopes are used to make peptides prepared by standard methods of automated peptide synthesis or recombinant DNA techniques. Scoring information provided from Epivax can provide an indication of how widespread a predicted epitope is recognized in the population. A lower score predicts a lower immunogenic potential.

As used herein, "T-regitopes" are amino acid sequences within the monoclonal antibody framework region that can potentially activate natural regulatory T cells and reduce unwanted immune responses. In some embodiments, an anti-E-selectin antibody, or antigen binding-fragment thereof, comprises 8, 7, 6, 5, 4, 3, 2, 1 or 0 non-germline T-cell epitopes. In some embodiments, an anti-E-selectin antibody, or antigen-binding fragment thereof, has a low immunogenicity risk, e.g., has a T-reg Adjusted Score of about −45.11, −45.32, −46.16 or −46.26. In some embodiments, anti-E-selectin antibody (e.g., antibody 1444), or antigen-binding fragment thereof, has a T-reg Adjusted Score of about −45.11 and 0 non-germline T-ell epitopes.

Nucleic Acids Encoding Anti-E-Selectin Antibodies

The disclosure also provides polynucleotides encoding any of the antibodies of the invention, including antibody portions and modified antibodies described herein. The invention also provides a method of making any of the polynucleotides described herein. Polynucleotides can be made and the proteins expressed by procedures known in the art.

A sequence of a desired antibody, or antigen-binding fragment thereof, and nucleic acid encoding such antibody, or antigen-binding fragment thereof, can be determined using standard sequencing techniques. A nucleic acid molecule encoding a desired antibody, or antigen-binding fragment thereof, may be inserted into various vectors (such as cloning and expression vectors) for recombinant production and characterization. A nucleic acid molecule encoding the heavy chain, or an antigen-binding fragment of the heavy chain, and a nucleic acid molecule encoding the light chain, or an antigen-binding fragment of the light chain, can be cloned into the same vector, or different vectors.

In some embodiments, the disclosure provides polynucleotides encoding the amino acid sequences of any of the following anti-E-selectin antibodies and antigen-binding fragments thereof: antibody 1444, 0841, 0978, 0164, 1448, 1284, 1282, 0525, 0039, 0265_0254, 0158, 0929_548, 0159, 0955_0300, 0170, 0564, 0180 and 0027. In one embodiment, the invention provides polynucleotides encoding the amino acid sequence of anti-E-selectin antibody 1444 and antigen-binding fragments thereof.

In some embodiments, the disclosure provides polynucleotides encoding one or more anti-E-selectin antibody HC polypeptides comprising an amino acid sequence selected from the group consisting of: SEQ ID NOs:7, 13, 22, 28, 34, 37, 40, 43, 51, 59, 62, 74, 76, 89, 91, 103, 110, 117 and 124. In some embodiments, the disclosure provides a polynucleotide encoding an anti-E-selectin antibody HC polypeptide comprising, or consisting of, the amino acid sequence of SEQ ID NO:7 or SEQ ID NO:13.

In some embodiments, the disclosure provides polynucleotides encoding one or more anti-E-selectin antibody LC polypeptides comprising an amino acid sequence selected from the group consisting of: SEQ ID NOs:1, 17, 26, 31, 46, 56, 67, 72, 81, 86, 96, 101, 105, 115 and 119. In some embodiments, the disclosure provides a polynucleotide encoding an anti-E-selectin antibody LC polypeptide comprising, or consisting of, the amino acid sequence of SEQ ID NO:1.

In some embodiments, the disclosure provides polynucleotides encoding one or more anti-E-selectin antibody VH domain polypeptides comprising an amino acid sequence selected from the group consisting of: SEQ ID NOs:11, 25, 30, 35, 39, 42, 45, 55, 60, 66, 75, 80, 90, 95, 104, 114, 118 and 128. In some embodiments, the disclosure provides a polynucleotide encoding an anti-E-selectin antibody VH domain polypeptide comprising, or consisting of, the amino acid sequence of SEQ ID NO:11.

In some embodiments, the disclosure provides polynucleotides encoding one or more anti-E-selectin antibody VL domain polypeptides comprising an amino acid sequence selected from the group consisting of: SEQ ID NOs:5, 21, 27, 32, 50, 57, 7, 73, 85, 87, 100, 102, 109, 116 and 122. In some embodiments, the disclosure provides a polynucleotide encoding an anti-E-selectin antibody VL domain polypeptide comprising, or consisting of, the amino acid sequence of SEQ ID NO:5.

The invention provides a polynucleotide comprising the nucleic acid sequence of the insert of the plasmid deposited with the ATCC and having Accession No. PTA-126529 encoding the HC domain of antibody 1444. The invention also provides a polynucleotide comprising the nucleic acid sequence of the insert of the plasmid deposited with the ATCC and having Accession No. PTA-126530 encoding the LC of antibody 1444. In addition, the invention provides a polypeptide comprising the amino acid sequence encoded by the DNA insert of the plasmid deposited with the ATCC and having Accession No. PTA-126529, encoding the VH domain of antibody 1444. The invention further provides a polypeptide comprising the amino acid sequence encoded by the insert of the plasmid deposited with the ATCC and having Accession No. PTA-126530 encoding the VL domain of antibody 1444.

The invention also provides a polynucleotide comprising the nucleic acid sequence of the insert of the plasmid deposited with the ATCC and having Accession No. PTA-126529, encoding the HCDR-1, HCDR-2 and HCDR-3 of antibody 1444 and the nucleic acid sequence of the insert of the plasmid deposited with the ATCC and having Accession No. PTA-126530, encoding the LCDR-1, LCDR-2 and LCDR-3 of antibody 1444.

The invention also provides a polynucleotide comprising the nucleic acid sequence of the insert of the plasmid deposited with the ATCC and having Accession No. PTA-126529, encoding the VH domain of antibody 1444 and the nucleic acid sequence of the insert of the plasmid deposited with the ATCC and having Accession No. PTA-126530, encoding the VL domain of antibody 1444.

The invention also provides a polynucleotide comprising the nucleic acid sequence of the insert of the plasmid deposited with the ATCC and having Accession No. PTA-126529, encoding the heavy chain of antibody 1444 and the nucleic acid sequence of the insert of the plasmid deposited with the ATCC and having Accession No. PTA-126530, encoding the light chain of antibody 1444.

In some embodiments, the disclosure provides polynucleotides and variants thereof encoding an anti-E-selectin antibody, wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% nucleic acid sequence identity to any of the nucleic acid sequences disclosed in Table 2. These amounts are not meant to be limiting and increments between the recited percentages are specifically envisioned as part of the disclosure.

In one embodiment, the VH and VL domains, or antigen-binding fragment thereof, or full-length HC or LC, are encoded by separate polynucleotides. Alternatively, both VH and VL, or antigen-binding fragment thereof, or HC and LC, are encoded by a single polynucleotide.

Polynucleotides complementary to any such sequences are also encompassed by the present disclosure. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present disclosure, and a polynucleotide may, but need not, be inked to other molecules and/or support materials.

Polynucleotides may comprise a nucleic acid sequence that encodes an antibody or a fragment thereof or may comprise a variant of such a sequence. Polynucleotide variants contain one or more substitutions, additions, deletions and/or insertions such that the binding characteristics of the encoded polypeptide is not diminished relative to a native antibody molecule. The effect on the binding characteristics of the polypeptide encoded by the variant nucleic acid sequence may generally be assessed as described herein. In some embodiments, polynucleotide variants exhibit at least about 70% identity, at least about 80% identity, at least about 90% identity, at least about 95% identity, at least 98% identity or at least 99% identity to a polynucleotide sequence that encodes the original (parent) antibody not comprising any substitution, addition, deletion and/or insertion, or a fragment thereof. These percent identities are not meant to be limiting and increments between the recited percentages are specifically envisioned as part of the disclosure.

Two polynucleotide or polypeptide sequences are said to be "identical" if the sequence of nucleotides or amino acids in the two sequences is the same when aligned for maximum correspondence as described herein. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned. In some embodiments, a polynucleotide is at least 70%, 75%, 80%, 85%, 90%, 95%, 98%, 99% identical to a polynucleotide disclosed herein.

In some embodiments, an anti-E-selectin antibody VL domain is encoded by a polynucleotide comprising a nucleic acid sequence selected from the group consisting of SEQ ID NO:137, 145, 147, 149, 154, 165, 158, 160, 162, 164, 166, 168, 170, 172 and 174. In some embodiments, an anti-E-selectin antibody VL domain is encoded by a polynucleotide comprising a nucleic acid sequence at least 80%, 85%, 90%, 95%, 98% or 99% identical to a nucleic acid selected from the group consisting of SEQ ID NO:137, 145, 147, 149, 154, 165, 158, 160, 162, 164, 166, 168, 170, 172 and 174.

In some embodiments, an anti-E-selectin antibody VL domain is encoded by a polynucleotide comprising a nucleic acid sequence at least 90% identical to the nucleic acid sequence of SEQ ID NO:137. In some embodiments, an anti-E-selectin antibody VL domain is encoded by a polynucleotide comprising, or consisting of, a nucleic acid sequence of SEQ ID NO:137.

In some embodiments, an anti-E-selectin antibody VH domain is encoded by a polynucleotide comprising a nucleic acid sequence selected from the group consisting of SEQ ID NO:136, 144, 146, 148, 150, 151, 152, 153, 155, 157, 159, 161, 163, 165, 167, 169, 171 and 173. In some embodiments, an anti-E-selectin antibody VH domain is encoded by a polynucleotide comprising a nucleic acid sequence at least 80%, 85%, 90%, 95%, 98% or 99% identical to a nucleic acid selected from the group consisting of SEQ ID NO: 136, 144, 146, 148, 150, 151, 152, 153, 155, 157, 159, 161, 163, 165, 167, 169, 171 and 173.

In some embodiments, an anti-E-selectin antibody VH domain is encoded by a polynucleotide comprising a nucleic acid sequence at least 90% identical to SEQ ID NO:136. In some embodiments, an anti-E-selectin antibody VH domain is encoded by a polynucleotide comprising, or consisting of, a nucleic acid sequence of SEQ ID NO:136.

In some embodiments, an anti-E-selectin antibody HC is encoded by a polynucleotide comprising a nucleic acid sequence at least 90% identical to SEQ ID NO:206 or 207. In some embodiments, an anti-E-selectin antibody HC is encoded by a polynucleotide comprising, or consisting of, a nucleic acid sequence of SEQ ID NO:206 or 138.

In some embodiments, an anti-E-selectin antibody LC is encoded by a polynucleotide comprising a nucleic acid sequence at least 90% identical to SEQ ID NO:139. In some embodiments, an anti-E-selectin antibody LC is encoded by a polynucleotide comprising a nucleic acid sequence of SEQ ID NO:139.

Polynucleotide variants may also, or alternatively, be substantially homologous to a gene, or a fragment or complement thereof. Such polynucleotide variants are capable of hybridizing under moderately stringent conditions to a naturally occurring DNA sequence encoding an antibody (or a complementary sequence).

Suitable "moderately stringent conditions" include pre-washing in a solution of 5×SSC, 0.5% SDS, 1.0 mM EDTA (pH 8.0); hybridizing at about 50° C. to 65° C., 5×SSC (0.75

M NaCl, 0.075 M sodium citrate), overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/ 0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC, 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1× SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode the amino acid sequence of a polypeptide as described herein. Some of these polynucleotides bear minimal homology to the nucleotide sequence of any native gene. That is, there are 64 different codons to encode 20 natural amino acids, with some amino acids having multiple codons that encode it (e.g., 6 different codons encode leucine). Therefore, a large number of nucleic acid sequences can encode the same protein sequence such that two nucleic acids encoding the same polypeptide amino acid sequence can share very low nucleic acid sequence identity. Therefore, polynucleotides that vary due to differences in codon usage are specifically contemplated by the present disclosure.

Further, alleles of the genes comprising the polynucleotide sequences provided herein are within the scope of the present disclosure. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, for example.

As used herein, the term "vector" means a construct, which is capable of delivering, and, preferably, expressing, one or more gene(s) or sequence(s) of interest (e.g., a nucleic acid encoding a HC, a LC, a VH, a VL and/or a fragment thereof, of an anti-E-selectin antibody) in a host cell. Examples of vectors include, but are not limited to, viral vectors (e.g. AAV), naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

Suitable cloning and expression vectors can include a variety of components, such as promoter, enhancer, and other transcriptional regulatory sequences. The vector may also be constructed to allow for subsequent cloning of an antibody variable domain into different vectors. Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors are further provided. Expression vectors generally are replicable polynucleotide constructs that contain a polynucleotide according to the disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

In some embodiments, a cell (e.g., isolated or within an organism) is transduced with a recombinant AAV (rAAV) comprising a recombinant nucleic acid encoding a heterologous polynucleotide (e.g., a HC, a LC, a VH domain, a VL domain, or an antigen-binding fragment thereof, of an anti-E-selectin antibody) and an AAV capsid. A recombinant nucleic acid may further comprise regulatory elements (e.g., a promoter, an enhancer, an intron, an exon, polyA) for expression of the heterologous polynucleotide within a transduced cell. A recombinant nucleic acid may further comprise viral inverted tandem repeat (ITR) sequences. In some embodiments, an AAV capsid is an AAV1, AAV2, AAV3, AAV4, AAV5, AAV6, AAV7, AAV8, AAV9, AAV10, or any other wild type or recombinant AAV capsid known in the art. ITR sequences may be AAV1, AAV2, AAV3, AAV4, AAV5, AAV6, AAV7, AAV8, AAV9, AAV10, or any other wild type or recombinant ITR sequences (e.g., AAV2) known in the art. In some embodiments, a rAAV comprises a recombinant nucleic acid encoding a HC, a LC, a VH domain, a VL domain, or an antigen-binding fragment thereof, of an anti-E-selectin antibody, a promoter, an AAV ITR and a viral capsid. Such rAAV is suitable for expression of an anti-E-selectin antibody, or antigen-binding fragment thereof in a cell to treat or prevent a disease, disorder or condition (e.g., SCD) mediated by E-selectin in a subject (e.g., a patient).

The vectors containing the polynucleotides of interest and/or the polynucleotides themselves, can be introduced into a host cell by any of a number of appropriate means, including electroporation, transfection employing calcium chloride or polyethylenimine (PEI), rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

In some embodiments, a vector comprises a polynucleotide comprising a nucleic acid sequence selected from the group consisting of SEQ ID NO: 137, 145, 147, 149, 154, 165, 158, 160, 162, 164, 166, 168, 170, 172 and 174. In some embodiments, a vector comprises a polynucleotide comprising a nucleic acid sequence at least 70%, 80%, 85%, 90%, 95%, 98% or 99% identical to the nucleic acid sequence of SEQ ID NO:137. In some embodiments, a vector comprises a polynucleotide comprising, or consisting of, a nucleic acid sequence of SEQ ID NO:137.

In some embodiments, a vector comprises polynucleotide comprising a nucleic acid sequence selected from the group consisting of SEQ ID NO: 136, 144, 146, 148, 150, 151, 152, 153, 155, 157, 159, 161, 163, 165, 167, 169, 171 and 173. In some embodiments, a vector comprises a polynucleotide comprising a nucleic acid sequence at least 70% 80%, 85%, 90%, 95%, 98% or 99% identical to SEQ ID NO:136. In some embodiments, a vector comprises a polynucleotide comprising, or consisting of, a nucleic acid sequence of SEQ ID NO:136.

In some embodiments, a vector comprises a polynucleotide comprising i) a nucleic acid sequence of SEQ ID NO:136; ii) a nucleic acid of SEQ ID NO:137; or ii) both.

In some embodiments, a vector comprises a polynucleotide comprising a nucleic acid sequence at least 70% 80%, 85%, 90%, 95%, 98% or 99% identical to SEQ ID NO:206 or 138. In some embodiments, a vector comprises a polynucleotide comprising, or consisting of, a nucleic acid sequence of SEQ ID NO:206 or 138.

In some embodiments, a vector comprises a polynucleotide comprising a nucleic acid sequence at least 70% 80%, 85%, 90%, 95%, 98% or 99% identical to SEQ ID NO:139. In some embodiments, a vector comprises a polynucleotide comprising, or consisting of, a nucleic acid sequence of SEQ ID NO:139.

In some embodiments, a vector comprises a polynucleotide comprising i) a nucleic acid sequence of SEQ ID NO:206 or 138; i) a nucleic acid of SEQ ID NO:139; or ii) both.

As used herein, the terms "host cell," "host cell line," and "host cell culture" are used interchangeable and mean an individual cell or cell culture that can be or has been a recipient for a polynucleotide and/or vector(s) for incorporation of polynucleotide inserts. Host cells include "transformants," "transformed cells," and "transduced cells," which include the primary transformed or transduced cell and progeny derived therefrom without regard to the number of passages. Host cell progeny may not necessarily be completely identical (in morphology or in genomic DNA complement) to the original parent cell due to natural, accidental, or deliberate mutation. A host cell includes cells transfected and/or transformed in vivo with a polynucleotide of this invention (e.g., a polynucleotide encoding an amino acid sequence of an anti-E-selectin antibody) or a vector comprising the same.

Host cells may be prokaryotic cells or eukaryotic cells. Exemplary eukaryotic cells include mammalian cells, such as primate or non-primate animal cells; fungal cells, such as yeast; plant cells; and insect cells.

An antibody, or antigen-binding fragment thereof, may be made recombinantly using a suitable host cell. A nucleic acid encoding an anti-E-selectin antibody, or antigen-binding fragment thereof, of the present disclosure can be cloned into an expression vector, which can then be introduced into a host cell, where the cell does not otherwise produce an immunoglobulin protein, to obtain the synthesis of an antibody in the recombinant host cell. Any host cell susceptible to cell culture, and to expression of protein or polypeptides, may be utilized in accordance with the present invention. In certain embodiments, the host cell is mammalian. Mammalian cell lines available as hosts for expression are well known in the art and include many immortalized cell lines available from the American Type Culture Collection (ATCC). Nonlimiting exemplary mammalian cells include, but are not limited to, NS0 cells, HEK 293 and Chinese hamster ovary (CHO) cells, and their derivatives, such as 293-6E and CHO DG44 cells, CHO DXB11, and Potelligent® CHOK1SV cells (BioWa/Lonza, Allendale, N.J.). Mammalian host cells also include, but are not limited to, human cervical carcinoma cells (HeLa, ATCC CCL 2), baby hamster kidney (BHK, ATCC CCL 10) cells, monkey kidney cells (COS), and human hepatocellular carcinoma cells (e.g., Hep G2). Other non-limiting examples of mammalian cells that may be used in accordance with the present invention include immortalized primary human embryonic retinal cells (PER.C6®; CruCell, Leiden, The Netherlands); monkey kidney CV1 line transformed by SV40 (COS-7, ATCC CRL 1651); human embryonic kidney line 293 (HEK 293) or 293 cells subcloned for growth in suspension culture (Graham et al., J. Gen Virol. 1997; 36:59); mouse sertoli cells (TM4, Mather, Biol. Reprod. 1980; 23:243-251); monkey kidney cells (CV1 ATCC CCL 70); African green monkey kidney cells (VERO-76, ATCC CRL-1 587); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 1982; 383:44-68); MRC 5 cells; FS4 cells; a human hepatoma line (Hep G2); and numerous myeloma cell lines, including, but not limited to, BALB/c mouse myeloma line (NS0/1, ECACC No: 85110503), NS0 cells and Sp2/0 cells.

Additionally, any number of commercially and non-commercially available cell lines that express polypeptides or proteins may be utilized in accordance with the present invention. One skilled in the art will appreciate that different cell lines might have different nutrition requirements and/or might require different culture conditions for optimal growth and polypeptide or protein expression, and will be able to modify conditions as needed.

Uses

Methods of Treatment

In some embodiments, the disclosure provides for therapeutic methods for reducing or inhibiting E-selectin activity using an anti-E-selectin antibody or antigen-binding fragment thereof, wherein the therapeutic method comprises administering a therapeutically effective amount of a pharmaceutical composition comprising an antibody or antigen-binding fragment thereof. The disorder treated is any disease or condition which is improved, ameliorated, inhibited or prevented by removal, inhibition or reduction of E-selectin activity (e.g., SCD).

Methods of treatment using anti-E-selectin antibodies, or antigen-binding fragments thereof, include, but are not limited to, methods of treating and/or preventing diseases, disorders and conditions associated with, or mediated by, E-selectin expression and/or E-selectin binding to a ligand (e.g., sLex A and/or X determinants), including, but not limited to, SCD, vaso-occlusive crisis, pain, organ infarction, ischemia, stroke, end organ dysfunction, acute chest and vascular obstruction. An anti-E-selectin antibody, or antigen-binding fragment thereof of the present disclosure, may also be used to treat and/or prevent other diseases, disorders and conditions such as, skin diseases (e.g., psoriasis), inflammatory diseases (e.g., rheumatoid arthritis) and complications of diabetes.

The present disclosure provides novel therapeutic antibodies that specifically bind to E-selectin and are capable of neutralizing E-selectin functional activity. These antibodies may be used advantageously to prevent, or reduce occurrence of, a VOC when utilized as a prophylactic treatment for SCD. In some embodiments, occurrence of a VOC in a subject (e.g., a patient with SCD) treated with an anti-E-selectin antibody, or antigen-binding fragment thereof, is reduced by about 10%, 20%, 30%, 40%, 50%, 60%, 70%, 80%, 90% or 100% as compared to occurrence of a VOC in a subject, or group of subjects, (e.g., patient(s) with SCD) who are not treated with an anti-E-selectin antibody, or antigen-binding fragment thereof. In some embodiments, occurrence of a VOC in subject (e.g., a patient with SCD) treated with an anti-E-selectin antibody, or antigen-binding fragment thereof, is reduced by about 10%, 20%, 30%, 40%, 50%, 60%, 70%, 80%, 90% or 100% as compared to occurrence of a VOC in the same subject prior to treatment with an anti-E-selectin antibody, or antigen-binding fragment thereof. In some embodiments, occurrence of a VOC in subject (e.g., a patient with SCD) treated with an anti-E-selectin antibody, or antigen-binding fragment thereof, is not significantly different from occurrence of VOC in a subject, or population of subjects, who do not have SCD. In some embodiments, occurrence of a VOC (e.g., number of VOC events) is measured over a period of time. In some embodiments, occurrence of a VOC (e.g., number of VOC events) is measured over days, weeks, months or years.

In some embodiments, an antibody, or antibody-binding fragment thereof, of the disclosure may reduce an annualized rate of sickle cell-related pain crisis. Sickle cell-related pain crises, as referred to herein, are acute episodes of pain, with no medically determined cause other than a vaso-occlusive event, that may result in a medical facility visit and/or may result in treatment with oral or parenteral narcotic agents or with a parenteral nonsteroidal anti-inflammatory drug. In some embodiments, acute chest syndrome, hepatic sequestration, splenic sequestration, and priapism are considered sickle cell-related pain crises.

In some embodiments, an annualized rate of sickle cell-related pain crisis in a subject (e.g., a patient with SCD) treated with an anti-E-selectin antibody, or antigen-binding fragment thereof, is about 10%, 20%, 30%, 40%, 50%, 60%, 70%, 80%, 90% or 100% lower than an annualized rate of sickle cell-related pain crisis in a subject, or group of subjects, (e.g., patient(s) with SCD) who are not treated with an anti-E-selectin antibody, or antigen-binding fragment thereof. In some embodiments, an annualized rate of sickle cell-related pain crisis in a subject (e.g., a patient with SCD) treated with an anti-E-selectin antibody, or antigen-binding fragment thereof, is about 10%, 20%, 30%, 40%, 50%, 60%, 70%, 80%, 90% or 100% lower than an annualized rate of sickle cell-related pain crisis in the same subject prior to treatment with an anti-E-selectin antibody, or antigen-binding fragment thereof. In some embodiments, an annualized rate of sickle cell-related pain crisis in a subject (e.g., a patient with SCD) treated with an anti-E-selectin antibody, or antigen-binding fragment thereof, is not significantly different from an annualized rate of sickle cell-related pain crisis in a subject, or population of subjects, who do not have SCD.

In some embodiments, a median time to a first sickle cell-related pain crisis in a subject (e.g., a patient with SCD) treated with an anti-E-selectin antibody, or antigen-binding fragment thereof, is about 10%, 20%, 30%, 40%, 50%, 60%, 70%, 80%, 90% or 100% longer than a median time to a first sickle cell-related pain crisis in a subject, or group of subjects, (e.g., patient(s) with SCD) who are not treated with an anti-E-selectin antibody, or antigen-binding fragment thereof. In some embodiments, a median time to a first sickle cell-related pain crisis in a subject (e.g., a patient with SCD) treated with an anti-E-selectin antibody, or antigen-binding fragment thereof, is about 10%, 20%, 30%, 40%, 50%, 60%, 70%, 80%, 90% or 100% longer than a median time to a first sickle cell-related pain crisis in the same subject prior to treatment with an anti-E-selectin antibody, or antigen-binding fragment thereof. In some embodiments, a median time to a first sickle cell-related pain crisis in a subject (e.g., a patient with SCD) treated with an anti-E-selectin antibody, or antigen-binding fragment thereof, is not significantly different from a median time to first sickle cell-related pain crisis in a subject, or population of subjects, who do not have SCD.

In some embodiments, a median time to a second sickle cell-related pain crisis in a subject (e.g., a patient with SCD) treated with an anti-E-selectin antibody, or antigen-binding fragment thereof, is about 10%, 20%, 30%, 40%, 50%, 60%, 70%, 80%, 90% or 100% longer than a median time to a second sickle cell-related pain crisis in a subject, or group of subjects, (e.g., patient(s) with SCD) who are not treated with an anti-E-selectin antibody, or antigen-binding fragment thereof. In some embodiments, a median time to a second sickle cell-related pain crisis in a subject (e.g., a patient with SCD) treated with an anti-E-selectin antibody, or antigen-binding fragment thereof, is about 10%, 20%, 30%, 40%, 50%, 60%, 70%, 80%, 90% or 100% longer than a median time to a second sickle cell-related pain crisis in the same subject prior to treatment with an anti-E-selectin antibody, or antigen-binding fragment thereof. In some embodiments, a median time to a second sickle cell-related pain crisis in a subject (e.g., a patient with SCD) treated with an anti-E-selectin antibody, or antigen-binding fragment thereof, is not significantly different from a median time to second sickle cell-related pain crisis in a subject, or population of subjects, who do not have SCD.

In some embodiments, a median rate of uncomplicated sickle cell-related pain crisis in a subject (e.g., a patient with SCD) treated with an anti-E-selectin antibody, or antigen-binding fragment thereof, is about 10%, 20%, 30%, 40%, 50%, 60%, 70%, 80%, 90% or 100% lower than a median rate of uncomplicated sickle cell-related pain crisis in a subject, or group of subjects, (e.g., patient(s) with SCD) who are not treated with an anti-E-selectin antibody, or antigen-binding fragment thereof. In some embodiments, an uncomplicated crisis was a crisis other than acute chest syndrome, hepatic sequestration, splenic sequestration and/or priapism. In some embodiments, a median rate of uncomplicated sickle cell-related pain crisis in a subject (e.g., a patient with SCD) treated with an anti-E-selectin antibody, or antigen-binding fragment thereof, is about 10%, 20%, 30%, 40%, 50%, 60%, 70%, 80%, 90% or 100% longer than a median rate of uncomplicated sickle cell-related pain crisis in the same subject prior to treatment with an anti-E-selectin antibody, or antigen-binding fragment thereof. In some embodiments, a median rate of uncomplicated sickle cell-related pain crisis in a subject (e.g., a patient with SCD) treated with an anti-E-selectin antibody, or antigen-binding fragment thereof, is not significantly different from a median rate of uncomplicated sickle cell-related pain crisis in a subject, or population of subjects, who do not have SCD.

Antibodies of the disclosure may also be used advantageously to treat an acute VOC in a patient with SCD by decreasing the duration (e.g., reduction in the time to resolve a VOC), severity and/or intensity of a VOC. In some embodiments, duration, severity and/or intensity of a VOC in a subject (e.g., a patient with SCD) treated with an anti-E-selectin antibody, or antigen-binding fragment thereof, is reduced by about 10%, 20%, 30%, 40%, 50%, 60%, 70%, 80%, 90% or 100% as compared to duration, severity and/or intensity of a VOC in a subject, or group of subjects, (e.g., patient(s) with SCD) who are not treated with an anti-E-selectin antibody, or antigen-binding fragment thereof. In some embodiments, duration, severity and/or intensity of a VOC in subject (e.g., a patient with SCD) treated with an anti-E-selectin antibody is reduced by about 10%, 20%, 30%, 40%, 50%, 60%, 70%, 80%, 90% or 100% as compared to duration, severity and/or intensity of a VOC in the same subject prior to treatment with an anti-E-selectin antibody, or antigen-binding fragment thereof. In some embodiments, duration, severity and/or intensity of a VOC in subject (e.g., a patient with SCD) treated with an anti-E-selectin antibody, or antigen-binding fragment thereof, is not significantly different from duration, severity and/or intensity of a VOC in a subject, or population of subjects, who do not have SCD.

An anti-E-selectin antibody, or antigen-binding fragment thereof, may also be used, to treat, prevent and/or ameliorate at least one sign and/or symptom of SCD, for example, those affecting the cardiothoracic system (e.g., chronic restrictive lung disease, left ventricular diastolic disease, pulmonary hypertension, acute chest syndrome, dysrhythmias, sudden death, vaso-occlusive crisis), the nervous system (e.g., hemorrhagic stroke, venous sinus thrombosis, silent cerebral Infarction of the brain, chronic pain, acute ischemic stroke of the brain, proliferative retinopathy, orbital infarction, cognitive impairment) the reticuloendothelial system (e.g., splenic sequestration, functional hyposplenism, anemia, hemolysis), the musculoskeletal system (e.g., avascular necrosis, skin ulcerations), the urogenital system (e.g., papillary necrosis, proteinuria, renal failure, hematuria, nocturnal enuresis, priapism) and the gastrointestinal system (e.g., cholelithiasis, cholangiopathy, hepatopathy, mesenteric vaso-occlusion).

In some embodiments, the present disclosure includes an isolated antibody, or antigen-binding fragment thereof, that specifically binds E-selectin and modulates at least one detectable E-selectin biological activity such that the antibody: (a) decreases leukocyte tethering to endothelial cells; (b) decreases activation of stable adhesion to endothelial cells; (c) reduces slow rolling of leukocytes to arrest; (d) reduces efficient trans-endothelial migration of leukocytes; (e) decreases affinity and avidity of CD18 integrins; (f) reduces trafficking of leukocytes to sites of acute inflammation; (g) decreases cytosolic calcium; (h) decreases tyrosine phosphorylation that activates p38 MAP kinase and Syk kinase; (i) reduces recruitment of platelets and leukocytes from the blood to the vascular endothelium; and/or (j) does not create a pro-inflammatory environment.

Methods of treating using an anti-E-selectin antibody, or antigen-binding fragment thereof, of the present disclosure includes prophylactic and/or therapeutic treatments. If a treatment is administered prior to clinical manifestation of a condition, the treatment is considered prophylactic. For example, administration of an anti-E-selectin antibody, or antigen-binding fragment thereof, may be used to prevent VOC (e.g., reduce the frequency of VOC events) when utilized as a prophylactic treatment (e.g., one or more doses, over a period of time) for SCD. Therapeutic treatment includes, e.g., ameliorating or reducing the severity of a disease, or shortening the length of the disease. For example, administration of an anti-E-selectin antibody, or antigen-binding fragment thereof, may be used to treat an acute VOC in patients with SCD by decreasing the duration, intensity and/or severity of the VOC.

In some embodiments, a subject to be treated may be mammal, and in particular a human patient, for example, a patient with SCD. A subject may be in need of treatment because, as a result of one or more mutations in the coding sequence of the HBB gene, the p-globin protein is expressed inappropriately, e.g., has an incorrect amino acid sequence. Administration of an anti-E-selectin antibody, or antigen-binding fragment thereof, may be used to treat and/or prevent at least one sign and/or symptom of SCD (e.g., VOC), a variant of SCD or SC disease. Administration of an anti-E-selectin antibody, or antigen-binding fragment thereof, may be used to treat and/or prevent at least one sign and/or symptom of disease in a subject who has a HBSS, HBSC, HBSE, HBS/$\beta^{\circ}$thal, HBS/$\beta^{+}$thal or HBS-variant genotype.

The disclosure further encompasses an anti-E-selectin antibody, or antigen binding fragment thereof, or pharmaceutical composition, as defined herein for use in the defined methods of treatment and/or prevention. In embodiments that refer to a method of treatment and/or prevention as described herein, such embodiments are also include further embodiments concerning an anti-E-selectin antibody, or antigen binding fragment thereof, or pharmaceutical composition, for use in that treatment and/or prevention, or alternatively use in the manufacture of a medicament for treatment and/or prevention of a symptom of SCD.

Combination Therapies

An antibody, or antigen-binding fragment thereof of the present disclosure, may be administered in combination with one or more additional therapeutically active compounds or treatment modalities which are effective in treating and/or preventing at least one sign and/or symptom of SCD. The disclosure encompasses a method of treating and/or preventing at least one sign and/or symptom of SCD comprising administering to a patient in need thereof an amount of an anti-E-selectin antibody, or antigen-binding fragment thereof, in combination with an amount of a therapeutically active compound or treatment modality which is effective in treating and/or preventing at least one sign and/or symptom of SCD. In some embodiments, treating a symptom of SCD includes decreasing the duration and intensity of an acute VOC. In some embodiments, preventing a symptom of SCD includes reducing the frequency of VOC events.

The invention also encompasses a method of treating and/or preventing at least one sign and/or symptom of SCD comprising administering to a patient in need thereof an amount of an anti-E-selectin antibody, or antigen-binding fragment thereof and an amount of a therapeutically active compound or treatment modality which is effective in treating and/or preventing at least one sign and/or symptom of SCD, wherein the amounts together are effective in treating and/or preventing at least one sign and/or symptom of SCD.

In another embodiment, the invention is related to a method of treating and/or preventing at least one sign and/or symptom of SCD comprising administering to a patient in need thereof an amount of an anti-E-selectin antibody, or antigen-binding fragment thereof, and an amount of a therapeutically active compound or treatment modality which is effective in treating and/or preventing at least one sign and/or symptom of SCD, wherein the amounts together achieve synergistic effects in the treatment and/or prevention of at least one sign and/or symptom of SCD, that is, the combination is "synergistic," (i.e., the combination provides an effect greater than a merely additive effect of two or more individual therapies). Such synergistic combination therapies may advantageously utilize lower dosages of the administered therapeutic agents, thus avoiding possible toxicities or complications associated with the various monotherapies.

Additional therapeutically active compounds useful for the treatment and/or prevention of at least one sign and/or symptom of SCD include, for example, penicillin prophylaxis to prevent pneumococcal infection, hydroxyurea (e.g., DROXIA, HYDREA), L-glutamine (e.g., ENDARI), crizanlizumab (ADAKVEO), voxelotor (OXBRYTA), apixaban (ELIQUIS), rivaroxaban (XARELTO), a non-steroidal anti-inflammatory drug, an analgesic generally, an opioid analgesic, IW-1701, riociguat (ADEMPAS), ticagrelor (BRILINTA), memantine (NAMENDA) and a combination thereof.

Additional therapeutically active compounds useful for the treatment and/or prevention of at least one sign and/or symptom of SCD include compounds such as an anti-P-selectin antibody (e.g., crizanlizumab (ADAKVEO)), a compound that modulates HbS, a compound that modulates oxygen affinity of HbS (e.g., voxelotor (OXBRYTA)), a compound that targets HbS polymerization by modulating generation of 2,3-disphosphoglyceric acid, a compound that targets HbS polymerization by inducing expression of fetal hemoglobin (HbF) (e.g., hydroxyurea), a compound that targets dysfunctional cellular adhesion, vascular dysfunction and/or inflammation (e.g., a phosphodiesterase-9 inhibitor), a compound that increases levels of nitric oxide in the blood (e.g., soluble guanylate cyclase stimulators, e.g., IW-1701, riociguat (ADEMPAS)), intravenous IG, a compound that targets hypercoagulability (e.g., riociguat (ADEMPAS), apixaban (ELIQUIS), rivaroxaban (XARELTO)), a compound that blocks NMDA receptor binding (e.g., memantine (NAMENDA)).

An additional therapeutically active compound useful for the treatment and/or prevention of at least one sign and/or symptom of SCD (e.g., a VOC) is a compound that modulates HbS so as to maintain it in its R state (i.e., oxygenated state), such as those described in WO 2020/109994, and incorporated herein by reference. In some embodiments, a compound that modulates HbS so as to maintain it in its R state includes a 2-aminoquinoline compound. In some embodiments, a compound that modulates HbS so as to maintain it in its R state is 6-{(1S)-1-[(2-amino-6-fluoroquinolin-3-yl)oxy]ethyl}-5-(1H-pyrazol-1-yl)pyridin-2-ol, optionally prepared in solid form as its amide tautomer (S)-6-(1-((2-amino-6-fluoroquinolin-3-yl)oxy)ethyl)-5-(1H-pyrazol-1-yl)pyridin-2(1H)-one,

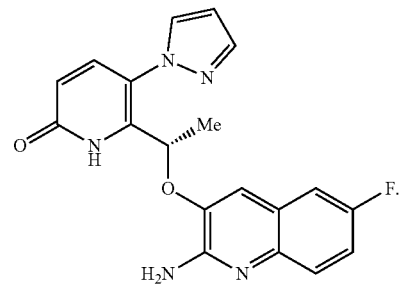 [SMILES: C[C@H](Oc1cc2cc(F)ccc2nc1N)c1[nH]c(=O)ccc1-n1cccn1]

A therapeutically active treatment modality useful for treatment and/or prevention of at least one sign and/or symptom of SCD includes supplemental oxygen, blood transfusion, optionally with iron chelation, bone marrow transplant, gene therapy (e.g., LentiGlobin®), a gene editing therapy by CRISPR (e.g., CTX001), a zinc finger technique and a combination thereof.

The present disclosure encompasses a pharmaceutical composition comprising an anti-E-selectin antibody, or antigen-binding fragment thereof, a therapeutically active compound or treatment modality which is effective in treating and/or preventing at least one sign and/or symptom of SCD, and a pharmaceutically acceptable carrier for use in the treatment and/or prevention of at least one sign and/or symptom of SCD (e.g., VOC). The disclosure encompasses a pharmaceutical composition comprising a synergistic, therapeutically effective amount of an anti-E-selectin antibody, a synergistic, therapeutically effective amount of a therapeutically active compound or treatment modality which is effective in treating and/or preventing at least one sign and/or symptom of SCD, and a pharmaceutically acceptable carrier for use in the treatment and/or prevention of at least one sign and/or symptom of SCD (e.g., VOC). The composition can further comprise an additional therapeutic agent, such as, but not limited to at least one other therapeutically active compound or treatment modality which is effective in treating and/or preventing at least one sign and/or symptom of SCD (e.g., VOC).

One skilled in the art would understand, based on the disclosure provided therein, that the method of treating and/or preventing at least one sign and/or symptom of SCD encompasses administering a synergistic, therapeutically effective amount of an anti-E-selectin antibody and a synergistic, therapeutically effective amount of a therapeutically active compound or treatment modality which is effective in treating and/or preventing at least one sign and/or symptom of SCD, to a patient either previously treated with, or currently receiving, at least one additional therapeutic agent to treat and/or prevent at least one sign and/or symptom of SCD (e.g., VOC).

Such additional therapeutic agent encompasses an agent that is standard of care to treat and/or prevent at least one sign and/or symptom of SCD. That is, the combination therapy of the invention may be added to the therapeutic regimen of a SCD patient already receiving a different therapy including, but not limited to, L-glutamine, hydroxyurea, a blood transfusion (optionally with iron chelation) and any other therapy known in the art.

Those skilled in the art will be able to determine, according to known methods, the appropriate amount, dose or dosage of each compound, as used in the combination of the present disclosure, to administer to a patient with SCD, taking into account factors such as age, weight, general health, the compound administered, the route of administration, the nature and advancement of the treatment of SCD, and the presence of other medications.

A prophylactic or therapeutic agent of the combination therapies, including an anti-E-selectin antibody, or antigen-binding fragment thereof, can be administered to a subject in the same pharmaceutical composition (e.g., the therapies are co-formulated). Alternatively, a prophylactic or therapeutic agent of the combination therapies can be administered concurrently to a subject in separate pharmaceutical compositions (e.g., the therapies are co-administered). Prophylactic or therapeutic agent of the combination therapies can be administered according to the same dosing regimen (e.g., both therapies are administered daily) or according to different dosing regimens (e.g., one therapy is administered daily, the other therapy is administered weekly). Prophylactic or therapeutic agents may be administered to a subject by the same or different routes of administration.

A prophylactic or therapeutic agent of the combination therapies, including an anti-E-selectin antibody, or an antigen-binding fragment thereof, and 6-((1S)-1-[(2-amino-6-fluoroquinolin-3-yl)oxy]ethyl-5-(1H-pyrazol-1-yl)pyridin-2-ol, optionally prepared in solid form as its amide tautomer (S)-6-(1-((2-amino-6-fluoroquinolin-3-yl)oxy)ethyl)-5-(1H-pyrazol-1-yl)pyridin-2(1H)-one, can be administered concurrently to a subject in separate pharmaceutical compositions (e.g., the therapies are co-administered). Such prophylactic or therapeutic agent of the combination therapies can be administered according to the same dosing regimen (e.g., both therapies are administered daily) or according to different dosing regimens (e.g., one therapy is administered daily, the other therapy is administered weekly). Furthermore, such prophylactic or therapeutic agents may be administered to a subject by the same or different routes of administration.

Prophylactic or therapeutic agents including an anti-E-selectin antibody, or an antigen-binding fragment thereof, and 6-{(1S)-1-[(2-amino-6-fluoroquinolin-3-yl)oxy]ethyl}-5-(1H-pyrazol-1-yl)pyridin-2-ol, optionally prepared in solid form as its amide tautomer (S)-6-(1-((2-amino-6-fluoroquinolin-3-yl)oxy)ethyl)-5-(1H-pyrazol-1-yl)pyridin-2(1H)-one, may be administered in combination to reduce the duration (e.g., reduction in the time to resolve a VOC), severity and/or intensity of a VOC, to reduce an annualized rate of sickle cell-related pain crisis, to Increase the median time to a first sickle cell-related pain crisis, to increase the median time to a second sickle cell-related pain crisis, and/or to reduce the median rate of uncomplicated sickle cell-related pain crisis in a subject.

The disclosure further encompasses a prophylactic or therapeutic agent of the combination therapies, including an anti-E-selectin antibody, or antigen-binding fragment thereof, as defined herein for use in the defined methods of treatment and/or prevention. In embodiments that refer to a method of treatment and/or prevention as described herein, such embodiments are also include further embodiments concerning a combination therapy, including an anti-E-selectin antibody, or antigen binding fragment thereof, or pharmaceutical composition, for use in that treatment and/or prevention, or alternatively for the manufacture of a medicament for use in that treatment and/or prevention of at least one sign and/or symptom of SCD.

The disclosure provides protocols for the administration of pharmaceutical composition comprising E-selectin antibodies, or antigen-binding fragments thereof, of the disclosure alone or in combination with other therapies to a subject in need thereof. The therapies (e.g., prophylactic or therapeutic agents) of the combination therapies of the present disclosure can be administered concomitantly or sequentially to a subject. The therapy (e.g., prophylactic or therapeutic agents) of the combination therapies of the present disclosure can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising E-selectin antibodies, or antigen-binding fragments thereof, of the disclosure are administered to a subject in a sequence and within a time interval such that the antibodies of the disclosure or conjugates thereof can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

Prophylactic or therapeutic agents of a combination therapy can be administered to a subject in the same pharmaceutical composition. Alternatively, a prophylactic or therapeutic agent of a combination therapy can be administered concurrently to a subject in separate pharmaceutical compositions. Prophylactic or therapeutic agents may be administered to a subject by the same or different routes of administration.

Diagnostic Uses

The anti-E-selectin antibodies, antibody compositions, and methods of the present invention have in vitro and in vivo utilities including immunoassays and use for the diagnosis and assessment of treatment of E-selectin mediated disorders. The methods are particularly suitable for diagnosing, assessing, and treating human patients having a disorder associated with the existence of E-selectin. This disorder associated with the existence of E-selectin includes, but is not limited to, SCD, skin diseases (e.g., psoriasis), inflammatory diseases (e.g., rheumatoid arthritis) and complications of diabetes.

The invention provides a method for detecting the presence of E-selectin in a sample, the method comprising contacting a sample suspected of comprising E-selectin with an antibody specific for E-selectin and detecting the presence of E-selectin bound with the antibody thereby detecting E-selectin in the sample. Methods for detecting E-selectin bound with the antibody are well-known in the art including, but not limited to, an assay where E-selectin is bound to a solid support and a sample is added thereto allowing the antibody to bind E-selectin in the sample. A second E-selectin antibody that is either the same or different from the antibody bound to the sold support is added and can be detected by either direct labeling (i.e., the second antibody is conjugated to a detectable label) or by adding a third antibody, e.g., from another species which reacts with the constant domain of the second antibody and which comprises a detectable label. Thus, the assay can be used to detect the presence or absence of E-selectin in a sample.

The invention also provides a method for determining the concentration of E-selectin in a sample, said method comprising providing a labeled competitor comprising E-selectin coupled to a detectable label; providing an antibody, or antigen binding fragment thereof, that specifically binds E-selectin; combining the sample, the antibody, and the labeled competitor, wherein the E-selectin in the sample competes with the labeled competitor for binding to the antibody; and determining the concentration of E-selectin in said sample by measuring the amount of labeled competitor not bound to antibody by detection of the label. The amount of labeled competitor bound to the antibody in the absence of the sample is compared with the amount of labeled competitor bound to the antibody when the sample is added. The amount of decrease of bound labeled-competitor in the presence of the sample is an indicator of the amount of non-labeled E-selectin present in the sample such that the assay can be used to assess the presence and level of E-selectin in a sample. In some embodiments, E-selectin is soluble E-selectin. In some embodiments, E-selectin is membrane bound E-selectin.

In one embodiment, the invention provides a method for assessing the effectiveness of a treatment for a disease or disorder associated with an increased level of E-selectin in a subject, the method comprising administering a treatment to the subject and comparing the level of E-selectin in a sample obtained from the subject prior to the treatment with the level of E-selectin in an otherwise identical sample obtained from the subject after the treatment, wherein the level of E-selectin in a sample is assessed using a E-selectin specific antibody, and further wherein a lower, level of E-selectin in the sample collected from the subject after the treatment compared with the level of E-selectin in a sample collected from the subject prior to treatment is an indication of the effectiveness of the course of treatment.

The term "labeled," with regard to the E-selectin specific antibody or labeled competitor, includes direct labeling by coupling (i.e., physically Inking) a detectable substance to the antibody or labeled competitor, as well as indirect labeling of the antibody or labeled competitor by coupling it with another reagent that is directly labeled. An example of indirect labeling includes detection of a primary antibody using a fluorescent-labeled secondary antibody. In vitro techniques for detection of a polypeptides of the invention include enzyme linked immunosorbent assays (ELISAs), Western blots, immunoprecipitation, and immunofluorescence.

The term "sample" is intended to include tissues, cells, and biological fluids (e.g., blood, CSF, urine, etc.) isolated from a subject, as well as tissues, cells, and fluids present within a subject.

The antibodies, labeled competitors, and potential therapeutic compounds described herein are also suitable for use with any of a number of other homogeneous and heterogeneous immunoassays with a range of detection systems.

Compositions

An anti-E-selectin antibody, or antigen-binding fragment thereof, of the disclosure may be formulated as a pharmaceutical composition. The pharmaceutical composition may further comprise a pharmaceutically acceptable carrier, excipient, and/or stabilizer (Remington: The Science and practice of Pharmacy 21st Ed., 2005, Lippincott Williams and Wilkins, Ed. K. E. Hoover), in the form of lyophilized formulation or aqueous solution. As used herein, the term "pharmaceutically acceptable carrier" or "pharmaceutically acceptable excipient" includes any material which, when combined with an active ingredient, allows the ingredient to retain biological activity and is non-reactive with the subject's immune system.

Examples include, but are not limited to, any of the standard pharmaceutical carriers such as phosphate buffered saline (PBS), water, normal saline (0.9%), emulsions (e.g., o/water emulsions) and various types of wetting agents. Preferred diluents for aerosol or parenteral administration are PBS and normal saline.

Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, polysorbate (e.g., polysorbate 80 (PS80), polysorbate 60 (PS60), polysorbate 20 (PS20)), or polyethylene glycol (PEG). Pharmaceutically acceptable excipients are further described herein.

Pharmaceutical compounds of the disclosure may include one or more pharmaceutically acceptable salts. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) ol-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, It will be suitable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

A pharmaceutical composition of the present disclosure may be prepared, packaged, or sold in a formulation suitable for ophthalmic administration. Such formulations may, for example, be in the form of eye drops including, for example, a 0.1%-1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; filers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the disclosure are known in the art and described, for example in Remington's Pharmaceutical Sciences, Genaro, ed., Mack Publishing Co., Easton, Pa. (1985), which is incorporated herein by reference.

In some embodiments, an anti-E-selectin antibody, or antigen-binding fragment thereof is formulated in a vial containing 100 mg of an anti-E-selectin antibody (e.g., antibody 1444), or an antigen binding fragment thereof, in 1 mL of an aqueous buffered solution. In some embodiments, an anti-E-selectin antibody, or antigen-binding fragment thereof is formulated in a vial containing 150 mg of an anti-E-selectin antibody (e.g., antibody 1444), or an antigen binding fragment thereof, in 1 mL of an aqueous buffered solution. In some embodiments, an anti-E-selectin antibody, or antigen-binding fragment thereof is formulated in a vial containing 15 mg, 40 mg, 100 mg, 300 mg, or 600 mg of an anti-E-selectin antibody (e.g., antibody 1444), or an antigen binding fragment thereof, in 1 mL of an aqueous buffered solution, optionally for subcutaneous administration. In some embodiments, an anti-E-selectin antibody, or antigen-binding fragment thereof is formulated in a vial containing 500 mg of an anti-E-selectin antibody (e.g., antibody 1444), or an antigen binding fragment thereof, in 1 mL of an aqueous buffered solution, optionally for intravenous administration.

In some embodiments, a pharmaceutical composition comprises about 25 mg/mL, 50 mg/mL, 75 mg/mL, 100 mg/mL, 125 mg/mL, 150 mg/ml antibody, or antigen binding fragment thereof. In some embodiments, a pharmaceutical composition comprises about 100 mg/mL antibody, or antigen binding fragment thereof. In some embodiments, a pharmaceutical composition suitable for SC and/or IV administration comprises about 100 mg/mL anti-E-selectin antibody (e.g., antibody 1444), or antigen binding fragment thereof.

In some embodiments, an anti-E-selectin antibody, or antigen-binding fragment thereof, is administered in an intravenous or subcutaneous formulation as a sterile aqueous solution comprising a polypeptide comprising the amino acid sequence of SEQ ID NO:7 or SEQ ID NO:13. In some embodiments, an anti-E-selectin antibody, or antigen-binding fragment thereof, is administered in an intravenous or subcutaneous formulation as a sterile aqueous solution comprising a polypeptide comprising the amino acid sequence of SEQ ID NO:1. In some embodiments, an anti-E-selectin antibody, or antigen-binding fragment thereof, is administered in an intravenous or subcutaneous formulation as a sterile aqueous solution comprising a polypeptide comprising the amino acid sequence of SEQ ID NO:7 or SEQ ID NO:13 and polypeptide comprising the amino acid sequence of SEQ ID NO:1.

In some embodiments, an anti-E-selectin antibody (e.g., antibody 1444), or antigen-binding fragment thereof, is administered as an intravenous or subcutaneous formulation that is a sterile aqueous solution containing about 5 mg/mL, about 10 mg/mL, about 15 mg/mL, about 20 mg/mL of antibody, about 25 mg/mL, about 50 mg/mL, about 75 mg/ml, about 100 mg/mL, about 125 mg/mL, or about 150 mg/mL of antibody or antigen-binding fragment thereof. In some embodiments, an intravenous or subcutaneous formulation Is a sterile aqueous solution comprising sodium acetate, polysorbate 80, and sodium chloride at a pH ranging from about 5 to 6. In some embodiments, an intravenous formulation is a sterile aqueous solution containing 5 or 10 mg/mL of antibody, with 20 mM sodium acetate, 0.2 mg/mL polysorbate 80, and 140 mM sodium chloride at pH 5.5. Further, a solution comprising an antibody, or antigen-binding fragment thereof, can comprise, among many other compounds, glutamic acid, histidine, mannitol, sucrose, trehalose, glycine, poly(ethylene) glycol, EDTA, methionine, polysorbate 80 and any combination thereof, and many other compounds known in the relevant art.

In one embodiment, a pharmaceutical composition of the present disclosure comprises the following components: 50 mg/mL or 100 mg/mL of an anti-E-selectin antibody (e.g., antibody 1444) or antigen-binding fragment of the present disclosure, 20 mM histidine, 8.5% sucrose, and 0.02% polysorbate 80, 0.005% EDTA at pH 5.8. In one embodiment, a pharmaceutical composition of the present invention comprises the following components: 100 mg/mL anti-E-selectin antibody (e.g., antibody 1444) or antigen-binding fragment of the present disclosure, 10 mM histidine, 5% sucrose, and 0.01% polysorbate 80 at pH 5.8.

In some embodiments, a pharmaceutical composition comprises an anti-E-selectin antibody, or antigen-binding fragment thereof (e.g., antibody 1444) at a concentration of 100 mg/mL, 1.12 mg/mL L-histidine, 2.67 mg/mL L-histidine hydrochloride monohydrate, 85 mg/mL sucrose, 0.05 mg/mL edetate disodium dihydrate and 0.2 mg/mL polysorbate 80 at pH 5.8 in a nominal fill volume of 1.0 mL. Such pharmaceutical composition is suitable for SC or IV administration.

Such pharmaceutical compositions may be provided as a liquid formulation or as a lyophilized powder. When a powder is reconstituted at full volume, the composition retains the same formulation. Alternatively, a powder may be reconstituted at half volume, in which case the composition comprises the same components but at twice the concentration.

With regard to a therapeutic agent, where the agent is, e.g., a small molecule to be used in a combination therapy, it can be present in a pharmaceutical composition in the form of a physiologically acceptable ester or salt, such as in combination with a physiologically acceptable cation or anion, as is well known in the art.

Formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In some embodiments, a composition of the disclosure is a pyrogen-free formulation which is substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. These substances can cause fever, hypotension and shock if administered to humans. Due to the potential harmful effects, it is advantageous to remove even low amounts of endotoxins from intravenously administered pharmaceutical drug solutions. The Food and Drug Administration ("FDA") has set an upper limit of 5 endotoxin units (EU) per dose per kilogram body weight in a single one-hour period for intravenous drug applications (The United States Pharmacopeial Convention, Pharmacopeial Forum 26 (1): 223 (2000)). When therapeutic proteins are administered in amounts of several hundred or thousand milligrams per kilogram body weight it is advantageous to remove even trace amounts of endotoxin. In one embodiment, endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg. In another embodiment, endotoxin and pyrogen levels in the composition are less than about 10 EU/mg, or less than about 5 EU/mg, or less than about 1 EU/mg, or less than about 0.1 EU/mg, or less than about 0.01 EU/mg, or less than about 0.001 EU/mg.

Dosing and Administration

To prepare a pharmaceutical or sterile composition including an anti-E-selectin antibody, or antigen-binding fragment thereof, of the disclosure, the antibody is mixed with a pharmaceutically acceptable carrier or excipient (see above). Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY;

Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of a symptom, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, 1996, Antibody Therapy, Bios Scientific Pub. Ltd, Oxfordshire, UK; Kresina (ed.), 1991, Monoclonal Antibodies, Cytokines and Arthritis, Marcel Dekker, New York, N.Y.; Bach (ed.), 1993, Monoclonal Antibodies and Peptide Therapy in Autoimmune Diseases, Marcel Dekker, New York, N.Y.; Baert, et al., New Engl. J. Med. 2003; 348:601-608; Milgrom, et al., New Engl. J. Med. 1999; 341:1966-1973; Slamon, et al., New Engl. J. Med. 2001; 344:783-792; Beniaminovitz, et al., New Engl. J. Med. 2000; 342:613-619; Ghosh, et al., New Engl. J. Med. 2003; 348:24-32; Lipsky, et al., New Engl. J. Med. 2000; 343:1594-1602).

Determination of the appropriate dose is made by a clinician, e.g., using parameters or factors known or suspected in the art to affect treatment or predicted to affect treatment. Generally, the dose begins with an amount somewhat less than the optimum dose and R is increased by small Increments thereafter until the desired or optimum effect is achieved relative to any negative side effects. A specific dose protocol may be one involving the maximal dose or dose frequency that avoids significant undesirable side effects.

"Reducing, decreasing, neutralizing or inhibiting interaction with E-selectin" as the terms are used herein, means to reduce, decrease, neutralize or inhibit interaction of E-selectin with a ligand as compared to the level of interaction prior to any therapeutic intervention. As used herein, "free E-selectin," means E-selectin that is not bound or otherwise in a complex with another molecule (e.g., a free or cell surface expressed E-selectin ligand).

The level of E-selectin includes the level of free E-selectin in a subject where the level is assessed using the methods disclosed herein or any other method for assessing the level of free E-selectin known in the art.

In one embodiment, a level of free E-selectin is reduced as compared to the level of E-selectin in a subject prior to administration of an anti-E-selectin antibody of the disclosure. In one embodiment, a level of free E-selectin is reduced compared to a standard level of free E-selectin that is associated with or indicates that a subject is afflicted with a disease, disorder or condition associated with or mediated by free E-selectin.

In some embodiments, the disclosure encompasses reducing the level of free E-selectin to a level where there is a decrease, or complete lack of, detectable deleterious effect(s) mediated by or associated with free E-selectin. In some embodiments, an effective dose of an anti-E-selectin antibody is administered to neutralize E-selectin functional activity, such as (a) leukocyte tethering to endothelial cells; (b) activation of stable adhesion to endothelial cells; (c) slow rolling of leukocytes to arrest; (d) trans-endothelial migration of leukocytes; (e) affinity and avidity of CD18 integrins; (f) trafficking of leukocytes to sites of acute inflammation; (g) increase in cytosolic calcium; (h) increase in tyrosine phosphorylation that activates p38 MAP kinase and Syk kinase; (i) recruitment of platelets and leukocytes from the blood to the vascular endothelium; and/or (j) does not create a pro-inflammatory environment.

As used herein, an "effective dosage," "effective dose," "effective amount," or "therapeutically effective amount" of a drug, compound, or pharmaceutical composition is an amount sufficient to effect any one or more beneficial or desired results. For prophylactic use, beneficial or desired results include eliminating or reducing the risk, reducing the frequency of occurrence (e.g., over a period of time, e.g., weekly, monthly, yearly), lessening the severity, and/or delaying the onset of the disease, including biochemical, histological and/or behavioral symptoms of the disease, its complications and intermediate pathological phenotypes presenting during development of the disease. For therapeutic use, beneficial or desired results include detectable clinical results such as reducing, or decreasing the rate of, VOC or reducing one or more symptoms resulting from expression of E-selectin, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

In some embodiments, an effective dose of an anti-E-selectin antibody is administered to a patient with SCD, skin diseases (e.g., psoriasis), inflammatory diseases (e.g., rheumatoid arthritis) and complications of diabetes.

In some embodiments, an effective dose on an anti-E-selectin antibody (e.g., antibody 1444) is administered to treat and/or prevent diseases, disorders and conditions associated with, or mediated by, E-selectin expression and/or E-selectin binding to a ligand (e.g., sLex A and/or X determinants), including, but not limited to, SCD, vaso-occlusive crisis, pain, organ infarction, ischemia, stroke, end organ dysfunction, acute chest and vascular obstruction.

In some embodiments, an effective dose on an anti-E-selectin antibody (e.g., antibody 1444) is administered to prevent, or reduce the occurrence of, a VOC when utilized as a prophylactic treatment for SCD. In some embodiments, prophylactic administration of an anti-E-selectin antibody (e.g., antibody 1444) is administered one time. In some embodiments, prophylactic administration of an anti-E-selectin antibody (e.g., antibody 1444) is administered on an on-going basis (e.g., one or more than one dose, over a period of time).

In some embodiments, an effective dose on an anti-E-selectin antibody (e.g., antibody 1444) is administered to treat acute VOC in patients with SCD by decreasing the duration, intensity and/or severity of the VOC.

In some embodiments, an effective dose on an anti-E-selectin antibody (e.g., antibody 1444) is administered to treat, prevent and/or ameliorate at least one sign and/or symptom of SCD, for example, those affecting the cardiothoracic system (e.g., chronic restrictive lung disease, left ventricular diastolic disease, pulmonary hypertension, acute chest syndrome, dysrhythmias, sudden death, vaso-occlusive crisis), the nervous system (e.g., hemorrhagic stroke, venous sinus thrombosis, silent cerebral infarction of the brain, chronic pain, acute ischemic stroke of the brain, proliferative retinopathy, orbital infarction, cognitive Impairment) the reticuloendothelial system (e.g., splenic sequestration, functional hyposplenism, anemia, hemolysis), the musculoskeletal system (e.g., avascular necrosis, skin ulcerations), the urogenital system (e.g., papillary necrosis, proteinuria, renal failure, hematuria, nocturnal enuresis, priapism) and the gastrointestinal system (e.g., cholelithiasis, cholangiopathy, hepatopathy, mesenteric vaso-occlusion).

In some embodiments, the method or use comprises administering a dose of about 1 mg to about 800 mg. In some embodiments, the method or use comprises administering a dose of about 1 mg to 800 mg as an initial fixed dose. In some embodiments, the method or use comprises administering a dose of about 1 mg to about 2 mg, about 2 mg to about 5 mg, about 5 mg to about 10 mg, about 10 mg to about 20 mg, about 20 mg to about 30 mg, about 30 mg to about 40 mg, about 40 mg to about 50 mg, about 50 mg to about 60 mg, about 60 mg to about 70 mg, about 70 mg to about 80 mg, about 80 mg to about 90 mg, about 90 mg to about 100 mg, about 100 mg to about 150 mg, about 150 mg to about 200 mg, about 200 mg to about 300 mg, about 300 mg to about 400 mg, about 400 mg to about 500 mg, about 500 mg to about 600 mg, about 600 mg to about 700 mg or about 700 mg to about 800 mg, optionally as an initial fixed dose. In some embodiments, the method or use comprises administering a dose of about 15 mg, 40 mg, 100 mg, 150 mg, 300 mg, 500 mg or 600 mg of an anti-E-selectin antibody, or antigen binding fragment thereof, or a pharmaceutical composition thereof, of the invention. In some embodiments, the dose is an initial fixed dose.

In some embodiments, the method or use comprises administering a dose of about 150 mg of an anti-E-selectin antibody, or antigen binding fragment thereof, or a pharmaceutical composition thereof, of the invention. In some embodiments, the method or use comprises administering a dose of about 150 mg of an anti-E-selectin antibody, or antigen binding fragment thereof, or a pharmaceutical composition thereof, of the invention on a weekly basis. In some embodiments, the method or use comprises administering a dose of about 150 mg of an anti-E-selectin antibody (e.g., antibody 1444), or antigen binding fragment thereof, or a pharmaceutical composition thereof, of the invention, subcutaneously, on a weekly basis.

In some embodiments, the method or use comprises administering dose of about 0.01 mg/kg to about 30 mg/kg of an antibody, or antigen binding fragment thereof, or a pharmaceutical composition of the invention, optionally as an initial dose. The initial dose may be followed by one or more subsequent doses. In some embodiments, one or more subsequent dose may be administered at least any of weekly, every other week, every three weeks, every four weeks, every five weeks, every six weeks, every seven weeks, every eight weeks, every nine weeks, every ten weeks, every eleven weeks, or every twelve weeks.

An initial dose may be followed by one or more subsequent doses. In some embodiments, a subsequent dose is the same dose, a lower dose or a higher dose of anti-E-selectin antibody as compared to the initial dose. In some embodiments, one or more subsequent dose may be administered at least any of weekly, every other week, every three weeks, every four weeks, every five weeks, every six weeks, every seven weeks, every eight weeks, every nine weeks, every ten weeks, every eleven weeks, or every twelve weeks. A specific dose protocol is one involving the maximal dose or dose frequency that avoids significant undesirable side effects.

A pharmaceutical composition of the present disclosure may also be administered via one or more routes of administration using one or more of a variety of methods known in the art. As will be appreciated by the skilled artisan, the route and/or mode of administration will vary depending upon the desired results. Selected routes of administration for antibodies of the disclosure include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the disclosure can be administered via a non-parenteral route, such as a topical, epidermal or mucosal route of administration, for example, intranasaly, orally, vaginally, rectally, sublingually or topically.

In some embodiments, an anti-E-selectin antibody, or antigen-binding fragment thereof of the disclosure is administered intravenously. In some embodiments, an anti-E-selectin antibody, or antigen-binding fragment thereof of the disclosure is administered subcutaneously.

In some embodiments, an anti-E-selectin antibody, or antigen-binding fragment thereof of the disclosure is administered intravenously or subcutaneously on a weekly basis. In some embodiments, an anti-E-selectin antibody, or antigen-binding fragment thereof of the disclosure is administered at a unit dose of about 15 mg, about 40 mg, about 100 mg, about 150 mg, about 300 mg, or about 600 mg subcutaneously on a weekly basis. In some embodiments, an anti-E-selectin antibody, or antigen-binding fragment thereof of the disclosure is administered at a unit dose of about 150 mg or about 500 mg intravenously on a weekly basis.

In some embodiments, a subject is administered an anti-E-selectin antibody, or antigen-binding fragments thereof, of the disclosure on a weekly basis and a therapeutically active compound or treatment modality which is effective in treating and/or preventing at least one sign and/or symptom of a disease (e.g., SCD) on a daily, weekly, biweekly, monthly, or on an as needed basis. The disclosure provides protocols for the administration of pharmaceutical composition comprising anti-E-selectin antibodies, or antigen-binding fragments thereof, of the disclosure alone or in combination with other therapies to a subject in need thereof. The therapies (e.g., prophylactic or therapeutic agents) of the combination therapies of the present disclosure can be administered concomitantly or sequentially to a subject. The therapy (e.g., prophylactic or therapeutic agents) of the combination therapies of the present disclosure can also be cyclically administered.

In some embodiments, an anti-E-selectin antibody, or antigen-binding fragment thereof, or a pharmaceutical composition comprising the same, is administered about twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, once every three months, once every four months, once every five months, once every six months, once every seven months, once every eight months, once every nine months, once every ten months, once every eleven months or once every twelve months.

In some embodiments, part of a dose is administered by an intravenous bolus and the rest of the dose is administered by infusion of the antibody formulation. For example, a 0.01 mg/kg intravenous injection of the anti-E-selectin antibody, or antigen-binding fragment thereof, may be given as a bolus, and the rest of the antibody dose may be administered by intravenous injection. A predetermined dose of the anti-E-selectin antibody, or antigen-binding fragment thereof, may be administered, for example, over a period of an hour and a half to two hours to five hours.

Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

Kits

The disclosure also provides a kit comprising any or all of the anti-E-selectin antibodies or antigen-binding fragments thereof described herein. A kit of the disclosure includes one or more containers comprising an anti-E-selectin antibody, or antigen-binding fragment thereof, described herein and instructions for use in accordance with any of the methods of the disclosure described herein. Generally, these instructions comprise a description of administration of an antibody for the above described therapeutic treatments. In some embodiments, a kit is provided for producing a single-dose administration unit. In certain embodiments, a kit can contain both a first container having a dried protein and a second container having an aqueous formulation. In certain embodiments, a kit containing an applicator, e.g., single and multi-chambered pre-filled syringe or device (e.g., liquid syringes and lyosyringes), is included.

In some embodiments, a kit contains an applicator comprising an anti-E-selectin antibody, or antigen-binding fragment thereof, wherein the applicator is designed, or acceptable for self-administration, by a patient (e.g., a patient with SCD). In some embodiments, self-administration is by subcutaneous administration.

Instructions relating to use of an anti-E-selectin antibody, or antigen-binding fragment thereof, generally include information as to dosage, dosing schedule, and route of administration (e.g., SC or IV) for the intended treatment. A container may be a unit dose, a bulk package (e.g., a multi-dose package) or a sub-unit dose. Instructions supplied in a kit of the disclosure are typically written instructions on a label or package insert (e.g., a paper sheet included in the kit), but machine-readable instructions (e.g., instructions carried on a magnetic or optical storage disk) are also acceptable.

A kit of this disclosure is in suitable packaging. Suitable packaging includes, but is not limited to, a vial, bottle, jar, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example a container may be an intravenous solution bag or a vial having a stopper pierceable by a hypodermic injection needle). A container may also have a sterile access port (for example a container may be an intravenous solution bag or a vial having a stopper pierceable by a hypodermic injection needle). At least one active agent in the composition is an anti-E-selectin antibody of the disclosure. A container may further comprise an additional therapeutic agent.

In one embodiment, the invention includes a kit further comprising a second therapeutically active compound, or treatment modality, which is effective in treating or preventing symptoms of SCD, wherein the amount of the anti-E-selectin antibody and the second compound or modality together achieve synergistic effects in the treatment or prevention of symptoms of SCD, that is, the combination is "synergistic," (i.e., the combination provides an effect greater than a merely additive effect of two or more individual therapies). Such a kit comprising synergistic combination therapies may advantageously utilize lower dosages of the administered therapeutic agents, thus avoiding possible toxicities or complications associated with the various monotherapies.

In some embodiments, a kit may further comprise at least one additional therapeutically active compound useful for the treatment or prevention of a sign and/or symptom of SCD including, for example, penicillin, hydroxyurea (e.g., DROXIA, HYDREA), L-glutamine (e.g., ENDARI), crizanlizumab (ADAKVEO), voxelotor (OXBRYTA), apixaban (ELIQUIS), rivaroxaban (XARELTO), a non-steroidal anti-inflammatory drug, an analgesic generally, an opioid analgesic, IW-1701, riociguat (ADEMPAS), ticagrelor (BRILINTA) or memantine (NAMENDA).

A kit may optionally provide additional components such as a buffer and interpretive information. Normally, a kit comprises a container and a label or package insert(s) on, or associated with, the container.

The disclosure also provides a diagnostic kit comprising any or all of the antibodies, or antigen-binding fragments thereof, described herein. A diagnostic kit is useful for, for example, detecting the presence of E-selectin in a sample. In some embodiments, a diagnostic kit can be used to identify an individual with a latent disease, disorder or condition that may put them at risk of developing an E-selectin-mediated disease, disorder or condition. In some embodiments, a diagnostic kit can be used to detect the presence and/or level of E-selectin in an individual suspected of having an E-selectin mediated disease, disorder or condition.

Diagnostic kits of the disclosure include one or more containers comprising an anti-E-selectin antibody, or antigen-binding fragment thereof, described herein and instructions for use in accordance with any of the methods of the disclosure described herein. Generally, the instructions comprise a description of use of an E-selectin antibody, or antigen-binding fragment thereof, to detect the presence of E-selectin in individuals at risk for, or suspected of having, an E-selectin mediated disease, disorder or condition, such as a VOC in a patient suspected or known to be afflicted with SCD and or any other condition associated with or mediated by an abnormal form of β-globin including: HbS, HbC, Hbβ$^+$-thalassemia, Hbβ$^0$-thalassemia or other Hb variant. In some embodiments, an exemplary diagnostic kit can be configured to contain reagents such as, for example, an E-selectin antibody, or antigen-binding fragment thereof, a negative control sample, a positive control sample, and directions for using the kit.

Biological Deposits

The heavy and light chains of anti-E-selectin antibody 1444 were deposited under terms in accordance with the Budapest Treaty with the American Type Culture Collection (ATCC), 10801 University Boulevard, Manassas, Va. 20110-2209, USA, on Dec. 6, 2019.

| Antibody | Description | ATCC Accession No. |
|---|---|---|
| 1444 | Ab 1444-HC (heavy chain of antibody 1444) | PTA-126529 |
| 1444 | Ab 1444-LC (light chain of antibody 1444) | PTA-126530 |

The deposits were made under the provisions the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer Inc. and ATCC, which assures permanent and unrestricted availability of the progeny of the culture of the deposit to the pubic upon Issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (Including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

General Techniques

It is to be understood that this invention is not limited to specific synthetic methods of making that may of course vary. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mulls et al., eds., 1994); Current Protocols in Immunology (J. E. Coligan et al., eds., 1991); Sambrook and Russell, Molecular Cloning: A Laboratory Manual, 3rd. ed., Cold Spring Harbor Laboratory Press, Cold Spring Harbor, N.Y. (2001); Ausubel et al., Current Protocols in Molecular Biology, John Wiley & Sons, NY (2002); Harlow and Lane Using Antibodies: A Laboratory Manual, Cold Spring Harbor Laboratory Press, Cold Spring Harbor, N.Y. (1998); Coligan et al., Short Protocols in Protein Science, John Wiley & Sons, NY (2003); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Enzymatic reactions and purification techniques are performed according to manufacturer's specifications, as commonly accomplished in the art or as described herein. The nomenclatures used in connection with, and the laboratory procedures and techniques of, analytical chemistry, biochemistry, immunology, molecular biology, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

EQUIVALENTS

The foregoing description and following Examples detail certain specific embodiments of the disclosure and describes the best mode contemplated by the inventors. It will be appreciated, however, that no matter how detailed the foregoing may appear in text, the disclosure may be practiced in many ways and the disclosure should be construed in accordance with the appended claims and any equivalents thereof.

Although the disclosed teachings have been described with reference to various applications, methods, kits, and compositions, it will be appreciated that various changes and modifications can be made without departing from the teachings herein and the claimed disclosure below. The following examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

EXAMPLES

In order that this invention may be better understood, the following examples are set forth. These examples are for purposes of illustration only and are not to be construed as limiting the scope of the invention in any manner.

Example 1: Isolation of Rat Monoclonal Antibodies that Bind to Human E-Selectin

Sprague Dawley Rats were immunized with soluable human E-selectin extracellular domain (Uniprot P16581 residues 22-556; SEQ ID NO:133) using a Rappid IP Immunization method. Hybridoma supernatants were screened for binding to soluable human (ID NO:133) and mouse (SEQ ID NO:135) E-selectin extracellular domain and truncated human E-selectin (UniProtKB P16581 residues 22-178; SEQ ID NO:197) and truncated mouse E-selectin (UniProtKB Q00690 residues 22-178; SEQ ID NO:199) E-selectin using a direct binding HRP-ELISA. Of the set of binders, 6 antibodies (0039, 0158, 0159, 0164, 0170 and 0180) were selected that bound to soluable and truncated human E-selectin and one antibody (0027) was selected that bound to soluable and truncated mouse E-selectin. These seven antibodies were chosen for molecular cloning and subsequence analysis.

Example 2: Cloning of Rat Anti-E-Selectin Antibody Heavy and Light Chain Variable Regions Heavy chain (HC) and light chain (LC) variable regions of the anti-E-selectin antibodies that bound to human E-selectin (antibodies 0039, 0158, 0159, 0164, 0170 and 0180) or mouse E-selectin (antibody 0027) were cloned using the SMART® cDNA synthesis system (Clontech Laboratories Inc. of Mountain View, Calif.) followed by PCR amplification. The cDNA was synthesized from 1 µg total RNA isolated from approximately 500,000 hybridoma cells for each clone 0027, 0039, 0158, 0159, 0164, 0170 and 0180), using the RNEasy kit (Qiagen) and the SMART® IIA oligo (Clontech Laboratories Inc.) with Superscript™ III reverse transcriptase (Invitrogen). The cDNA was then amplified by PCR using a primer that anneals to the SMART® IIA oligo sequence and rat constant region-specific primer (rat Kappa for the light chain and rat IgG1 for the heavy chain) with Q5S High-Fidelity 2× Master Mix (New England Biolabs Inc.). Heavy and light chain PCR products were subcloned into the pCR4-TOPO vector (Invitrogen) and the nucleic acid sequence was determined. This method is advantageous in that no prior knowledge of the DNA sequence is required. In addition, the resultant DNA sequence is not altered by use of degenerate PCR primers.

The variable heavy regions (VH for antibody 0039 (amino acid sequence of SEQ ID NO-60), VH for antibody 0158 (amino acid sequence of SEQ ID NO:75), VH for antibody 0159 (amino acid sequence of SEQ ID NO:90), VH for antibody 0164 (amino acid sequence of SEQ ID NO:35), VH for antibody 0170 (amino acid sequence of SEQ ID NO:104), VH for antibody 0180 (amino acid sequence of SEQ ID NO:118), and VH for antibody 0027 (amino acid sequence of SEQ ID NO:128)) were cloned into the pTT5 mammalian expression vector containing the human IgG1 constant region that was mutated to abolish effector function (Leu234Aa, Leu235Ala and Gly237Aa, EU numbering; U.S. Pat. No. 5,624,821) (amino acid sequence of SEQ ID NO:15), producing chimeric heavy chains. Variable light regions (VL for antibody 0039 (amino acid sequence of SEQ ID NO:57), VL for antibody 0158 (amino acid sequence of SEQ ID NO:73), VL for antibody 0159 (amino acid sequence of SEQ ID NO:87), VL for antibody 0164 (amino acid sequence of SEQ ID NO:32), VL for antibody 0170 (amino acid sequence of SEQ ID NO:102), VL for antibody 0180 (amino acid sequence of SEQ ID NO:116) and VL for antibody 0027 (amino acid sequence of SEQ ID NO:122)) were cloned into the pTT5 mammalian expression vectors containing the constant region of human kappa (amino acid sequence of SEQ ID NO:14) to produce chimeric light chains.

Example 3: Binding and Neutralization of Anti-E-Selectin Antibodies

The binding of anti-E-selectin antibodies to human (amino acid sequence of SEQ ID NO:133 plus a 10 His purification tail) and mouse (amino acid sequence of SEQ ID NO:135 plus a 10 His purification tail) E-selectin extracellular domains was measured using a recombinant antigen binding ELISA with HPR detection. 384-well Maxisorp plates were used to capture the human and mouse His-tagged recombinant E-selectin polypeptides. The polypeptides were incubated with chimeric antibodies of varying concentrations and detected with HRP-labeled anti-human IgG1 antibodies. Antibodies 0039, 0158, 0159, 0164, 0170 and 0180 bound to human E-selectin with $EC_{50}$s of 0.02 nM, 0.03 nM, 0.02 nM, 0.02 nM, 0.01 nM and 0.01 nM, respectively. None of these antibodies bound to mouse E-selectin, with $EC_{50}$ of >133 nM. Antibody 0027 bound to mouse E-selectin with an $EC_{50}$ of 0.02 nM, but did not bind to human E-selectin, with an $EC_{50}$ of >133 nM.

The neutralization ability of anti-E-selectin antibodies was measured in an AlphaLISA homogenous competition assay. Here the antibodies competed against the interaction of human E-selectin extracellular domain (amino acid sequence of SEQ ID NO:133 plus 10 His purification tail), mouse E-selectin extracellular domain (amino acid sequence of SEQ ID NO:135 plus 10 His purification tail), or cynomolgus E-selectin extracellular domain (amino acid sequence of SEQ ID NO:175 plus 10 His purification tail) to a sialyl-Lewis A ligand. For this experiment 1 µL of an antibody was added to a well of a 384-well plate followed by 1 µL of sialyl Lewis A-PAA-biotin to a final concentration of 1.75 nM. This was incubated at room temperature for 15 minutes, followed by addition of 1.4 µL of human, mouse or cynomolgus monkey E-selectin added to a final concentration of 7 nM. This was again incubated at room temperature for 15 minutes. To this, 1.4 µL AlphaLISA beads was added (Ni-donor/SA-acceptor) for a final assay concentration of 10 µg/mL. This was incubated in the dark at room temperate for at least 10 hours. The plates were then read using the AlphaLISA protocol (Envision).

The $EC_{50}$ of neutralization of human, mouse and cynomolgus monkey E-selectin was measured for chimeric anti-E-selectin antibodies 0027, 0158, 0159, 0164, 0170 and 0180. Antibodies 0039, 0158, 0159, 0164, 0170 and 0180 had $EC_{50}$ values to human E-selectin of <1 nM, while antibody 0027 did not neutralize human E-selectin and had an $EC_{50}$ of >133 nM. Antibodies 0158, 0159, 0164, 0170 and 0180 had $EC_{50}$ values to cynomolgus E-selectin of <1 nM, antibody 0039 had an $EC_{50}$ to cynomolgus E-selectin of >63 nM and antibody 0027 didn't neutralize cynomolgus E-selectin and had an $EC_{50}$ of >133 nM. Antibody 0027 had an $EC_{50}$ value of 1 nM to mouse E-selectin while antibodies 0039, 0158, 0159, 0164, 0170 and 0180 did not neutralize mouse E-selectin and had an $EC_{50}$ of >133 nM (Table 4).

TABLE 4

Binding and neutralization of anti-E-selectin chimeric antibodies to human, mouse and cynomolgus monkey E-selectin using an HRP binding ELISA and AlphaLISA neutralization assay.

| anti-body | HC SEQ ID NO | LC SEQ ID NO | HRP binding $EC_{50}$ (nM) | | alphaLISA neutralization $EC_{50}$ (nM) | | |
|---|---|---|---|---|---|---|---|
| | | | human E-selectin | mouse E-selectin | human E-selectin | mouse E-selectin | cynomolgus monkey E-selectin |
| 0027 | 124 | 119 | >133 | 0.02 | >133 | 1 | >133 nM |
| 0039 | 59 | 56 | 0.02 | >133 | <1 | >133 nM | >63 |
| 0158 | 74 | 72 | 0.03 | >133 | <1 | >133 nM | <1 |
| 0159 | 89 | 86 | 0.02 | >133 | <1 | >133 nM | <1 |
| 0164 | 34 | 31 | 0.02 | >133 | <1 | >133 nM | <1 |
| 0170 | 103 | 101 | 0.01 | >133 | <1 | >133 nM | <1 |
| 0180 | 117 | 115 | 0.01 | >133 | <1 | >133 nM | <1 |

Example 4: Kinetic Evaluation of Anti-E-selectin Using Surface Plasmon Resonance (SPR)

Human (amino acid sequence of SEQ ID NO:133), mouse (amino acid sequence of SEQ ID NO:135), and cynomolgus monkey (amino acid sequence of SEQ ID NO:175) E-selectin extracellular domain proteins were prepared. Each protein contained a C-terminal 10 residue histidine tag utilized for purification. An anti-human Fc sensor chip was prepared by amine coupling of anti-human IgG antibody (catalog number BR-1008-39, GE Healthcare) to all four flow cells of a carboxymethylated dextran coated sensor chip (CM5) (catalog number BR100530, GE Healthcare) according to the manufacturer's protocols. The flow cells were activated by injecting a 1:1 mixture of 400 mM 1-Ethyl-3-(3-dimethylaminopropyl) carbodiimide hydrochloride (EDC) and 100 mM N-hydroxysuccinimide (NHS) for 7 minutes at a flow rate of 10 µL/minute. Anti-human IgG antibody was diluted to 25 µg/m in 10 mM sodium acetate pH 5.0 and injected over all flow cells for 7 minutes at 10 µL/minute. All flow cells were blocked with 1M Ethanolamine-HCl (ETH) for 7 minutes at 10 µL/minute. Final immobilization level of the capture antibody was approximately 10,000 resonance units (RU). The running buffer for immobilization and kinetics was HBS-EP+ (10 mM 4-(2-hydroxyethyl)-1-piperazineethanesulfonic acid (HEPES) pH 7.4, 150 mM sodium chloride, 3 mM ethylenediaminetetraacetic acid (EDTA), 0.05% (v/v) Tween-20).

To characterize binding of antibodies to human, cynomolgus monkey, and mouse E-selectin, an antibody was diluted to 0.5 µg/mL in HBS-EP+ and captured by the anti-human IgG immobilized on flow cells 2, 3 and 4 for 30 seconds to 1 minute at a flow rate of 10 µL/minute to achieve a capture level of 70 to 300 RU. Flow cell 1 was used as a reference surface. After antibody capture, the flow rate was increased to 50 µL/minute and buffer or E-selectin proteins ranging in concentration from 15 nM to 405 nM in HBS-EP+ were injected over all flow cells for a 1.0 minute association period and then allowed to dissociate for 6 to 15 minutes. HBS-EP+ buffer cycles collected for each captured antibody were used for double-referencing (Myszka D G. J. Mol. Recognition 1999; 12(5):279-84). At the end of each cycle, the entire anti-IgG surface was regenerated by a 30 second pulse of 3 M $MgCl_2$ and a 30 second pulse of ionic buffer (1.83 M $MgCl_2$, 0.92 M Urea, 1.83 M Guanidine HCl, pH 7.4) (Andersson K. Analy. Chem. 1999; 71(13): 2475-81). Kinetic assays were conducted at 25° C. at a collection rate of 10 Hertz (Hz) on a BIAcore™ T200 instrument (GE Healthcare). Rate constants and affinities were determined by fitting the data to a 1:1 binding model in BIAcore™ 200 Evaluation software version 3.0 (GE Healthcare).

Binding affinities were determined for human and cynomolgus monkey E-selectin for antibodies 0039, 0158, 0159, 0164, 0170 and 0180, and for mouse E-selectin antibody 0027 by first binding the antibody to immobilized anti-human IgG. After antibody capture, dilutions of the E-selectin proteins were flowed over and the association rate constant (ka), disassociation rate constant (kd), t½, and $k_D$ values were determined for binding to human, cynomolgus and mouse E-selectin (Tables 5-7). In this SPR analysis the affinity ($K_D$) of antibodies 0039, 0158, 0159, 0164, 0170 and 0180 to human E-selectin was 68.0 nM, 21.6, 324 nM, 54.4 nM, 628 nM and 2940 nM, respectively. The affinity of chimeric antibodies 0039, 0159, 0164, 0170 and 0180 to cynomolgus monkey E-selectin was 45.8 nM, 243.5 nM, 45.4 nM, 492 nM, and 3145 nM, respectively. Antibody 0158 did not show binding to cynomolgus monkey E-selectin. The affinity $K_D$ of chimeric antibody 0027 to mouse E-selectin was 1.2 nM.

TABLE 5

Affinity of anti-E-selectin antibodies to human E-selectin measured by surface plasmon resonance.

| | | | analyte human E-selectin | | | |
|---|---|---|---|---|---|---|
| antibody | HC SEQ ID NO | LC SEQ ID NO | ka (1/Ms) | kd (1/s) | t½ (s) | $K_D$ (nM) |
| 0039 | 59 | 56 | 6.42E+04 | 4.21E−03 | 173.64 | 68.0 |
| 0158 | 74 | 72 | 8.10E+04 | 1.75E−03 | 397.16 | 21.6 |
| 0159 | 89 | 86 | 1.15E+05 | 3.71E−02 | 18.71 | 324 |
| 0164 | 34 | 31 | 2.07E+05 | 1.13E−02 | 61.61 | 54.4 |
| 0170 | 103 | 101 | 8.74E+04 | 5.49E−02 | 12.64 | 628.5 |
| 0180 | 117 | 115 | 2.62E+05 | 6.66E−01 | 1.05 | 2940 |

TABLE 6

Affinity of anti-E-selectin antibodies to cynomolgus monkey E-selectin measured by surface plasmon resonance.

| | | | analyte cynomolgus monkey E-selectin | | | |
|---|---|---|---|---|---|---|
| antibody | HC SEQ ID NO | LC SEQ ID NO | ka (1/Ms) | kd (1/s) | t½ (s) | $K_D$ (nM) |
| 0039 | 59 | 56 | 8.24E+04 | 3.77E−03 | 184.07 | 45.8 |
| 0158 | 74 | 72 | ND | ND | | weak |
| 0159 | 89 | 86 | 1.54E+05 | 3.74E−02 | 18.53 | 243.5 |
| 0164 | 34 | 31 | 2.65E+05 | 1.20E−02 | 57.75 | 45.4 |
| 0170 | 103 | 101 | 1.15E+05 | 5.64E−02 | 12.30 | 492 |
| 0180 | 117 | 115 | 2.45E+05 | 7.49E−01 | 0.93 | 3145 |

ND: not detected

TABLE 7

Affinity of anti-mouse E-selectin antibody to mouse E-selectin measured by surface plasmon resonance.

| antibody | HC SEQ ID NO | LC SEQ ID NO | analyte mouse E-selectin | | | |
|---|---|---|---|---|---|---|
| | | | ka (1/Ms) | kd (1/s) | t½ (s) | $K_D$ (nM) |
| 0027 | 124 | 119 | 1.92E+05 | 2.31E−04 | 3010.95 | 1.2 |

Example 5: Neutralization of Ligand Binding of Anti-E-Selectin Antibodies in a Static Binding Assay The ability of anti-E-selectin antibodies to neutralize ligand binding was assessed in a static neutralization assay using a competition enzyme-linked immunosorbent assay (ELISA) to evaluate the neutralization of the sialyl Lewis antigen to Chinese hamster ovary cells (CHO) engineered to express E-selectin.

Briefly, CHO cells expressing human E-selectin were grown in culture medium (MEM (Minimum Essential Medium) Alpha Medium, supplemented with 10% dialyzed fetal bovine serum, 100 nM methotrexate and 100 Units/mL penicillin and 100 μg/mL streptomycin) and were seeded at 12,500 cells per well into a 96 well tissue culture plate and incubated at 37° C., 5% $CO_2$ for 48 hours to form a confluent monolayer. Plates were subsequently washed twice with 200 μL of calcium magnesium free phosphate buffered saline (PBS). Anti-E-selectin antibodies 0039, 0158, 0159, 0164, 0170 and 0180 or an IgG1 isotype control were added to the assay in the presence of a small synthetic conjugate of biotinylated, sialyl Lewis A polyacrylamide (Carbosynth LLC; OS45446) with a streptavidin/horseradish peroxidase (100 μL total) and incubated at 37° C., 5% $CO_2$ for 2 hours. Plates were then washed twice with 200 μL of calcium magnesium free PBS. Following the incubation, the cells were washed twice with 200 μL of wash buffer containing 2 mM of calcium chloride (50 mM TRIS [trisaminomethane], 150 mM sodium chloride; 0.05% polysorbate 20, pH 7.4; 2 mM of calcium chloride). Signal was developed by adding 100 μL of 1-Step Ultra TMB substrate (Thermo Scientific, 34028) and incubating for 30 minutes at room temperature. Reactions were stopped using 2 M of sulfuric acid and absorbance read at 450 nm (Spectramax M5e). Data were analyzed and graphed using GraphPad Prism software (Version 8.0.2). Estimated half maximal inhibitory concentration ($IC_{50}$) values derived from the analysis (Table 8).

The tested antibodies dose-dependently neutralized ligand binding to cell surface expressed human E-selectin. The estimated $IC_{50}$ values in the neutralization assay for chimeric antibodies 0039, 0164, 0158, 0159, 0170 and 0180 were 3.76 nM, 2.77 nM, 2.87 nM, 3.24 nM, 2.3 nM and 3.83 nM, respectively. Antibody 0027 did not neutralize binding of the sialyl Lewis A polyacrylamide ligand binding to cell surface expressed human E-selectin. A human IgG control antibody did not demonstrate an effect in these assays.

Example 6: Inhibition of Cellular Binding in a Static Adhesion Assay of Anti-E-Selectin Antibodies The ability of chimeric anti-E-selectin antibodies 0039, 0164, 0158, 0159, 0170 and 0180 to inhibit adhesion of cells expressing an E-selectin ligand, under a static condition, to CHO cells expressing human E-selectin was evaluated.

CHO cells expressing human E-selectin were cultured in Alpha medium (MEM [Minimum Essential Medium]) Alpha Medium, Corning)/10% dialyzed fetal bovine serum (GIBCO)/100 Units/mL penicillin and 100 μg/mL streptomycin (Gibco)/100 nM methotrexate and were maintained at 37° C. with 5% $CO_2$ and 95% humidity. HL-60 cells (a human promyelocytic cell line which expresses the E selectin ligand, PSGL-1 and other sialyl Lewis ligands) were maintained at 37° C. with 5% $CO_2$ and 95% humidity in RPMI/Glutamine growth medium (Gibco)/10% fetal bovine serum (Gibco)/100 Units/mL penicillin and 100 μg/mL streptomycin (Gibco). CHO cells expressing human E-selectin were seeded in 96-well flat bottom black plates at a density of 11,500 cells/well and incubated to form a confluent monolayer for 48 hours at 37° C., 5% $CO_2$ and 95% air in a humidified incubator.

For the static adhesion neutralization assay, HL-60 cells at log phase were washed three times in PBS and resuspended in 500 μL of PBS and an equal volume of 2 μM carboxyfluorescein diacetate succinimidyl ester fluorescent dye [(CFSE) (ThemoFisher)]. The cells were incubated for 10 minutes at room temperature in the dark. The labeling was stopped with the addition of 4 mLs of cold HL-60 growth medium on ice for 5 minutes. The labeled HL-60 cells were washed three times in Hanks Balanced Salt Solution (HBSS)/1% Bovine Serum Albumin (BSA)/0.1% sodium azide, resuspended at a density of 400,000 cells/mL for use in the static adhesion assays.

Anti-E-selectin chimeric antibodies 0039, 0164, 0158, 0159, 0154, 0170 and 0180, negative control anti-P-selectin antibodies and a control human IgG were serially (concentrations ranging from 1333 nM to 1.83 nM) diluted in HBSS/1% BSA/0.1% sodium azide. A no antibody control was prepared for each antibody. The E-selectin CHO cell monolayer was gently washed three times with HBSS/1% BSA/0.1% sodium azide and 100 μL of the cellular suspension was added to the wells and incubated for one hour on ice. Fifty μL (20,000) CFSE-labeled HL-60 cells were added per well without removing the antibody. The labeled HL-60 cells were incubated with the CHO cell monolayer for 1 hour at 37° C. at 5% $CO_2$ and 95% air in a humidified incubator. The plate was washed three times with HBSS/1% BSA/0.1% sodium azide, a 100 μL of HBSS/1% Triton-X100 was added and incubated for 10 minutes in the dark. The fluorescence of the bound HL-60 cells was measured at excitation/emission wavelengths of 494/521 nanometer using Spectramax i3X (Molecular Devices) to determine the number of adhered HL-60 cells. Background binding was subtracted using the signal from the no cell control wells and the % adhesion was determined using the human IgG control as 100%. The estimated $EC_{50}$ values were determined in the GraphPad Prism suite.

Under static adhesion conditions, antibodies 0158 and 0164 inhibited HL-60 cell adhesion to CHO cells expressing human E-selectin with >50% inhibition at 16.5 nM. Antibody 0159 inhibited HL-60 cell adhesion to CHO cells expressing human E-selectin with >50% inhibition at 49.4 nM. Antibodies 0170 and 0180 inhibited HL-60 adhesion to CHO cells expressing human E-selectin with >50% inhibition at 444 nM. Antibody 0039 at a concentration up to 1333 nM did not inhibit HL-60 cell adhesion to CHO cells expressing human E-selectin. Negative control antibodies did not inhibit the adhesion of HL-60 cells (Table 8).

Example 7: Cell Surface Binding (FACS) of the Anti-E-Selectin Antibodies

Antibody binding was evaluated using Fluorescence Activated Cell Sorting (FACS) to cells engineered to express E-selectin or P-selectin. Species cross-reactivity to cynomolgus monkey was also evaluated.

CHO cells expressing human E-selectin or P-selectin were cultured in Alpha medium (MEM [Minimum Essential Medium]) Alpha Medium, Corning) supplemented with 10% dialyzed fetal bovine serum (GIBCO), 100 Units/mL penicillin and 100 µg/mL streptomycin (Gibco). For the CHO cells expressing human E-selectin, the growth media was also supplemented with 100 nM methotrexate. CHO cells expressing cynomolgus monkey E-selectin were cultured in R1 medium (RI Dulbecco's Modifies Eagle's Medium/Ham's F12 modification) supplemented with 10% heat inactivated fetal bovine serum (GIBCO), 100 Units/mL penicillin and 100 µg/mL streptomycin and 125 µg/mL Zeocin (GIBCO). Cells were maintained in growth medium at 37° C., 5% $CO_2$ and 95% air in a humidified incubator. Methotrexate or Zeocin were removed from the medium prior to culture for experiments. CHO-E selectin cells or P-selectin cells were detached from T-150 flasks using citric saline (135 mM KCl, 15 mM sodium citrate) and immediately re-calcified with the addition of $CaCl_2$ to the detached cells to a final concentration of 1 mM. Growth media was immediately added to the detached cells, then centrifuged at 300×g for 5 minutes at room temperature to pellet the cells. Cells were plated into 96-well V-bottom plates in cold CHO buffer consisting of phosphate buffered saline (PBS), pH 7.4 containing bovine serum albumin (BSA; Sigma-Aldrich) at final concentration of 1%, calcium chloride at final concentration of 1 mM, and sodium azide at a final concentration of 0.1%, for 5 minutes on wet ice. After incubation, the cells were centrifuged at 300×g for 2 minutes at 4° C. to remove the buffer.

Test antibody solutions were prepared with serial dilutions (ranging from 1333.3 nM to 0.0022 nM) using CHO buffer as diluent and 100 µL was added and incubated in the designated volume of serially-diluted antibody and incubated for 45 minutes on ice. After incubation, antibodies were removed and the cells were washed three times by centrifugation at 300×g for 1 minute at 4° C. and resuspended in cold CHO buffer. The washed cells were incubated for 30 minutes on wet ice with 100 µL of a 1:1000 dilution of APC-conjugated AffiniPure F(ab)₂ Fragment Goat Anti-human IgG, Fcγ (Jackson Immunoresearch). The cells were washed three or four times prior to resuspension in CHO buffer for flow cytometric analysis. A Becton Dickinson LSRFortessa instrument using 640 nanometer laser line was used to acquire cell fluorescence data. Geometric mean fluorescence of cells was analyzed by FlowJo software package (FlowJo, LLC) and plotted against antibody concentration. The estimated $EC_{50}$ values were calculated using nonlinear regression analysis in the Prism suite (GraphPad, version 8) (Table 8).

Chimeric antibodies 0039, 0164, 0158, 0159, 0154, 0170 and 0180 exhibited binding to cell surface expressed human E-selectin on CHO cells with estimated $EC_{50}$ values ranging from 1.99 nM to 4.99 nM (Table 8). Antibodies 0039, 0164, 0158, 0159, 0170 and 0180 also bound to CHO cells expressing cynomolgus monkey E-selectin with estimated $EC_{50}$ values ranging from 3.37 to 13.98. Antibodies 0164, 0158, 0159, 0154, 0170 and 0180 did not bind to CHO-expressed human P-selectin, indicating selectivity for E-selectin. Antibody 0039 exhibited minimal binding to CHO-expressed human P-selectin with an estimated $EC_{50}$ value>354 nM.

TABLE 8

Cell binding and neutralization of anti-E-selectin antibodies.

| | static neutralization | | cell surface antibody binding by FACS | | |
|---|---|---|---|---|---|
| antibody | sialyl Lewis ligand adhesion CHO-human E-selectin cells $IC_{50}$ (nM) | HL-60 Cell adhesion CHO-Human E-selectin cells $IC_{50}$ (nM) | binding to CHO-human E-selectin cells $EC_{50}$ (nM) | binding to CHO-cynomolgus monkey E-selectin cells $EC_{50}$ (nM) | binding to CHO-human P-selectin cells $EC_{50}$ (nM) |
| 0039 | 3.76 | ND | 4.99 | 4.07 | >354 nM |
| 0164 | 2.77 | >50% at 16.5 nM | 4.43 | 1.73 | ND |
| 0158 | 2.87 | >50 % at 16.5 nM | 3.75 | 13.98 | ND |
| 0159 | 3.24 | >50% at 49.4 nM | 2.44 | 3.37 | ND |
| 0170 | 2.30 | >50% at 444 nM | 1.99 | 3.76 | ND |
| 0180 | 3.83 | >50% at 444 nM | 4.31 | 3.66 | ND |

ND = Not Detected

Example 8: Ex Vivo Neutralization of Anti-E-Selectin Antibodies Using a Physiological Flow Assay Ex vivo cellular adhesion was analyzed under physiological flow conditions using a BioFlux™ system (Fluxion, San Francisco, Calif., USA) using BioFlux™ plates/chambers (Fluxion Biosciences, 48-well low shear, 0-20 dynes/cm²; 910-0004). Adhesion assays were performed using recombinant purified soluble E- or P-selectin proteins and human HL-60 cells (ATCC CCL-240). HL-60 cells express the E selectin ligand, PSGL-1 and other sialyl Lewis ligands. HL-60 cells were maintained at 37° C. with 5% $CO_2$ and 95% humidity in RPMI/Glutamine growth medium (Gibco) with 10% fetal bovine serum (Gibco); 1× penicillin/streptomycin (Gibco). The cells were maintained at 37° C. prior to perfusion and BioFlux™ assays were performed at room temperature. First, to mimic a surface of an activated endothelial cell, the flow chambers were coated with equal amounts of both human E- and P-selectin soluble recombinant proteins. BioFlux™ flow microchannels were coated with 10 µg/mL each of soluble recombinant human P-selectin (R & D Systems, ADP3) and E-selectin (R & D Systems, ADP1) prepared in PBS, perfused at 1 dyne/cm² for 5 minutes, incubated at room temperature for 1 hour and washed with PBS for 3-5 minutes at 1 dyne/cm². The E-selectin chimeric antibodies, 0039, 0158, 0159, 0164, 0170 and 0180, were diluted in PBS and the plates were treated with the test articles (concentrations from 1.6 to 1000 nM), or the vehicle control for 1 hour at 1 dyne/cm². The HL-60 cells were centrifuged at 1000 rpm for 5 minutes, stained with Calcein AM (Calcein; Life Technologies™; C3099) for 30 minutes, washed twice with phosphate buffered saline (PBS; Gibco) and resuspended to a concentration of ~3×10⁶ cells/mL in PBS. Diluted antibody stocks were also added to the cellular suspension prior to perfusion in the flow chambers. An aliquot of 100 µL of HL-60 cells was perfused in each channel for 10 minutes at physiological shear flow of 1 dyne/cm$^2$. PBS was perfused for 2-3 minutes at 1 dyne/cm$^2$ to remove the non-adherent cells. Adherent cells were visualized and counted using a Nikon Eclipse Ti-S (NIS-Elements BR 3.2 64-bit) inverted-stage phase-contrast fluorescent microscope with 40× magnification. Cellular counts were normalized to phosphate buffer vehicle control. Each experiment has two wells per conditions. Data was graphed and analyzed using GraphPad Prism (8.0.2). Estimated hag-maximal inhibitory concentration (IC$_{50}$) values were derived from the analysis.

In these studies, which were designed to mimic blood flow through the vasculature ex vivo, E-selectin antibodies 0039, 0164, 0158, 0159, 0170 and 0180 neutralized the adhesion of HL-60 cells to soluble recombinant E-selectin protein with estimated IC$_{50}$ values of 264.7 nM, 1.7 nM, 17.9 nM, 21 nM, 74.2 nM, and 224.7 nM, respectively (Table 9).

TABLE 9

Neutralization of HL-60 binding to soluble human E-selectin protein under physiological flow.

| antibody | neutralization of HL-60 cell binding under physiological flow to soluble human E-selectin protein IC$_{50}$ (nM) |
| --- | --- |
| 0039 | 264.7 |
| 0164 | 1.7 |
| 0158 | 17.9 |
| 0159 | 21 |
| 0170 | 74.2 |
| 0180 | 224.7 |

Example 9: Epitope Grouping of Anti-E-Selectin Antibodies

The six neutralizing chimeric antibodies (0039, 0158, 0159, 0164, 0170 and 0180) were grouped into epitope bins based on a competition assay using an Octet biosensor. Anti-human FC (AHC) coated tips were transferred to a well containing 20 μg/mL of one of the seven antibodies for 600 seconds to allow the first antibody to bind to the anti-human FC. The tips were transferred to a second well with 300 nM human E-selectin extracellular domain (SEQ ID NO:133 plus a 10 His purification tail) and allowed to associate for 100 seconds. Finally, the tips were transferred to a third well containing a second antibody for 100 seconds. Antibodies were scored as non-competing if the second antibody showed an increase in biosensor signal above that produced by the first antibody, and they were scored as competing if the second antibody did not produce an additional increase in signal (Table 10).

Based on these competition data, antibodies 0159, 0164, 0170 and 0180 defined one epitope group, 0158 defined a second epitope group and 0039 defined a third epitope group. The first group and the second group partially overlap, the second and third groups partially overlap, and the first and third group are non-overlapping. In Table 10 a "+" indicates that the second antibody (Indicated by the column heading) bound in the presence of the first antibody (indicated by row headings). A "−" indicates that no increase in signal was observed upon addition of the second antibody.

TABLE 10

Epitope grouping of anti-IL-E-selectin antibodies by Octet biosensor

| 2$^{nd}$ Ab (column) | 1$^{st}$ Ab (rows) | | | | | |
| --- | --- | --- | --- | --- | --- | --- |
| | 0039 | 0158 | 0159 | 0164 | 0170 | 0180 |
| 0039 | − | − | + | + | + | + |
| 0158 | − | − | − | − | − | − |
| 0159 | + | − | − | − | − | − |
| 0164 | + | − | − | − | − | − |
| 0170 | + | − | − | − | − | − |
| 0180 | + | − | − | − | − | − |

Example 10: Crystal Structure and Epitope

The Fab fragment of the anti-E-selectin chimeric antibody 0164 was obtained by cleaving the full-length IgG with papain and removing the Fc using a Protein A resin. The Fab was mixed with truncated human E-selectin (described in Example 1) at a 1:1 molar ratio and the resulting complex was purified by size exclusion chromatography (SEC). Crystals of the complex formed in 200 mM calcium acetate pH 7.5, 20% PEG 3350. Data was collected to 2.68 Å at beamline 17-ID at the Advanced Photon Source. The structure was solved by molecular replacement and refined to R/Rfree of 0.243/0.252 (FIG. 1). The crystal structure has a single copy of E-selectin bound to a single 0164 Fab fragment in the asymmetric unit in space group P3121.

Based upon the crystal structure, the residues of E-selectin that interacted with antibody 0164 were determined based upon: I) residues that were within 3.8 Å, ) normalized surface area (Å$^2$) buried due to interactions between pairs of 0164 antibody residues and E-selectin residues of >5 Å$^2$, iii) formation of a salt bridge, iv) formation of a hydrogen bond or v) formation of a water-mediated hydrogen bond. The list of residues, whose numbering is based upon the mature human E-selectin sequence (SEQ ID NO:132) includes T7, E8, A9, M10, T11, P46, S47, Y48, N82, N83, Q85, E88, E92, Y94, R97, N105, E107, R108, S110, K111, K112 and K113 (Table 11).

The interaction of E-selectin with its natural ligand Sialyl-Lewis X (sLeX) by x-ray crystallography is shown in the PDB structure (1g1t) (see www.rcsb.org/structure/1g1t). In this structure, the E-selectin residues that are within 3.8 Å of sLeX and are similar to the interaction with antibody 0164 are Y48, N82, N83, E92, Y94, R97, N105, and E107 based on the numbering of SEQ ID NO:132. Additional residues that are also within 3.8 angstroms of sLex are E80, E98 and D106 (based on the numbering of SEQ ID NO:132). Given the significant overlap of the epitopes of sLex and antibody 0164, it is likely that the neutralization activity demonstrated by this antibody is a result of directly blocking the interaction of sLeX and other similar ligands like Sialyl-Lewis A (sLeA) with E-selectin.

TABLE 11

Interaction of E-selectin with anti-E-selectin antibody 0164 or sLeX.

| E-selection position | amino acid | Interaction with Antibody 0164 | | | | | Interaction with sLeX within 3.8 Å |
|---|---|---|---|---|---|---|---|
| | | within 3.8 Å | buried surface area (Å2) | hydrogen bond | salt bridge | $H_2O$ mediated interaction | |
| 7 | T | X | 13.3 | | | | |
| 8 | E | X | 94.5 | 1 | | | |
| 9 | A | X | 39.2 | | | | |
| 10 | M | | 5 | | | | |
| 11 | T | X | 7.3 | | | | |
| 46 | P | X | 56.2 | | | | |
| 47 | S | X | 36.1 | 1 | | | |
| 48 | Y | X | 13.1 | | | | X |
| 82 | N | X | 29.5 | 1 | | | X |
| 83 | N | X | 29.4 | 1 | | | X |
| 85 | Q | X | 35.7 | | | | |
| 88 | E | | 9.9 | 1 | | | |
| 92 | E | X | 6.9 | 1 | | | X |
| 94 | Y | X | 9.3 | 1 | | | X |
| 97 | R | | 29.7 | | X | | X |
| 105 | N | X | 1.4 | 1 | | | X |
| 107 | E | X | 30.6 | 1 | | | X |
| 108 | R | X | 72.6 | 2 | | | |
| 110 | S | X | 29.3 | 1 | | | |
| 111 | K | X | 63.9 | | X | | |
| 112 | K | X | 112.6 | 1 | X | X | |
| 113 | K | | 15.1 | | | | |
| 80 | E | | | | | | X |
| 98 | E | | | | | | X |
| 106 | D | | | | | | X |

Example 11: Humanization of Rat Anti-E-Selectin Antibodies

Humanized versions of neutralizing rat chimeric antibodies 0039, 0158, 0159, 0164, 0170 and 0180 were generated by complementarity determining region (CDR) grafting (referred to hereafter as "CDR-grafted"). For antibodies 0039, 0158, 0164 and 0180, heavy chain CDRs were grafted onto a human DP-54 framework region (VH3 sub-group). Humanized antibody 0039 contained rat amino acid residues including methionine at position 48, glycine at position 49, and valine at position 78. Humanized antibody 0158 contained rat amino acid residues including valine at position 24, methionine at position 48, glycine t position 49, threonine at position 73, and valine at position 78. Humanized antibody 0164 contained rat amino acid residues including alanine at position 71, alanine at position 78 and methionine at position 94. Humanized antibody 0180 contained rat amino acid residues including isoleucine at position 48, glycine at position 49, leucine at position 69, serine at position 71 threonine at position 73, alanine at position 78 and isoleucine at position 94.

For antibody 0159, heavy chain CDRs were grafted onto DP-7 framework region (VH1 sub-group). Humanized antibody 0159 contained rat amino acid residues including valine at position 24, leucine at position 69, alanine at position 78 and methionine at position 94.

For antibody 0170, heavy chain CDRs were grafted onto DP-10 framework region (VH1 sub-group). Humanized antibody 0170 contained rat amino acid residues including valine at position 24, isoleucine at position 69, threonine at position 73, and valine at position 94.

All 6 humanized antibodies were grafted with the JH4 J-segment (amino acid sequence of SEQ ID NO:6).

For antibodies 0039, 0158, 0164, 0170 and 0180, light chain CDRs were grafted onto human DPK9 framework region (VKI sub-group). Humanized antibody 0039 contained rat amino acid residue cysteine at L87. Humanized antibody 0158, contained rat amino acid residue methionine at position 4. Humanized antibodies 0164 and 180 contained rat amino acid residue phenylalanine at position 87. Humanized antibody 0170 contained rat amino acid residues including methionine at position 48 and phenylalanine at position 87.

For antibody 0159, light chain CDRs were grafted onto human DPK1 framework region (VKI sub-group).

The humanized $V_H$ regions were joined to the effector-function mutated human IgG1 constant region (amino acid sequence of SEQ ID NO:16) and then sub-cloned into a proprietary expression vector to generate the CDR-grafted heavy chains SEQ ID NO:51 (0039 CDR graft; heavy chain of antibody 0525), SEQ ID NO:62 (0158 CDR graft; heavy chain of antibody 265_254), SEQ ID NO:76 (0159 CDR graft; heavy chain of antibody 0929_0548), SEQ ID NO:22 (0164 CDR graft; heavy chain of antibody 0841), SEQ ID NO:91 (0170 CDR graft; heavy chain of antibody 0955_0300) and SEQ ID NO:110 (0180 CDR graft; heavy chain of antibody 0564).

The humanized $V_L$ regions were fused to the human kappa constant region (amino acid sequence of SEQ ID NO:14) and then sub-cloned into a proprietary expression vector to create the CDR-grafted light chains SEQ ID NO:46 (0039 CDR graft; light chain of antibody 0525), SEQ ID NO:67 (0158 CDR graft; light chain of antibody 0265_0254), SEQ ID NO:81 (0159 CDR graft; light chain of antibody 0929_0548), SEQ ID NO:17 (0164 CDR graft; light chain of antibody 0841), SEQ ID NO:96 (0170 CDR graft; light chain of antibody 0955_0300) and SEQ ID NO:105 (0180 CDR graft; light chain of antibody 0564).

TABLE 12

Anti-E-selectin antibodies.

| Chimeric antibody | Humanized antibody | Optimized Antibody |
|---|---|---|
| 0164 | 0841 | |
| | 0978 | 1444 |
| | | 1448 |
| | | 1282 |
| | | 1284 |
| 0039 | 0525 | |
| 0158 | 0265_0254 | |
| 0159 | 0929_0548 | |
| 0170 | 0955_0300 | |
| 0180 | 0564 | |
| 0027 | | |

Example 12: Kinetic Evaluation of Humanized Anti-E-Selectin Using Surface Plasmon Resonance Binding affinity was determined for human and cynomolgus monkey E-selectin for the humanized antibody 0841 (HC SEQ ID NO:22, LC SEQ ID NO:17) using SPR in a method similar to the method described in Example 4. This was done by first binding the antibody to immobilized anti-human IgG. After antibody capture, dilutions of the E-selectin proteins were flowed over and the association rat constant (ka), disassociation rat constant (kd), t½, and $K_D$ values were determined for binding to human and cynomolgus E-selectin (Table 13). In this SPR analysis, the affinity of humanized anti-E-selectin antibody 0841 to human E-selectin and cynomolgus monkey E-selectin was 92.85 nM and 138.5 nM, respectively.

TABLE 13

Affinity of anti-E-selectin antibodies to human and cynomolgus monkey E-selectin measured by surface plasmon resonance.

| | analyte | | | | | | | |
|---|---|---|---|---|---|---|---|---|
| | human E-selectin | | | | cynomolgus monkey E-selectin | | | |
| antibody | Ka (1/Ms) | kd (1/s) | t½ (s) | $K_D$ (nM) | ka (1/Ms) | kd (1/s) | t½ (s) | $K_D$ (nM) |
| 0841 | 2.55E+05 | 2.37E−02 | 29.31 | 92.85 | 1.82E+05 | 2.52E−02 | 27.56 | 138.5 |

Example 13: Cell Surface Binding (FACS) of Humanized Anti-E-Selectin Antibody (0841)

Antibody binding was evaluated using flow cytometry (FACS) of cells engineered to express E-selectin. Species cross-reactivity to cynomolgus monkey was also evaluated.

CHO cells expressing human E-selectin were cultured in Alpha medium (MEM [Minimum Essential Medium]) Alpha Medium, Corning) supplemented with 10% dialyzed fetal bovine serum (GIBCO) and 100 Units/mL penicillin and 100 µg/mL streptomycin in the culture medium (Gibco). For the CHO cells expressing human E-selectin, the growth media was also supplemented with 100 nM methotrexate. CHO cells expressing cynomolgus monkey E-selectin were cultured in R1 medium (RI Dulbecco's Modifies Eagle's Medium/Ham's F12 modification) supplemented with 10% heat inactivated fetal bovine serum (GIBCO), 100 Units/mL penicillin and 100 µg/mL streptomycin and 125 µg/mL Zeocin (GIBCO). Cells were maintained in growth medium at 37° C., 5% $CO_2$ and 95% air in a humidified incubator. Methotrexate or Zeocin were removed from the medium prior to culture for experiments. CHO-E selectin cells were detached from T-150 flasks using citric saline (135 mM KCl, 15 mM sodium citrate) and immediately re-calcified with the addition of $CaCl_2$ to the detached cells to a final concentration of 1 mM. Growth media was immediately added to the detached cells, then centrifuged at 300×g for 5 minutes at room temperature to pellet the cells. Cells were plated into 96-well round-bottom plates in cold CHO buffer consisting of phosphate buffered saline (PBS), pH 7.4 containing bovine serum albumin (BSA; Sigma-Aldrich) at final concentration of 1%, calcium chloride at final concentration of 1 mM and sodium azide at a final concentration of 0.1%, for 5 minutes on wet ice. After incubation, the cells were centrifuged at 300×g for 2 minutes at 4° C. to remove the buffer.

Test antibody solutions were prepared with serial dilutions (ranging from 1333.3 nM to 0.0022 nM) using CHO buffer as diluent, 100 µL was added in the designated volume of serially-diluted antibody and incubated for 45 minutes on ice. After incubation, the antibodies were removed and the cells were washed three times by centrifugation at 300×g for 1 minute at 4° C. and resuspended in cold CHO buffer. The washed cells were resuspended and incubated for 30 minutes on wet ice with 100 µL of 1:1000 dilution of APC-conjugated AffiniPure F(ab')₂ Fragment Goat Anti-human IgG, Fcγ (Jackson Immunoresearch). The cells were washed three or four times prior to resuspension in CHO buffer for flow cytometric analysis. A Becton Dickinson LSRFortessa instrument using 640 nanometer laser line was used to acquire cell fluorescence data. Geometric mean fluorescence of cells was analyzed by FlowJo software package (FlowJo, LLC) and plotted against antibody concentration. The estimated $EC_5$ values were calculated using nonlinear regression analysis in the GraphPad Prism suite.

Binding of humanized antibody 0841 to human and cynomolgus monkey E-selectin expressed on the surface of CHO cells was similar with estimated $EC_{50}$ values of 1.62 and 1.54 nM, respectively (Table 14). The estimated $EC_5$ values for antibody 0164 in the same assay were similar with estimated $EC_5$ values of 1.39 and 1.73 nM for CHO expressed human and cynomolgus monkey E-selectin, respectively (Table 14).

Example 14: Humanized Anti-E-Selectin Antibody Neutralization of Ligand Binding to CHO Cells Expressing Human or Cynomolgus Monkey E-Selectin In a static ligand cellular adhesion assay, horse radish peroxidase (HRP) conjugated E-selectin ligand and E-selectin antibodies compete for binding to human or cynomolgus E-selectin expressed on Chinese hamster ovary (CHO) cells. The ability of anti-E-selectin antibodies to neutralize the ligand binding was assessed in a static neutralization assay using a competition enzyme-inked immunosorbent assay (ELISA) to evaluate the neutralization of the sialyl Lewis antigen to Chinese hamster ovary cells (CHO) engineered to express human or cynomolgus monkey E-selectin.

CHO cells expressing human E-selectin were grown in culture medium (MEM (Minimum Essential Medium) Alpha Medium, supplemented with 10% dialyzed fetal bovine serum, 100 nM Methotrexate and 100 Units/mL penicillin and 100 µg/mL streptomycin) and CHO cells expressing cynomolgus monkey E-selectin were cultured in R1 medium (RI Dulbecco's Modifies Eagle's Medium/ Ham's F12 modification) supplemented with 10% heat inactivated fetal bovine serum (GIBCO), 100 Units/mL penicillin and 100 µg/mL streptomycin and 125 µg/mL Zeocin (GIBCO). CHO cells expressing E-selectin were seeded at 12,500 cells per well into a 96 well tissue culture plate and incubated at 37° C., 5% $CO_2$ for 48 hours to form a confluent monolayer. Plates were subsequently washed twice with 200 µL of calcium magnesium free PBS. Anti- E-selectin antibodies, or an IgG1 isotype control, were added to the assay in the presence of a small synthetic conjugate of biotinylated, sialyl Lewis A polyacrylamide (Carbosynth LLC, OS45446) or sialyl Lewis X polyacrylamide (Glycotech, 01-045) with a streptavidin/horseradish peroxidase (100 µL total) and incubated at 37° C., 5% $CO_2$ for 2 hours. Plates were then washed twice with 200 µL of calcium magnesium free PBS. Following the incubation, the cells were washed twice with 200 µL of wash buffer containing 2 mM calcium chloride (50 mM TRIS [trisaminomethane], 150 mM sodium chloride; 0.05% polysorbate 20, pH 7.4; 2 mM of calcium chloride). Signal was developed by adding 100 µL of 1-Step Ultra TMB substrate (Thermo Scientific, 34028) and incubating for 30 minutes at room temperature. Reactions were stopped using 2 M of sulfuric acid and absorbance was read at 450 nm (Spectramax M5e). Data was analyzed and graphed using GraphPad Prism software (Version 8.0.2). Estimated half maximal inhibitory concentration ($IC_{50}$) values were derived from the analysis.

Neutralization of sialyl Lewis ligand binding by humanized antibody 0841 to human and cynomolgus monkey E-selectin expressed on the surface of CHO cells was similar with estimated $IC_{50}$ values of 3.81 and 1.74 nM, respectively (Table 14). The estimated $IC_{50}$ values for 0164 in the same assay were similar with estimated $IC_{50}$ values of 5.17 and 2.00 nM for CHO expressed human and cynomolgus monkey E-selectin, respectively.

Example 15: Humanized Anti-E-Selectin Antibody Neutralization of Cellular Adhesion Under Physiological Flow Ex vivo cellular rolling/adhesion studies were conducted to evaluate the potency and the neutralizing activity of antibodies 0841 and 0164 to inhibit the adhesion of HL-60 cells to CHO-human E-selectin cells using a physiological flow system.

CHO-human E-selectin cells were maintained in Alpha medium/10% dialyzed fetal bovine serum (GIBCO)/penicillin/streptomycin (1×) and 100 nM methotrexate at 37° C. with 5% $CO_2$ and 95% humidity. The BioFlux™ plates were coated with 50 µg/mL of fibronectin in PBS at a flow rate of 1 dyne/$cm^2$ and incubated for 1 hour at room temperature. Chinese Hamster Ovary cells expressing human E-selectin (human CHO-E-selectin cells) were prepared for assay by treatment with a 1:1 ratio of 0.05% Trypsin-Ethylenediaminetetraacetic acid (EDTA), and StemPro Accutase (Gibco; A1110501) for 5 minutes at 37° C., neutralized with an equal volume of growth medium, collected, centrifuged at 1000 rpm for 5 minutes and re-suspended to a final concentration of ~30×$10^6$ cells/mL in growth medium. The plates were perfused twice with CHO-human E-selectin growth medium at 1 dyne/$cm^2$ for 2-3 minutes at room temperature. All medium was removed and 30 µL of CHO-human E-selectin cells (at ~30×$10^6$ cells/mL) were perfused for 25 seconds at 3-4 dyne/$cm^2$. The plates were removed from the instrument and were incubated at 37° C. in a 5% $CO_2$ incubator for 1 hour. Medium was removed and 500 µL of fresh growth medium was added and the cells were incubated at 37° C. in a 5% $CO_2$ incubator overnight. Following the incubation, the CHO-E monolayers were washed (3-4 dynes/$cm^2$) on the BioFlux instrument with fresh growth medium. Antibody 0841 (serial dilutions), isotype control antibody, and IgG1 control antibody (200 nM), in PBS and the vehicle control were perfused at 1 dyne/$cm^2$ for 1 hour.

HL-60 cells were maintained at 37° C. with 5% $CO_2$ and 95% humidity in RPMI/Glutamine growth medium (Gibco) with 10% fetal bovine serum (Gibco); and 1× penicillin/streptomycin (Gibco). The cells were maintained at 37° C. prior to perfusion. The HL-60 cells were centrifuged at 1000 rpm for 5 minutes, stained with Calcein AM (Life Technologies™; C3099) for 30 minutes, washed twice with phosphate buffered saline (PBS; Gibco) and resuspended to a concentration of ~3×$10^6$ cells/mL in PBS. Diluted antibody stocks were also added to the cellular suspension prior to perfusion in the flow chambers. An aliquot of 100 µL of HL-60 cells, plus inhibitor, were perfused in each channel for 10 minutes at physiological shear flow of 1 dyne/$cm^2$. PBS was perfused for 2-3 minutes at 1 dyne/$cm^2$ to remove the non-adherent cells and the plates were imaged and analyzed. Assays were performed at room temperature.

Antibodies 0841 and 0164 inhibited the neutralization of HL-60 cells to CHO cells expressing human E-selectin under physiological flow conditions with estimated $IC_{50}$ values of 4.17 and 3.73 nM receptively (Table 14).

TABLE 14

Binding and neutralization by antibody 0841 and 0164.

| | static neutralization | | neutralization | cell surface antibody binding by FACS | |
| --- | --- | --- | --- | --- | --- |
| antibody | sialyl Lewis ligand adhesion CHO-human E-selectin cells $IC_{50}$ (nM) | sialyl Lewis ligand adhesion CHO-cynomolgus monkey E-selectin cells $IC_{50}$ (nM) | under physiological flow HL-60 cell adhesion to CHO-human E-selectin cells $IC_{50}$ (nM) | binding to CHO-human E-selectin cells $EC_{50}$ (nM) | binding to CHO-cynomolgus monkey E-selectin cells $EC_{50}$ (nM) |
| 0841 | 3.81 | 1.74 | 4.17 | 1.62 | 1.54 |
| 0164 | 5.17 | 2.00 | 3.73 | 1.39 | 1.73 |

Example 16: Biophysical Characterization of Humanized Anti-E-Selectin

Thermal Stability

Differential scanning calorimetry was used to determine the stability of humanized antibody 0841 (comprising HC amino acid sequence of SEQ ID NO:22 and LC amino acid sequence of SEQ ID NO:17). For this analysis, samples at 0.3 mg/mL were dispensed into a sample tray of a MicroCal VP-Capillary DSC with an Autosampler (Malvern Instruments, Inc.), equilibrated for 5 minutes at 10° C. and then scanned up to 110° C. at a rate of 100° C. per hour. A filtering period of 16 seconds was selected. Raw data was baseline corrected and the protein concentration was normalized. Origin Software 7.0 (OriginLab Corporation, Northampton, Mass.) was used to fit the data to an MN2-State Model with an appropriate number of transitions. Table 15 below shows the melting temperatures ($T_m1$-$T_m4$ and FAB) of the molecule in Tris/Suc buffer (20 mM Tris, 8.5% sucrose, at pH 7.5) His/Suc buffer (20 mM histidine, 8.5% sucrose, 0.005% EDTA, at pH 5.8) and Glu/Tre buffer (20 mM glutamic acid, 8.5% trehalose, at pH 4.5). This molecule showed good stability, with the first transition in the CH2 domain ($T_m1$) of greater than 65° C. in Tris/Suc and Glu/Tre buffers and just under 65° C. in the Glu/Tre buffer.

TABLE 15

Thermal transitions of humanized antibody 0841.

| formulation | Tm1 (° C.) | Tm2 (° C.) | Tm3 (° C.) | Tm4 (° C.) | Tm Fab (° C.) |
|---|---|---|---|---|---|
| Tris/Suc | 75.04 ± 0.24 | 77.99 ± 0.04 | 85.31 ± 0.03 | — | 77.8 |
| His/Suc | 68.65 ± 0.05 | 77.48 ± 0.24 | 79.44 ± 0.08 | 84.65 ± 0.09 | 78.9 |
| Glu/Tre | 64.78 ± 0.13 | 77.44 ± 0.21 | 79.71 ± 0.10 | — | 79.0 |

Forced Degradation

Humanized antibody 0841 was dialyzed extensively into three buffers: Tris (20 mM Tris at pH 7.5), His (20 mM histidine at pH 5.8) and Glu (20 mM glutamic acid at pH 4.5) for a 4 week forced degradation study at 40° C. After dialysis, sample concentrations were adjusted to 5 mg/mL. At T0, T2 and T4 weeks, samples were taken for analytical size exclusion chromatography (aSEC), imaged capillary electrophoresis (iCE) and bioassay testing.

The aggregation state of the heated samples was determined by aSEC. Samples were injected onto a YMC-Pack Diol-200 column (300×8.0 mm, pore size 200 Å) connected to the Agilent 1260 HPLC system (Agilent Technologies, Santa Clara, Calif.) with 20 mM sodium phosphate, 400 mM arginine at pH 7.2 as the mobile phase. An isocratic program at a flow rate of 0.75 mL/minute for 20 minutes was applied to the aSEC column for sample elution and the data was analyzed using the Agilent OpenLAB Data Analysis software to integrate and quantify peak area of aggregate, protein of interest and low molecular weight species. All samples showed minimal change in % HMMS (high molecular mass species) and % LMMS (low molecular mass species), i.e., the percentage was less than 5% (Table 16).

TABLE 16 aSEC of a T4-week forced degradation sample of humanized 0841.

| | antibody 0841 (HC SEQ ID NO: 22; LC ID SEQ NO: 17) | | |
|---|---|---|---|
| formulation | concentration (mg/mL) | % HMMS | % LMMS |
| Tris pH 7.5 | 5 | 3.05 | 0.48 |
| His pH 5.8 | 5.2 | 2.75 | 0.39 |
| Glu pH 4.5 | 5.3 | 2.73 | 0.84 | iCE was used to detect the charge-based heterogeneity of the forced degradation samples. iCE separates the protein charge species under high voltage and detection at absorbance 280 nm. Carrier ampholytes produce a pH gradient and proteins migrate until their net charge is zero. Electropherograms were analyzed to determine pI values and peak areas for acidic, main, and basic species. Protein Simple iCE3 instrument with PrinCE Autosampler was used to analyze samples. Proteins were diluted to 2 mg/mL in water. Sample diluent contained 0.01 mg/mL pI marker 4.65, 0.01 mg/mL pI marker 9.5, 4.0% Pharmalyte pH 3-10, 0.25% methyl cellulose, and 2.0 M urea. Samples contained 15 µL protein at 2 mg/mL and 85 µL sample diluent. Samples were focused for 1 minute at 1500 Volts and then 6 minutes at 3000 Volts. Empower software was used for data analysis.

For samples with a high percentage of acidic/basic species in iCE analysis, additional mass spectroscopy analysis was required to identify sequence liabilities on CDR regions. Analysis of samples in the histidine and glutamic acid buffers showed typical increases in acidic and basic species. However, there was a larger increase in basic species than expected for a stable antibody in the Tris buffer, suggesting a possible chemical modification (Table 17). Samples in all three buffers were further analyzed using mass spectroscopy three-part analysis and peptide mapping.

TABLE 17 iCE analysis of forced degradation samples of humanized antibody 0841 (HC SEQ ID NO: 22 and LC SEQ ID NO: 17).

| antibody 0841 | 40° C. | pI | % acidic species | % main species | % basic species |
|---|---|---|---|---|---|
| Tris, pH 7.5 | T0wks | 8.8 | 23.6 | 72.1 | 4.3 |
| | T2wks | 8.8 | 37.4 | 51.9 | 10.7 |
| | T4wks | 8.8 | 45.3 | 41.4 | 13.3 |
| His, pH 5.8 | T0wks | 8.9 | 24.3 | 71.5 | 4.2 |
| | T2wks | 8.9 | 32.9 | 60.8 | 6.3 |
| | T4wks | 8.9 | 40.9 | 51.7 | 7.4 |
| Glu, pH 4.5 | T0wks | 8.8 | 24.2 | 71.3 | 4.4 |
| | T2wks | 8.8 | 35.1 | 56.0 | 8.9 |
| | T4wks | 8.8 | 42.0 | 47.3 | 10.8 |

Mass Spectroscopy Analysis

For 3-part mass spectroscopy analysis antibodies were digested using FabALACTICA. 50 µg of antibody mAb was added to 100-150 mM NaPO4 pH 7.0 for a volume of 25 µL. 1.5 µLs of FabALACTICA enzyme (40 U/µL) was added and incubated overnight (16-18 hours) at 37° C. with gentle shaking. Following this, 50 µL of 8M Guan-HCl, 12.5 µL 1 M DTT and 12.5 µL 150 mM sodium phosphate buffer pH 7.0 was added. This was incubated for 1 hour at 37° C. with gentle shaking. 7-8 µg (about 15 µL) were used for 3-part Liquid Chromatography Mass Spectrometry (LC-MS) analysis.

Figure 2:
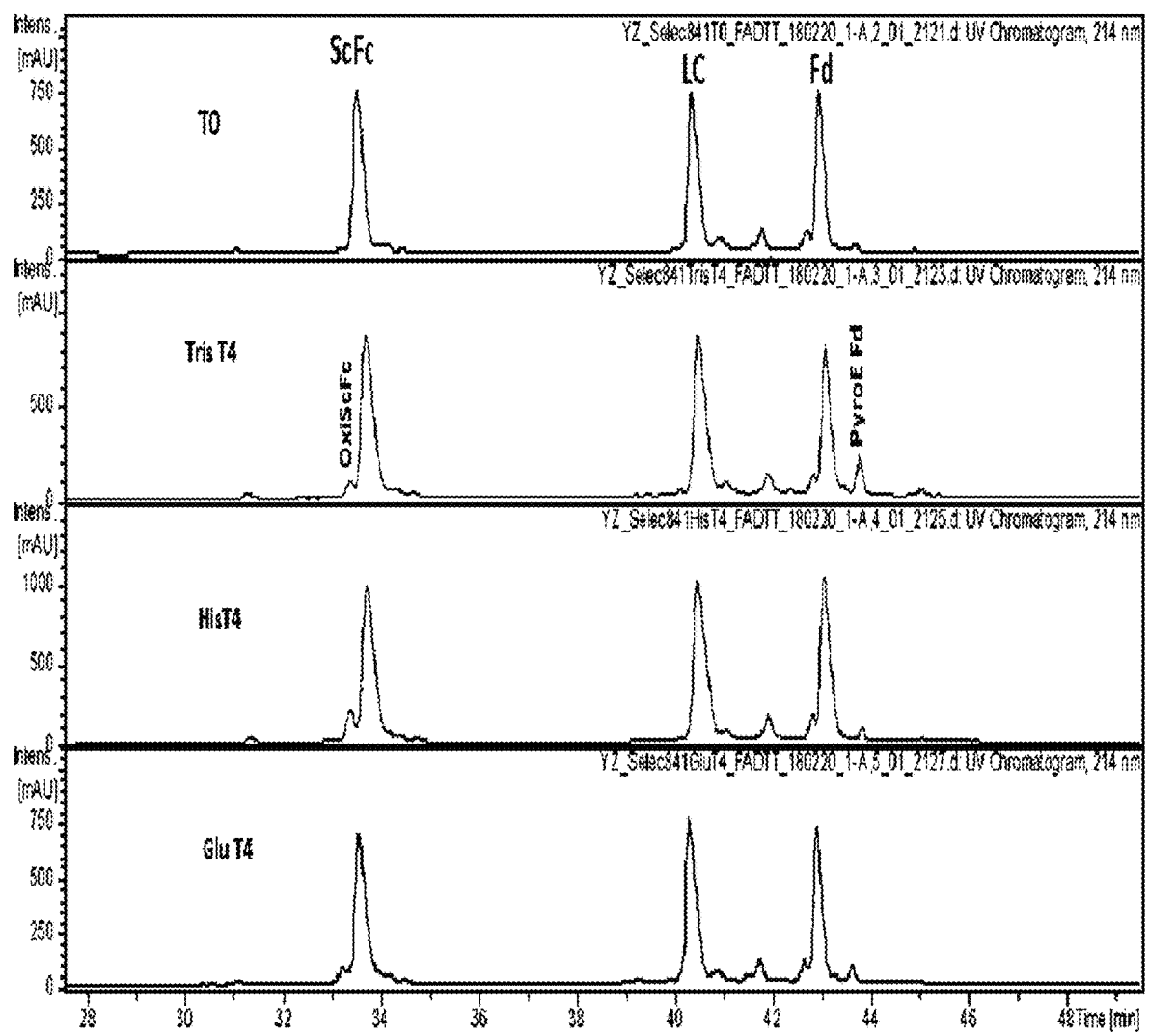
FIG. 2 depicts exemplary data from a three-part mass spectroscopy analysis of optimized anti-E-selectin antibody 0841 at time 0 (T0) and following storage at 40° C. for 4 weeks in Tris buffer (TrisT4), histidine buffer (HisT4) or glutamic acid (Glu4) buffer.

LC-MS analysis was performed using a Bruker maXis II mass spectrometer (Bruker, Billerica, Mass.) coupled to a Waters H-Class (Waters, Milord, Mass.) UPLC. The FabA-LACTICA digested and reduced samples were separated over a Waters BEH C4 (1.7 Å, 2.1×150 mM) column maintained at 65° C. with a flow rate of 300 µL/min. Mobile phase A was water with 5% acetonitrile and 0.05% TFA, mobile phase B was 50:50 acetonitrile:2-Propanol and 0.05% TFA. The mass spectrometer was run in positive MS only mode and the data were acquired with oTOF control software. The TOF-MS signal was deconvoluted using Maximum Entropy in Compass DataAnalysis v 4.2 (Bruker). Analysis of the forced degradation 0841 samples in glutamic acid, histidine and Tris buffer at time four weeks (T4W) showed similar profiles as compared to samples at time 0 (T0) (FIG. 2). PyroE-Fd (Fd fragment from the IgG heavy chain with pyroglutamic acid (PyroE) at the N-termini) showed a slight increase in T4W samples particularly in the Tris buffer (~3.5%). In addition, about 5% Fd D/P clip (Fd fragment with cleaved aspartic acid/proline (D/P) site) was detected in the T0 and T4W samples.

Peptide Mapping by LC-MS

To further investigate sample stability, peptide mapping LC-MS was utilized. For peptide mapping, denaturation and reduction of antibody 0841 was carried out in 5 M Guan:HCl NaAc, pH 5.0, 10 mM TCEP at 37° C. for 1 hour. The reaction mixture was diluted 10 times with 100 mM MES, pH 6.0, 0.5 mM TCEP buffer. Next, LysC/Trypsin mix was added at a 1:10 ratio followed by a 37° C. overnight digestion. The reaction was quenched with 0.5% TFA/H$_2$O (final concentration). This digestion mixture was then injected onto Thermo Scientific Orbitrap Fusion Lumos for LC-MS analysis LC-MS peptide mapping analysis was performed using an Orbitrap Fusion Lumos mass spectrometer (Thermo Scientific, Waltham, Mass.) coupled to a Waters H-Class (Waters, Milford, Mass.) UPLC. The digested samples were separated over a Waters BEH C18 (300 Å, 1.7 um 2.1×150 mM) column maintained at 60° C. with a flow rate of 200 μL/min. Mobile phase A was 0.05% TFA in water and mobile phase B was 0.05% TFA in acetonitrile. Peptides were eluted from the column using a gradient: 0.5% to 35% B in 135 minutes. The mass spectrometer was run in positive MS only mode scanning from 300 to 1600 m/z and data was acquired with Xcalibur software. The data analysis and database search were performed using both Xcalibur software (Thermo Fisher Scientific, Waltham Mass.) and Peaks AB (Bioinformatics Solutions Inc, Toronto, Canada).

High fidelity peptide mapping analysis of T4W samples for Tris, histidine and glutamic acid buffer Identified trace amounts of deamidation (<1%) in a HC CDR2 peptide with the sequence IDPAN*GNTIYAEK (NG deamidation site is underlined; SEQ ID NO:176). NG is a common deamidation site, but in this case was mostly stable. Potential deamidation (in the form of succinimide-N) was detected in a LC CDR1 peptide with the sequence TSQNI N*RYLNWYQQKPGK (NR deamidation site is underlined; SEQ ID N:177), the deamidation increased to about 5.1% in the Tris T4W sample (MS2 spectrum indicted the N(30)R site was the most likely deamidation site, however, N28 and N34 could also potentially have trace amounts of deamidation) (Table 18).

TABLE 18

LC/MS peptide mapping of forced degradation samples of humanized antibody 0841.

| | % regular peptide | % deamidation | % succinimide peptide | total deamidated peptide |
|---|---|---|---|---|
| HC CDR2 peptide | | | | |
| T0 | 99.74% | 0.07% | 0.15% | 0.26% |
| Glu T4W | 99.62% | 0.18% | 0.16% | 0.38% |
| His T4W | 99.59% | 0.16% | 0.17% | 0.41% |
| Tris T4W | 99.36% | 0.30% | 0.15% | 0.65% |
| LC CDR1 peptide | | | | |
| T0 | 99.12% | 0.00% | 0.88% | 88.00% |
| Glut T4W | 98.08% | 0.00% | 1.48% | 1.48% |
| His T4W | 95.20% | 0.08% | 3.95% | 4.03% |
| Tris T4W | 93.46% | 0.27% | 4.85% | 5.12% |

Competition Binding ELISA

To additionally asses stability of the forced degradation samples, the activity of the stressed samples was evaluated in a competition binding ELISA. Here the stability of the T0, T2W and T4W samples were compared for their ability to compete with biotinylated chimeric antibody 0164 (comprising HC SEQ ID NO:34 and LC SEQ ID NO:31) for binding to human E-selectin. The human E-selectin was stored in PBS with Ca/Mg at 500 μg/mL and was diluted with PBS with Ca/Mg to a concentration of 1 μg/mL. This was added to a 384 well MaxiSorp plate, sealed and incubated at 4° C. with gentle shaking overnight. The next day the reagents in each well were removed, followed by addition of 50 μL of blocking buffer (1% BSA in PBS with Ca/Mg) to each well. The wells were sealed and incubated at room temperature for about 1 hour with gentle shaking. At a starting concentration of 0.2 mg/mL, antibody 0841 was serially diluted in steps of 1/3 dilutions with PBS with Ca/Mg for a total of 12 concentrations.

Biotinylated antibody 0164 was diluted to 0.04 μg/mL in 2% BSA/PBS with Ca/Mg. Equal volumes of diluted antibody 0841 were mixed with biotinylated antibody 0164. Next, the wash plate was blocked with 1% BSA with PBST (0.05% Tween) on a TITERTEK for 3 cycles using 80 μL for each wash. The plate was tapped on a paper towel to drain. Twenty-five μL of the mixture of antibody 0841 and Biotin-labeled antibody 0164 was added to each well of the 384-well plate, in duplicate wells and incubated at room temperature with gentle shaking for 2-4 hours. The wash step was repeated with 3 cycles of 2 washes. Then, dilute Streptavidin-HRP (~1/7500 diluted in blocking buffer) was added to each well and the plate was incubated at room temperature with gentle shaking ~40 minutes to 1 hour. The wash step was again repeated with 3 cycles of 2 washes, tapped dry and followed by the addition of 25 μL of TMB substrate (one component HRP microwell substrate). This was followed by the addition of 25 μL of 0.18 M sulfuric acid to stop the reaction when the color reached saturation (determined by observing the color development). The OD450 measurement of the plate was then read on the Envision plate reader, and the data was analyzed with GraphPad, Prism7.

Figure 3:
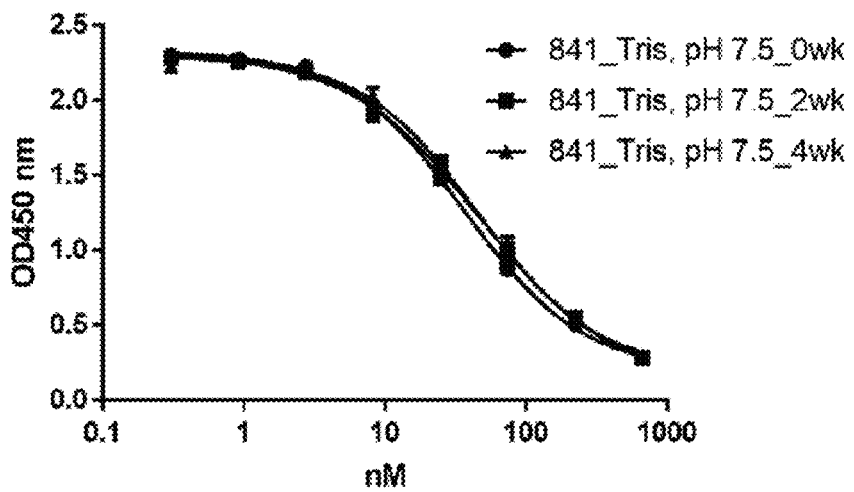
FIG. 3 depicts an exemplary competition ELISA analysis of antibody 841 (also known as 0841) following forced degradation. Antibody 841 was analyzed at time 0 (0 wk) and following incubation in Tris, His or Glu buffer for 2 weeks (2 wk) or 4 weeks (4 wk) at 40° C.
Figure 3:
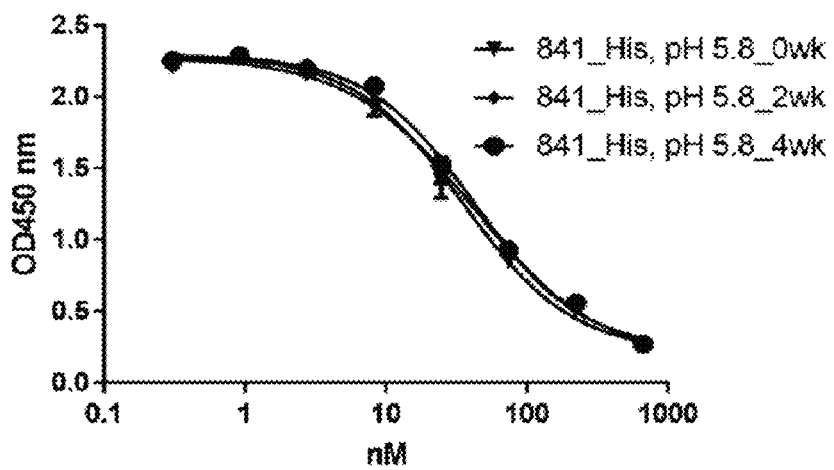
Figure 3:
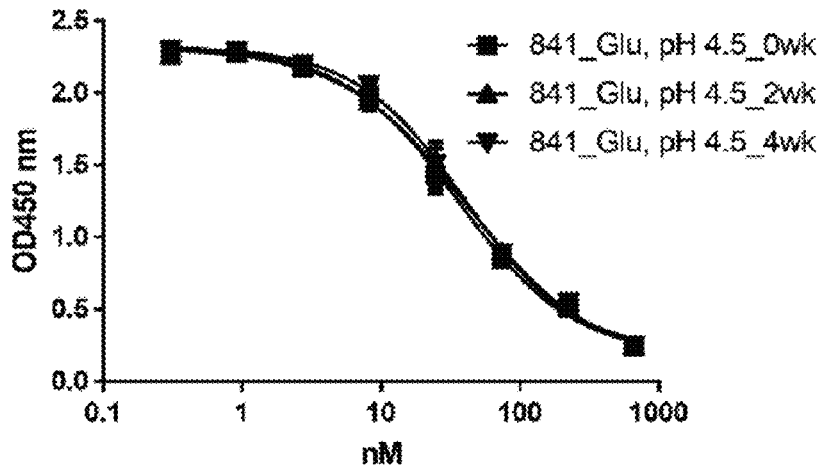
Figure 5:
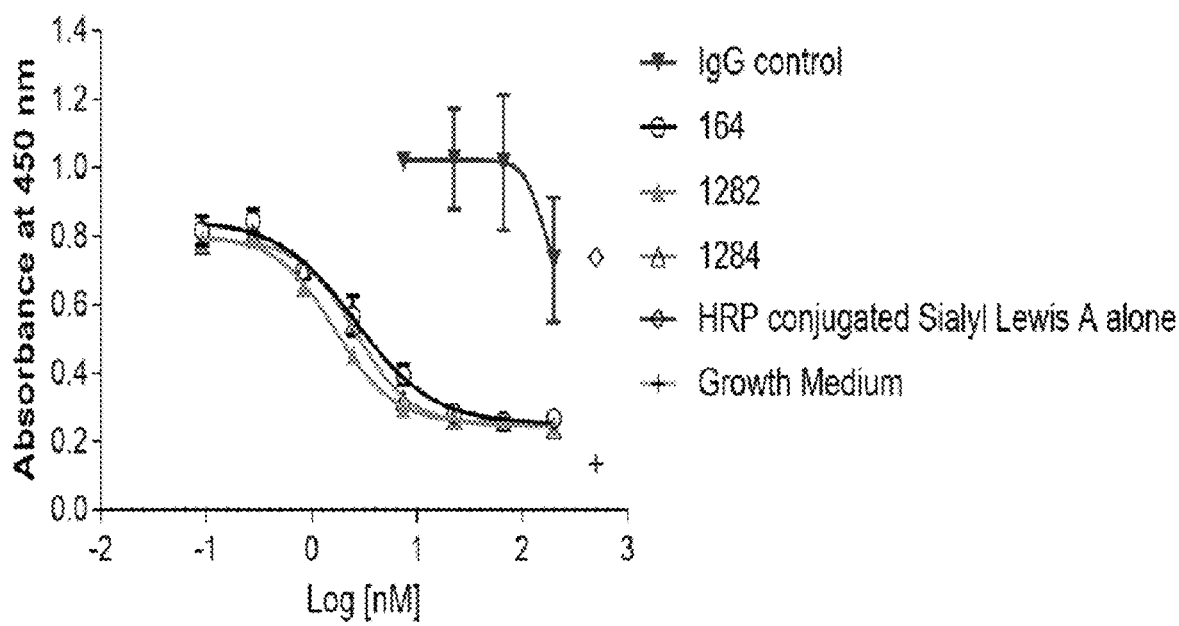
Figure 5:
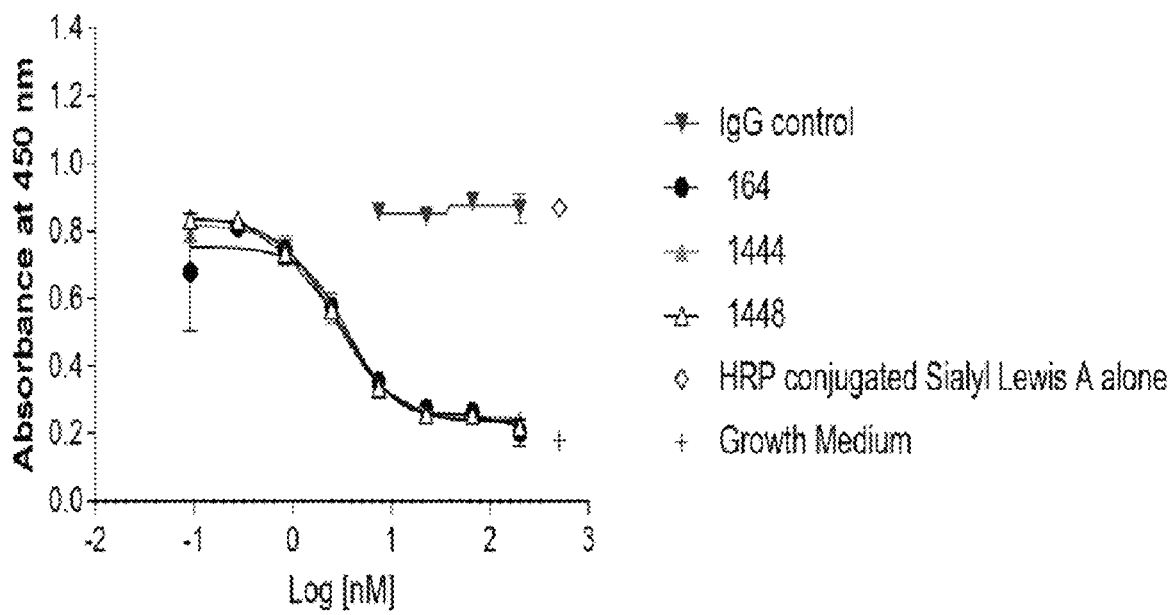

The competition binding results are shown in FIG. 3 and no difference was seen between the T0, T2W and T4W samples in any of the three buffers. These data demonstrate that antibody 0841 retained its ability to bind to E-selectin following storage under high-temperature conditions (i.e., 40° C.).

High Concentration Stability

Humanized antibody 0841 was dialyzed extensively into three buffers, Tris/Suc (20 mM Tris, 8.5% sucrose, at pH 7.5), His/Suc (20 mM histidine, 8.5% sucrose, 0.005% EDTA, at pH 5.8) and Glu/Tre (20 mM glutamic acid, 8.5% trehalose, at pH 4.5). After dialysis, the samples were concentrated to 150 mg/mL using a spin filter concentrator and stored at 4° C. and 25° C. At T0, T1, T2, T4 and T6 weeks, samples were taken for real time aSEC analysis.

The aggregation state of the high concentration samples was determined by aSEC as described above for the forced degradation analysis. Samples stored at 4° C. and 25° C. were stable at high concentration at T6 weeks (T6W) with little increase in percentage of HMMS (<5%) under all three buffer conditions (Table 19).

TABLE 19 aSEC analysis of high concentration samples of humanized antibody 0841 (HC SEQ ID NO: 22, LC SEQ ID NO: 17) at T0 and T6 weeks.

| | antibody 0841 | | | |
|---|---|---|---|---|
| formulation | concentration (mg/mL) | % HMMS T0 | % HMMS T6W 4° C. | % HMMS T6W 25° C. |
| Tris/Suc, pH 7.5 | 149.6 | 3.3 | 3.99 | 4.66 |
| His/Suc, pH 5.8 | 157.1 | 3.2 | 3.34 | 3.56 |
| Glu/Tre, pH 4.5 | 150.5 | 3.1 | 3.24 | 3.37 |

At T0, T3 (T3W) and T6 weeks, samples were analyzed by iCE and capillary gel electrophoresis (CGE). iCE was used to detect charge-based heterogeneity of the high concentration samples using a method similar to the method used in the forced degradation study. Minimal changes in the % acidic species and the % basic species were observed over 6 weeks of storage at 25° C. in His/Suc and Glu/Tre buffers with larger changes associated with the Tris/Suc buffer in the acidic and basic species (Table 20).

TABLE 20 iCE analysis of high concentration samples of humanized antibody 0841 (HC SEQ ID NO: 22, LC SEQ ID NO: 17).

| antibody 0841 | 25°C sampling time | pI | % acidic species | % main species | % basic species |
|---|---|---|---|---|---|
| Tris/Suc, pH 7.5 | T0wks | 9.0 | 25.8 | 69.9 | 4.3 |
|  | T3wks | 9.0 | 32.3 | 60.7 | 6.9 |
|  | T6wks | 9.0 | 37.6 | 53.1 | 9.3 |
| His/Suc, pH 5.8 | T0wks | 9.0 | 25.9 | 69.4 | 4.7 |
|  | T3wks | 9.0 | 27.6 | 67.2 | 5.1 |
|  | T6wks | 9.0 | 28.7 | 65.6 | 5.7 |
| Glu/Tre, pH 4.5 | T0wks | 9.0 | 25.6 | 69.6 | 4.8 |
|  | T3wks | 9.0 | 28.0 | 65.8 | 6.2 |
|  | T6wks | 9.0 | 30.1 | 63.1 | 6.7 |

CGE was performed to determine the fragmentation of the high concentration samples of antibody 0841. Samples were analyzed using LabChip Touch HT Protein Express Assay from Perkin Elmer. The assay was set up according to manufacturer instruction and samples were prepared using a modified method. Briefly, 5 µL of sample at 1 mg/mL was mixed with 35 µL of sample buffer containing either iodoacetamide for non-reducing (nrCGE), or dithiothreitol for reducing CGE, and incubated at 70° C. for 10 minutes. After heating, 70 µL of de-ionized water was added to each sample prior to analysis on the Touch system. The size and level of fragmentation for each sample was quantified using the LabChip GX software.

Quantification of the % fragmentation and % HMMS demonstrated that antibody 0841, at a high concentration, was stable in all three buffers (Table 21).

TABLE 21

CGE analysis of high concentration samples of humanized antibody 0841 (HC SEQ ID NO:22, LC SEQ ID NO:17).

| nrCGE | | Tris/Suc pH 7.5 | His/Suc pH 5.8 | Glu/Tre pH 4.5 |
|---|---|---|---|---|
| | | % fragmentation (25° C.) | | |
| antibody 0841 | T0wks | 0.49 | 0.87 | 0.51 |
|  | T3wks | 0.75 | 0.3 | 0.75 |
|  | T6wks | 1.1 | 0.31 | 1.69 |
| | | % HMMS (25° C.) | | |
| antibody 0841 | T0wks | 0.03 | 0.03 | 0 |
|  | T3wks | 0.31 | 0 | 0 |
|  | T6wks | 0 | 0.38 | 0 |

Example 17: In Silico Immunogenicity Risk and t-Cell Epitope Prediction of Humanized Anti-E-Selectin Immunogenicity risk of the humanized anti-E-selectin antibody 0841 was predicted using in silico tools for prediction of MHCII peptide binding. These tools were used: (1) for epitope identification of potential MHCII binding for each individual peptide in the sequence, (2) for epitope classification, to assess the risk of potential MHCII peptide binders and (3) for overall sequence score, to predict the overall risk of the entire sequence having MHCII binding associated immunogenicity risk. The methods are described below.

Epitope Identification

Sequences were analyzed using two protocols (described below) to identify epitopes. Any sequence flagged by the rules described herein for either protocol was considered an epitope. These methods examine sequences primarily at the level of amino acid 9-mers.

Protocol 1: ISPRI/EpiMatrix

Sequences were submitted for EpiMatrix analysis in the ISPRI software package (ISPRI v 1.8.0, EpiVax Inc., Providence, R.I. (2017); Schafer J R A et al. (1998) Vaccine 16(19): 1880-84). The raw results provided ranking of likelihood of binding of each 9-mer amino acid fragment against 8 different HLA types. Thus, there were 8 predictions ("observations") for each 9-mer. The 9-mers were generated starting at each individual linear numbering position of the sequence (thus, it was possible for the same 9-mer to occur more than once in the same sequence). If any 4 observations indicated that the 9-mer was in the top 5% of binders (meaning it was predicted to be in the top 5% of binders for at least 4 HLA types), the 9-mer was considered a predicted epitope ("epitope"). Alternatively, if any 1 of the 8 predictions indicated that the 9-mer was in the top 1% of binders, the 9-mer was also considered a predicted epitope.

Protocol 2: IEDB Consensus Method

Sequences were submitted for analysis using the MHC-II binding Consensus method (Wang P. et al. (2010) BMC Bioinformatics 11: 568; Wang P. et al. (2008) PLoS Comput. Biol. 4(4),e1000048) in IEDB (Vita R. et al., Nucleic Acids Res. 2015; 28 (43): D405-12; IEDB MHC-II Binding Predictions, www.iedb.org). The output of the software arranged results by 15-mer. A consensus score and percentile ranking were provided for each combination of 15-mer and HLA type. Individual scores from which each 15-mer's consensus was derived were rankings of certain 9-mers found in the 15-mer: each method used for the consensus reported a percentile rank for a 9-mer within the 15-mer. The consensus taken as the value for the overall 15-mer was the prediction for the 9-mer having the median score. A 9-mer was classified as an epitope if (a) it was chosen as the consensus representative for the 15-mer AND (b) had a percentile ranking in the top 10% of binders for the HLA type being considered, AND if criteria (a) and (b) occurred for three or more distinct HLA types for the same 9-mer (i.e., three observations). The HLA types considered were DRB1*01, 1*03, 1*04, 1*07, 1*08, 1*11, 1*13, and 1*15, which were the same HLA types in a standard ISPRI/EpiMatrix report. Thus, although the primary output of the method was a ranking of 15-mers, we reinterpreted the data to obtain a list of predicted 9-mer epitopes, for ease of comparison with Protocol 1.

Epitope Classification

Each epitope was classified as a germline or non-germline epitope. For antibodies, we further classified each epitope based on its location within the antibody (CDR or non-CDR). We filtered sequences of human V domains obtained from IMGT (www.imgt.org) to remove germlines annotated as pseudogenes or open reading frames (ORFs). Any predicted 9-mer epitopes found in the remaining sequences were considered a germline epitope. Epitopes found in the J or C regions (including IgG1, IgG2, IgG3, and IgG4), or the junctions between these regions, were also classified as germline epitopes. Otherwise, an epitope was classified as a non-germline epitope. Variable domain residues were numbered based on the numbering system of Kabat (Kabat E A, et al. (1991) US Department of Health and Human Services, NIH Publication No. 91-3242). After numbering, CDRs were defined to include the following residues: CDR-H1 (H26-H35 including insertions such as H35A, up to but not including H36), CDR-H2 (H50-H65 inclusive), CDR-H3 (H95-H102 inclusive) CDR-L1 (L24-L34 inclusive), CDR-L2 (L50-L56 inclusive), CDR-L3 (L89-L97, inclusive). A predicted 9-mer epitope was a CDR epitope if any one of its amino acids was part of a CDR region. Note that our chosen start position (H26) for CDR-H1 differs from some other publications using Kabat annotation.

Overall Sequence Score (T-reg Adjusted Score)

For an individual chain, or for a pairing of an antibody VH and VL domain, an overall score was calculated by summing over each of the constituent 9-mers as follows. All individual combinations of 9-mer and HLA type ("observations") were examined, regardless of whether the 9-mer was an epitope. If a particular observation indicated that the peptide is in the top 5% of binders for the given HLA type, the EpiMatrix Z-score for this observation was added to a running total associated with the entire protein sequence. The total number of observations examined was also recorded. The only exception was that all observations of 9-mers Identified by ISPRI as "T-regitopes" were assumed to have EpiMatrix scores of zero. In the running total, a baseline score of 0.05*2.2248 was subtracted from each observation (including T-regitopes). The final score was computed as follows:

T-reg Adjusted Score=(Running total)*1000/(Number of observations)

Lower scores indicated lower predicted immunogenic potential. Note that the score only included predictions from ISPRI/EpiMatrix, and did not include information from IEDB. Therefore, any strong HLA binders predicted by IEDB but not ISPRI did not contribute to the score. In theory, sequences may contain many IEDB-predicted HLA binders and still have a favorable T-reg Adjusted Score if EpiMatrix does not also predict the same sequences to be likely binders.

These tools were used to predict the number of non-germline T-cell epitopes and the overall sequence score in the humanized antibody 0841 (comprising VH amino acid sequence of SEQ ID NO:25 and VL amino acid sequence of SEQ ID NO: 21). Using the two protocols, 8 non-germline epitopes were identified in the VH and VL sequences (H27: YNIRSSYMH (SEQ ID NO:178), H63: FKIRFTISA (SEQ ID NO:179), H65: IRFTISADN (SEQ ID NO:180), L29: INRYLNWYQ (SEQ ID NO:181), L46: LLIYNANSL (SEQ ID NO:182), L47: LIYNANSLQ (SEQ ID NO:183), L48: IYNANSLQT (SEQ ID NO:184), and L49: YNANSLQTG (SEQ ID NO:185) (FIG. 4). Additionally, the overall sequence score was -30.34. Reduction in the number of epitopes and the overall sequence score is predicted to decrease the overall immunogenicity risk of the sequence.

Example 18: Optimization of Humanized Anti-E-Selectin Antibodies

Structure-Based Rational Mutagenesis of Antibody 0841

Anti-E-selectin antibody 0841 contained several predicted T-cell epitopes that may increase the risk for immunogenicity when administered to a subject. These included 8 non-germline epitopes contained in the VH and VL sequences (H27: YNIRSSYMH, H63: FKIRFTISA, H65: IRFTISADN, L29: INRYLNWYQ, L46: LLIYNANSL, L47: LIYNANSLQ, L48: IYNANSLQT, and L49: YNANSLQTG). In addition, peptide mapping of the antibody following heat forced degradation identified an NR deamidation liability at the L30 position. In addition to the NR deamidation liability at L30, other potential liability sites were identified including a NG site at heavy chain position H54, a NS site at position L52 and a NS site at position L92. Structure based optimization methods were utilized to remove the predicted T-cell epitopes and sequence liability sites.

Initially though, a further humanized antibody, 0978 (comprising a HC amino acid sequence of SEQ ID NO:28 and a LC amino acid sequence of SEQ ID NO:26), was generated that germlines the CDR-L2 to the DPK9 CDR-L2 (AASSLQS (SEQ ID NO:3) and the end of the CDR-H2 to the DP-54 sequence of (H59-H65 YVDSVKG (SEQ ID NO:186)). Antibody 0978 was shown to maintain binding similar to antibody 0841 using the competition binding assay described in Example 16. Germlining these two stretches removed 5 of the predicted T-cell epitopes (H63: FKIRFTISA (SEQ ID NO:179), L46: LLIYNANSL (SEQ ID NO:182), L47: LIYNANSLQ (SEQ ID NO:183), L48: IYNANSLQT (SEQ ID NO:184), and L49: YNANSLQTG (SEQ ID NO:185) but introduced a new predicted T-cell epitope (H63: VKGRFTISA (SEQ ID NO:187)). Additionally, mutation of the L2 removed the potential NS liability site at position L52, but mutation of the end of H2 added a DS site at position H61 that was another potential liability site. Structure based optimization was performed on antibody 0978 using an x-ray crystal structure of antibody 0164 bound to o-type lectin domain of E-selectin (residues 22-178) to remove the remaining 3 predicted T-cell epitopes and the sequence liabilities.

To determine suitable positions for mutagenesis, computational prediction of mutations for both the changes in affinity and changes in stability were made using Discovery Studio 4.5 (Dassault Systems Biovia Corp.) and FoldX. Tolerated mutations are those that are not predicted to have a ΔΔG>1 kcal/mol for both the Discovery Studio and FoldX methods. From these predictions, a set of residues that would be predicted to have a minimal impact on binding and stability, while removing the predicted T-cell epitopes and sequence liabilities, were identified and shown in Table 22.

TABLE 22

List of mutations predicted to remove sequence liabilities motifs or predicted T-cell epitopes identified through structure based rational design.

| Feature | WT | Mutant |
| --- | --- | --- |
| L30 deamidation site motif NR | L30 NR | L30 ER |
| L92 deamidation site motif NS | L92 NS | L92 NA |
| H61 isomerization site motif DS | H61 DS | H61 ES |
| H27 predicted T-cell epitope | H27: YNIRSSYMH (SEQ ID NO:178) | H27: YAIRSAYMH (SEQ ID NO:188) |
| H63 predicted T-cell epitope | H63: VKGRFTISA (SEQ ID NO:187) | H63: VEGRFTISA (SEQ ID NO:189) |
| | H63: VKGRFTISA (SEQ ID NO:187) | H63: VTGRFTISA (SEQ ID NO: 190) |

TABLE 22-continued

List of mutations predicted to remove sequence
liabilities motifs or predicted T-cell epitopes
identified through structure based rational design.

| Feature | WT | Mutant |
|---|---|---|
| | H63: VKGRFTISA (SEQ ID NO: 187) | H63: VKERFTISA (SEQ ID NO:191) |
| L29 predicted T-cell epitope | L29: INRYLNWYQ (SEQ ID NO:181) | L29: IERYLNWYQ (SEQ ID NO: 192) |

Using this set of mutations, 4 optimized constructs were generated which removed the 3 sequence liabilities and the 3 T-cell epitopes identified in Table 22. These constructs are antibody 1282 (comprising HC amino acid sequence of SEQ ID NO:43 and LC amino acid sequence of SEQ ID NO:1), antibody 1284 (comprising HC amino acid sequence of SEQ ID NO:40 and LC amino acid sequence of SEQ ID NO:1), antibody 1444 (comprising HC amino acid sequence of SEQ ID NO:13 and LC amino acid sequence of SEQ ID NO:1) and antibody 1448 (comprising HC amino acid sequence of SEQ ID NO:37 and LC amino acid sequence of SEQ ID NO:1). Mutations relative to antibody 0978 are shown in Table 23. The binding affinity of these mutants were confirmed to be similar to antibody 0978 using the competition binding assay described in Example 16.

TABLE 23

List of new sequences optimized to remove t-cell epitopes and sequence liabilities.

| antibody | HC mutants | LC mutants |
|---|---|---|
| 1282 | K64E | N30E, S93A |
| 1284 | D61E, K64E | N30E, S93A |
| 1444 | K64T | N30E, S93A |
| 1448 | G64E | N30E, S93A |

Example 19: Neutralization of Optimized Anti-E-Selectin Antibodies. (0164, 0841, 1282, 1284, 1444, 1448)

Neutralization of Ligand Binding to CHO Expressing Cell Surface E-Selectin

In a static ligand cellular adhesion assay, horse radish peroxidase (HRP) conjugated E-selectin ligand (sialyl Lewis antigen) and E-selectin antibodies compete for binding to human or cynomolgus E-selectin expressed on Chinese hamster ovary (CHO) cells. The ability of anti-E-selectin antibodies to neutralize ligand binding was assessed in a static neutralization assay using a competition enzyme-linked immunosorbent assay (ELISA) to evaluate the neutralization of the sialyl Lewis antigen to Chinese hamster ovary cells (CHO) engineered to express human or cynomolgus monkey E-selectin.

CHO cells expressing human E-selectin were grown in culture medium (MEM (Minimum Essential Medium) Alpha Medium, supplemented with 10% (volume/volume) dialyzed fetal bovine serum, 100 nM methotrexate and 100 Units/mL penicillin and 100 μg/mL streptomycin). CHO cells expressing cynomolgus monkey E-selectin were cultured in R1 medium (RI Dulbecco's Modifies Eagle's Medium/Ham's F12 modification) supplemented with 10% heat inactivated fetal bovine serum (GIBCO), 100 Units/mL penicillin and 100 μg/mL streptomycin and 125 μg/mL Zeocin (GIBCO).

Figure 6:
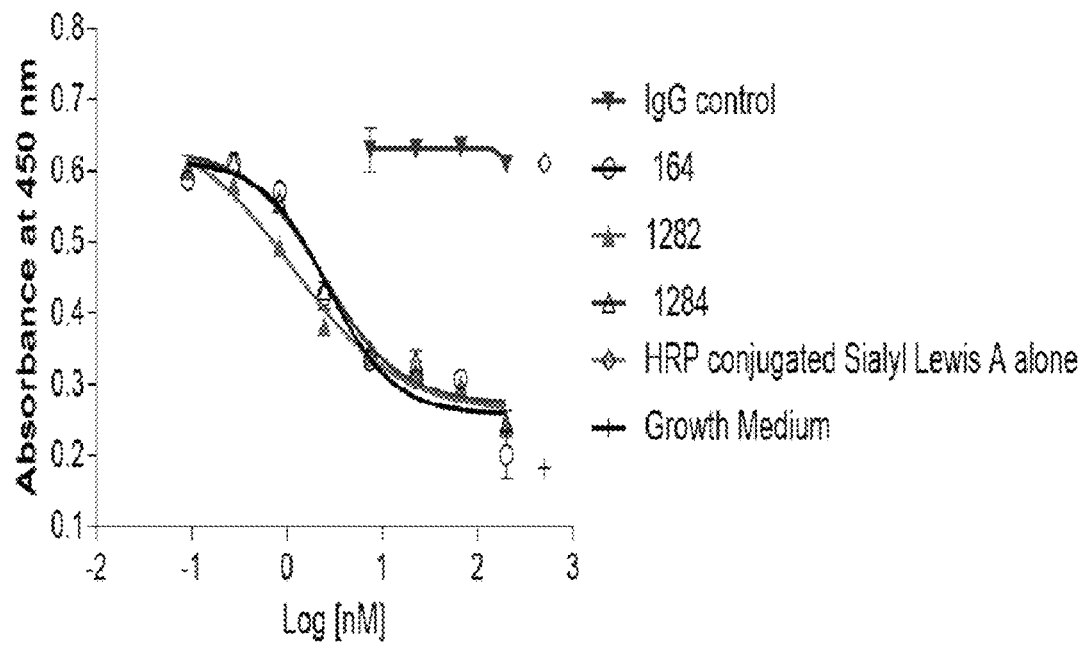
FIG. 6 depicts exemplary neutralization of sialyl Lewis A ligand adhesion to Chinese hamster ovary (CHO) cells expressing human E-selectin. Antibodies tested included anti-E-selectin antibodies 164 (also known as 0164), 1282, 1284, 1444 and 1448 and an IgG isotype control.
Figure 6:
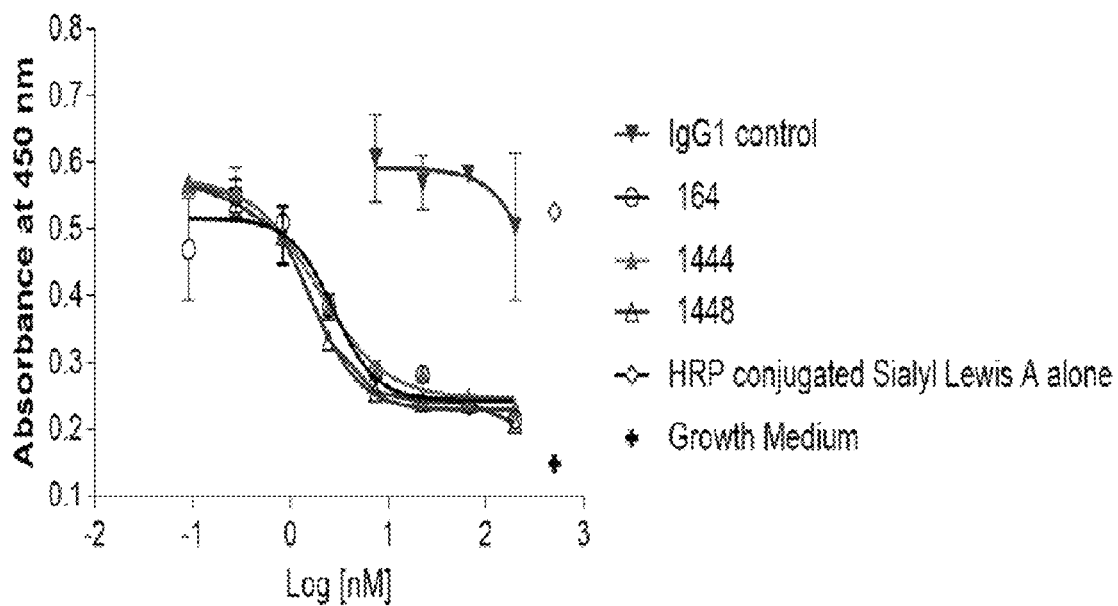

CHO cells expressing E-selectin were seeded at 12,500 cells per well into a 96 well tissue culture plate and incubated at 37° C. 5% $CO_2$ for 48 hours to form a confluent monolayer. Plates were subsequently washed twice with 200 μL of calcium magnesium free PBS. Anti-E-selectin antibodies or an IgG1 isotype control (IgG control) were added to the assay in the presence of a small synthetic conjugate of biotinylated, sialyl Lewis A polyacrylamide (Carbosynth LLC, OS45446) or sialyl Lewis X polyacrylamide (Glycotech, 01-045) with streptavidin/horseradish peroxidase (100 μL total) and incubated at 37° C., 5% $CO_2$ for 2 hours. Plates were then washed twice with 200 μL of calcium and magnesium free PBS. Following the incubation, the cells were washed twice with 200 μL of wash buffer containing 2 mM of calcium chloride (50 mM TRIS [trisaminomethane], 150 mM sodium chloride; 0.05% polysorbate 20, pH 7.4; 2 mM calcium chloride). Signal was developed by adding 100 μL of 1-Step Ultra TMB substrate (Thermo Scientific, 34028) and incubating for 30 minutes at room temperature. Reactions were stopped using 2 M of sulfuric acid and absorbance was read at 450 nm (Spectramax M5e). Data were analyzed and graphed using GraphPad Prism software (Version 8.0.2). Estimated half maximal inhibitory concentration ($IC_{50}$) values derived from the analysis ranged from 1.38 to 2.89 nM for human E-selectin and from 1.85 to 2.65 nM for cynomolgus monkey E-selectin (FIG. 6 and FIG. 6) (Table 24).

TABLE 24

Neutralization of ligand binding to CHO expressing cell surface E-selectin

| | static neutralization of sialyl Lewis ligand adhesion | |
|---|---|---|
| antibody | CHO-human E-selectin cells $IC_{50}$ (nM) | CHO-cynomolgus monkey E-selectin cells $IC_{50}$ (nM) |
| 0164 | 2.69 | 2.25 |
| 0841 | 2.56 | NT |
| 1282 | 1.38 | 1.29 |
| 1284 | 2.77 | 1.91 |
| 1444 | 2.89 | 2.65 |
| 1448 | 2.78 | 1.85 |

NT = Not determined in this assay

In further static neutralization assays, using methods similar to those described above, antibody 1444 neutralized ligand binding to both human or cynomolgus E-selectin protein expressed by CHO cells with an estimated $IC_{50}$ value of 1.88 nM-2.33 nM and 1.47 nM-1.49 nM, respectively.

Neutralization of Ligand Binding to Soluble Recombinant Proteins

Recombinant histidine-tagged E-selectin; cynomolgus monkey E-selectin (Sino Biologicals; 190169-C08H) and human E-selectin (Sino Biologicals; 13025-H08H) stock solutions were prepared to a final concentration of 3 μg/mL in phosphate buffered saline (PBS) without calcium and magnesium. One hundred μL per well of the diluted recombinant E-selectin protein was added into a Ni-NTA HisSorb 96 well plate (Qiagen, 35061) and plates were incubated on an orbital shaker at room temperature for 2 hours. Sialyl Lewis A polyacrylamide biotin, a synthetic E-selectin ligand (GlycoTech corporation 01-044), was conjugated to streptavidin HRP (horse radish peroxidase) (Ultra Streptavidin HRP, Thermo Scientific N504) and diluted in assay diluent containing 2 mM calcium chloride (BD OptEIA buffer; BD Biosciences, 555213).

Two-fold concentrated stock solutions of antibodies (IgG1 control, 0160, 1282, 1284, 1444 and 1448) were also made in assay diluent containing 2 mM calcium chloride. Following the incubation, the plates were washed 5 times with 200 μL of wash buffer containing 2 mM of calcium chloride (50 mM TRIS [trisaminomethane]; 150 mM sodium chloride, 0.05% polysorbate 20, pH 7.4; 2 mM of calcium chloride). Following this, 100 μL of a mixture of antibody (IgG1 control, 0160, 1282, 1284, 1444 and 1448) and HRP conjugated Sialyl Lewis A were added in duplicate and the plates were incubated on an orbital shaker at room temperature for 2 hours. The final antibody concentration ranged from 200 nM to 0.09 nM and the final concentration of HRP conjugated Sialyl Lewis A was 5 μg/mL. Plates were washed as mentioned before, and 100 μL per well of 1-Step Ultra TMB substrate (Thermo Scientific, 34028) was added and incubated for 5 minutes at room temperature. Reactions were stopped with 100 μl of 2M sulfuric acid and absorbance read at 450 nm (Spectramax M5e). Data were analyzed and graphed using GraphPad Prism software (Version 8.0.2).

Estimated half-maximal inhibitory concentration ($IC_{50}$) values derived from the analysis (Table 25).

The estimated half maximal inhibitory concentration ($IC_{50}$) values derived from the analysis and ranged 2.96 nM to 3.59 nM for antibody neutralization of ligand binding to soluble recombinant human E-selectin and 2.74 nM to 3.29 nM for antibody neutralization of ligand binding to soluble recombinant cynomolgus monkey E-selectin.

TABLE 25

Neutralization of ligand binding to soluble recombinant E-selectin

| antibody | static neutralization of sialyl Lewis ligand adhesion | |
|---|---|---|
| | recombinant human E-selectin-$IC_{50}$ (nM) | recombinant cynomolgus monkey E-selectin-$IC_{50}$ (nM) |
| 0164 | 3.39 | 3.29 |
| 1282 | 3.39 | 3.23 |
| 1284 | 3.59 | 3.39 |
| 1444 | 3.01 | 2.91 |
| 1448 | 2.96 | 2.74 |

In further static neutralization assays, using methods similar to those described above, antibody 1444 neutralized ligand binding to both human or cynomolgus E-selectin protein with an estimated $IC_{50}$ value of 2.87 nM-2.91 nM and 2.39 nM-2.45 nM, respectively.

Example 20: Kinetic Evaluation of Optimized Anti-E-Selectin Using Surface Plasmon Resonance Binding affinities were determined for human and cynomolgus monkey E-selectin for the optimized antibodies 1282, 1284, 1444, and 1448 using SPR in a method similar to Example 4. This was done by first binding the antibody to immobilized anti-human IgG. After antibody capture, dilutions of the E-selectin proteins were flowed over and the association rate constant (ka), disassociation rate constant (kd), t½, and $K_D$ values were determined for binding to human and cynomolgus (Table 26). In this SPR analysis, the affinity of 1282, 1284, 1444 and 1448 to human E-selectin was 70.3 nM, 65.2 nM, 61.8 nM, and 60.5 nM, respectively. The affinity of 1282, 1284, 1444 and 1448 to cynomolgus monkey E-selectin was 78.3 nM, 76.5 nM, 81.5 nM, and 67.8 nM, respectively.

TABLE 26

Affinity of anti-E-selectin antibodies to human and cynomolgus monkey E-selectin measured by surface plasmon resonance.

| antibody | analyte | | | | | | | |
|---|---|---|---|---|---|---|---|---|
| (HC SEQ ID NO.; LC SEQ ID NO.) | human E-selectin | | | | cynomolgus monkey E-selectin | | | |
| | ka (1/Ms) | Kd (1/s) | t½ (s) | $K_D$ (nM) | ka (1/Ms) | kd (1/s) | t½ (s) | $K_D$ (nM) |
| 1282 (43; 1) | 2.01E+05 | 1.41E−02 | 49.3 | 70.3 | 2.27E+05 | 1.76E−02 | 39.4 | 78.3 |
| 1284 (40; 1) | 2.22E+05 | 1.45E−02 | 48 | 65.2 | 2.36E+05 | 1.80E−02 | 38.5 | 76.5 |
| 1444 (13; 1) | 2.64E+05 | 1.63E−02 | 42.7 | 61.8 | 2.11E+05 | 1.71E−02 | 40.5 | 81.5 |
| 1448 (37; 1) | 2.10E+05 | 1.26E−02 | 55 | 60.5 | 2.22E+05 | 1.50E−02 | 46.2 | 67.8 |

Example 21: Cell Surface Binding (FACS) and Neutralization of Optimized Anti-E-Selectin Antibodies (0164, 0841, 1282, 1284, 1444 and 1448)

Cell Surface Binding by FACS

The binding of antibodies 0841, 0164, 1282, 1284, 1444 and 1448 to membrane-bound E-selectin was analyzed by FACS. CHO cells expressing human E-selectin were cultured in Alpha medium (MEM [Minimum Essential Medium]) Alpha Medium, 50-012-PC, Corning;) supplemented with dialyzed fetal bovine serum (GIBCO,) at a final concentration of 10% and penicillin/streptomycin (1×) and supplemented with methotrexate. Briefly, the thawed cells were initially grown in the presence of 100 nM methotrexate. For subsequent cultures, the methotrexate was omitted from the growth media.

Endothelial cells were thawed from frozen stocks and initially plated in T-25 flasks (Corning, 353108) re-coated with sterile 0.1% gelatin solution (Sigma, ES-006-B). Human umbilical vein endothelial cells (HUVEC) were grown in Endothelial Cell Growth Medium (Sigma Aldrich, 211-500) while cynomolgus monkey lung microvascular endothelial cells (CLMEC) were grown in Complete Monkey Endothelial Cell Medium (Cell Biologics, MK1168). Cells were split upon reaching 90% confluency and plated into three T-175 flasks precoated with 0.1% gelatin.

CHO cell lines expressing human E-selectin were detached from confluent flasks using enzyme-free Cell Dissociation Buffer (GIBCO, 13151014). Growth media was immediately added to the detached cells, then centrifuged at 300×g for 5 minutes at room temperature to pellet the cells. The cells were then resuspended in cold CHO buffer consisting of phosphate buffered saline (PBS), pH 7.4 containing bovine serum albumin (BSA; Sigma-Aldrich, A3059) at final concentration of 1%, calcium chloride at final concentration of 1 mM, and sodium azide at a final concentration of 0.1%.

For primary cells, HUVEC or CLMEC, cultures at 90% confluency were serum-starved by replacing the growth media with Endothelial Cell Basal Medium (Sigma-Aldrich, 210-500). Cells were incubated at 37° C., 5% $CO_2$ and 95% air in a humidified incubator for 2 hours. Immediately after serum starvation, Endothelial Cell Basal Medium containing 10 ng/mL of human tissue necrosis factor-alpha (TNF-α; GIBCO,) was added to the cells to induce E-selectin expression. Following 4 hours of TNF-α stimulation, the cells were detached using citric saline (135 mM potassium chloride, 15 mM sodium citrate) and immediately recalcified by addition of calcium chloride to 1 mM final concentration. The cells were centrifuged at 300×g at 4° C. and fixed by resuspension in PBS containing 4% paraformaldehyde (PFA; Electron Microscopy Sciences, 15710) in wet ice for 15 minutes. The PFA was removed by centrifugation and the cells resuspended in CHO buffer overnight.

Binding studies with CHO cells were performed in duplicate using two rows of a 96-well round bottom plate, whereas, binding studies with primary endothelial cells were performed in a single row of a 96-well V-bottom plate. The plates were centrifuged at 300×g for 2 minutes at 4° C. and the cells were resuspended and blocked by incubation in the CHO buffer for 10 minutes on wet ice. After incubation, the cells were centrifuged at 300×g for 2 minutes at 4° C. to remove the buffer. The cell pellet in each well was then resuspended and incubated in the designated volume of serially-diluted antibody (human IgG1 control, 0841, 1282, 1284, 1444 and 1448) and allowed to incubate for 30 minutes on wet ice. The test antibody solutions were prepared by three-fold dilution series (1333 nM to 0.0226 nM) using CHO buffer as diluent. After incubation with the antibody, the cells were washed three times by centrifugation at 300×g for 1 minute at 4° C. and resuspended in cold CHO buffer. The washed cells were resuspended and incubated with 100 µL of 1:1000 dilution of AlexaFluor647-conjugated goat anti-human F(ab')$_2$ Fragment (Fcγ fragment specific antibody, [Jackson Immunoresearch, 109-606-170] for 45 minutes (CHO cells) or 30 minutes (endothelial cells) on wet ice. The cells were washed three or four times prior to resuspension in CHO buffer for flow cytometric analysis. A Becton Dickinson LSRFortessa instrument using 640 nanometer laser line was used to acquire cell fluorescence data. Geometric mean fluorescence of cells was analyzed by FlowJo software package (FlowJo, LLC) and plotted against antibody concentration. The estimated $EC_{50}$ values were calculated using nonlinear regression analysis in the Prism suite (GraphPad, version 8).

Antibodies 0841, 1282, 1284, 1444 and 1448 bound to CHO cells engineered to express human E-selectin with similar estimated $EC_{50}$ values in the sub to low nM range (Table 27). The control human IgG did not exhibit any binding to the CHO cells expressing human E-selectin.

Antibodies 0164, 1282, 1284, 1444 and 1448 bound to cell surface human and cynomolgus monkey E-selectin on HUVECs and CLMECs that were treated for 4 hours with TNF-α to induce expression of E-selectin. Compared to the IgG1 isotype control, in which no binding was detected, binding to endogenously expressed E-selectin on the cell surface of TNF-α activated HUVEC or CLMEC was observed. A high fluorescence background was observed and $EC_{50}$ values were not calculated (Table 27).

TABLE 27

| Cell surface antibody binding by FACS | | | |
|---|---|---|---|
| antibody | binding to CHO-human E-selectin cells $EC_{50}$ (nM) | binding to activated HUVEC cells | binding to activated CLMEC cells |
| 0164 | NT | binding | binding |
| 0841 | 0.71 | NT | NT |
| 1282 | 0.85 | binding | binding |
| 1284 | 0.64 | binding | binding |
| 1444 | 0.66 | binding | binding |
| 1448 | 0.75 | binding | binding |

Example 22: Static Neutralization of Cellular Adhesion by Optimized Anti-E-Selectin Antibodies E-selectin binds to sialylated Lewis modified ligands expressed on the surfaces of blood cells. In this study, the human promyelocytic cell line (HL-60) was used as a cellular source for E-selectin ligands. The neutralizing activity of antibodies 0164, 1282, 1284, 1444 and 1448 on the adhesion of HL-60 cells to cell surface E-selectin (on CHO cells) was evaluated in a static neutralization adhesion assay.

CHO cells expressing human E-selectin, were grown in fresh growth media supplemented with 100 nM Methotrexate. After this initial passage of the cells, the methotrexate was omitted from the growth media for subsequent cultures. CHO cells expressing cynomolgus monkey E-selectin were cultured in R1 medium. After this initial passage of cells, the Zeocin was omitted from the growth media for subsequent cultures.

HL-60 cells at log phase were labeled using carboxyfluorescein diacetate succinimidyl ester fluorescent dye (CFSE) labeling kit (ThemoFisher, 65-0850-84). The labeled HL-60 cells were resuspended in CHO buffer (PBS, pH 7.4/1% bovine serum albumin (BSA)/1 mM calcium chloride ($CaCl_2$)/0.1% sodium azide ($NaN_3$)) at density of 400,000 cells/mL for use in the static adhesion assays.

The ability of antibodies 0164, 1282, 1284, 1444 and 1448 to inhibit cellular adhesion of HL-60 cells to E-selectin expressing CHO cells under static condition was evaluated. Briefly, CHO cells were seeded on two rows of a 96-well (technical replicates) flat bottom black plates at a density of 100,000 cells/well and were allowed to form a confluent monolayer (typically after 24 hours) at 37° C., 5% $CO_2$ and 95% air in a humidified incubator. The cell monolayer was gently washed using CHO buffer then designated wells were incubated with antibody solution (0164, 1282, 1284, 1444 and 1448) in a three-fold dilution series (ranging from 200 µg/mL or 1333 nM to 0.003 µg/mL or 0.022 nM). An appropriate volume of the CFSE-labeled HL-60 cell suspension (400,000 cells/mL) was immediately added to the wells so that the final antibody concentration was maintained (ranging from 200 µg/mL or 1333 nM to 0.003 µg/mL or 0.022 nM). The labeled HL-60 cells were incubated with the CHO cell monolayer for 45 minutes at 37° C. at 5% $CO_2$ and 95% air in a humidified incubator. After incubation, the plate was washed three times with CHO buffer and the fluorescence of the bound HL-60 cells was measured at excitation/emission wavelengths of 494/521 nanometer using Spectramax i3X (Molecular Devices). Fluorescence units were plotted as a function of the antibody concentration and $IC_{50}$ was estimated using nonlinear regression analysis using GraphPad Prism software (Version 8.0.2).

Figure 7:
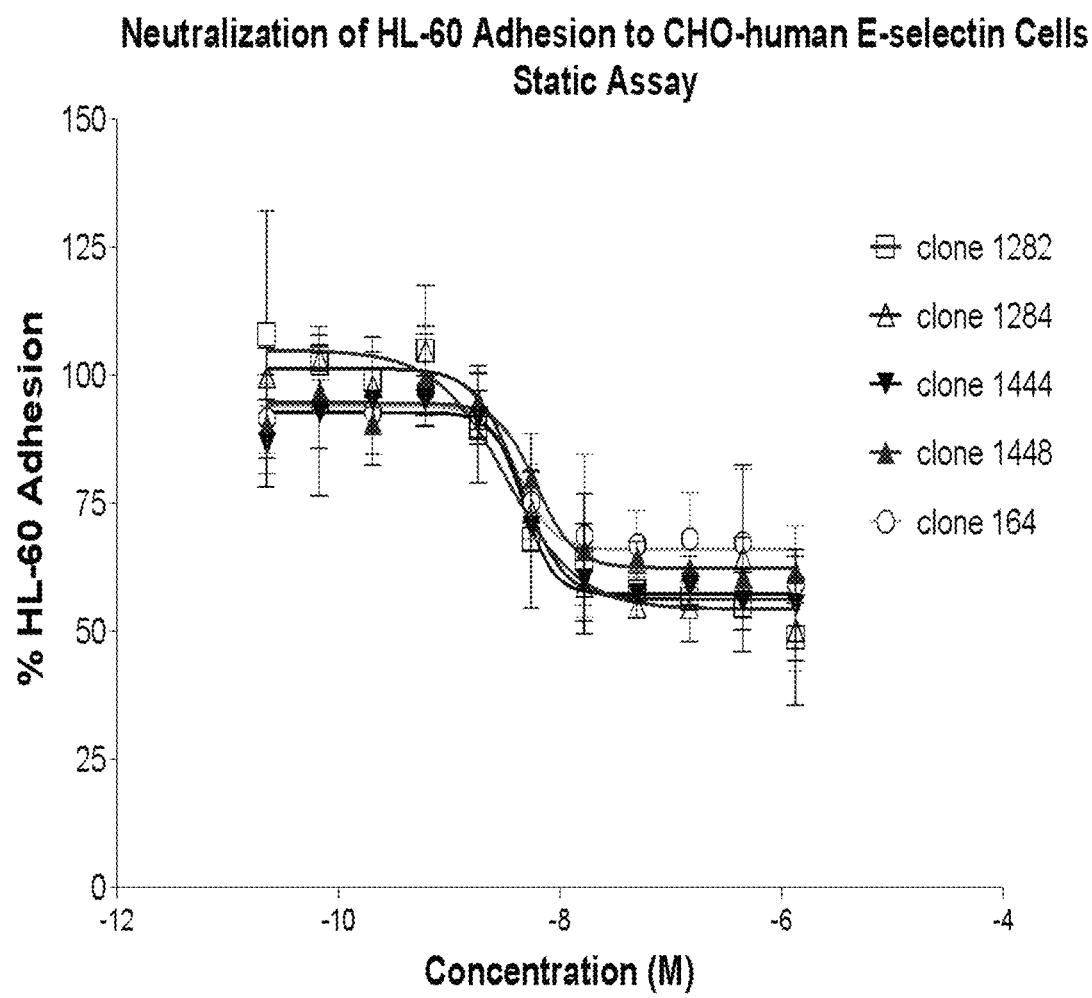
FIG. 7 depicts exemplary neutralization of HL-60 cell adhesion to CHO cells expressing human E-selectin by antibodies 1282, 1284, 1444, 1448 and 164 (also known as 0164).

Estimated $IC_{50}$ values for the antibodies were similar and ranged from 3.4 nM to 6.2 nM (FIG. 7) (Table 28).

TABLE 28

Static neutralization of HL-60 cell adhesion.
static neutralization of HL-60 cell adhesion

| antibody | CHO-human E-selectin cells-$IC_{50}$ (nM) |
|---|---|
| 0164 | 4.4 |
| 1282 | 3.4 |
| 1284 | 4.4 |
| 1444 | 4.7 |
| 1448 | 6.2 |

In a further static neutralization assay, using methods similar to those described above, antibody 1444 neutralized HL-60 adhesion to both cell surface human and cynomolgus monkey E-selectin with estimated $IC_{50}$ values of 3.36 nM and 3.84 nM, respectively (Table 38).

Example 23: Endogenous Human E-Selectin Binding of Optimized Anti-E-Selectin Antibodies Analysis of E-selectin binding inhibition in human plasma by optimized anti-E-selectin antibodies 1282, 1284, 1444 and 1448 was performed using an IP-LC/MS/MS method. This method quantified free soluble human E-selectin in human serum or free soluble monkey E-selectin in cynomolgus monkey serum. The method used 50 µL of serum in 250 µL of PBS which was incubated overnight at 4° C. (in cold room, shaking at 500 rpm) with 1.0 µg of biotinylated anti-E-selectin antibody 0164. After incubation, 30 µL of Invitrogen T1 streptavidin magnetic beads were added to each sample followed by incubation for 40 minutes at room temperature (shaking at 1000 rpm). Using a Hamilton Microlabstar, the magnetic beads were then washed two times with PBS/0.05% Tween-20 followed by one wash with PBS. Soluble E-selectin was then eluted from the beads with 145 µL of 30 mM hydrochloric acid (HCl) and neutralized with 32 µL of 1 M Tris HCl, pH 8. Subsequently 50 fmol of stable isotope labeled (SIL) internal standard was added, followed by the addition of dithiothreitol (DTT, 10 µL×50 mM). After incubating 35 minutes at 60° C. the samples were allowed to cool to room temperature prior to the addition of iodoacetamide (IAA, 10 µL×100 mM). Samples were then placed in the dark for 30 minutes to which 1 µg of Promega LysC/trypsin (10 µL×100 µg/mL) was added and then digested overnight at 37° C.

After overnight incubation, 50 µL of prepared sample was injected onto the nano ESILC-MS/MS. Quantification occurred by monitoring tryptic peptides for soluble E-selectin (CSSLAVLEK (SEQ ID NO:193)). This quantification showed that antibodies 1282, 1284, 1444 and 1448 had similar inhibition of human E-selectin with $IC_{50}$s of 2.4 nM, 1.1 nM, 1.2 nM and 1.8 nM, respectively, and $IC_{90}$s of 4.9 nM, 4.8 nM, 6.5 nM and 8.6 nM, respectively.

Example 24: Biophysical Characterization of Humanized Anti-E-Selectin

Thermal Stability

Differential scanning calorimetry was used to determine the stability of the four optimized anti-E-selectin antibodies 1282, 1284, 1444 and 1448. The DSC method similar to the method described in Example 16 was used. Table 29 below shows the melting temperatures ($T_m1$-$T_m3$ and FAB) of these molecules in Tris/Sucrose ("Tris/Suc") buffer (20 mM Tris, 8.5% sucrose, at pH 7.5), Histidine/Sucrose ("His/Suc") buffer (20 histidine, 8.5% sucrose, 0.005% EDTA, at pH 5.8) and Glutamic Acid/Trehalose ("Glu/Tre") buffer (20 M glutamic acid, 8.5% trehalose, at pH 4.5). All four molecules demonstrated good stability, with the first transition in the CH2 domain ($T_m1$) of greater than 65° C. in the Tris/Suc, His/Suc and Glu/Tre buffers. These molecules showed a slight increase in stability in the His/Suc and Glu/Tre buffers, and a slight decrease in stability in the Tris/Suc buffer.

TABLE 29

Thermal stability of optimized anti-E-selectin antibodies determined by differential scanning calorimetry.

| antibody | formulation | Tm1 (° C.) | Tm2 (° C.) | Tm3 (° C.) | apparent Tm of Fab (° C.) |
|---|---|---|---|---|---|
| 1282 | Tris/Suc, pH 7.5 | 71.41 ± 0.01 | 77.23 ± 0.04 | 85.86 ± 0.02 | 71.7 |
|  | His/Suc/EDTA, pH 5.8 | 71.70 ± 0.02 | 77.64 ± 0.05 | 84.42 ± 0.01 | 72.0 |
|  | Glu/Tre, pH 4.5 | 65.99 ± 0.02 | 74.81 ± 0.01 | 82.99 ± 0.02 | 74.9 |
| 1284 | Tris/Suc, pH 7.5 | 71.56 ± 0.01 | 78.12 ± 0.02 | 85.52 ± 0.02 | 71.7 |
|  | His/Suc/EDTA, pH 5.8 | 71.52 ± 0.06 | 76.09 ± 0.16 | 84.23 ± 0.02 | 73.0 |
|  | Glu/Tre, pH 4.5 | 65.95 ± 0.02 | 75.42 ± 0.01 | 83.07 ± 0.02 | 75.5 |
| 1444 | Tris/Suc, pH 7.5 | 71.25 ± 0.01 | 77.78 ± 0.02 | 85.47 ± 0.02 | 71.4 |
|  | His/Suc/EDTA, pH 5.8 | 71.69 ± 0.01 | 78.17 ± 0.02 | 84.34 ± 0.01 | 71.8 |
|  | Glu/Tre, pH 4.5 | 65.79 ± 0.01 | 74.28 ± 0.01 | 82.88 ± 0.02 | 74.3 |
| 1448 | Tris/Suc, pH 7.5 | 72.06 ± 0.01 | 77.70 ± 0.02 | 85.47 ± 0.01 | 72.2 |
|  | His/Suc/EDTA, pH 5.8 | 73.10 ± 0.10 | 76.24 ± 1.54 | 84.34 ± 0.02 | 73.5 |
|  | Glu/Tre, pH 4.5 | 65.65 ± 0.01 | 74.62 ± 0.03 | 76.58 ± 0.02 | 75.2 |

Forced Degradation

Optimized anti-E-selectin antibodies 1282, 1284, 1444 and 1448 were prepared for the 4 week forced degradation study at 40° C. by extensive dialysis into three buffers: Tris (20 mM Tris at pH7.5), His (20 mM histidine at pH5.8) and Glu (20 mM glutamic acid at pH4.5). After dialysis, sample concentrations are adjusted to 5 mg/mL. At T0, T2 and T4 weeks, samples were aliquoted for aSEC, iCE and bioassay testing.

The aggregation state of the forced degradation samples was determined by aSEC as described in Example 16. All samples showed minimal change, less than 5% LMMS and less than 1% HMMS species at T4 weeks (Table 30).

TABLE 30 aSEC of forced degradation samples of optimized anti-E-selectin antibodies.

| Week 4, 40° C. | % HMMS | % main | % LMMS |
|---|---|---|---|
| antibody 1282 | | | |
| Tris (pH 7.5) | 0.38 | 97.18 | 2.43 |
| His (pH 5.8) | 0.33 | 97.44 | 2.23 |
| Glu (pH 4.5) | 0.47 | 95.91 | 3.62 |
| antibody 1284 | | | |
| Tris (pH 7.5) | 0.62 | 96.38 | 3.00 |
| His (pH 5.8) | 0.34 | 97.51 | 2.15 |
| Glu (pH 4.5) | 0.51 | 95.65 | 3.84 |
| antibody 1444 | | | |
| Tris (pH 7.5) | 0.56 | 95.55 | 3.89 |
| His (pH 5.8) | 0.31 | 97.70 | 2.00 |
| Glu (pH 4.5) | 0.59 | 95.63 | 3.78 |
| antibody 1448 | | | |
| Tris (pH 7.5) | 0.68 | 94.96 | 4.36 |
| His (pH 5.8) | 0.33 | 97.56 | 2.11 |
| Glu (pH 4.5) | 0.61 | 95.68 | 3.72 |

Imaged capillary isoelectric focusing (iCE) was used to detect the charge-based heterogeneity of the forced degradation samples. This was done using a method similar to the method used in Example 16. For samples with a high % acidic/basic species in iCE analysis, additional mass spectroscopy analysis was required to identify sequence liabilities in CDR regions. Analysis of the samples in the Tris, His and Glu buffers showed typical increases in the acidic and basic species (Table 31). Antibody 1444 was further analyzed using Mass spectroscopy three-part analysis and peptide mapping for comparison to humanized 0841.

TABLE 31 iCE Analysis of forced degradation samples of optimized anti-E-selectin antibodies.

| 40° C. | | iCE pI | % acidic species | % main | % basic species |
|---|---|---|---|---|---|
| antibody 1282 | | | | | |
| Tris, pH 7.5 | T0W | 7.66 | 19.7 | 75.4 | 5.0 |
| | T2W | 7.66 | 38.8 | 48.4 | 12.8 |
| | T4W | 7.66 | 45.6 | 38.5 | 15.9 |
| His, pH 5.8 | T0W | 7.74 | 18.2 | 77.7 | 4.1 |
| | T2W | 7.73 | 25.9 | 65.2 | 8.9 |
| | T4W | 7.74 | 33.7 | 55.9 | 10.4 |
| Glu, pH 4.5 | T0W | 7.67 | 20.2 | 74.5 | 5.3 |
| | T2W | 7.67 | 31.5 | 55.5 | 13.0 |
| | T4W | 7.66 | 40.6 | 42.8 | 16.6 |
| antibody 1284 | | | | | |
| Tris, pH 7.5 | T0W | 7.66 | 22.3 | 73.4 | 4.4 |
| | T2W | 7.66 | 36.3 | 51.7 | 12.0 |
| | T4W | 7.66 | 49.2 | 36.0 | 14.8 |
| His, pH 5.8 | T0W | 7.74 | 19.5 | 76.8 | 3.7 |
| | T2W | 7.75 | 27.5 | 65.6 | 6.9 |
| | T4W | 7.74 | 35.6 | 55.7 | 8.8 |
| Glu, pH 4.5 | T0W | 7.67 | 21.1 | 74.3 | 4.6 |
| | T2W | 7.67 | 32.1 | 56.6 | 11.4 |
| | T4W | 7.67 | 41.9 | 43.8 | 14.2 |
| antibody 1444 | | | | | |
| Tris, pH 7.5 | T0W | 8.02 | 25.1 | 71.3 | 3.6 |
| | T2W | 8.02 | 36.2 | 52.3 | 11.5 |
| | T4W | 8.02 | 51.4 | 34.2 | 14.4 |
| His, pH 5.8 | T0W | 8.08 | 25.7 | 70.8 | 3.6 |
| | T2W | 8.08 | 33.2 | 59.7 | 7.1 |
| | T4W | 8.09 | 44.6 | 47.1 | 8.4 |
| Glu, pH 4.5 | T0W | 8.03 | 20.7 | 75.8 | 3.6 |
| | T2W | 8.03 | 36.3 | 52.4 | 11.3 |
| | T4W | 8.03 | 44.3 | 40.9 | 14.8 |
| antibody 1448 | | | | | |
| Tris, pH 7.5 | T0W | 8.01 | 24.5 | 71.8 | 3.7 |
| | T2W | 8.01 | 39.1 | 50.4 | 10.5 |
| | T4W | 8.01 | 54.0 | 33.0 | 13.0 |
| His, pH 5.8 | T0W | 8.07 | 25.6 | 70.7 | 3.8 |
| | T2W | 8.07 | 34.8 | 57.2 | 8.0 |
| | T4W | 8.08 | 40.0 | 51.0 | 9.0 |
| Glu, pH 4.5 | T0W | 8.02 | 22.3 | 73.8 | 3.9 |
| | T2W | 8.02 | 31.6 | 54.5 | 13.9 |
| | T4W | 8.02 | 39.9 | 42.3 | 17.8 |

Figure 8:
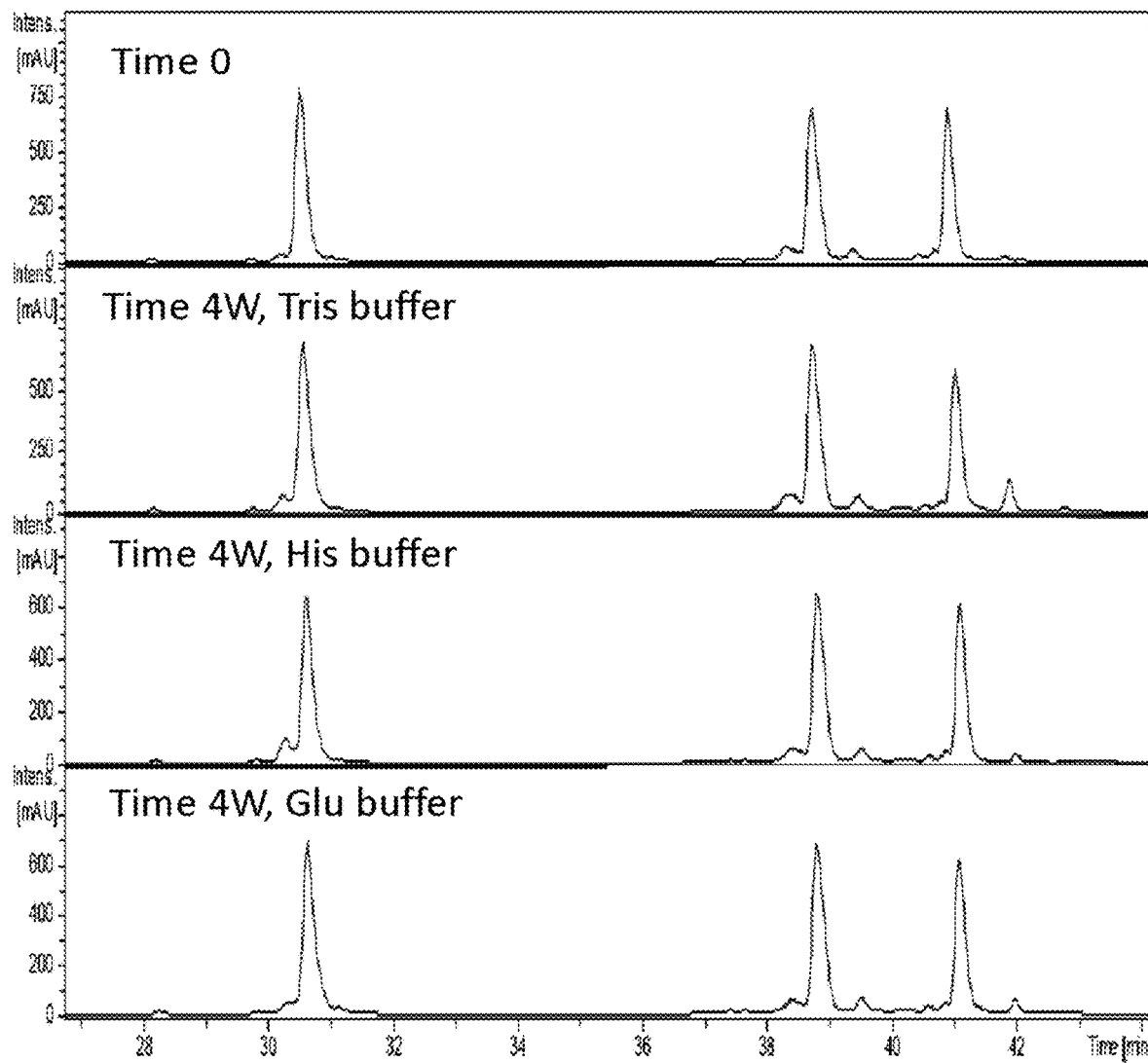
FIG. 8 depicts exemplary data from a three-part mass spectroscopy analysis of optimized anti-E-selectin antibody 1444 at time 0 (top panel) and following storage at 40° C. for 4 weeks in Tris, His or Glu buffer.
Figure 9A:
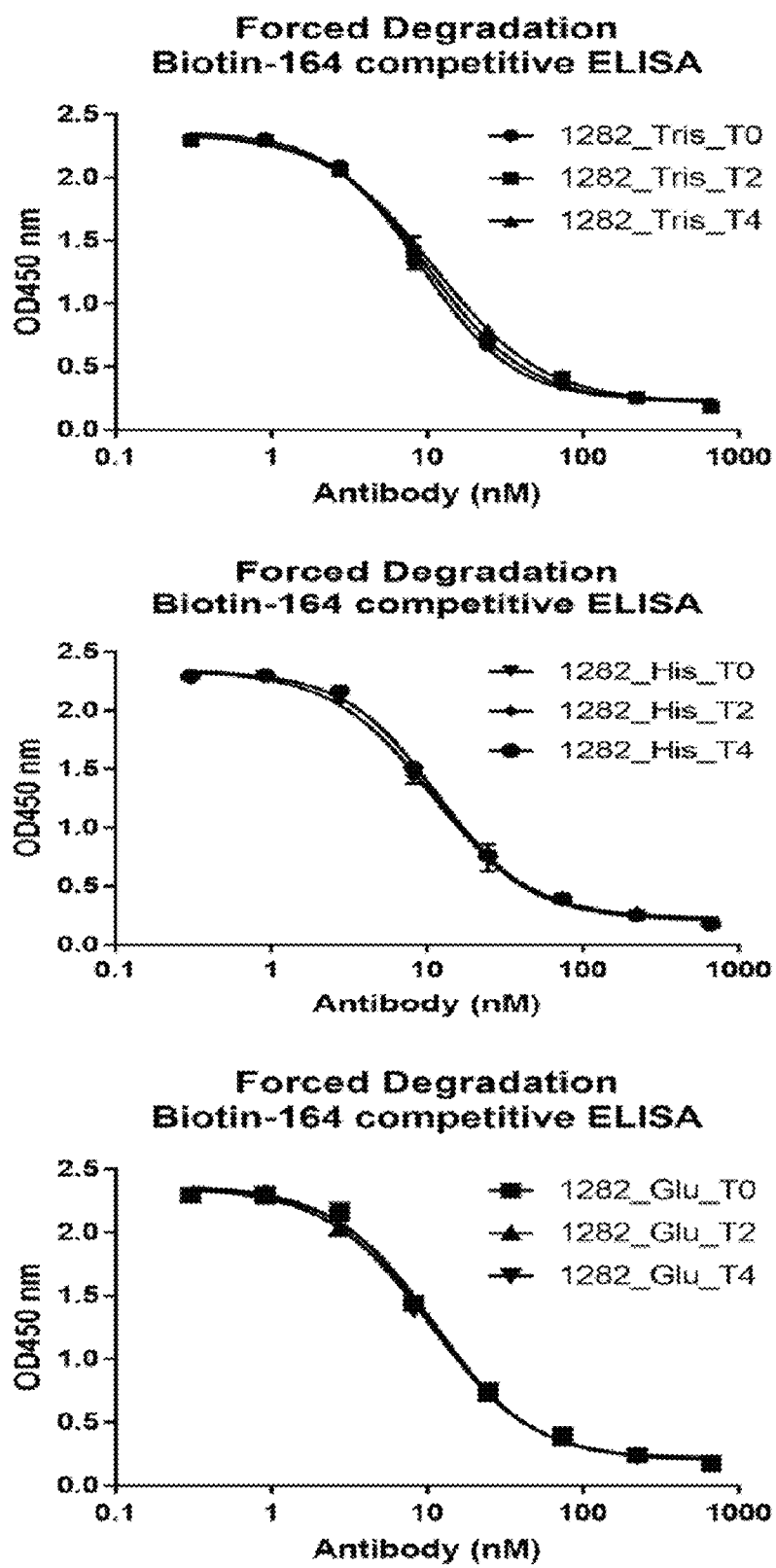
FIG. 9A-9D depicts exemplary competition ELISA analysis of antibodies 1282 (FIG. 9A), 1284 (FIG. 9B), 1444 (FIG. 9C) and 1448 (FIG. 9D) following forced degradation. Antibodies were analyzed at time 1 (T0) and following incubation in Tris, His or Glu buffer for 2 weeks (T2) or 4 weeks (T4) at 40° C.
Figure 9B:
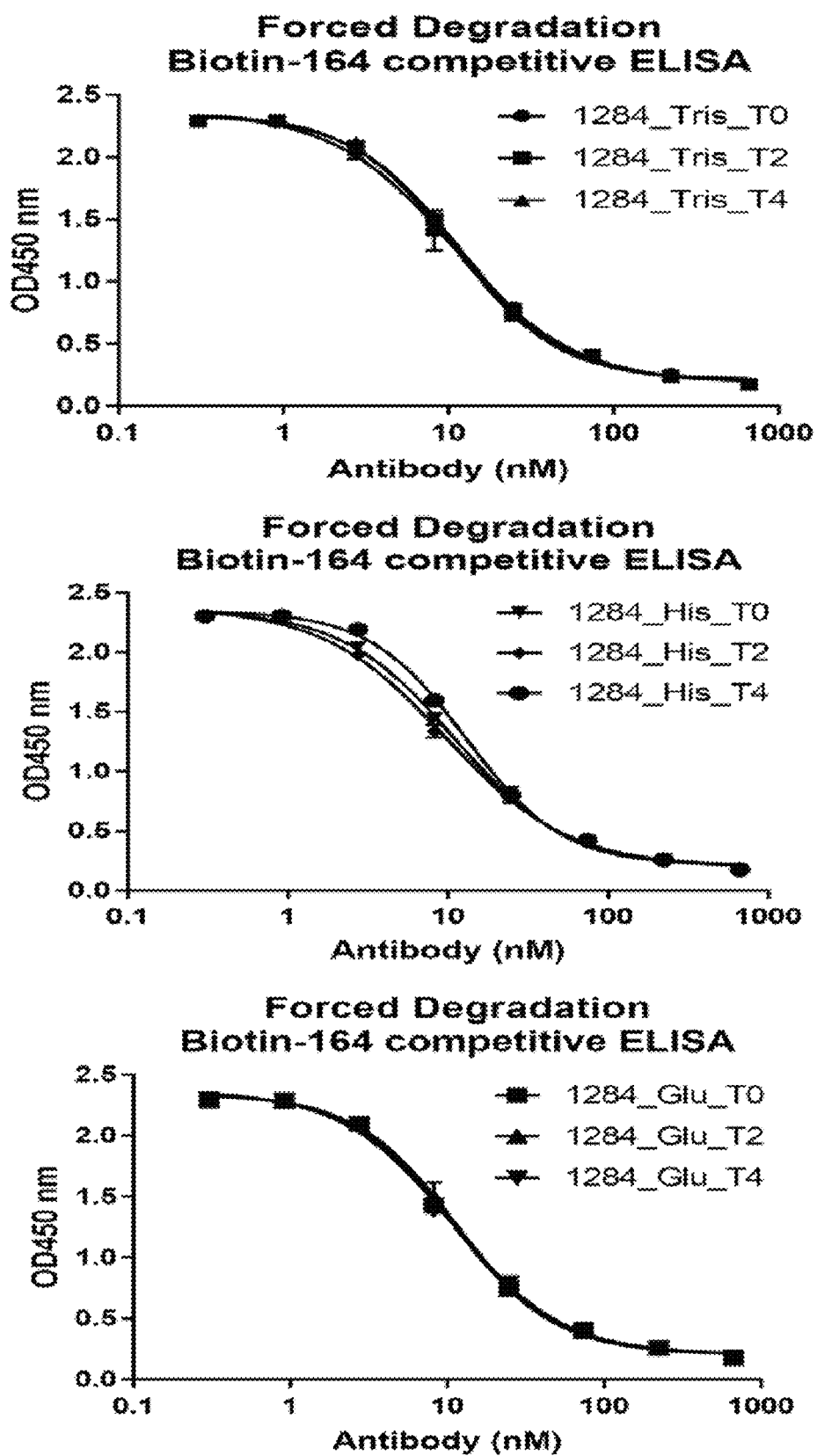
Figure 9C:
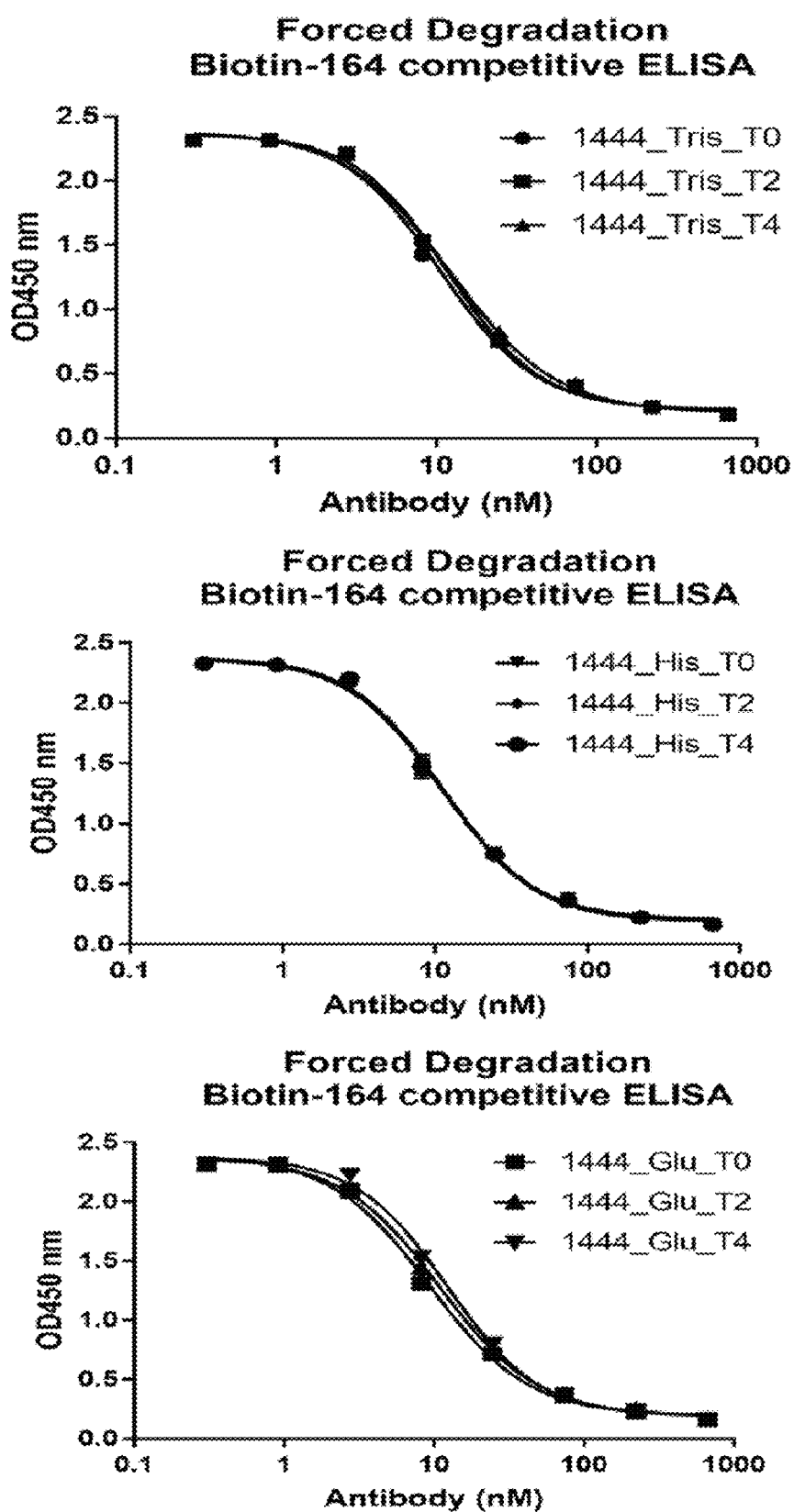
Figure 9D:
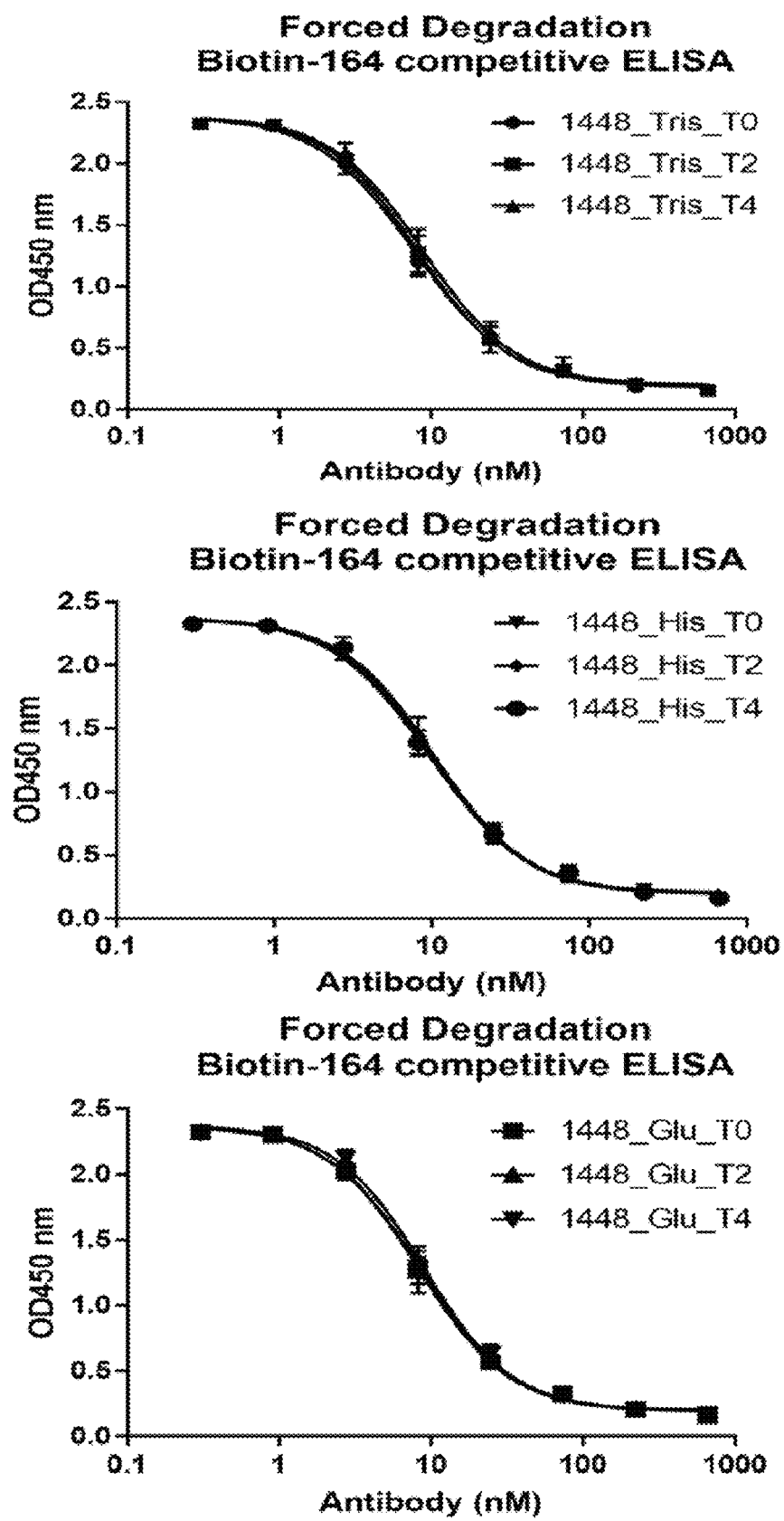
Figure 10A:
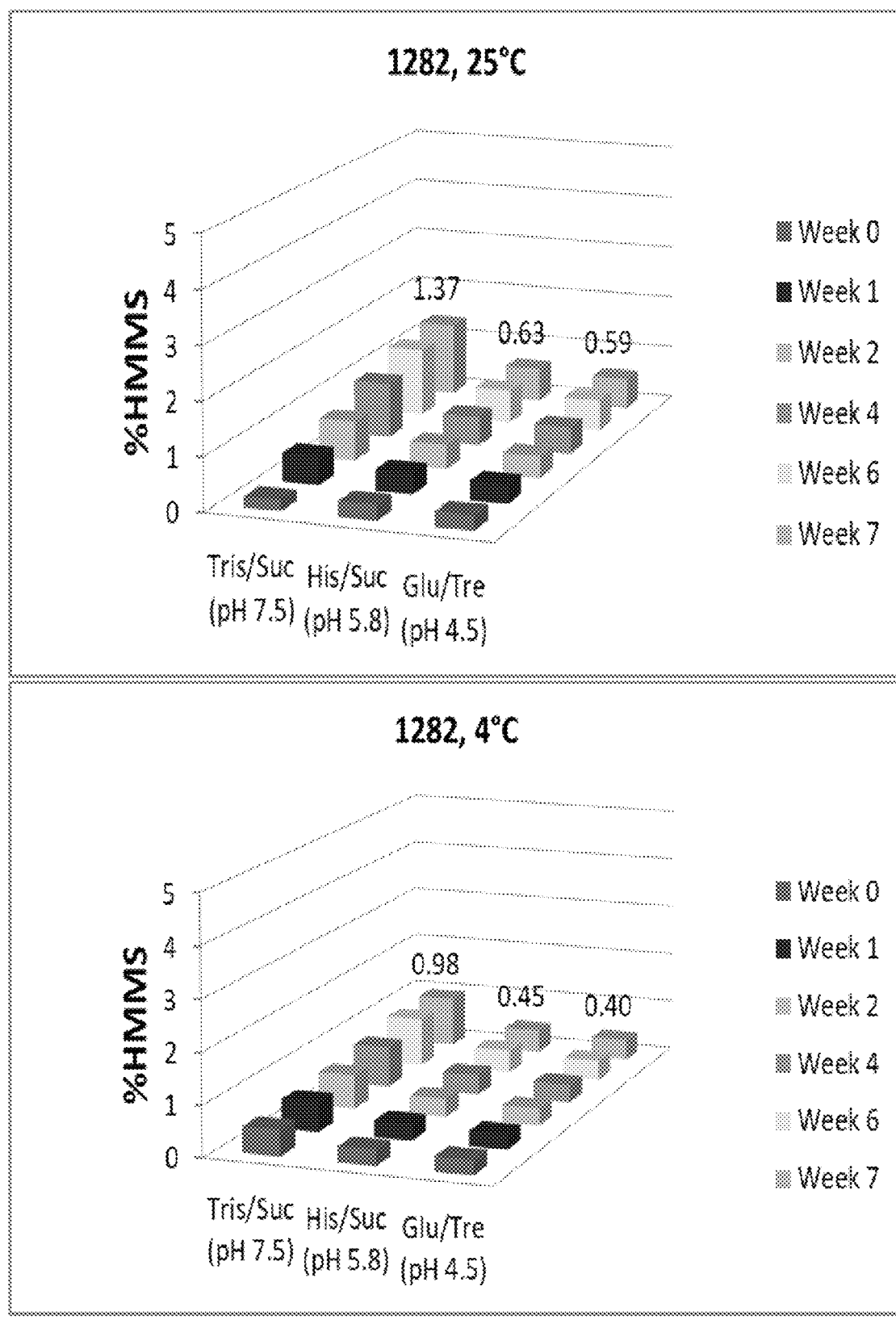
FIG. 10A-10D depicts aSEC analysis of high concentration samples of optimized anti-E-selectin antibody samples. Antibodies at a concentration of 150 mg/mL were analyzed at time 0 (0) and following storage at 4° C. or 25° C. in Tris/Suc, His/Suc or Glu/Tre buffer for 1, 2, 4, 6 and 7 weeks. The percentage of high molecular mass species (% HMMS) was quantified.
Figure 10B:
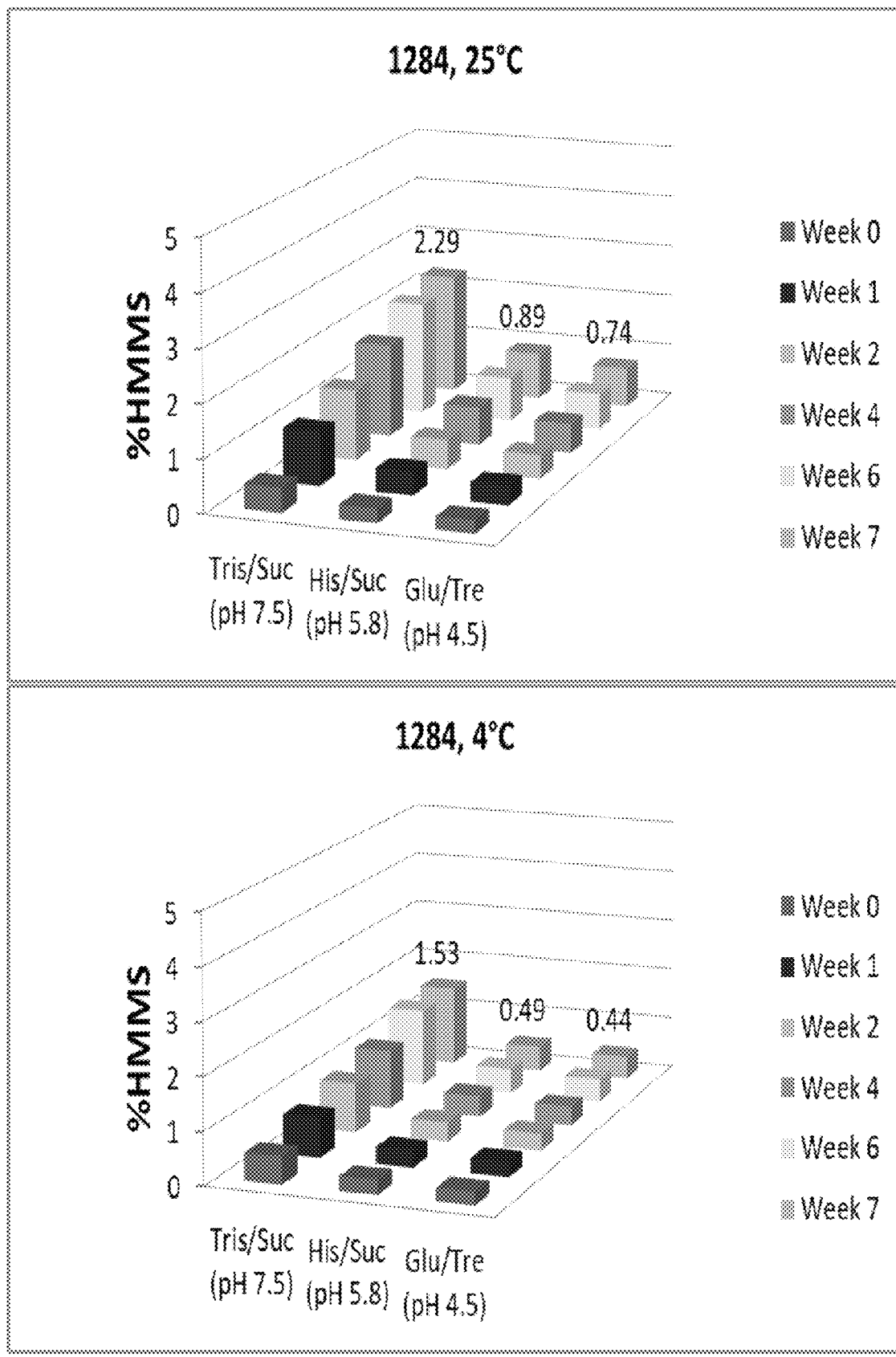
Figure 10C:
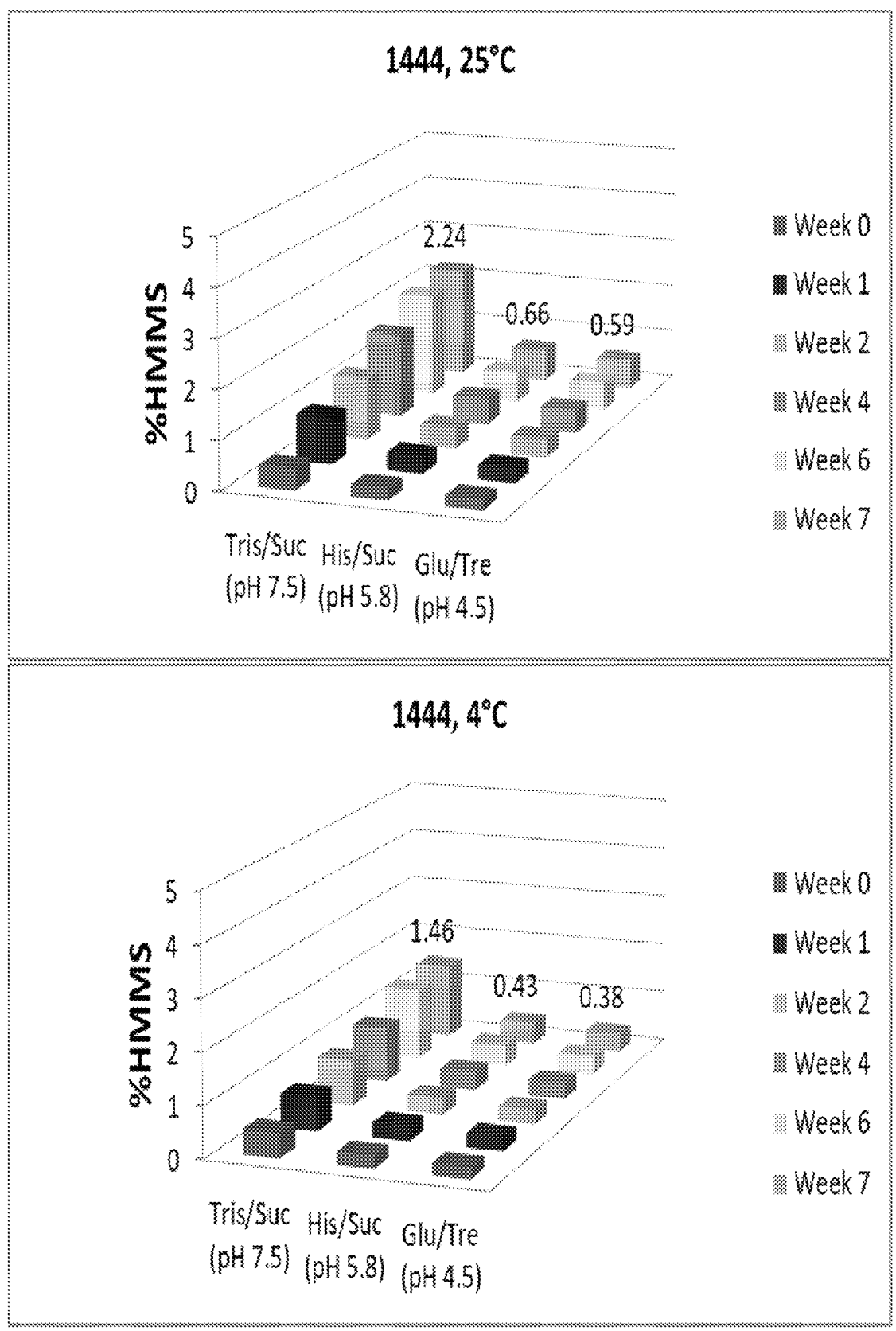
Figure 10D:
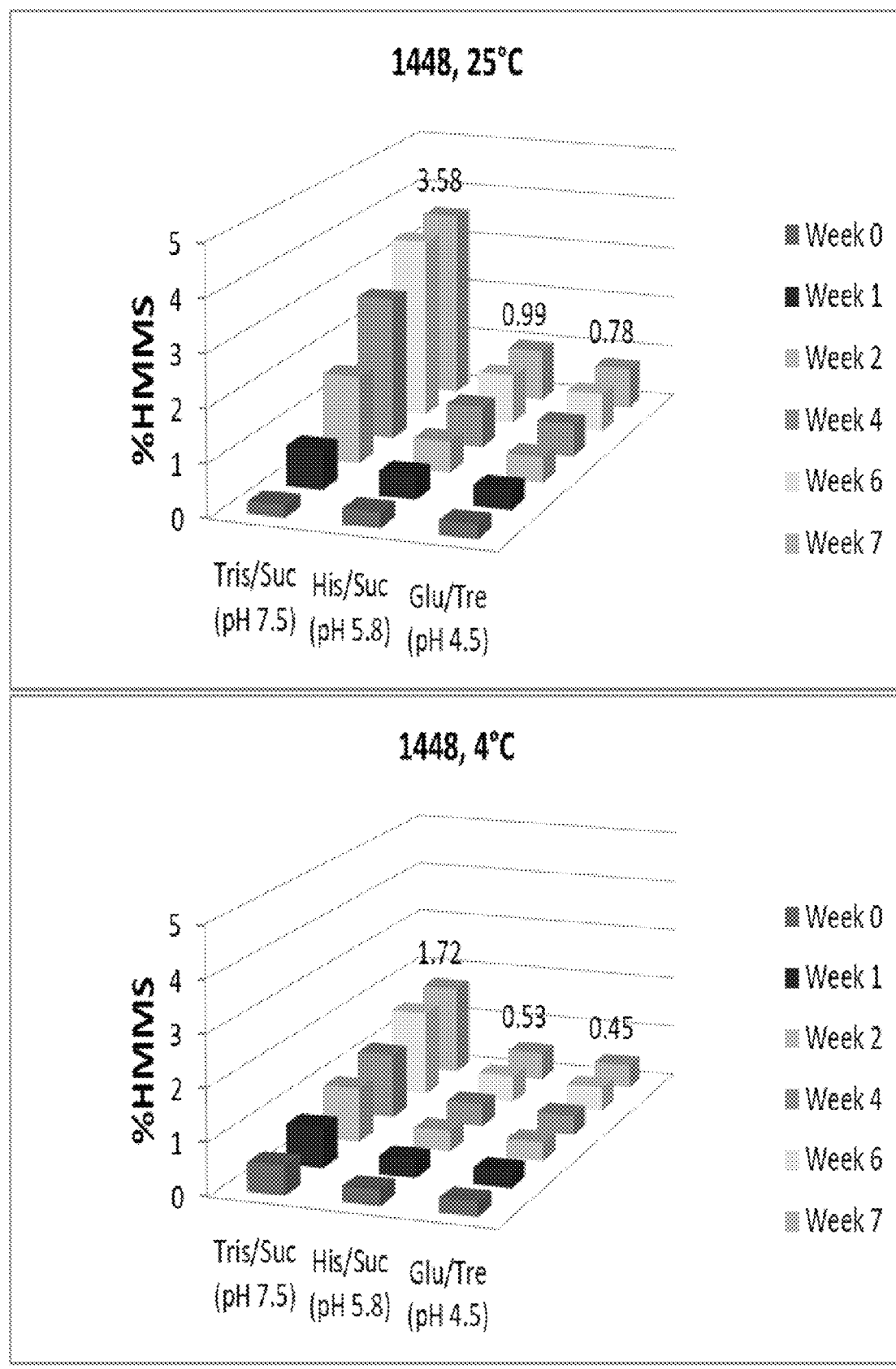

Mass Spectroscopy Analysis 3-pert mass spectroscopy analysis was performed on optimized antibody 1444. Analysis of the forced degradation of antibody 1444 at T4W in Glu, His and Tris buffer showed similar profiles as compared to T0. There were low levels of scFc (single chain Fc) oxidation and D/P Clip observed, low levels of oxi_Fd (oxidized Fd) detected, trace Fd+ HexNAc (glycated Fd) detected, trace amount Fd D/P clip (Fd fragment with cleaved D/P site) detected, and low level PyroE Fd (Fd fragment with pyroglutamic acid at the N-termini) observed in stressed samples (FIG. 8).

Peptide mapping was carried out for antibody 1444 using a method similar to the method used in Example 16. High fidelity peptide mapping analysis of T0 and T4 week forced degradation samples in Tris, His or Glu buffer indicated that only trace level isomerization and deamidation was detected in anti-E-selectin antibody 1444 HC CDR2 peptide IDPANGNTIYVDSVTGR (SEQ ID NO:194), (Table 32). All samples had >96% regular peptide with less than 1% found as a deamidated peptide and less than 2% found as peptide containing isomerization (IsoD). This optimized variant no longer contains a chemically labile motif at light chain position 30 which was mutated to Glu. For LC CDR1 peptide TSQNIERYLNWQQKPGK (SEQ ID NO: 195), no modification was detected.

TABLE 32

LC/MS peptide mapping of forced degradation samples of HC CDR2 peptide from optimized anti-E-selectin antibody 1444.

| HC CDR2 peptide | % regular peptide | % deamidation peptide | % IsoD peptide |
|---|---|---|---|
| T0 | 99.00% | 0.07% | 0.32% |
| Glu T4W | 98.30% | 0.18% | 0.56% |
| His T4W | 96.60% | 0.16% | 0.65% |
| Tris T4W | 97.80% | 0.30% | 1.20% |

To additionally asses the stability of the forced degradation samples, the activity of the stressed samples (antibodies 1282, 1284, 1444, 1448) was evaluated in a competition binding ELISA. Here the T0, T2W and T4W samples were compared for their ability to compete with biotinylated chimeric antibody 0164 for binding to human E-selectin. This method was similar to the method described in Example 16. The competition binding results are shown in FIGS. 9A-9D and no difference was seen between the T0, T2W and T4W samples, indicating that the ability of the antibodies to bind to E-selectin was stable following high-temperature incubation.

High Concentration Stability

Optimized anti-E-selectin antibodies 1282, 1284, 1444 and 1448 were dialyzed extensively into three buffers, Tris/Suc (20 mM Tris, 8.5% sucrose, at pH 7.5), His/Suc (20 mM histidine, 8.5% sucrose, 0.005% EDTA, at pH 5.8) and Glu/Tre (20 mM glutamic acid, 8.5% trehalose, at pH 4.5). After dialysis, the samples were concentrated to 150 mg/mL using spin filter concentrator and store at 4° C. and 25° C. At time zero (T0), one week (T1W), two weeks (T2W), four weeks (T4W), six weeks (T6W) and seven weeks (17W), samples were aliquoted for real time aSEC analysis, with iCE and CGE analysis at T0, T3 and T7 weeks performed at the end of study.

The aggregation state of the high concentration samples was determined by aSEC as described in Example 16. Samples at 4° C. and 25° C. showed good high concentration stability at all time points with little increase in HMMS (<5% of the total) in al three buffer conditions (FIG. 10A-10D).

iCE was used to detect the charge-based heterogeneity of the high concentration samples using a method similar to the method described in Example 16. Minimal change in the % acidic and the % basic species was seen in antibodies stored at 25° C. in Tris/Suc, His/Suc and Glu/Tre buffers over the 7 week study (Table 33).

TABLE 33 iCE analysis of 25° C. high concentration samples of optimized anti-E-selectin antibodies.

| buffer/time | % acidic species | % main | % basic species |
|---|---|---|---|
| antibody 1282 | | | |
| Tris/Suc T0 | 17.7 | 77.5 | 4.8 |
| Tris/Suc T3W | 25.1 | 67.0 | 7.9 |
| Tris/Suc T7W | 35.1 | 54.1 | 10.8 |
| His/Suc T0 | 13.2 | 82.7 | 4.1 |
| His/Suc T3W | 15.4 | 79.1 | 5.5 |
| His/Suc T7W | 18.3 | 75.6 | 6.1 |
| Glu/Tre T0 | 16.9 | 77.3 | 5.8 |
| Glu/Tre T3W | 18.1 | 74.6 | 7.3 |
| Glu/Tre T7W | 21.1 | 69.5 | 9.5 |
| antibody 1284 | | | |
| Tris/Suc T0 | 22.4 | 73.2 | 4.4 |
| Tris/Suc T3W | 29.6 | 63.3 | 7.1 |
| Tris/Suc T7W | 37.2 | 53.4 | 9.4 |
| His/Suc T0 | 16.5 | 79.8 | 3.7 |
| His/Suc T3W | 19.3 | 76.1 | 4.6 |
| His/Suc T7W | 22.4 | 71.9 | 5.7 |
| Glu/Tre T0 | 18.6 | 77.0 | 4.5 |
| Glu/Tre T3W | 20.0 | 73.7 | 6.2 |
| Glu/Tre T7W | 22.7 | 69.9 | 7.4 |
| antibody 1444 | | | |
| Tris/Suc T0 | 24.0 | 72.4 | 3.6 |
| Tris/Suc T3W | 31.9 | 61.0 | 7.1 |
| Tris/Suc T7W | 39.2 | 51.1 | 9.8 |
| His/Suc T0 | 24.7 | 71.1 | 4.3 |
| His/Suc T3W | 24.4 | 70.9 | 4.7 |
| His/Suc T7W | 29.5 | 64.1 | 6.5 |
| Glu/Tre T0 | 24.0 | 72.4 | 3.6 |
| Glu/Tre T3W | 26.7 | 67.0 | 6.4 |
| Glu/Tre T7W | 29.7 | 63.0 | 7.3 |
| antibody 1448 | | | |
| Tris/Suc T0 | 30.4 | 65.3 | 4.4 |
| Tris/Suc T3W | 35.1 | 58.6 | 6.3 |
| Tris/Suc T7W | 43.3 | 48.0 | 8.7 |
| His/Suc T0 | 28.1 | 67.5 | 4.4 |
| His/Suc T3W | 30.7 | 63.5 | 5.8 |
| His/Suc T7W | 32.4 | 61.2 | 6.3 |
| Glu/Tre T0 | 27.9 | 68.4 | 3.8 |
| Glu/Tre T3W | 29.2 | 63.9 | 6.9 |
| Glu/Tre T7W | 32.8 | 57.9 | 9.2 |

CGE analysis was conducted to determine the fragmentation of the high concentration samples of optimized antibodies 1282, 1284, 1444 and 1448. The analysis was done using a method similar to the method described in Example 16. The quantification of the % fragmentation and % HMMS demonstrated good high concentration stability for antibodies 1282, 1284, 1444 and 1448 in all three buffers at 25° C. (Table 34).

TABLE 34

CGE analysis of 25° C. high concentration samples of optimized anti-E-selectin antibodies.

| buffer/time | sum of % HLC | % non HLC | % fragment (LMMS) | % other (HMMS) |
|---|---|---|---|---|
| antibody 1282 | | | | |
| Tris/Suc, T0 | 99.89 | 0.11 | 0.07 | 0.04 |
| Tris/Suc, T3W | 99.88 | 0.12 | 0.05 | 0.07 |
| Tris/Suc, T7W | 99.86 | 0.14 | 0.07 | 0.07 |
| His/Suc, T0 | 99.92 | 0.08 | 0.04 | 0.04 |
| His/Suc, T3W | 99.95 | 0.05 | 0.04 | 0.01 |
| His/Suc, T7W | 99.90 | 0.10 | 0.07 | 0.03 |
| Glu/Tre, T0 | 99.96 | 0.04 | 0.00 | 0.04 |
| Glu/Tre, T3W | 99.84 | 0.16 | 0.11 | 0.05 |
| Glu/Tre, T7W | 99.77 | 0.23 | 0.20 | 0.03 |
| antibody 1284 | | | | |
| Tris/Suc, T0 | 99.99 | 0.01 | 0.00 | 0.01 |
| Tris/Suc, T3W | 99.79 | 0.21 | 0.10 | 0.11 |
| Tris/Suc, T7W | 99.79 | 0.21 | 0.11 | 0.10 |
| His/Suc, T0 | 99.92 | 0.08 | 0.05 | 0.03 |
| His/Suc, T3W | 99.90 | 0.10 | 0.05 | 0.05 |
| His/Suc, T7W | 99.75 | 0.25 | 0.19 | 0.06 |
| Glu/Tre, T0 | 99.86 | 0.14 | 0.09 | 0.05 |
| Glu/Tre, T3W | 99.84 | 0.16 | 0.11 | 0.05 |
| Glu/Tre, T7W | 99.76 | 0.24 | 0.19 | 0.05 |
| antibody 1444 | | | | |
| Tris/Suc, T0 | 99.68 | 0.32 | 0.19 | 0.13 |
| Tris/Suc, T3W | 99.79 | 0.21 | 0.07 | 0.14 |
| Tris/Suc, T7W | 99.03 | 0.97 | 0.66 | 0.31 |
| His/Suc, T0 | 99.70 | 0.30 | 0.20 | 0.10 |
| His/Suc, T3W | 99.85 | 0.15 | 0.05 | 0.10 |
| His/Suc, T7W | 99.43 | 0.57 | 0.42 | 0.15 |
| Glu/Tre, T0 | 99.76 | 0.24 | 0.12 | 0.12 |
| Glu/Tre, T3W | 99.57 | 0.43 | 0.32 | 0.11 |
| Glu/Tre, T7W | 99.31 | 0.69 | 0.59 | 0.10 |
| antibody 1448 | | | | |
| Tris/Suc, T0 | 99.74 | 0.26 | 0.14 | 0.12 |
| Tris/Suc, T3W | 99.52 | 0.48 | 0.20 | 0.28 |
| Tris/Suc, T7W | 99.28 | 0.72 | 0.35 | 0.37 |
| His/Suc, T0 | 99.62 | 0.38 | 0.27 | 0.11 |
| His/Suc, T3W | 99.29 | 0.71 | 0.56 | 0.15 |
| His/Suc, T7W | 99.25 | 0.75 | 0.57 | 0.18 |
| Glu/Tre, T0 | 99.59 | 0.41 | 0.27 | 0.14 |
| Glu/Tre, T3W | 99.18 | 0.82 | 0.68 | 0.14 |
| Glu/Tre, T7W | 99.23 | 0.77 | 0.65 | 0.12 |

Viscosity

Viscosity of the optimized antibodies 1282, 1284, 1444 and 1448 were measured using the following DLS (dynamic light-scattering) bead-based method. Proteins in PBS were extensively dialyzed against 20 mM histidine, 85 mg/mL sucrose, 0.05 mg/mL EDTA, pH 6.0 using membrane cassette devices 10K MWCO (Thermo Scientific). Proteins were harvested from dialysis and filtered using a 0.2 µM syringe filter. Proteins were concentrated using Vivaspin centrifugal concentrators 10K MWCO (GE Healthcare). Sample aliquots (12 µL) were removed from the concentrator retentate as the protein volume was reduced and the protein concentration increased. 300 nm beads (Nanosphere, Thermo Scientific) were added to the protein samples and buffer blank. The beads were diluted 1:10 in 20 mM histidine, 85 mg/mL sucrose, 0.05 mg/mL EDTA, pH 6.0 and 0.75 µL diluted beads were spiked into the protein sample. The protein/bead and buffer/bead samples were mixed by gently vortexing. Eight µL of sample was transferred to 1536 well plate (SensoPlate, glass bottom, Greiner Bio-One) for analysis by DLS. The plate was sealed with optically clear tape and centrifuged at 2000 RPM for 2 minutes to remove bubbles.

The DLS measurements were made using a DynaPro Plate Reader (Wyatt Technology, Santa Barbara, Calif.). Samples were incubated at 25° C. and measured with 15 consecutive 25 second acquisitions. Radius of the bead was averaged for data acquisitions that had acceptable decay curves. The viscosity was calculated based on the Stokes-Einstein equation. Sample viscosity was calculated as the measured apparent radius divided by the nominal bead radius times 0.893 centipoise (cP), the viscosity of water at 25° C.

High concentration formulation is a desirable property for antibodies, allowing higher and less frequent dosing. Optimized antibodies al showed good viscosity profiles with their viscosity not reaching 20 cP until approximately 160 mg/mL. To confirm this measurement, an additional viscosity measurement at a single concentration for each optimized antibody was done using the Anton Paar method described below.

Figure 11:
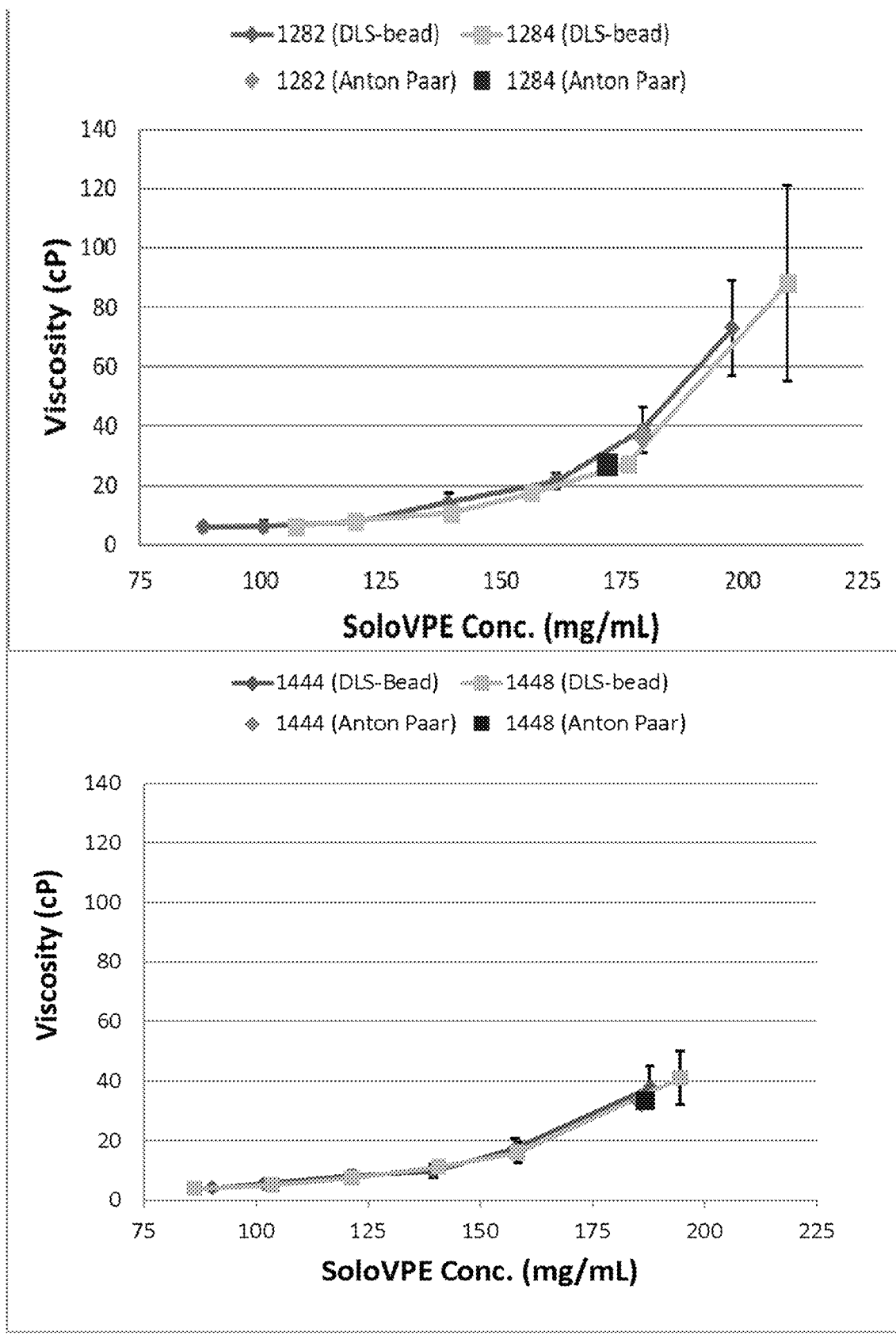
FIG. 11 depicts exemplary viscosity curves of optimized anti-E-selectin antibodies. The viscosity of optimized antibodies 1282, 1284, 1444 and 1448 was measured using a DLS bead-based method. Additional single data points are provided for each using an Anton Paar cone and plate method.

Protein samples were concentrated to a target of 170-180 mg/mL using 50 kDa molecular weight cut-off Amicon centrifugal filter units (EMD Millipore, Bilerica, Mass.). Protein concentrations were determined by 280 nm analysis on the SoloVPE Variable Pathlength System (C Technologies, Inc, Bridgewater, N.J.). Viscosity measurements were performed using the CP25-1 cone and plate on the MCR-302 rheometer (Anton Paar USA Inc., Ashland, Va.) at a constant rotational speed of 150 rpm at 25° C. A total of 10 measurements of 10 seconds each were collected per sample and the data was analyzed using the Rheoplus (Anton Paar USA Inc.) V 3.62 software. The viscosity of 1282 was measured to be 36.29 cP at 179.5 mg/mL. The viscosity of 1284 was measured to be 27.38 cP at 171.9 mg/mL. The viscosity of 1444 was measured to be 33.43 cP at 185.7 mg/mL. The viscosity of 1448 was measured to be 33.35 cP at 186.8 mg/mL. All of these measurements fit well to the curve fit of the DLS viscosity measurements, reinforcing their accuracy (FIG. 11).

Example 25: In Silico Immunogenicity Risk and T-Cell Epitope Prediction of Optimized Anti-E-Selectin The immunogenicity risk of optimized anti-E-selectin antibodies 1282, 1284, 1444 and 1448 was predicted using in silico tools to predict MHCII peptide binding. The method used was similar to the method described in Example 17. The optimized antibodies showed improved overall sequence score decreasing from −30.34 for humanized antibody 0841 to scores of −46.26 for antibody 1282, −46.16 for antibody 1284, −45.11 for antibody 1444 and −45.32 for antibody 1448. Additionally, 8 predicted non-germline T-cell epitopes were removed in the optimized antibodies (Table 35). P6

TABLE 35

In silico immunogenicity analysis of optimized anti-E-selectin antibodies.

| antibody | VH Seq ID NO | VL Seq ID NO | overall sequence score | epitopes all | non-germline | CDR | non-germline CDR |
|---|---|---|---|---|---|---|---|
| 0841 | 25 | 21 | −30.34 | 15 | 8 | 9 | 8 |
| 1282 | 45 | 5 | −46.26 | 10 | 0 | 4 | 0 |
| 1284 | 42 | 5 | −46.16 | 10 | 0 | 4 | 0 |
| 1444 | 11 | 5 | −45.11 | 10 | 0 | 4 | 0 |
| 1448 | 39 | 5 | −45.32 | 10 | 0 | 4 | 0 |

Example 26: Self-Interaction and Polyreactivity of Optimized Anti-E-Selectin Antibodies The optimized antibodies 1444 (comprising HC amino acid sequence of SEQ ID NO:13 and LC amino acid sequence of SEQ ID NO:1), 1282 (comprising HC amino acid sequence of SEQ ID NO 43 and LC amino acid sequence of SEQ ID NO:1), 1284 (comprising HC amino acid sequence of SEQ ID NO:40 and LC amino acid sequence of SEQ ID NO:1) and 1448 (comprising HC amino acid sequence of SEQ ID NO:37 and LC amino acid sequence of SEQ ID NO:1) were tested for binding to DNA and insulin, and in addition were tested for self-interaction in an AC-SINS assay (affinity-capture self-interaction nanoparticle spectroscopy; Liu et al. (2014) mAbs 6:483-92). In the AC-SINS assay, mAbs captured on gold nanospheres induce a shift in the absorbance maximum if they bind to one another and thereby cause the beads to cluster. High scores in this assay have been suggested to correlate with low or poor solubility and nonspecific membrane Interactions (Liu et al., mAbs 2014; 6:483-92). Antibodies 1282, 1284, 1444 and 1448 had very low AC-SINS scores and DNA/Insulin scores, comparable to those of the negative control (Table 36). These data indicate that these antibodies are at low risk for polyreactivity, similar to that of the negative control.

TABLE 36

Non-specific binding and self-interaction of E-selectin antibodies.

| antibody | AC-SINS (wavelength of maximum absorbance relative to blank, nm) | DNA binding normalized to blank | insulin binding normalized to blank |
|---|---|---|---|
| 1282 | 1 | 2 | 1 |
| 1284 | 1 | 2 | 2 |
| 1444 | 1 | 3 | 2 |
| 1448 | 1 | 2 | 2 |
| Polyreactivity negative control | 1 | 2 | 4 |
| Polyreactivity positive control (MJ4-2 v1.1/P33) | 22 | 34 | 36 |

Figure 12:
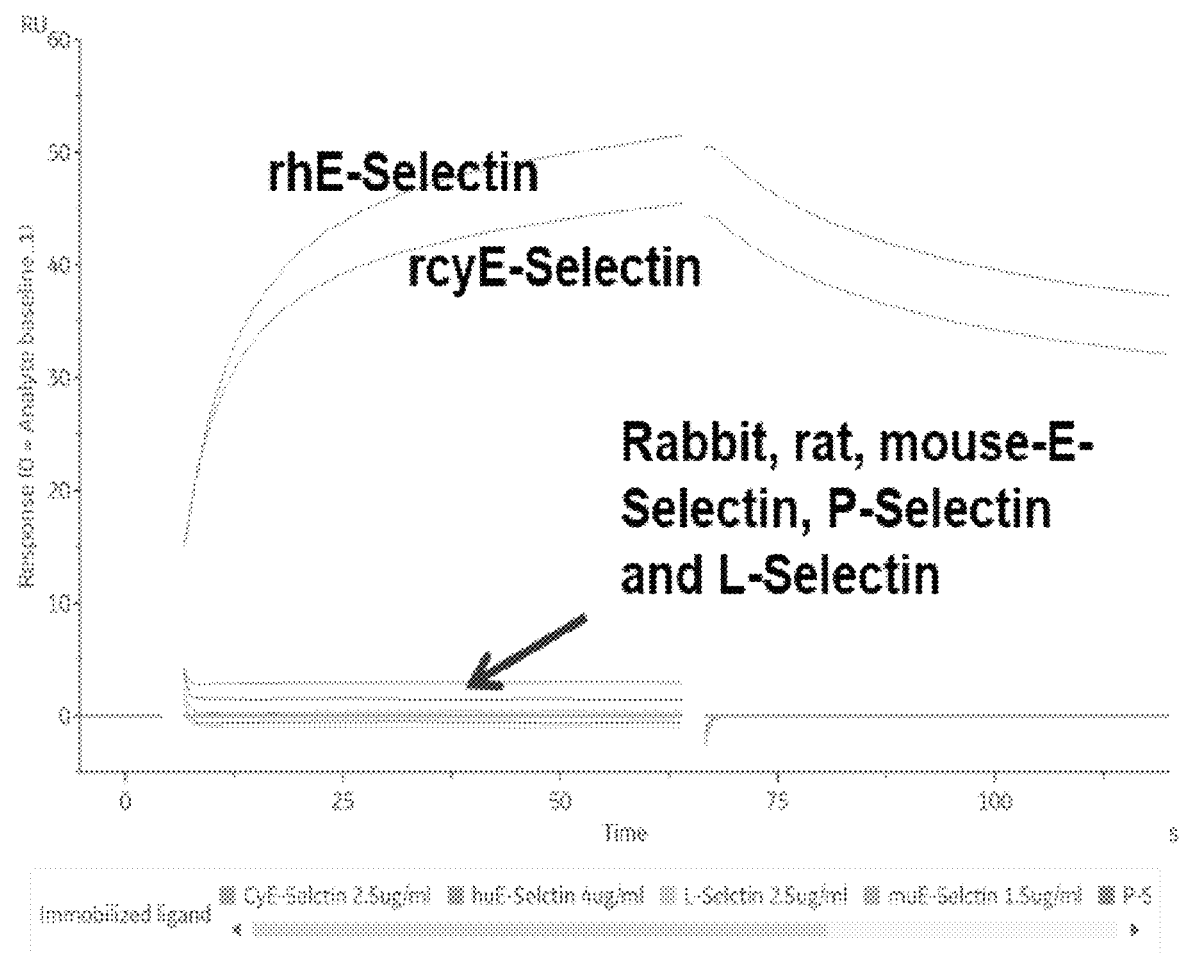
FIG. 12 depicts exemplary SPR analysis of optimized antibody 1444 binding to human E-selectin (rhE-Selectin), homologs P-selectin and L-selectin, and species homologs of rabbit, rat, mouse (muE-Selectin), and cynomolgus monkey (rcyE-Selectin).

Example 27: Cross-Reactivity Evaluation of Optimized Anti-E-Selectin Using Surface Plasmon Resonance Binding affinities were determined for human and cynomolgus monkey E-selectin for the optimized antibody 1444 (comprising HC amino acid sequence of SEQ ID NO:13 and LC amino acid sequence of SEQ ID NO:1) using SPR as described in Example 20. Using a similar method with a high analyte concentration of 405 nM, we also evaluated the biding affinity of this antibody to homologs of rat E-selectin, mouse E-selectin, rabbit E-selectin, human L-selectin and human P-selectin using a method similar to the method described in Example 5. A 25° C. no binding of antibody 1444 to rat E-selectin, mouse E-selectin, rabbit E-selectin, human L-selectin and human P-selectin was observed up to 405 nM (FIG. 12). Antibody 1444 bound to human E-selectin with a $K_D$ of 68.35+/−3.18 nM and bound to cynomolgus monkey E-selectin with a $K_D$ of 64.9+/−1.13 nM.

Example 28: Plate Based Direct Binding ELISA Analysis of Antibodies 1282, 1284, 1444 and 1448

Direct binding ELISAs were used to characterize the binding of antibodies 0841, 1282, 1284, 1444 and 1448 to various immobilized soluble recombinant selectins. Recombinant histidine tagged human P-, E- or L-selectin (Sino Biologicals), mouse E-selectin (Sino Biologicals), rat E-selectin (Sino Biologicals) and Cynomolgus monkey E-selectin (Sino Biologicals) stock solutions were prepared to a final concentration of 1 μg/mL in phosphate buffered saline without calcium and magnesium. Controls included an L-selectin directed antibody (BioLegend; 304811) or P-selectin directed antibody or a negative control IgG. One hundred μL per well of the diluted recombinant selectin proteins were added into a Ni-NTA HisSorb 96 well plate (Qiagen; 35061). Plates were incubated on an orbital shaker at room temperature for 2 hours. Following the incubation, the plates were washed 3 times with 200 μL of wash buffer (50 mM TRIS [trisaminomethane]; 150 mM sodium chloride; 0.05% polysorbate 20, pH 7.4). To decrease nonspecific binding, plates were treated with 200 μL of blocking buffer (BD OptEIA buffer; 555213; BD Biosciences), incubated on an orbital shaker for 1 hour at room temperature and washed as described above. Antibodies (IgG1 control antibody, anti-E-selectin antibodies, anti-P-selectin antibody or anti L-selectin antibody) were added to the reaction at 100 μL per well in duplicate with a four-fold dilution series (ranging from 133.33 nM to 0.004 nM made in BD OptEIA buffer), incubated for 1 hour on an orbital shaker and washed as described above. One hundred μL specific detection antibodies (described below) were added and incubated for 1 hour:

IgG1 control, 0841, 1282, 1284, 1444, 1448, anti-mouse-E-selectin and anti P-selectin antibodies were detected using 1 to 25000 or 1 to 50000 dilution of Peroxidase-conjugated Goat anti-human IgG Fc gamma (Jackson ImmunoResearch Lab; 109-035-008);

Anti L-selectin and anti-rat-E-selectin antibodies were detected using 1 to 25000 dilution of Peroxidase-conjugated AffiniPure Goat Anti-Mouse IgG (H+L); (Jackson ImmunoResearch Lab;).

Plates were washed and 100 μL per well of 1-Step Ultra TMB substrate (Thermo Scientific,) was added and incubated for 5 minutes at room temperature. Reactions were stopped with 100 μL of 2 M sulfuric acid and absorbance read at 450 nm (Spectramax M5e). Data was analyzed and graphed using GraphPad Prism software (8.0.2). Estimated half-maximal concentration ($EC_{50}$) values derived from the analysis.

Figure 13:
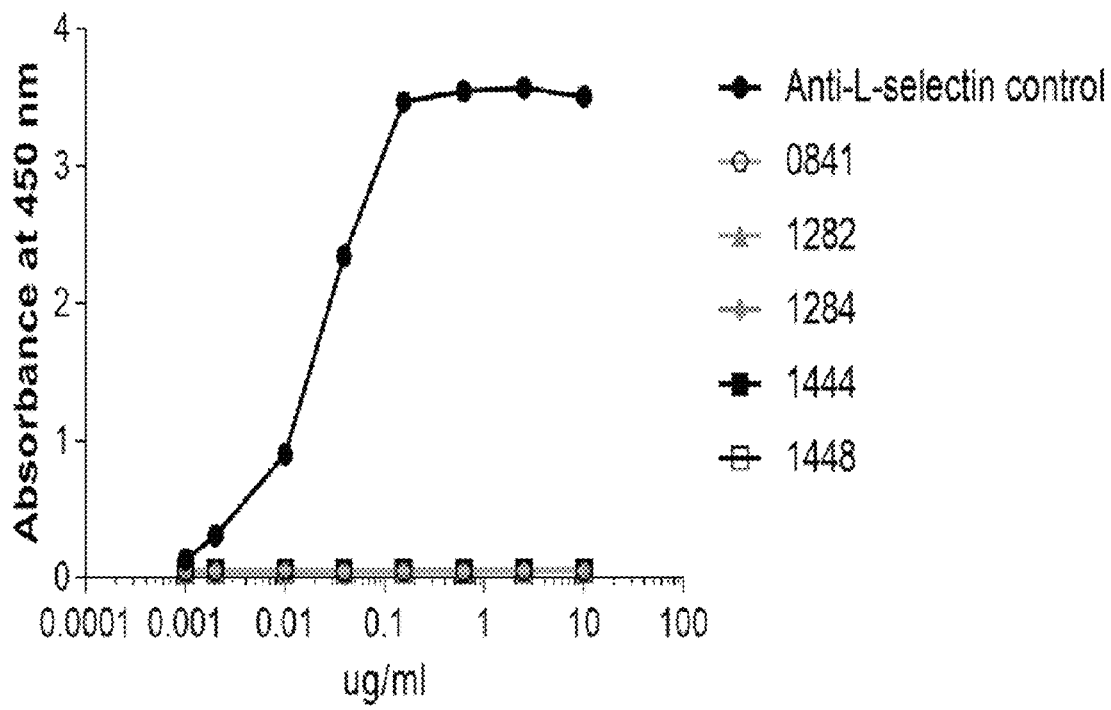
FIG. 13 depicts exemplary binding of anti-E-selectin antibodies (0841, 1282, 1284, 1444 and 1448) to immobilized human L-selectin and human P-selectin. An anti-L-selectin control antibody and an anti-P-selectin control antibody bound human L-selectin and human P-selectin, respectively.
Figure 13:
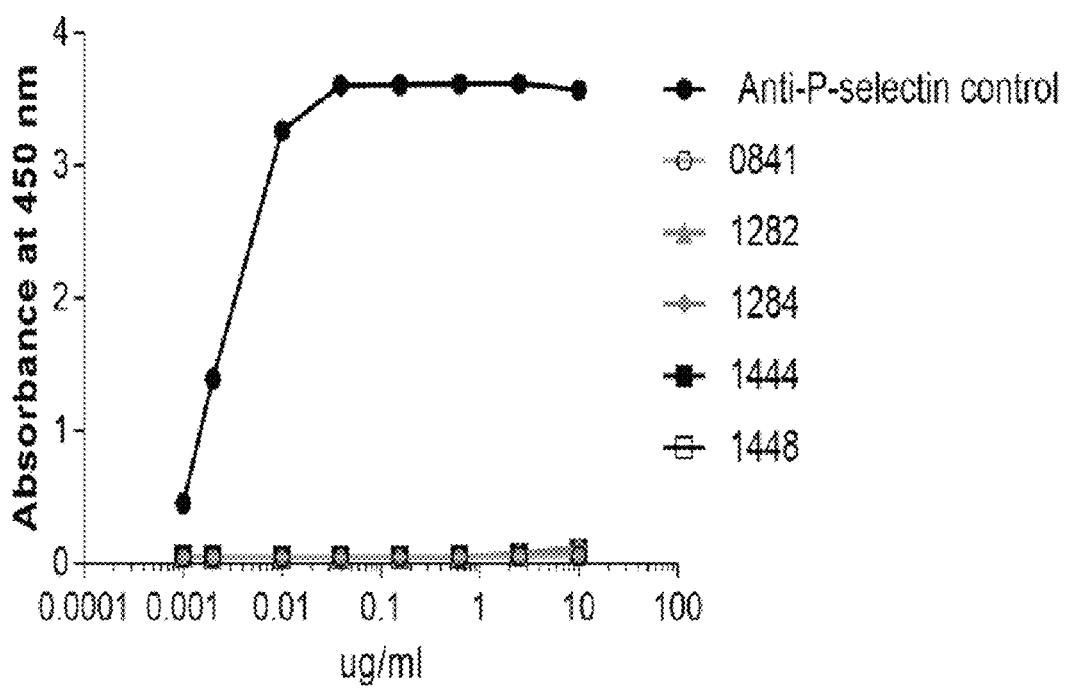

Dose-dependent binding to immobilized human L-selectin or human P-selectin was observed with L-, or P-selectin directed antibodies, with estimated $EC_{50}$ (values of 0.362 nM and 0.081 nM, respectively). In contrast, no cross reactivity of 0841, 1282, 1284, 1444 or 1448 to soluble human L- or P-selectin protein was observed (FIG. 13). These studies demonstrate that the antibodies (e.g., 1444) bind to E-selectin selectively with no observed binding to human L- or P-selectin.

Dose-dependent binding to mouse E-selectin and rat E-selectin was observed with control rat or mouse anti-E-selectin antibodies with low to sub-nanomolar binding (0.153 nM and 0.0139 nM, respectively). In contrast, weak binding of 0841, 1282, 1284, 1444 or 1448 to mouse and rat E-selectin was observed, and the binding curves were right shifted as compared to the positive control antibodies. The binding curves indicated weaker, non-saturable or variable binding compared to control rat or mouse E-selectin directed antibodies (Table 37).

TABLE 37

Antibody cross reactivity to soluble recombinant E- selectin proteins.

| antibody | human E-selectin $EC_{50}$ (nM) | cynomolgus monkey E-selectin $EC_{50}$ (nM) | mouse E-selectin $EC_{50}$ (nM) | rat E-selectin $EC_{50}$ (nM) |
|---|---|---|---|---|
| 0841 | 0.17 | 0.081 | Weak, non-saturable | Weak, variable |
| 1282 | NT | NT | Weak, non-saturable | Weak, variable |
| 1284 | 0.10 | 0.082 | Weak, non-saturable | Weak, variable |
| 1444 | 0.12 | 0.093 | Weak, non-saturable | Weak, variable |
| 1448 | NT | NT | Weak, non-saturable | Weak, variable |

NT = not determined

In a further direct binding ELISA, using methods similar to those described above, antibody 1444 bound to immobilized soluble recombinant human E-selectin with an EC50 of 0.085 and to immobilized soluble recombinant cynomolgus monkey E-selectin with an EC50 of 0.071 to 0.075 nM (Table 38).

Example 29: Pharmacokinetics of Optimized Antibody 1444 in Monkey Following Intravenous or Subcutaneous Administration A pharmacokinetics study of optimized antibody 1444 was conducted in cynomolgus monkeys using intravenous and subcutaneous administration. The quantification of serum antibody 1444 (comprising HC amino acid sequence of SEQ ID NO:7 (which includes a terminal lysine) and LC amino acid sequence of SEQ ID NO:1) concentrations were determined using an immunoassay on the Meso-Scale Discovery® (MSD) assay platform. In the assay, to quantify anti-E-selectin antibody 1444, biotinylated goat anti-human immunoglobulin G (IgG) was bound onto a blocked streptavidin-coated small spot plate. Anti-E-selectin antibody 1444 was captured by the ligand, recombinant human soluble E-selectin. Bound anti-E-selectin antibody 1444 was detected with a ruthenylated goat anti-human IgG. Plates were read on the MSD SECTOR Imager 6000, and final detection was conducted by using the ruthenium labeled goat anti-human IgG antibody and Tripropylamine (TPA) to produce an electrochemiluminescent signal within the MSD instrument that is representative of the amount of bound anti-E-selectin antibody 1444. Sample concentrations were determined by interpolation from a standard curve that is fit using a 5-parameter logistic equation (weighting formula for standard curve is 1/y^2). The range of quantitation in 100% serum was 40.0 ng/mL to 2560 ng/mL.

Following intravenous (IV) administration at 0.3, 0.6, 1, 3 or 10 mg/kg to two animals each, antibody 1444 exhibited a mean systemic clearance calculated from time 0 to the last measurable concentration ($CL_{0-tlast}$) of 0.39, 0.31, 0.15, 0.18 and 0.18 mL/h/kg, respectively, and an apparent volume of distribution at steady state ($V_{ss(0-tlast)}$) of 25, 22, 27, 35 and 36 mL/kg, respectively. Antibody 1444 displayed dose dependent pharmacokinetics, the clearance decreased as the dose increased indicating a target-mediated drug disposition. The mean half-life ($t_{1/2}$) for the IV administration at 0.3, 0.6, 1, 3 or 10 mg/kg was 102, 264, 188, 287 and 345 hours respectively.

After subcutaneous (SC) administration at 1 or 3 mg/kg to two animals each, antibody 1444 had a mean bioavailability (% F) of 50% following SC administration at 1 mg/kg when comparing to the IV administration of the antibody at 1 mg/kg. Following SC administration of antibody 1444 at 3 mg/kg, antibody 1444 had a mean % F of 65% when compared to IV administration of antibody 1444 at 3 mg/kg. The mean half-life ($t_{1/2}$) for SC administration of antibody 1444 at 1 and 3 mg/kg was 243 and 518 hours, respectively.

A ligand binding assay was validated to detect the presence of anti-drug antibodies (ADA) in cynomolgus monkey serum on the Meso Scale Discovery platform. In this method, positive controls at 2 different concentrations, consisting of a mouse monoclonal anti-antibody 1444 antibody spiked into cynomolgus monkey serum, and a negative control, consisting of pooled normal cynomolgus monkey serum, were included on each plate to monitor assay performance. The overall incidence of ADA induction to antibody 1444 was 0% (0/18 animals) across all dose groups.

Example 30: Ex Vivo Neutralization of Cellular Adhesion by Optimized Antibody 1444 in Physiological Flow Assays Ex vivo cellular adhesion experiments were performed inside microfluidic channels coated with recombinant proteins or cell monolayers to evaluate the potency and the neutralization activity of antibody 1444 to inhibit adhesion of cells that express E-selectin ligands. Cellular adhesion was analyzed under physiological flow conditions using a BioFlux™ (S/N-008-0180-08) system (Fluxion, San Francisco, Calif., USA). Adhesion assays were performed using recombinant purified soluble E- or P-selectin proteins or Chinese Hamster Ovary (CHO) cells engineered to express E-selectin (human or cynomolgus monkey) on the cell surface. Human HL-60 cells, which express the E-selectin ligand, PSGL-1 and other sialyl Lewis X ligands, purified human neutrophils, which express E-selectin ligands, or whole blood obtained from patients with sickle cell disease were used to test adhesion to recombinant E- and P-selectin proteins and CHO cells that expressed E-selectin.

BioFlux™ plates/chambers (Fluxion Biosciences, 48-well low shear, 0-20 dynes/cm²; 910-0004) were used in these studies. CHO cells expressing human E-selectin (human CHO-E, Pfizer) or cynomolgus monkey E-selectin (cynomolgus monkey CHO-E, Pfizer) and HL-60 cells were maintained at 37° C. with 5% $CO_2$ and 95% humidity in their respective growth medium. In studies using HL-60 cells, or purified human neutrophils, the cells were centrifuged at 1000 rpm for 5 minutes, stained with Calcein AM (Calcein; Life Technologies™; C3099) for 30 minutes, washed twice with phosphate buffered saline (PBS) with calcium and magnesium (Gibco; Catalog number 14040-133) and resuspended to a concentration of $3\times10^1$ cells/mL in PBS prior to perfusion in the flow chambers. The cells were maintained at 37° C. prior to perfusion and BioFlux™ assays were performed at room temperature. Adherent cells were visualized and counted using a Nikon Eclipse Ti-S (NIS-Elements BR 3.2 64-bit) inverted-stage phase-contrast fluorescent microscope with 40× magnification. Cellular counts were normalized to phosphate buffer vehicle control. Each experiment had two wells per condition. Data were graphed and analyzed using GraphPad Prism (8.0.2). Estimated half-maximal inhibitory concentration ($IC_{50}$) values derived from the analysis were rounded to two significant digits from the decimal point. The estimated $IC_{50}$ values were calculated by normalizing data to vehicle control (=100%, with no inhibition).

Neutralization of Cellular Adhesion to Recombinant E-Selectin

First, to mimic the surface of an activated endothelial cell, the flow chambers were coated with equal amounts of both human E- and P-selectin soluble recombinant proteins. BioFlux™ low microchannels were coated with 20 µg/mL each of soluble recombinant human P-selectin and E-selectin (Sino Biologicals) prepared in PBS, perfused at 1 dyne/cm² for 5 minutes, incubated at room temperature for 1 hour and washed with 0.1% bovine serum albumin (BSA)/PBS for 3-5 minutes at 1 dyne/cm². The plates were treated with test articles including antibody 1444 (concentrations from 0.78 to 200 nM), isotype negative control antibody (200 nM), positive control anti-E selectin antibody (200 nM) in PBS and the vehicle control for 1 hour at 1 dyne/cm². An aliquot of 100 µL of HL-60 cells were perfused in each channel for 10 minutes at physiological shear flow of 1 dyne/cm². PBS was perfused for 2-3 minutes at 1 dyne/cm² to remove the non-adherent cells and analyzed as described.

Antibody 1444 (0.78 to 200 nM), isotype negative control antibody, or vehicle were perfused in the chambers to inhibit E-selectin binding. In these studies, HL-60 cells, which express the E-selectin ligand, PSGL-1 and other sialyl Lewis X ligands, were flowed at 1 dyne/cm. Antibody 1444 reduced HL-60 cellular adhesion to purified soluble human E-selectin protein, with an estimated $IC_{50}$ value of 15.26 nM. The isotype negative control had no effect in the assay. The positive control anti-E selectin antibody reduced HL-60 adhesion by about 43%.

In further flow adhesion neutralization assays, using methods similar to those described above, antibody 1444 neutralized HL-60 adhesion to recombinant human E-selectin protein with an estimated $IC_{50}$ value of 13.28 nM-15.94 nM (Table 38).

Neutralization of Cellular Adhesion to Chinese Hamster Ovary Cells Expressing E-Selectin The BioFlux™ plates were coated with 100 µg/mL of fibronectin (Advanced BioMatrix, Catalog number 5050-1MG) in PBS at a flow rate of 1 dyne/cm² and incubated for 1 hour at room temperature. Chinese Hamster Ovary cells expressing E-selectin (human or cynomolgus monkey CHO-E) cells were prepared for assay by treatment with a 1:1 ratio of 0.05% Trypsin-Ethylenediaminetetraacetic acid (EDTA), (Gibco, 25300054) and StemPro Accutase (Gibco; A1110501) for 5 minutes at 37° C., neutralized with an equal volume of growth medium, collected, centrifuged at 1000 rpm for 5 minutes and re-suspended to a final concentration of $60\times10^6$ cells/mL in their respective growth medium. The plates were perfused twice with 250 µL of CHO growth medium at 1 dyne/cm² for 2-3 minutes at room temperature, all medium was removed and 10-20 µL of CHO-E cells (at $60\times10^6$ cells/mL) were perfused for 15 seconds at 2-3 dyne/cm². The plates were removed from the instrument and were incubated at 37° C. in a 5% $CO_2$ incubator for 1 hour. Medium was removed and 500 µL of fresh growth medium was added and the cells were incubated at 37° C. in a 5% $CO_2$ incubator overnight. Following the incubation, the CHO-E monolayers were washed (3-4 dynes/cm²) on the BioFlux instrument with fresh growth medium. The plates were treated with test articles including antibody 1444 (concentrations from 0.78 to 200 nM), isotype negative control antibody (200 nM), positive control commercial anti-E selectin antibody (200 nM) in PBS and vehicle control by perfusion at 1 dyne/cm² for 1 hour. An aliquot of 100 µL of HL-60 cells was perfused in each channel for 10 minutes at physiological shear flow of 1 dyne/cm². PBS was perfused for 2-3 minutes at 1 dyne/cm² to remove the non-adherent cells and the plates were imaged and analyzed as described.

E-selectin is expressed on the endothelial cell surface. CHO cells that express E-selectin (human or cynomolgus monkey) were attached to the surface of the flow chambers to form a cellular monolayer. Antibody 1444 was perfused in the chambers (0.78 to 200 nM) and HL-60 cells were perfused under physiological flow at 1 dyne/cm². Negative controls included isotype negative control antibody and vehicle. Anti-E-selectin antibody 1444, neutralized cellular adhesion of HL-60 cells to human CHO-E-selectin cells with an estimated $IC_{50}$ value of 4.41 nM. In addition, the estimated $IC_{50}$ value for the neutralization of HL-60 to cells expressing cynomolgus monkey E-selectin was 4.34 nM. The isotype negative control antibody did not neutralize HL-60 binding to CHO cells expressing either human or cynomolgus monkey E-selectin. The positive control antibody testing at 200 nM reduced HL-60 adhesion to cells expressing human E-selectin by about 44%

In further flow adhesion neutralization assays, using methods similar to those described above, antibody 1444 neutralized HL-60 adhesion to human or cynomolgus monkey E-selectin expressing CHO cells with an estimated $IC_{50}$ value of 4.25 nM-4.56 nM and 4.32 nM-4.35 nM, respectively (Table 38).

Neutralization of Purified Neutrophils Adhesion Chinese Hamster Ovary Cells Expressing E-Selectin Human and cynomolgus monkey CHO cell monolayers were prepared on the Bioflux plates as described. Whole blood was obtained from four healthy volunteer donors (Pfizer) and 3 mL of each were pooled and neutrophils were purified using Miltenyi Kit (MACSxpress whole blood neutrophil isolation kit, human, 130-104-434) according to the manufacturer's protocol.

Test articles including antibody 1444 (concentrations from 0.78 to 200 nM), isotype negative control antibody (200 nM), positive control anti-E selectin antibody (200 nM) in PBS and the vehicle control were perfused at 1 dyne/cm² for 1 hour. The purified neutrophils were stained with Calcein and treated with tumor necrosis factor-alpha (TNF-α) (Biotang Inc, 50-751-5681) for 10 minutes at 37° C., prior to assay. The neutrophils were collected, 300×g for 10 minutes at room temperature and resuspended in PBS (with calcium and magnesium). The neutrophils were perfused at 1 dyne/cm² for 10 minutes. PBS was perfused for 2-3 minutes at 1 dyne/cm² to remove the non-adherent cells and the plates were imaged and analyzed.

Neutrophils express E-selectin ligands and E-selectin mediates neutrophil adherence to the endothelium. Anti-E-selectin antibody neutralization of human neutrophils to CHO monolayers that express E-selectin (human or cynomolgus monkey) under ex vivo physiological flow was assessed. Antibody 1444, isotype negative control antibody or vehicle were perfused into the chambers. Human neutrophils were purified from 4 healthy donors, pooled and TNF-α activated (10 ng/mL) neutrophils were evaluated in the assay. Antibody 1444 neutralized the adhesion of activated human neutrophils to human CHO-E-selectin cells with estimated $IC_{50}$ values of 2.87 nM. The estimated $IC_{50}$ for neutralization of adhesion of activated human neutrophils to cynomolgus monkey CHO-E-selectin cells was 16.33 nM.

In a further flow adhesion neutralization assay, using methods similar to those described above, antibody 1444 neutralized adhesion of activated human neutrophils to human or cynomolgus monkey E-selectin expressing CHO cells with an estimated $IC_{50}$ value of 4.65 nM and 9.45 nM, respectively (Table 38).

Neutralization of SCD Blood Cell Adhesion

A pro-inflammatory response in SCD is promoted by alterations in the sickled red blood cell and the activated endothelial cell (Manwani D and Frenette PS Blood 2013; 122(24):3892-98). Red blood cell sickling, hemolysis, and endothelial cell dysfunction lead to inflammation and cellular activation and contribute to SCD pathogenesis. Whole blood from 2 donors with SCD, were labeled with Calcien and Hoechst to visualize rolling and adhesion. Briefly, the blood was assayed 24 hours after arrival and diluted to a hematocrit of 15% with HBSS (Hank's Balanced Salt Solution) buffer containing 1 mM calcium chloride, 1 mM magnesium chloride, 10 mM N-2-hydroxyethylpiperazine-N-2-ethane sulfonic acid, 0.25% BSA, 0.1% glucose, pH 7.4. Blood cells were stained with Calcein and Hoechst (Thermo Scientific, catalog number 33342) dye (1:1000) for 30 minutes at 37° C. prior to assay. The flow chambers were coated with 20 µg/mL each of soluble recombinant human E- and P-selectin protein (Sino Biologicals) prepared in PBS at 1 dyne/cm² for 5 minutes, incubated at room temperature for 1-2 hours and washed with 0.1% BSA/PBS for 3-5 minutes at 1 dyne/cm².

Blood from both donors was evaluated for adhesion to recombinant human E- and P-selectin proteins. Test articles including antibody 1444, anti-P-selectin antibody control in PBS (0.78-200 nM), isotype negative control antibody (200 nM), control anti-E-selectin antibody (200 nM), or vehicle were flowed at 1 dyne/cm² for 1 hour. Diluted SCD blood was flowed for 10 minutes at 0.6 dyne/cm². PBS was perfused for 2-3 minutes at 1 dyne/cm² to remove the non-adherent cells and the plates were imaged and analyzed. The estimated $IC_{50}$ values were calculated as described above. The estimated $IC_{20}$, $IC_{80}$ and $IC_{90}$ were calculated based on the formula: $(IC_{50}*\text{effect})/(100-\text{effect})$. The calculation is based on an $E_{max}$ Tmodel $[E=(E_{max}+C)/(C+EC_{50})]$.

Figure 14:
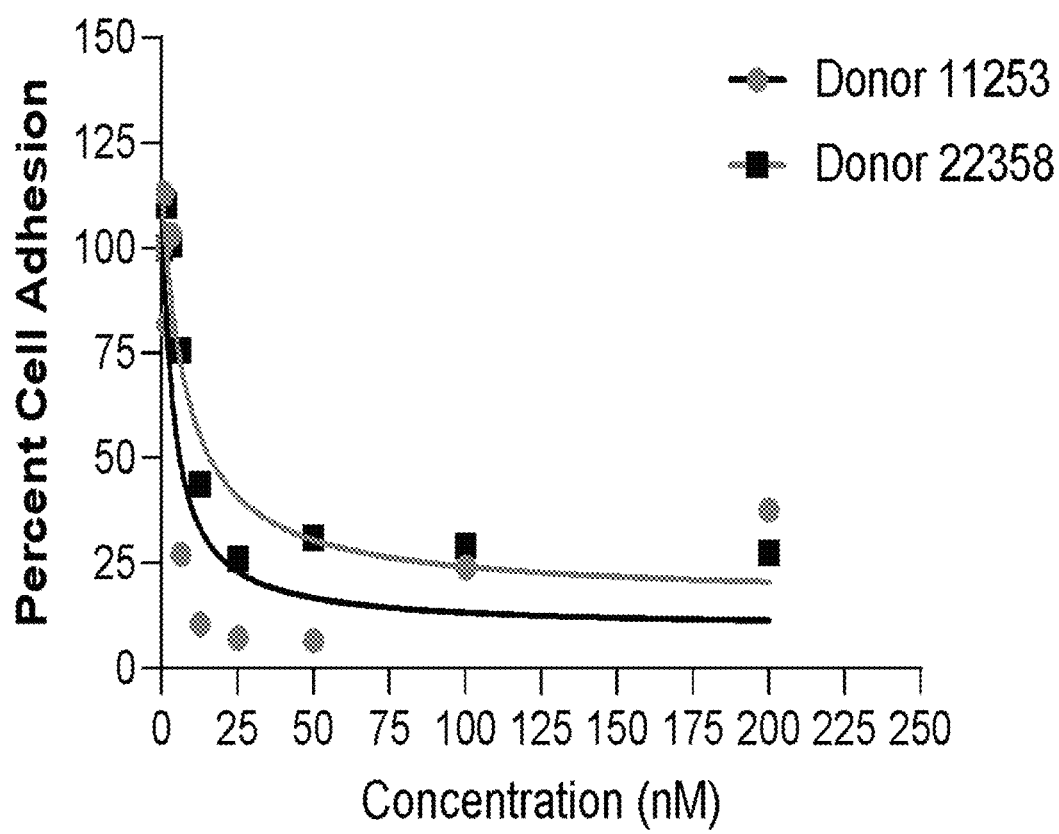
FIG. 14 depicts exemplary neutralization of adhesion of SCD patient cells (Donor 11253 and Donor 22358) to recombinant E-selectin under physiological flow.

The isotype negative control antibody did not neutralize binding. The positive control antibody, tested at 200 mM, reduced cell binding adhesion between 10-35%. Antibody 1444 neutralized the binding of human SCD cells to recombinant E-selectin with an estimated $IC_{50}$ value of 6.17 nM and 18.66 nM, with a mean of 12.4 nM (FIG. 14). The $IC_{20}$, $IC_{80}$, and $IC_{90}$ values were estimated to be 3.1 nM, 49.6 nM, and 111.6 nM, respectively. Greater neutralization of cellular adhesion was observed with E-selectin inhibition compared to P-selectin inhibition under similar physiological flow conditions using soluble E- and P-selectin protein coated chambers.

TABLE 38

Summary of key pharmacologic properties of antibody 1444.

| assay | pharmacodynamic activity |
|---|---|
| In vitro assays | |
| *SPR binding to soluble recombinant protein* | |
| human E-selectin | $K_D$ = 68.4 +/− 3.18nM |
| cynomolgus monkey E-selectin | $K_D$ = 64.9 +/− 1.13nM |
| mouse E-selectin | no binding (up to 405 nM) |
| rat E-selectin | no binding |
| rabbit E-selectin | no binding |
| *Direct binding ELISA binding to soluble recombinant protein* | |
| human E-selectin | $EC_{50}$ = 0.085 nM − 0.12 nM |
| cynomolgus E-selectin | $EC_{50}$ = 0.071 nM − 0.093 nM |
| human P-selectin | no binding |
| human L-selectin | no binding |
| mouse E-selectin | weak non-saturable binding (up to 133.3 nM) |
| rat E-selectin | weak non-saturable binding (up to 133.3 nM) |
| *FACS binding to cell surface expressed E-selectin CHO cells* | |
| human E-selectin | $EC_{50}$ = 0.66 nM − 2.33 nM |
| cynomolgus monkey E-selectin | $EC_{50}$ = 0.75 nM − 1.37 nM |
| *Primary cells - TNFa activated* | |
| Human - HUVECS | binding |
| Cynomolgus monkey -CLMEC | binding |
| Selectivity | |
| CHO human P-selectin cells | no binding |
| CHO DUKX parental | no binding |
| *Functional assay* | |
| *Neutralization of ligand binding (sialyl Lewis A) CHO cells* | |
| human E-selectin | $IC_{50}$ = 1.88 nM − 2.89 nM |
| cynomolgus monkey E-selectin | $IC_{50}$ = 1.47 nM − 2.65 nM |
| Soluble recombinant protein | |
| human E-selectin | $IC_{50}$ = 2.87 nM − 3.01 nM |
| cynomolgus monkey E-selectin | $IC_{50}$ = 2.39 nM − 2.91 nM |
| *Static adhesion neutralization of HL-60 cells (endogenous ligand)* | |
| human E-selectin | $IC_{50}$ = 3.36 nM − 4.7nM |
| cynomolgus monkey E-selectin | $IC_{50}$ = 3.84 nm |
| *Flow adhesion neutralization of HL-60 cells (endogenous ligand) Soluble recombinant protein* | |
| human E-selectin | $IC_{50}$ = 13.28 nM − 15.94 nM |
| CHO cells | |
| human E-selectin | $IC_{50}$ = 4.25 nM − 4.56 nM |
| cynomolgus monkey E-selectin | $IC_{50}$ = 4.32 nM − 4.35 nM |
| *Neutralization of Human Neutrophils (endogenous ligand)* | |
| human E- selectin | $IC_{50}$ = 2.87 nM − 4.65 nM |
| cynomolgus E-selectin | $IC_{50}$ = 9.45 nM − 16.33 nM |
| *Neutralization of SCD patient cells* | |
| Soluble human recombinant protein | $IC_{50}$ = 12.4 nM |
| | $IC_{20}$ = 3.2 nM |
| | $IC_{80}$ = 49.6 nM |
| | $IC_{90}$ = 111.6 nM |

Example 31: Cell Surface Binding (FACS) and Neutralization of Optimized Anti-E-Selectin Antibody 1444

E-selectin is expressed on the endothelial cell surface and under conditions of endothelial cell dysfunction, such as an inflammatory response, circulating blood cells adhere to the vascular endothelium through ligand-adhesion molecule interactions. The ability of antibody 1444 to bind cell surface expressed E-selectin was assessed. In these studies, CHO cell lines expressing membrane-bound human or cynomolgus E-selectin were used to characterize binding of antibody 1444 to cell surface expressed E-selectin.

CHO cells that express E-selectin (human of cynomolgus monkey) or human P-selectin on the cell surface and control non-transfected CHO cells (CHO-DUKX) were evaluated by FACS analysis using antibody 1444, isotype control IgG1 and two control P-selectin antibodies. Antibody 1444 bound to human E-selectin with estimated $EC_{50}$ of 0.66 to 2.33 nM (based on 6 experiments). Antibody 1444 bound to cynomolgus E-selectin with an estimated $EC_{50}$ of 0.75 to 1.37 nM (based on 6 experiments). Antibody 1444 did not bind to control CHO-DUKX indicating absence of detectable cell surface binding. Furthermore, antibody 1444 did not bind cell-surface P-selectin. Dose dependent binding of the control anti-P-selectin antibody was observed to the CHO-P-selectin cells indicating expression of P-selectin. No binding was observed with the isotype control IgG1 (Table 38).

Example 32: Tolerability and Toxicokinetic Study in Cynomolgus Monkeys

The cynomolgus monkey was the only pharmacologically relevant nonclinical species based on in vitro pharmacology studies designed to assess the ability of antibody 1444 to inhibit E-selectin binding and/or biological activity. The binding affinity to human and cynomolgus monkey E-selectin were similar across assays evaluated, in contrast to the absence of potent binding to E-selectin from mouse, rabbit, or rat. In in vitro functional assays, antibody 1444 dose-dependently neutralized cellular adhesion of human promyelocytic cells to soluble recombinant human E-selectin protein and cellularly expressed recombinant human or cynomolgus monkey E-selectin. In addition, antibody 1444 neutralized the adhesion of purified neutrophils to both human and cynomolgus monkey cellular E-selectin with estimated 50% inhibitive concentration ($IC_5O$) values in the low nM range. An SC dose of 30 mg/kg was associated with an overall maximum observed concentration ($C_{max}$) of 353 μg/mL and area under the concentration-time curve from time 0 to 336 hours ($AUC_{336}$) of 92,500 μg·h/mL; while the IV dose of 100 mg/kg was associated with overall $C_{max}$ of 693 μg/mL and $AUC=_{336}$ of 108,000 μg·h/mL. Antibody 1444 was administered to male and female cynomolgus monkeys at doses up to 200 mg/kg/week IV once weekly for 1 month and as well tolerated. In vitro human complement component 1q (C1q) and fragment crystallizable gamma Fc receptor (FcγR) binding assays and a tissue cross reactivity evaluation did not yield safety concerns Example 33: Pharmacokinetic and Product Metabolism in Animals Single-dose PK and repeat-dose TK were evaluated in cynomolgus monkeys following IV and/or SC dosing of antibody 1444. After single IV dosing in cynomolgus monkeys, dose dependent clearance (CL) was observed and was consistent with saturable target mediated drug dispositions (TMDD). After single IV dosing at a dose range from 0.3 to 10 mg/kg, antibody 1444 exhibited a mean CL and mean $V_{SS}$ from approximately 0.39 to 0.15 mL/h/kg and 22 to 36 mL/kg, respectively. After single SC doses of antibody 1444 at 1 mg/kg or 3 mg/kg, $T_{max}$ was observed at 72 and 96 hours, respectively and SC bioavailability was >50%. The estimated $T_{1/2}$ of antibody 1444 at 3 mg/kg IV was approximately 12 days.

In a 1-month GLP repeat-dose toxicity study, there were no apparent sex-related differences in systemic exposure (as assessed by the maximum observed concentration [$C_{max}$] an area under the concentration-time curve [AUC]) following repeat SC and IV dosing. Systemic exposure increased with increasing dose (SC) and was higher after repeat SC and IV dosing. Antibody 1444 was administered to male and female cynomolgus monkeys at doses of 15 or 50 mg/kg/week SC or 200 mg/kg/week IV once weekly for 1 month (5 total doses). After once weekly repeat dosing at 15 and 50 mg/kg/week, mean $T_{max}$ was between 72 and 112 hours post dose on Days 1 and 22. Systemic exposure was higher after repeat dosing with mean accumulation rations (AUC$_{168}$, Day22/Day1) of 5.5, 3.2 and 1.9 for 15 (SC), 50 (SC) and 200 (IV) mg/kg/week, respectively.

The predicted efficacious dose in humans is a single SC administration of antibody 1444 at 150 mg. The predicted minimal effective concentration and exposure at 150 mg SC dosing are 14 μg/mL for average concentration ($C_{av}$ [1 to 168 hours]) and 2400 μg·h/mL for AUC$_{168}$, respectively.

Example 34: E-selectin Levels, Aggregates and ICAM-1 Expression in Animals

Soluble E-selectin was characterized in serum from cynomolgus monkeys following doses of antibody 1444 ranging from 0.3 to 10 mg/kg by liquid chromatography-mass-spectrometry (LC-MS). Antibody 1444 showed effective binding of E-selectin in a concentration-dependent manner, and a >90% inhibitory effect on soluble E-selectin was observed at all dose groups indicating in vivo E-selectin binding activity of antibody 1444.

Following dosing with antibody 1444, blood was collected from cynomolgus monkeys and analyzed using fluorescent activated cell sorting (FACS) to detect cellular aggregates and adhesion markers. The monocyte-platelet aggregate and neutrophil-platelet aggregates were examined. In this FACS analysis, CD14 was used to differentiate monocytes and neutrophils using size scan, and CD41 was used to detect monocyte-platelet aggregates and neutrophil-platelet aggregates. Antibody 1444 showed effects on decrease in monocyte-platelet and neutrophil-platelet aggregates in cynomolgus monkeys after treatment.

Leukocyte Intercellular Adhesion Molecule 1 (CAM-1) expression was examined in leukocytes from cynomolgus monkeys after antibody 1444 dosing using FACS analysis. A decrease in ICAM-1 was observed following dosing.

We claim:

1. An isolated antibody that specifically binds to human E-selectin, comprising at least one of the following:
    (a) a light chain complementarity determining region 1 (LCDR-1) comprising the amino acid sequence of SEQ ID NO:2, a LCDR-2 comprising the amino acid sequence of SEQ ID NO:3, a LCDR-3 comprising the amino acid sequence of SEQ ID NO:4, a heavy chain complementarity determining region 1 (HCDR-1) comprising the amino acid sequence of SEQ ID NO:8, a HCDR-2 comprising the amino acid sequence of SEQ ID NO:9, and a HCDR-3 comprising the amino acid sequence of SEQ ID NO:10;
    (b) a heavy chain variable domain (VH) comprising the amino acid sequence of SEQ ID NO:11 and a light chain variable domain (VL) comprising the amino acid sequence of SEQ ID NO:5; and
    (c) a heavy chain (HC) comprising the amino acid sequence of SEQ ID NO:7 or SEQ ID NO:13, and a light chain (LC) comprising the amino acid sequence of SEQ ID NO:1.

2. The isolated antibody of claim 1, wherein the antibody heavy chain isotype is IgG1, wherein the light chain constant region is a kappa light chain, or both.

3. The isolated antibody of claim 1, wherein the antibody comprises a VH comprising the amino acid sequence of SEQ ID NO:11 and a VL comprising the amino acid sequence of SEQ ID NO:5.

4. The isolated antibody of claim 1, wherein the antibody binds human E-selectin with a $K_D$ of about 60 nM to about 72 nM and wherein the antibody binds cynomolgus monkey E-selectin with a $K_D$ of about 63 nM to about 82 nM.

5. The isolated antibody of claim 1 that specifically binds E-selectin and demonstrates at least one detectable characteristic selected from the following:
    (i) binds to human E-selectin with a $K_D$ of 200 nM or less;
    (ii) binds to cynomolgus monkey E-selectin with a $K_D$ of 200 nM or less;
    (iii) binds with an $EC_{50}$ of 50 nM or less to cell-surface expressed E-selectin;
    (iv) binds with an $EC_{50}$ of 2 nM or less to soluble human E-selectin;
    (v) neutralizes binding with an $EC_{50}$ of 2 nM or less as measured by AlphaLisa competition assay, of a sialyl-Lewis A ligand to soluble human E-selectin;
    (vi) binds with an $IC_{50}$ of about 1 nM to about 3 nM to free soluble human E-selectin in human serum;

(vii) neutralizes binding with an $IC_{50}$ of 100 nM or less as measured by competition ELISA under static conditions, of a sialyl-Lewis A ligand to soluble human E-selectin;

(viii) neutralizes binding with an $IC_{50}$ of 50 nM or less as measured by competition ELISA under static conditions, of a sialyl-Lewis A ligand to cell-surface expressed human E-selectin;

(ix) inhibits adhesion with an $IC_{50}$ of 100 nM or less as measured under static conditions, of cells expressing an E-selectin ligand to cell-surface expressed human E-selectin;

(x) inhibits adhesion with an $IC_{50}$ of 100 nM or less as measured under physiological flow conditions, of cells expressing an E-selectin ligand to cell-surface expressed human E-selectin;

(xi) inhibits adhesion with an $IC_{50}$ of about 6.17 nM to about 18.66 nM as measured under physiologic flow conditions, of blood cells from SCD patients to soluble human E-selectin;

(xii) has a mean half-life of about 14.4 days (345 hours) following IV administration at a dose of 10 mg/kg;

(xiii) has a mean half-life of about 21.5 days (518 hours) following SC administration at a dose of about 3 mg/kg;

(xiv) has a viscosity of 33.4 cP at 185.7 mg/mL when measured at 25° C.;

(xv) exhibits commercially suitable formulation properties, including a high degree of thermal stability and minimal aggregation at high concentration; and (xvi) exhibits reproducible expression and purity under large-scale manufacturing conditions.

6. A pharmaceutical composition comprising an antibody of claim 1, and a pharmaceutically acceptable carrier or excipient.

7. The pharmaceutical composition of claim 6, comprising i) an antibody comprising an antibody HC comprising the amino acid sequence of SEQ ID NO:7 and an antibody LC comprising the amino acid sequence of SEQ ID NO:1, ii) an antibody comprising an antibody HC comprising the amino acid sequence of SEQ ID NO:13 and an antibody LC comprising the amino acid sequence of SEQ ID NO:1, or iii) both.

8. A method of treating a medical condition, disease or disorder mediated by or associated with expression of E-selectin, binding of E-selectin to a ligand, or both, in a subject in need thereof, the method comprising administering a therapeutically effective amount of an antibody of claim 1 that specifically binds to human E-selectin and ameliorates the medical condition, disease or disorder.

9. A method of treating Sickle Cell disease (SCD), in a subject in need thereof, the method comprising administering a therapeutically effective amount of an antibody of claim 1, that specifically binds to human E-selectin and ameliorates at least one sign or symptom of SCD selected from the group consisting of those affecting the cardiothoracic system, the nervous system, the reticuloendothelial system, the musculoskeletal system, the urogenital system, the gastrointestinal system and a combination thereof.

10. The method of treating SCD in a subject in need thereof of claim 9, wherein the sign or symptom of SCD affecting the cardiothoracic system includes chronic restrictive lung disease, left ventricular diastolic disease, pulmonary hypertension, acute chest syndrome, dysrhythmias, sudden death, vaso-occlusive crisis (VOC) or a combination thereof.

11. The method of treating SCD in a subject in need thereof of claim 9, wherein the sign or symptom of SCD affecting the nervous system includes hemorrhagic stroke, venous sinus thrombosis, silent cerebral infarction of the brain, chronic pain, acute ischemic stroke of the brain, proliferative retinopathy, orbital infarction, cognitive impairment or a combination thereof.

12. A method of decreasing an E-selectin biological activity in a subject in need thereof, wherein the method comprises administering a therapeutically effective amount of an antibody of claim 1, that specifically binds to human E-selectin.

13. A kit for the treatment of SCD, comprising a therapeutically effective amount of an anti-E-selectin antibody of claim 1.

14. The kit of claim 13, further comprising a therapeutically effective amount of an at least one additional therapeutically active compound or treatment modality which is effective in ameliorating at least one sign or symptom of SCD.

15. A method of treating SCD in a subject in need thereof, the method comprising administering a therapeutically effective amount of an antibody of claim 1, that specifically binds to human E-selectin and treats, prevents or ameliorates vaso-occlusive crisis (VOC).

16. An isolated antibody that specifically binds to human E-selectin, comprising:
a VL amino acid sequence comprising a LCDR-1, a LCDR-2 and a LCDR-3 of the amino acid sequence of SEQ ID NO:5; and
a VH amino acid sequence comprising a HCDR-1, a HCDR-2 and a HCDR-3 of the amino acid sequence of SEQ ID NO:11.

17. The isolated antibody of claim 16, comprising an antibody heavy chain constant region (CH) comprising the amino acid sequence of SEQ ID NO: 15 or SEQ ID NO:16, and an antibody light chain constant region (CL) comprising the amino acid sequence of SEQ ID NO:14.

18. An isolated antibody that specifically binds to human E-selectin, comprising a LC comprising the amino acid sequence of SEQ ID NO:1, and a HC comprising the amino acid sequence of SEQ ID NO:7 or SEQ ID NO:13.

19. An isolated nucleic acid molecule encoding an antibody that specifically binds human E-selectin comprising the amino acid sequence of SEQ ID NO:5 and SEQ ID NO:11.

20. An isolated nucleic acid molecule comprising at least one of the following:
a) the nucleic acid sequence of SEQ ID NO:136 and the nucleic acid sequence of SEQ ID NO:137; and
b) a nucleic acid sequence of SEQ ID NO:138 or SEQ ID NO:206, and the nucleic acid sequence of SEQ ID NO:139.

21. A vector comprising a nucleic acid molecule comprising (a) the nucleic acid sequence of SEQ ID NO:136 and the nucleic acid sequence of SEQ ID NO:137 or (b) the nucleic acid sequence of SEQ ID NO:138 or SEQ ID NO:206, and the nucleic acid sequence of SEQ ID NO:139.

22. A host cell comprising a vector comprising a nucleic acid molecule comprising (a) the nucleic acid sequence of SEQ ID NO:136 and the nucleic acid sequence of SEQ ID NO:137 or (b) the nucleic acid sequence of SEQ ID NO:138 or SEQ ID NO:206, and the nucleic acid sequence of SEQ ID NO:139.

23. The host cell of claim 22, wherein said host cell is a mammalian cell selected from the group consisting of a CHO cell, a COS cell, a HEK-293 cell, an NS0 cell, an immortalized primary human embryonic retinal cell, or an Sp2.0 cell.

24. A method of making an antibody comprising culturing a host cell under a condition wherein an antibody comprising a VH comprising the amino acid sequence of SEQ ID NO:11 and a VL comprising the amino acid sequence of SEQ ID NO:5 is produced by the host cell.

* * * * *

SEQUENCE LISTING

<160> NUMBER OF SEQ ID NOS: 206

<210> SEQ ID NO 1
<211> LENGTH: 214
<212> TYPE: PRT
<213> ORGANISM: Artificial Sequence
<220> FEATURE:
<223> OTHER INFORMATION: Synthetic Construct

<400> SEQUENCE: 1

```
Asp Ile Gln Met Thr Gln Ser Pro Ser Ser Leu Ser Ala Ser Val Gly
1               5                   10                  15

Asp Arg Val Thr Ile Thr Cys Lys Thr Ser Gln Asn Ile Glu Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Leu Gln Asp Asn Ala Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                    165                 170                 175
Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 2
<211> LENGTH: 11
<212> TYPE: PRT
<213> ORGANISM: Artificial Sequence
<220> FEATURE:
<223> OTHER INFORMATION: Synthetic Construct

<400> SEQUENCE: 2

Lys Thr Ser Gln Asn Ile Glu Arg Tyr Leu Asn
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Synthetic Construct

<400> SEQUENCE: 3

Ala Ala Ser Ser Leu Gln Ser
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Construct

<400> SEQUENCE: 4

Leu Gln Asp Asn Ala Trp Pro Leu Thr
1               5

<210> SEQ ID NO 5
<211> LENGTH: 107
<212> TYPE: PRT
<213> ORGANISM: Artificial Sequence
<220> FEATURE:
<223> OTHER INFORMATION: Synthetic Construct

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Thr Ser Gln Asn Ile Glu Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Leu Gln Asp Asn Ala Trp Pro Leu
                85                  90                  95

Thr Phe Gly Gln Gly Thr Lys Val Glu Ile Lys
```

```
                100             105

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

Phe Gly Gln Gly Thr Lys Val Glu Ile Lys
1               5                   10

<210> SEQ ID NO 7
<211> LENGTH: 447
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Ile Arg Ser Ala
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Thr Ile Tyr Val Asp Ser Val
    50                  55                  60

Thr Gly Arg Phe Thr Ile Ser Ala Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Met Asp Leu Tyr Ser Thr Ser Glu Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

```
                    Thr Lys Pro Arg Glu Glu Gln Tyr Asn Ser Thr Tyr Arg Val Val Ser
                        290                 295                 300

Val Leu Thr Val Leu His Gln Asp Trp Leu Asn Gly Lys Glu Tyr Lys
                    305                 310                 315                 320

Cys Lys Val Ser Asn Lys Ala Leu Pro Ala Pro Ile Glu Lys Thr Ile
                                    325                 330                 335

Ser Lys Ala Lys Gly Gln Pro Arg Glu Pro Gln Val Tyr Thr Leu Pro
                                340                 345                 350

Pro Ser Arg Glu Glu Met Thr Lys Asn Gln Val Ser Leu Thr Cys Leu
                            355                 360                 365

Val Lys Gly Phe Tyr Pro Ser Asp Ile Ala Val Glu Trp Glu Ser Asn
                    370                 375                 380

Gly Gln Pro Glu Asn Asn Tyr Lys Thr Thr Pro Pro Val Leu Asp Ser
                    385                 390                 395                 400

Asp Gly Ser Phe Phe Leu Tyr Ser Lys Leu Thr Val Asp Lys Ser Arg
                                    405                 410                 415

Trp Gln Gln Gly Asn Val Phe Ser Cys Ser Val Met His Glu Ala Leu
                                420                 425                 430

His Asn His Tyr Thr Gln Lys Ser Leu Ser Leu Ser Pro Gly Lys
                            435                 440                 445

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

Gly Tyr Ala Ile Arg Ser Ala Tyr Met His
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Synthetic Construct

<400> SEQUENCE: 9

Arg Ile Asp Pro Ala Asn Gly Asn Thr Ile Tyr Val Asp Ser Val Thr
1               5                   10                  15

Gly

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

Asp Leu Tyr Ser Thr Ser Glu Tyr
1               5

<210> SEQ ID NO 11
<211> LENGTH: 117
<212> TYPE: PRT
<213> ORGANISM: Artificial Sequence
<220> FEATURE:
<223> OTHER INFORMATION: Synthetic Construct
```

-continued

```
<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Ile Arg Ser Ala
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Thr Ile Tyr Val Asp Ser Val
    50                  55                  60

Thr Gly Arg Phe Thr Ile Ser Ala Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Met Asp Leu Tyr Ser Thr Ser Glu Tyr Trp Gly Gln Gly Thr Leu
            100                 105                 110

Val Thr Val Ser Ser
        115

<210> SEQ ID NO 12
<211> LENGTH: 11
<212> TYPE: PRT
<213> ORGANISM: Artificial Sequence
<220> FEATURE:
<223> OTHER INFORMATION: Synthetic Construct

<400> SEQUENCE: 12

Trp Gly Gln Gly Thr Leu Val Thr Val Ser Ser
1               5                   10

<210> SEQ ID NO 13
<211> LENGTH: 446
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Ile Arg Ser Ala
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Thr Ile Tyr Val Asp Ser Val
    50                  55                  60

Thr Gly Arg Phe Thr Ile Ser Ala Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Met Asp Leu Tyr Ser Thr Ser Glu Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160
```

```
Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 14
<211> LENGTH: 107
<212> TYPE: PRT
<213> ORGANISM: Artificial Sequence
<220> FEATURE:
<223> OTHER INFORMATION: Synthetic Construct

<400> SEQUENCE: 14

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80
```

Lys His Lys Val Tyr Ala Cys Glu Val Thr His Gln Gly Leu Ser Ser
                        85                  90                  95

Pro Val Thr Lys Ser Phe Asn Arg Gly Glu Cys
            100                 105

<210> SEQ ID NO 15
<211> LENGTH: 330
<212> TYPE: PRT
<213> ORGANISM: Artificial Sequence
<220> FEATURE:
<223> OTHER INFORMATION: Synthetic Construct

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 16
<211> LENGTH: 329
<212> TYPE: PRT
<213> ORGANISM: Artificial Sequence
<220> FEATURE:
<223> OTHER INFORMATION: Synthetic Construct

<400> SEQUENCE: 16

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 17
<211> LENGTH: 214
<212> TYPE: PRT
<213> ORGANISM: Artificial Sequence
<220> FEATURE:

<223> OTHER INFORMATION: Synthetic Construct

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Lys Thr Ser Gln Asn Ile Asn Arg Tyr
            20                  25                  30

Leu Asn Trp Tyr Gln Gln Lys Pro Gly Lys Ala Pro Lys Leu Leu Ile
        35                  40                  45

Tyr Asn Ala Asn Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Leu Gln Asp Asn Ser Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct

<400> SEQUENCE: 18

Lys Thr Ser Gln Asn Ile Asn Arg Tyr Leu Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic Construct

<400> SEQUENCE: 19

Asn Ala Asn Ser Leu Gln Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Leu Gln Asp Asn Ser Trp Pro Leu Thr
1               5

<210> SEQ ID NO 21
<211> LENGTH: 107
<212> TYPE: PRT
<213> ORGANISM: Artificial Sequence
<220> FEATURE:
<223> OTHER INFORMATION: Synthetic Construct

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Thr Ser Gln Asn Ile Asn Arg Tyr
            20                  25                  30

Leu Asn Trp Tyr Gln Gln Lys Pro Gly Lys Ala Pro Lys Leu Leu Ile
        35                  40                  45

Tyr Asn Ala Asn Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Leu Gln Asp Asn Ser Trp Pro Leu
                85                  90                  95

Thr Phe Gly Gln Gly Thr Lys Val Glu Ile Lys
            100                 105

<210> SEQ ID NO 22
<211> LENGTH: 446
<212> TYPE: PRT
<213> ORGANISM: Artificial Sequence
<220> FEATURE:
<223> OTHER INFORMATION: Synthetic Construct

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asn Ile Arg Ser Ser
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Thr Ile Tyr Ala Glu Lys Phe
    50                  55                  60

Lys Ile Arg Phe Thr Ile Ser Ala Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Met Asp Leu Tyr Ser Thr Ser Glu Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 23
<211> LENGTH: 10
<212> TYPE: PRT
<213> ORGANISM: Artificial Sequence
<220> FEATURE:
<223> OTHER INFORMATION: Synthetic Construct

<400> SEQUENCE: 23

Gly Tyr Asn Ile Arg Ser Ser Tyr Met His
1               5                   10

<210> SEQ ID NO 24
<211> LENGTH: 17
<212> TYPE: PRT
<213> ORGANISM: Artificial Sequence
<220> FEATURE:
<223> OTHER INFORMATION: Synthetic Construct

<400> SEQUENCE: 24

Arg Ile Asp Pro Ala Asn Gly Asn Thr Ile Tyr Ala Glu Lys Phe Lys
1               5                   10                  15

Ile

```
<210> SEQ ID NO 25
<211> LENGTH: 117
<212> TYPE: PRT
<213> ORGANISM: Artificial Sequence
<220> FEATURE:
<223> OTHER INFORMATION: Synthetic Construct

<400> SEQUENCE: 25
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asn Ile Arg Ser Ser
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Thr Ile Tyr Ala Glu Lys Phe
    50                  55                  60

Lys Ile Arg Phe Thr Ile Ser Ala Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Met Asp Leu Tyr Ser Thr Ser Glu Tyr Trp Gly Gln Gly Thr Leu
            100                 105                 110

Val Thr Val Ser Ser
        115

```
<210> SEQ ID NO 26
<211> LENGTH: 214
<212> TYPE: PRT
<213> ORGANISM: Artificial Sequence
<220> FEATURE:
<223> OTHER INFORMATION: Synthetic Construct

<400> SEQUENCE: 26
```

Asp Ile Gln Met Thr Gln Ser Pro Ser Ser Leu Ser Ala Ser Val Gly
1               5                   10                  15

Asp Arg Val Thr Ile Thr Cys Lys Thr Ser Gln Asn Ile Asn Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Leu Gln Asp Asn Ser Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr

```
                    180                 185                 190
Ala Cys Glu Val Thr His Gln Gly Leu Ser Ser Pro Val Thr Lys Ser
            195                 200                 205

Phe Asn Arg Gly Glu Cys
        210
```

<210> SEQ ID NO 27
<211> LENGTH: 107
<212> TYPE: PRT
<213> ORGANISM: Artificial Sequence
<220> FEATURE:
<223> OTHER INFORMATION: Synthetic Construct

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Lys Thr Ser Gln Asn Ile Asn Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Leu Gln Asp Asn Ser Trp Pro Leu
                85                  90                  95

Thr Phe Gly Gln Gly Thr Lys Val Glu Ile Lys
            100                 105
```

<210> SEQ ID NO 28
<211> LENGTH: 446
<212> TYPE: PRT
<213> ORGANISM: Artificial Sequence
<220> FEATURE:
<223> OTHER INFORMATION: Synthetic Construct

<400> SEQUENCE: 28

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asn Ile Arg Ser Ser
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Thr Ile Tyr Val Asp Ser Val
    50                  55                  60

Lys Gly Arg Phe Thr Ile Ser Ala Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Met Asp Leu Tyr Ser Thr Ser Glu Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160
```

```
Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
    195                 200                 205

Thr Lys Val Asp Lys Lys Val Glu Pro Lys Ser Cys Asp Lys Thr His
210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 29
<211> LENGTH: 17
<212> TYPE: PRT
<213> ORGANISM: Artificial Sequence
<220> FEATURE:
<223> OTHER INFORMATION: Synthetic Construct

<400> SEQUENCE: 29

Arg Ile Asp Pro Ala Asn Gly Asn Thr Ile Tyr Val Asp Ser Val Lys
1               5                   10                  15

Gly

<210> SEQ ID NO 30
<211> LENGTH: 117
<212> TYPE: PRT
<213> ORGANISM: Artificial Sequence
<220> FEATURE:
<223> OTHER INFORMATION: Synthetic Construct

<400> SEQUENCE: 30
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asn Ile Arg Ser Ser
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Thr Ile Tyr Val Asp Ser Val
    50                  55                  60

Lys Gly Arg Phe Thr Ile Ser Ala Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Met Asp Leu Tyr Ser Thr Ser Glu Tyr Trp Gly Gln Gly Thr Leu
            100                 105                 110

Val Thr Val Ser Ser
            115

<210> SEQ ID NO 31
<211> LENGTH: 214
<212> TYPE: PRT
<213> ORGANISM: Artificial Sequence
<220> FEATURE:
<223> OTHER INFORMATION: Synthetic Construct

<400> SEQUENCE: 31

Asp Ile Gln Met Thr Gln Ser Pro Ser Phe Leu Ser Ala Ser Val Gly
1               5                   10                  15

Asp Arg Val Thr Ile Asn Cys Lys Thr Ser Gln Asn Ile Asn Arg Tyr
            20                  25                  30

Leu Asn Trp Tyr Gln Gln Lys Leu Gly Glu Ala Pro Lys Leu Leu Ile
        35                  40                  45

Tyr Asn Ala Asn Ser Leu Gln Thr Gly Ile Pro Ser Arg Phe Ser Ala
    50                  55                  60

Ser Gly Ser Gly Thr Asp Phe Thr Leu Thr Ile Asn Ser Leu Gln Pro
65                  70                  75                  80

Glu Asp Val Ala Thr Tyr Phe Cys Leu Gln Asp Asn Ser Trp Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 32
<211> LENGTH: 107
```

<212> TYPE: PRT
<213> ORGANISM: Artificial Sequence
<220> FEATURE:
<223> OTHER INFORMATION: Synthetic Construct

<400> SEQUENCE: 32

Asp Ile Gln Met Thr Gln Ser Pro Ser Phe Leu Ser Ala Ser Val Gly
1               5                   10                  15

Asp Arg Val Thr Ile Asn Cys Lys Thr Ser Gln Asn Ile Asn Arg Tyr
            20                  25                  30

Leu Asn Trp Tyr Gln Gln Lys Leu Gly Glu Ala Pro Lys Leu Leu Ile
        35                  40                  45

Tyr Asn Ala Asn Ser Leu Gln Thr Gly Ile Pro Ser Arg Phe Ser Ala
    50                  55                  60

Ser Gly Ser Gly Thr Asp Phe Thr Leu Thr Ile Asn Ser Leu Gln Pro
65                  70                  75                  80

Glu Asp Val Ala Thr Tyr Phe Cys Leu Gln Asp Asn Ser Trp Pro Leu
                85                  90                  95

Thr Phe Gly Ser Gly Thr Lys Leu Glu Ile Lys
            100                 105

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

Phe Gly Ser Gly Thr Lys Leu Glu Ile Lys
1               5                   10

<210> SEQ ID NO 34
<211> LENGTH: 447
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Gln Gln Ser Gly Ala Glu Phe Gly Lys Pro Gly Thr
1               5                   10                  15

Ser Val Lys Leu Ser Cys Lys Val Ser Gly Tyr Asn Ile Arg Ser Ser
            20                  25                  30

Tyr Met His Trp Val Asn Gln Arg Pro Gly Lys Gly Leu Glu Trp Ile
        35                  40                  45

Gly Arg Ile Asp Pro Ala Asn Gly Asn Thr Ile Tyr Ala Glu Lys Phe
    50                  55                  60

Lys Ile Lys Ala Ile Leu Thr Ala Asp Ser Ser Asn Thr Ala Tyr
65                  70                  75                  80

Met Gln Leu Ser Gln Leu Lys Ser Asp Asp Thr Ala Ile Tyr Phe Cys
                85                  90                  95

Ala Met Asp Leu Tyr Ser Thr Ser Glu Tyr Trp Gly Gln Gly Val Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser

```
                145                 150                 155                 160
        Gly Ala Leu Thr Ser Gly Val His Thr Phe Pro Ala Val Leu Gln Ser
                        165                 170                 175

Ser Gly Leu Tyr Ser Leu Ser Ser Val Val Thr Val Pro Ser Ser Ser
                        180                 185                 190

Leu Gly Thr Gln Thr Tyr Ile Cys Asn Val Asn His Lys Pro Ser Asn
                        195                 200                 205

Thr Lys Val Asp Lys Lys Val Glu Pro Lys Ser Cys Asp Lys Thr His
                210                 215                 220

Thr Cys Pro Pro Cys Pro Ala Pro Glu Ala Ala Gly Ala Pro Ser Val
        225                 230                 235                 240

Phe Leu Phe Pro Pro Lys Pro Lys Asp Thr Leu Met Ile Ser Arg Thr
                        245                 250                 255

Pro Glu Val Thr Cys Val Val Val Asp Val Ser His Glu Asp Pro Glu
                        260                 265                 270

Val Lys Phe Asn Trp Tyr Val Asp Gly Val Glu Val His Asn Ala Lys
                        275                 280                 285

Thr Lys Pro Arg Glu Glu Gln Tyr Asn Ser Thr Tyr Arg Val Val Ser
                290                 295                 300

Val Leu Thr Val Leu His Gln Asp Trp Leu Asn Gly Lys Glu Tyr Lys
        305                 310                 315                 320

Cys Lys Val Ser Asn Lys Ala Leu Pro Ala Pro Ile Glu Lys Thr Ile
                        325                 330                 335

Ser Lys Ala Lys Gly Gln Pro Arg Glu Pro Gln Val Tyr Thr Leu Pro
                        340                 345                 350

Pro Ser Arg Glu Glu Met Thr Lys Asn Gln Val Ser Leu Thr Cys Leu
                        355                 360                 365

Val Lys Gly Phe Tyr Pro Ser Asp Ile Ala Val Glu Trp Glu Ser Asn
                        370                 375                 380

Gly Gln Pro Glu Asn Asn Tyr Lys Thr Thr Pro Pro Val Leu Asp Ser
        385                 390                 395                 400

Asp Gly Ser Phe Phe Leu Tyr Ser Lys Leu Thr Val Asp Lys Ser Arg
                        405                 410                 415

Trp Gln Gln Gly Asn Val Phe Ser Cys Ser Val Met His Glu Ala Leu
                        420                 425                 430

His Asn His Tyr Thr Gln Lys Ser Leu Ser Leu Ser Pro Gly Lys
                        435                 440                 445

<210> SEQ ID NO 35
<211> LENGTH: 117
<212> TYPE: PRT
<213> ORGANISM: Artificial Sequence
<220> FEATURE:
<223> OTHER INFORMATION: Synthetic Construct

<400> SEQUENCE: 35

Glu Val Gln Leu Gln Gln Ser Gly Ala Glu Phe Gly Lys Pro Gly Thr
        1               5                   10                  15

Ser Val Lys Leu Ser Cys Lys Val Ser Gly Tyr Asn Ile Arg Ser Ser
                        20                  25                  30

Tyr Met His Trp Val Asn Gln Arg Pro Gly Lys Gly Leu Glu Trp Ile
                        35                  40                  45

Gly Arg Ile Asp Pro Ala Asn Gly Asn Thr Ile Tyr Ala Glu Lys Phe
                50                  55                  60

Lys Ile Lys Ala Ile Leu Thr Ala Asp Ser Ser Ser Asn Thr Ala Tyr
```

```
                65                  70                  75                  80
Met Gln Leu Ser Gln Leu Lys Ser Asp Asp Thr Ala Ile Tyr Phe Cys
                    85                  90                  95

Ala Met Asp Leu Tyr Ser Thr Ser Glu Tyr Trp Gly Gln Gly Val Met
                    100                 105                 110

Val Thr Val Ser Ser
            115

<210> SEQ ID NO 36
<211> LENGTH: 11
<212> TYPE: PRT
<213> ORGANISM: Artificial Sequence
<220> FEATURE:
<223> OTHER INFORMATION: Synthetic Construct

<400> SEQUENCE: 36

Trp Gly Gln Gly Val Met Val Thr Val Ser Ser
1               5                   10

<210> SEQ ID NO 37
<211> LENGTH: 446
<212> TYPE: PRT
<213> ORGANISM: Artificial Sequence
<220> FEATURE:
<223> OTHER INFORMATION: Synthetic Construct

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Ile Arg Ser Ala
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Thr Ile Tyr Val Asp Ser Val
    50                  55                  60

Lys Glu Arg Phe Thr Ile Ser Ala Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Met Asp Leu Tyr Ser Thr Ser Glu Tyr Trp Gly Gln Gly Thr Leu
                    100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                    180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Ala Ala Gly Ala Pro Ser Val
225                 230                 235                 240
```

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 38
<211> LENGTH: 17
<212> TYPE: PRT
<213> ORGANISM: Artificial Sequence
<220> FEATURE:
<223> OTHER INFORMATION: Synthetic Construct

<400> SEQUENCE: 38

Arg Ile Asp Pro Ala Asn Gly Asn Thr Ile Tyr Val Asp Ser Val Lys
1               5                   10                  15

Glu

<210> SEQ ID NO 39
<211> LENGTH: 117
<212> TYPE: PRT
<213> ORGANISM: Artificial Sequence
<220> FEATURE:
<223> OTHER INFORMATION: Synthetic Construct

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Ile Arg Ser Ala
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Thr Ile Tyr Val Asp Ser Val
    50                  55                  60

Lys Glu Arg Phe Thr Ile Ser Ala Asp Asn Ala Lys Asn Ser Ala Tyr
65                  70                  75                  80

```
Leu Gln Met Asn Ser Leu Arg Ala Glu Asp Thr Ala Val Tyr Tyr Cys
                85                  90                  95

Ala Met Asp Leu Tyr Ser Thr Ser Glu Tyr Trp Gly Gln Gly Thr Leu
            100                 105                 110

Val Thr Val Ser Ser
        115

<210> SEQ ID NO 40
<211> LENGTH: 446
<212> TYPE: PRT
<213> ORGANISM: Artificial Sequence
<220> FEATURE:
<223> OTHER INFORMATION: Synthetic Construct

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Ile Arg Ser Ala
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Thr Ile Tyr Val Glu Ser Val
50                  55                  60

Glu Gly Arg Phe Thr Ile Ser Ala Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Met Asp Leu Tyr Ser Thr Ser Glu Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 41
<211> LENGTH: 17
<212> TYPE: PRT
<213> ORGANISM: Artificial Sequence
<220> FEATURE:
<223> OTHER INFORMATION: Synthetic Construct

<400> SEQUENCE: 41

Arg Ile Asp Pro Ala Asn Gly Asn Thr Ile Tyr Val Glu Ser Val Glu
1               5                   10                  15

Gly

<210> SEQ ID NO 42
<211> LENGTH: 117
<212> TYPE: PRT
<213> ORGANISM: Artificial Sequence
<220> FEATURE:
<223> OTHER INFORMATION: Synthetic Construct

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Ile Arg Ser Ala
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Thr Ile Tyr Val Glu Ser Val
    50                  55                  60

Glu Gly Arg Phe Thr Ile Ser Ala Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Met Asp Leu Tyr Ser Thr Ser Glu Tyr Trp Gly Gln Gly Thr Leu
            100                 105                 110

Val Thr Val Ser Ser
        115

<210> SEQ ID NO 43
<211> LENGTH: 446
<212> TYPE: PRT
<213> ORGANISM: Artificial Sequence
<220> FEATURE:
```

-continued

<223> OTHER INFORMATION: Synthetic Construct

<400> SEQUENCE: 43

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Ile Arg Ser Ala
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Thr Ile Tyr Val Asp Ser Val
    50                  55                  60

Glu Gly Arg Phe Thr Ile Ser Ala Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Met Asp Leu Tyr Ser Thr Ser Glu Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

-continued

```
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly
        435                 440                 445

<210> SEQ ID NO 44
<211> LENGTH: 17
<212> TYPE: PRT
<213> ORGANISM: Artificial Sequence
<220> FEATURE:
<223> OTHER INFORMATION: Synthetic Construct

<400> SEQUENCE: 44

Arg Ile Asp Pro Ala Asn Gly Asn Thr Ile Tyr Val Asp Ser Val Glu
1               5                   10                  15
Gly

<210> SEQ ID NO 45
<211> LENGTH: 117
<212> TYPE: PRT
<213> ORGANISM: Artificial Sequence
<220> FEATURE:
<223> OTHER INFORMATION: Synthetic Construct

<400> SEQUENCE: 45

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Ala Ile Arg Ser Ala
            20                  25                  30
Tyr Met His Trp Val Arg Gln Ala Pro Gly Lys Gly Leu Glu Trp Val
        35                  40                  45
Ala Arg Ile Asp Pro Ala Asn Gly Asn Thr Ile Tyr Val Asp Ser Val
    50                  55                  60
Glu Gly Arg Phe Thr Ile Ser Ala Asp Asn Ala Lys Asn Ser Ala Tyr
65                  70                  75                  80
Leu Gln Met Asn Ser Leu Arg Ala Glu Asp Thr Ala Val Tyr Tyr Cys
                85                  90                  95
Ala Met Asp Leu Tyr Ser Thr Ser Glu Tyr Trp Gly Gln Gly Thr Leu
            100                 105                 110
Val Thr Val Ser Ser
        115

<210> SEQ ID NO 46
<211> LENGTH: 214
<212> TYPE: PRT
<213> ORGANISM: Artificial Sequence
<220> FEATURE:
<223> OTHER INFORMATION: Synthetic Construct

<400> SEQUENCE: 46

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Thr Val Gly Ile Asn
            20                  25                  30
Val Asp Trp Tyr Gln Gln Lys Pro Gly Lys Ala Pro Lys Leu Leu Ile
        35                  40                  45
Tyr Gly Ala Ser Asn Arg His Thr Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Cys Cys Leu Gln Tyr Gly Ser Ile Pro His
            85                  90                  95

Thr Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 47
<211> LENGTH: 11
<212> TYPE: PRT
<213> ORGANISM: Artificial Sequence
<220> FEATURE:
<223> OTHER INFORMATION: Synthetic Construct

<400> SEQUENCE: 47

Lys Ala Ser Gln Thr Val Gly Ile Asn Val Asp
1               5                   10

<210> SEQ ID NO 48
<211> LENGTH: 7
<212> TYPE: PRT
<213> ORGANISM: Artificial Sequence
<220> FEATURE:
<223> OTHER INFORMATION: Synthetic Construct

<400> SEQUENCE: 48

Gly Ala Ser Asn Arg His Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Construct

<400> SEQUENCE: 49

Leu Gln Tyr Gly Ser Ile Pro His Thr
1               5

<210> SEQ ID NO 50
<211> LENGTH: 107
<212> TYPE: PRT
<213> ORGANISM: Artificial Sequence
<220> FEATURE:
<223> OTHER INFORMATION: Synthetic Construct

<400> SEQUENCE: 50

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Thr Val Gly Ile Asn
            20                  25                  30

Val Asp Trp Tyr Gln Gln Lys Pro Gly Lys Ala Pro Lys Leu Leu Ile
        35                  40                  45

Tyr Gly Ala Ser Asn Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Cys Cys Leu Gln Tyr Gly Ser Ile Pro His
                85                  90                  95

Thr Phe Gly Gln Gly Thr Lys Val Glu Ile Lys
                100                 105
```

<210> SEQ ID NO 51
<211> LENGTH: 453
<212> TYPE: PRT
<213> ORGANISM: Artificial Sequence
<220> FEATURE:
<223> OTHER INFORMATION: Synthetic Construct

<400> SEQUENCE: 51

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Gly Tyr
            20                  25                  30

Tyr Met Gln Trp Val Arg Gln Ala Pro Gly Lys Gly Leu Glu Trp Met
        35                  40                  45

Gly Phe Ile Arg Ser Ser Gly Ser Thr Glu Tyr Asn Ser Glu Phe Lys
    50                  55                  60

Ser Arg Phe Thr Ile Ser Arg Asp Asn Ala Lys Asn Ser Val Tyr Leu
65              70                  75                  80

Gln Met Asn Ser Leu Arg Ala Glu Asp Thr Ala Val Tyr Tyr Cys Ala
                85                  90                  95

Arg Cys Pro Tyr Lys Tyr Ser Ser Phe Val Tyr Val Gly Val Met Asp
                100                 105                 110

Ala Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Ala Ala Gly Ala Pro Ser Val Phe Leu Phe Pro Pro Lys Pro Lys Asp
                245                 250                 255
```

```
Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 52
<211> LENGTH: 10
<212> TYPE: PRT
<213> ORGANISM: Artificial Sequence
<220> FEATURE:
<223> OTHER INFORMATION: Synthetic Construct

<400> SEQUENCE: 52

Gly Phe Ser Leu Thr Gly Tyr Tyr Met Gln
1               5                   10

<210> SEQ ID NO 53
<211> LENGTH: 16
<212> TYPE: PRT
<213> ORGANISM: Artificial Sequence
<220> FEATURE:
<223> OTHER INFORMATION: Synthetic Construct

<400> SEQUENCE: 53

Phe Ile Arg Ser Ser Gly Ser Thr Glu Tyr Asn Ser Glu Phe Lys Ser
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Synthetic Construct

<400> SEQUENCE: 54

Cys Pro Tyr Lys Tyr Ser Ser Phe Val Tyr Val Gly Val Met Asp Ala
1               5                   10                  15
```

```
<210> SEQ ID NO 55
<211> LENGTH: 124
<212> TYPE: PRT
<213> ORGANISM: Artificial Sequence
<220> FEATURE:
<223> OTHER INFORMATION: Synthetic Construct

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Gly Tyr
            20                  25                  30

Tyr Met Gln Trp Val Arg Gln Ala Pro Gly Lys Gly Leu Glu Trp Met
        35                  40                  45

Gly Phe Ile Arg Ser Ser Gly Ser Thr Glu Tyr Asn Ser Glu Phe Lys
    50                  55                  60

Ser Arg Phe Thr Ile Ser Arg Asp Asn Ala Lys Asn Ser Val Tyr Leu
65                  70                  75                  80

Gln Met Asn Ser Leu Arg Ala Glu Asp Thr Ala Val Tyr Tyr Cys Ala
                85                  90                  95

Arg Cys Pro Tyr Lys Tyr Ser Ser Phe Val Tyr Val Gly Val Met Asp
            100                 105                 110

Ala Trp Gly Gln Gly Thr Leu Val Thr Val Ser Ser
        115                 120

<210> SEQ ID NO 56
<211> LENGTH: 214
<212> TYPE: PRT
<213> ORGANISM: Artificial Sequence
<220> FEATURE:
<223> OTHER INFORMATION: Synthetic Construct

<400> SEQUENCE: 56

Glu Ile Val Met Thr Gln Ser Pro Thr Ser Met Ser Thr Ser Ile Gly
1               5                   10                  15

Glu Arg Val Thr Leu Asn Cys Lys Ala Ser Gln Thr Val Gly Ile Asn
            20                  25                  30

Val Asp Trp Tyr Gln Gln Thr Pro Gly Gln Pro Lys Leu Leu Ile
        35                  40                  45

Tyr Gly Ala Ser Asn Arg His Thr Gly Val Pro Asp Arg Phe Thr Gly
    50                  55                  60

Ser Gly Phe Gly Arg Asp Phe Thr Leu Thr Ile Ser Asn Val Glu Ala
65                  70                  75                  80

Glu Asp Leu Ala Val Tyr Cys Cys Leu Gln Tyr Gly Ser Ile Pro His
                85                  90                  95

Thr Phe Gly Pro Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205
Phe Asn Arg Gly Glu Cys
        210

<210> SEQ ID NO 57
<211> LENGTH: 107
<212> TYPE: PRT
<213> ORGANISM: Artificial Sequence
<220> FEATURE:
<223> OTHER INFORMATION: Synthetic Construct

<400> SEQUENCE: 57

Glu Ile Val Met Thr Gln Ser Pro Thr Ser Met Ser Thr Ser Ile Gly
1               5                   10                  15
Glu Arg Val Thr Leu Asn Cys Lys Ala Ser Gln Thr Val Gly Ile Asn
            20                  25                  30
Val Asp Trp Tyr Gln Gln Thr Pro Gly Gln Pro Pro Lys Leu Leu Ile
        35                  40                  45
Tyr Gly Ala Ser Asn Arg His Thr Gly Val Pro Asp Arg Phe Thr Gly
    50                  55                  60
Ser Gly Phe Gly Arg Asp Phe Thr Leu Thr Ile Ser Asn Val Glu Ala
65                  70                  75                  80
Glu Asp Leu Ala Val Tyr Cys Cys Leu Gln Tyr Gly Ser Ile Pro His
                85                  90                  95
Thr Phe Gly Pro Gly Thr Lys Leu Glu Leu Lys
            100                 105

<210> SEQ ID NO 58
<211> LENGTH: 10
<212> TYPE: PRT
<213> ORGANISM: Artificial Sequence
<220> FEATURE:
<223> OTHER INFORMATION: Synthetic Construct

<400> SEQUENCE: 58

Phe Gly Pro Gly Thr Lys Leu Glu Leu Lys
1               5                   10

<210> SEQ ID NO 59
<211> LENGTH: 454
<212> TYPE: PRT
<213> ORGANISM: Artificial Sequence
<220> FEATURE:
<223> OTHER INFORMATION: Synthetic Construct

<400> SEQUENCE: 59

Gln Val Gln Leu Lys Glu Thr Gly Pro Gly Leu Val Gln Pro Thr Gln
1               5                   10                  15
Thr Leu Ser Ile Thr Cys Thr Val Ser Gly Phe Ser Leu Thr Gly Tyr
            20                  25                  30
Tyr Met Gln Trp Val Arg Gln Thr Pro Gly Lys Gly Leu Glu Trp Met
        35                  40                  45
Gly Phe Ile Arg Ser Ser Gly Ser Thr Glu Tyr Asn Ser Glu Phe Lys
    50                  55                  60
Ser Arg Leu Ser Ile Ser Arg Asp Thr Ser Lys Asn Gln Val Phe Leu
65                  70                  75                  80
Lys Met Asn Ser Leu Lys Thr Glu Asp Thr Gly Val Tyr Tyr Cys Ala
                85                  90                  95
```

Arg Cys Pro Tyr Lys Tyr Ser Ser Phe Val Tyr Val Gly Val Met Asp
            100                 105                 110

Ala Trp Gly Gln Gly Ala Pro Val Thr Val Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Ala Ala Gly Ala Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 60
<211> LENGTH: 124
<212> TYPE: PRT
<213> ORGANISM: Artificial Sequence
<220> FEATURE:
<223> OTHER INFORMATION: Synthetic Construct

<400> SEQUENCE: 60

Gln Val Gln Leu Lys Glu Thr Gly Pro Gly Leu Val Gln Pro Thr Gln
1               5                   10                  15

Thr Leu Ser Ile Thr Cys Thr Val Ser Gly Phe Ser Leu Thr Gly Tyr
                20                  25                  30

Tyr Met Gln Trp Val Arg Gln Thr Pro Gly Lys Gly Leu Glu Trp Met
            35                  40                  45

Gly Phe Ile Arg Ser Ser Gly Ser Thr Glu Tyr Asn Ser Glu Phe Lys
        50                  55                  60

Ser Arg Leu Ser Ile Ser Arg Asp Thr Ser Lys Asn Gln Val Phe Leu
65                  70                  75                  80

Lys Met Asn Ser Leu Lys Thr Glu Asp Thr Gly Val Tyr Tyr Cys Ala
                85                  90                  95

Arg Cys Pro Tyr Lys Tyr Ser Ser Phe Val Tyr Val Gly Val Met Asp
            100                 105                 110

Ala Trp Gly Gln Gly Ala Pro Val Thr Val Ser Ser
        115                 120

<210> SEQ ID NO 61
<211> LENGTH: 11
<212> TYPE: PRT
<213> ORGANISM: Artificial Sequence
<220> FEATURE:
<223> OTHER INFORMATION: Synthetic Construct

<400> SEQUENCE: 61

Trp Gly Gln Gly Ala Pro Val Thr Val Ser Ser
1               5                   10

<210> SEQ ID NO 62
<211> LENGTH: 444
<212> TYPE: PRT
<213> ORGANISM: Artificial Sequence
<220> FEATURE:
<223> OTHER INFORMATION: Synthetic Construct

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Ile Ser Thr Tyr
                20                  25                  30

Asn Val His Trp Leu Arg Gln Ala Pro Gly Lys Gly Leu Glu Trp Met
            35                  40                  45

Gly Met Met Trp Ser Gly Gly Ser Pro Asp Tyr Asn Ser Ala Leu Lys
        50                  55                  60

Ser Arg Phe Thr Ile Ser Arg Asp Thr Ala Lys Asn Ser Val Tyr Leu
65                  70                  75                  80

Gln Met Asn Ser Leu Arg Ala Glu Asp Thr Ala Val Tyr Tyr Cys Ala
                85                  90                  95

Arg Trp Gly Gly Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

```
Leu Tyr Ser Leu Ser Ser Val Thr Val Pro Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 63
<211> LENGTH: 10
<212> TYPE: PRT
<213> ORGANISM: Artificial Sequence
<220> FEATURE:
<223> OTHER INFORMATION: Synthetic Construct

<400> SEQUENCE: 63

Gly Phe Ser Ile Ser Thr Tyr Asn Val His
1               5                   10

<210> SEQ ID NO 64
<211> LENGTH: 16
<212> TYPE: PRT
<213> ORGANISM: Artificial Sequence
<220> FEATURE:
<223> OTHER INFORMATION: Synthetic Construct

<400> SEQUENCE: 64

Met Met Trp Ser Gly Gly Ser Pro Asp Tyr Asn Ser Ala Leu Lys Ser
1               5                   10                  15
```

```
<210> SEQ ID NO 65
<211> LENGTH: 7
<212> TYPE: PRT
<213> ORGANISM: Artificial Sequence
<220> FEATURE:
<223> OTHER INFORMATION: Synthetic Construct

<400> SEQUENCE: 65

Trp Gly Gly Gly Phe Asp Tyr
1               5

<210> SEQ ID NO 66
<211> LENGTH: 115
<212> TYPE: PRT
<213> ORGANISM: Artificial Sequence
<220> FEATURE:
<223> OTHER INFORMATION: Synthetic Construct

<400> SEQUENCE: 66

Glu Val Gln Leu Val Glu Ser Gly Gly Leu Val Gln Pro Gly Gly
1               5                   10                  15

Ser Leu Arg Leu Ser Cys Ala Val Ser Gly Phe Ser Ile Ser Thr Tyr
            20                  25                  30

Asn Val His Trp Leu Arg Gln Ala Pro Gly Lys Gly Leu Glu Trp Met
        35                  40                  45

Gly Met Met Trp Ser Gly Gly Ser Pro Asp Tyr Asn Ser Ala Leu Lys
    50                  55                  60

Ser Arg Phe Thr Ile Ser Arg Asp Thr Ala Lys Asn Ser Val Tyr Leu
65                  70                  75                  80

Gln Met Asn Ser Leu Arg Ala Glu Asp Thr Ala Val Tyr Tyr Cys Ala
                85                  90                  95

Arg Trp Gly Gly Gly Phe Asp Tyr Trp Gly Gln Gly Thr Leu Val Thr
            100                 105                 110

Val Ser Ser
        115

<210> SEQ ID NO 67
<211> LENGTH: 214
<212> TYPE: PRT
<213> ORGANISM: Artificial Sequence
<220> FEATURE:
<223> OTHER INFORMATION: Synthetic Construct

<400> SEQUENCE: 67

Asp Ile Gln Leu Thr Gln Ser Pro Ser Ser Leu Ser Ala Ser Val Gly
1               5                   10                  15

Asp Arg Val Thr Ile Thr Cys Arg Ala Ser His Ser Ile Gly Thr Asn
            20                  25                  30

Leu His Trp Tyr Gln Gln Lys Pro Gly Lys Ala Pro Lys Leu Leu Ile
        35                  40                  45

Tyr Phe Thr Ser Gln Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Gln Ser Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 68
<211> LENGTH: 11
<212> TYPE: PRT
<213> ORGANISM: Artificial Sequence
<220> FEATURE:
<223> OTHER INFORMATION: Synthetic Construct

<400> SEQUENCE: 68

```
Arg Ala Ser His Ser Ile Gly Thr Asn Leu His
1               5                   10
```

<210> SEQ ID NO 69
<211> LENGTH: 7
<212> TYPE: PRT
<213> ORGANISM: Artificial Sequence
<220> FEATURE:
<223> OTHER INFORMATION: Synthetic Construct

<400> SEQUENCE: 69

```
Phe Thr Ser Gln Ser Ile Ser
1               5
```

<210> SEQ ID NO 70
<211> LENGTH: 9
<212> TYPE: PRT
<213> ORGANISM: Artificial Sequence
<220> FEATURE:
<223> OTHER INFORMATION: Synthetic Construct

<400> SEQUENCE: 70

```
Gln Gln Thr Gln Ser Trp Pro Leu Thr
1               5
```

<210> SEQ ID NO 71
<211> LENGTH: 107
<212> TYPE: PRT
<213> ORGANISM: Artificial Sequence
<220> FEATURE:
<223> OTHER INFORMATION: Synthetic Construct

<400> SEQUENCE: 71

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser His Ser Ile Gly Thr Asn
            20                  25                  30

Leu His Trp Tyr Gln Gln Lys Pro Gly Lys Ala Pro Lys Leu Leu Ile
        35                  40                  45

Tyr Phe Thr Ser Gln Ser Ile Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Gln Ser Trp Pro Leu
                 85                  90                  95

Thr Phe Gly Gln Gly Thr Lys Val Glu Ile Lys
            100                 105
```

<210> SEQ ID NO 72
<211> LENGTH: 214
<212> TYPE: PRT
<213> ORGANISM: Artificial Sequence
<220> FEATURE:
<223> OTHER INFORMATION: Synthetic Construct

<400> SEQUENCE: 72

```
Asp Ile Val Leu Thr Gln Ser Pro Thr Thr Leu Ser Val Thr Pro Gly
  1               5                  10                  15

Glu Thr Val Ser Leu Ser Cys Arg Ala Ser His Ser Ile Gly Thr Asn
                 20                  25                  30

Leu His Trp Tyr Gln Gln Lys Thr Asn Glu Ser Pro Arg Leu Leu Ile
             35                  40                  45

Lys Phe Thr Ser Gln Ser Ile Ser Gly Ile Pro Ser Arg Phe Ser Ala
 50                  55                  60

Ser Gly Ser Gly Thr Asp Phe Thr Leu Asn Ile Asn Asn Val Glu Phe
 65                  70                  75                  80

Asp Asp Val Ser Ser Tyr Phe Cys Gln Gln Thr Gln Ser Trp Pro Leu
                 85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 73
<211> LENGTH: 107
<212> TYPE: PRT
<213> ORGANISM: Artificial Sequence
<220> FEATURE:
<223> OTHER INFORMATION: Synthetic Construct

<400> SEQUENCE: 73

```
Asp Ile Val Leu Thr Gln Ser Pro Thr Thr Leu Ser Val Thr Pro Gly
  1               5                  10                  15

Glu Thr Val Ser Leu Ser Cys Arg Ala Ser His Ser Ile Gly Thr Asn
                 20                  25                  30

Leu His Trp Tyr Gln Gln Lys Thr Asn Glu Ser Pro Arg Leu Leu Ile
```

```
                35                  40                  45
Lys Phe Thr Ser Gln Ser Ile Ser Gly Ile Pro Ser Arg Phe Ser Ala
 50                  55                  60

Ser Gly Ser Gly Thr Asp Phe Thr Leu Asn Ile Asn Asn Val Glu Phe
65                  70                  75                  80

Asp Asp Val Ser Ser Tyr Phe Cys Gln Gln Thr Gln Ser Trp Pro Leu
                85                  90                  95

Thr Phe Gly Ser Gly Thr Lys Leu Glu Ile Lys
            100                 105

<210> SEQ ID NO 74
<211> LENGTH: 445
<212> TYPE: PRT
<213> ORGANISM: Artificial Sequence
<220> FEATURE:
<223> OTHER INFORMATION: Synthetic Construct

<400> SEQUENCE: 74

Gln Val Gln Leu Lys Glu Ser Gly Pro Gly Leu Val Gln Pro Ser Glu
1               5                   10                  15

Thr Leu Ser Leu Thr Cys Thr Val Ser Gly Phe Ser Ile Ser Thr Tyr
            20                  25                  30

Asn Val His Trp Leu Arg Gln Pro Pro Gly Lys Gly Leu Glu Trp Met
        35                  40                  45

Gly Met Trp Ser Gly Gly Ser Pro Asp Tyr Asn Ser Ala Leu Lys
 50                  55                  60

Ser Arg Leu Ser Ile Ser Arg Asp Thr Ser Lys Asn Gln Val Phe Leu
65                  70                  75                  80

Lys Met Asn Ser Leu Gln Ser Glu Asp Thr Thr Thr Tyr Tyr Cys Ala
                85                  90                  95

Arg Trp Gly Gly Gly Phe Asp Tyr Trp Gly Gln Gly Val Met Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
```

```
                290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 75
<211> LENGTH: 115
<212> TYPE: PRT
<213> ORGANISM: Artificial Sequence
<220> FEATURE:
<223> OTHER INFORMATION: Synthetic Construct

<400> SEQUENCE: 75

Gln Val Gln Leu Lys Glu Ser Gly Pro Gly Leu Val Gln Pro Ser Glu
1               5                   10                  15

Thr Leu Ser Leu Thr Cys Thr Val Ser Gly Phe Ser Ile Ser Thr Tyr
            20                  25                  30

Asn Val His Trp Leu Arg Gln Pro Pro Gly Lys Gly Leu Glu Trp Met
        35                  40                  45

Gly Met Met Trp Ser Gly Gly Ser Pro Asp Tyr Asn Ser Ala Leu Lys
    50                  55                  60

Ser Arg Leu Ser Ile Ser Arg Asp Thr Ser Lys Asn Gln Val Phe Leu
65                  70                  75                  80

Lys Met Asn Ser Leu Gln Ser Glu Asp Thr Thr Thr Tyr Tyr Cys Ala
                85                  90                  95

Arg Trp Gly Gly Gly Phe Asp Tyr Trp Gly Gln Gly Val Met Val Thr
            100                 105                 110

Val Ser Ser
        115

<210> SEQ ID NO 76
<211> LENGTH: 446
<212> TYPE: PRT
<213> ORGANISM: Artificial Sequence
<220> FEATURE:
<223> OTHER INFORMATION: Synthetic Construct

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Val Ser Gly Tyr Asn Ile Arg Ser Thr
            20                  25                  30
```

```
Tyr Met His Trp Val Arg Gln Ala Pro Gly Gln Gly Leu Glu Trp Met
         35                  40                  45

Gly Arg Ile Asp Pro Ala Asn Gly Asn Thr Ile Tyr Ala Glu Lys Phe
 50                  55                  60

Lys Arg Arg Val Thr Leu Thr Arg Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Met Glu Val Arg Val Ser Phe Glu Tyr Trp Gly Gln Gly Thr Leu
                 100                 105                 110

Val Thr Val Ser Ser Ala Ser Thr Lys Gly Pro Ser Val Phe Pro Leu
         115                 120                 125

Ala Pro Ser Ser Lys Ser Thr Ser Gly Gly Thr Ala Ala Leu Gly Cys
 130                 135                 140

Leu Val Lys Asp Tyr Phe Pro Glu Pro Val Thr Val Ser Trp Asn Ser
 145                 150                 155                 160

Gly Ala Leu Thr Ser Gly Val His Thr Phe Pro Ala Val Leu Gln Ser
                 165                 170                 175

Ser Gly Leu Tyr Ser Leu Ser Ser Val Val Thr Val Pro Ser Ser Ser
                 180                 185                 190

Leu Gly Thr Gln Thr Tyr Ile Cys Asn Val Asn His Lys Pro Ser Asn
         195                 200                 205

Thr Lys Val Asp Lys Lys Val Glu Pro Lys Ser Cys Asp Lys Thr His
 210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                 245                 250                 255

Pro Glu Val Thr Cys Val Val Asp Val Ser His Glu Asp Pro Glu
                 260                 265                 270

Val Lys Phe Asn Trp Tyr Val Asp Gly Val Glu Val His Asn Ala Lys
                 275                 280                 285

Thr Lys Pro Arg Glu Glu Gln Tyr Asn Ser Thr Tyr Arg Val Val Ser
 290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                 325                 330                 335

Ser Lys Ala Lys Gly Gln Pro Arg Glu Pro Gln Val Tyr Thr Leu Pro
                 340                 345                 350

Pro Ser Arg Glu Glu Met Thr Lys Asn Gln Val Ser Leu Thr Cys Leu
                 355                 360                 365

Val Lys Gly Phe Tyr Pro Ser Asp Ile Ala Val Glu Trp Glu Ser Asn
 370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                 405                 410                 415

Trp Gln Gln Gly Asn Val Phe Ser Cys Ser Val Met His Glu Ala Leu
                 420                 425                 430

His Asn His Tyr Thr Gln Lys Ser Leu Ser Leu Ser Pro Gly
                 435                 440                 445
```

```
<210> SEQ ID NO 77
<211> LENGTH: 10
<212> TYPE: PRT
<213> ORGANISM: Artificial Sequence
<220> FEATURE:
<223> OTHER INFORMATION: Synthetic Construct

<400> SEQUENCE: 77

Gly Tyr Asn Ile Arg Ser Thr Tyr Met His
1               5                   10

<210> SEQ ID NO 78
<211> LENGTH: 17
<212> TYPE: PRT
<213> ORGANISM: Artificial Sequence
<220> FEATURE:
<223> OTHER INFORMATION: Synthetic Construct

<400> SEQUENCE: 78

Arg Ile Asp Pro Ala Asn Gly Asn Thr Ile Tyr Ala Glu Lys Phe Lys
1               5                   10                  15

Arg

<210> SEQ ID NO 79
<211> LENGTH: 8
<212> TYPE: PRT
<213> ORGANISM: Artificial Sequence
<220> FEATURE:
<223> OTHER INFORMATION: Synthetic Construct

<400> SEQUENCE: 79

Glu Val Arg Val Ser Phe Glu Tyr
1               5

<210> SEQ ID NO 80
<211> LENGTH: 117
<212> TYPE: PRT
<213> ORGANISM: Artificial Sequence
<220> FEATURE:
<223> OTHER INFORMATION: Synthetic Construct

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Val Ser Gly Tyr Asn Ile Arg Ser Thr
                20                  25                  30

Tyr Met His Trp Val Arg Gln Ala Pro Gly Gln Gly Leu Glu Trp Met
            35                  40                  45

Gly Arg Ile Asp Pro Ala Asn Gly Asn Thr Ile Tyr Ala Glu Lys Phe
        50                  55                  60

Lys Arg Arg Val Thr Leu Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Met Glu Val Arg Val Ser Phe Glu Tyr Trp Gly Gln Gly Thr Leu
            100                 105                 110

Val Thr Val Ser Ser
        115

<210> SEQ ID NO 81
<211> LENGTH: 213
<212> TYPE: PRT
<213> ORGANISM: Artificial Sequence
```

```
<220> FEATURE:
<223> OTHER INFORMATION: Synthetic Construct

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys Tyr
            20                  25                  30

Leu Asp Trp Tyr Gln Gln Lys Pro Gly Lys Ala Pro Lys Leu Leu Ile
        35                  40                  45

Tyr Tyr Thr Asn Asn Leu His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Asp Ser Gly Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 82
<211> LENGTH: 11
<212> TYPE: PRT
<213> ORGANISM: Artificial Sequence
<220> FEATURE:
<223> OTHER INFORMATION: Synthetic Construct

<400> SEQUENCE: 82

Lys Ala Ser Gln Asn Ile Asn Lys Tyr Leu Asp
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Synthetic Construct

<400> SEQUENCE: 83

Tyr Thr Asn Asn Leu His Thr
1               5

<210> SEQ ID NO 84
<211> LENGTH: 8
<212> TYPE: PRT
<213> ORGANISM: Artificial Sequence
<220> FEATURE:
```

```
<223> OTHER INFORMATION: Synthetic Construct

<400> SEQUENCE: 84

Leu Gln His Asp Ser Gly Tyr Thr
1               5

<210> SEQ ID NO 85
<211> LENGTH: 106
<212> TYPE: PRT
<213> ORGANISM: Artificial Sequence
<220> FEATURE:
<223> OTHER INFORMATION: Synthetic Construct

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys Tyr
            20                  25                  30

Leu Asp Trp Tyr Gln Gln Lys Pro Gly Lys Ala Pro Lys Leu Leu Ile
        35                  40                  45

Tyr Tyr Thr Asn Asn Leu His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Asp Ser Gly Tyr Thr
                85                  90                  95

Phe Gly Gln Gly Thr Lys Val Glu Ile Lys
            100                 105

<210> SEQ ID NO 86
<211> LENGTH: 213
<212> TYPE: PRT
<213> ORGANISM: Artificial Sequence
<220> FEATURE:
<223> OTHER INFORMATION: Synthetic Construct

<400> SEQUENCE: 86

Asp Ile Gln Met Thr Gln Ser Pro Ser Phe Leu Ser Ala Ser Val Gly
1               5                   10                  15

Asp Arg Val Thr Ile Asn Cys Lys Ala Ser Gln Asn Ile Asn Lys Tyr
            20                  25                  30

Leu Asp Trp Tyr Gln Gln Lys Leu Gly Glu Gly Pro Lys Leu Leu Ile
        35                  40                  45

Tyr Tyr Thr Asn Asn Leu His Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Leu Gln His Asp Ser Gly Tyr Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
```

```
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210

<210> SEQ ID NO 87
<211> LENGTH: 106
<212> TYPE: PRT
<213> ORGANISM: Artificial Sequence
<220> FEATURE:
<223> OTHER INFORMATION: Synthetic Construct

<400> SEQUENCE: 87

Asp Ile Gln Met Thr Gln Ser Pro Ser Phe Leu Ser Ala Ser Val Gly
1               5                   10                  15
Asp Arg Val Thr Ile Asn Cys Lys Ala Ser Gln Asn Ile Asn Lys Tyr
            20                  25                  30
Leu Asp Trp Tyr Gln Gln Lys Leu Gly Glu Gly Pro Lys Leu Leu Ile
        35                  40                  45
Tyr Tyr Thr Asn Asn Leu His Thr Gly Ile Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Val Ala Thr Tyr Phe Cys Leu Gln His Asp Ser Gly Tyr Thr
                85                  90                  95
Phe Gly Ala Gly Thr Lys Leu Glu Leu Lys
            100                 105

<210> SEQ ID NO 88
<211> LENGTH: 10
<212> TYPE: PRT
<213> ORGANISM: Artificial Sequence
<220> FEATURE:
<223> OTHER INFORMATION: Synthetic Construct

<400> SEQUENCE: 88

Phe Gly Ala Gly Thr Lys Leu Glu Leu Lys
1               5                   10

<210> SEQ ID NO 89
<211> LENGTH: 447
<212> TYPE: PRT
<213> ORGANISM: Artificial Sequence
<220> FEATURE:
<223> OTHER INFORMATION: Synthetic Construct

<400> SEQUENCE: 89

Glu Val Gln Leu Gln Gln Ser Gly Ala Glu Leu Gly Lys Pro Gly Thr
1               5                   10                  15
Ser Val Lys Leu Ser Cys Lys Val Ser Gly Tyr Asn Ile Arg Ser Thr
            20                  25                  30
Tyr Met His Trp Val Ser Gln Arg Pro Gly Lys Gly Leu Glu Trp Ile
        35                  40                  45
Gly Arg Ile Asp Pro Ala Asn Gly Asn Thr Ile Tyr Ala Glu Lys Phe
    50                  55                  60
Lys Arg Lys Ala Thr Leu Thr Ala Asp Thr Ser Ser Asn Thr Ala Tyr
65                  70                  75                  80
```

```
Met Gln Leu Ser Gln Leu Lys Ser Asp Asp Arg Ala Ile Tyr Phe Cys
                85                  90                  95

Ala Met Glu Val Arg Val Ser Phe Glu Tyr Trp Gly Gln Gly Val Met
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 90
<211> LENGTH: 117
<212> TYPE: PRT
<213> ORGANISM: Artificial Sequence
<220> FEATURE:
<223> OTHER INFORMATION: Synthetic Construct

<400> SEQUENCE: 90
```

```
Glu Val Gln Leu Gln Gln Ser Gly Ala Glu Leu Gly Lys Pro Gly Thr
 1               5                  10                  15

Ser Val Lys Leu Ser Cys Lys Val Ser Gly Tyr Asn Ile Arg Ser Thr
            20                  25                  30

Tyr Met His Trp Val Ser Gln Arg Pro Gly Lys Gly Leu Glu Trp Ile
        35                  40                  45

Gly Arg Ile Asp Pro Ala Asn Gly Asn Thr Ile Tyr Ala Glu Lys Phe
    50                  55                  60

Lys Arg Lys Ala Thr Leu Thr Ala Asp Thr Ser Ser Asn Thr Ala Tyr
65                  70                  75                  80

Met Gln Leu Ser Gln Leu Lys Ser Asp Asp Arg Ala Ile Tyr Phe Cys
                85                  90                  95

Ala Met Glu Val Arg Val Ser Phe Glu Tyr Trp Gly Gln Gly Val Met
            100                 105                 110

Val Thr Val Ser Ser
            115

<210> SEQ ID NO 91
<211> LENGTH: 446
<212> TYPE: PRT
<213> ORGANISM: Artificial Sequence
<220> FEATURE:
<223> OTHER INFORMATION: Synthetic Construct

<400> SEQUENCE: 91

Gln Val Gln Leu Val Gln Ser Gly Ala Glu Val Lys Lys Pro Gly Ser
 1               5                  10                  15

Ser Val Lys Val Ser Cys Lys Val Ser Gly Tyr Ser Ile Arg Ser Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Thr Ile Tyr Ala Glu Arg Phe
    50                  55                  60

Lys Asn Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Val Glu Ile Leu Gly Ile Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Ala Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 92
<211> LENGTH: 10
<212> TYPE: PRT
<213> ORGANISM: Artificial Sequence
<220> FEATURE:
<223> OTHER INFORMATION: Synthetic Construct

<400> SEQUENCE: 92

Gly Tyr Ser Ile Arg Ser Thr Tyr Met His
1               5                   10

<210> SEQ ID NO 93
<211> LENGTH: 17
<212> TYPE: PRT
<213> ORGANISM: Artificial Sequence
<220> FEATURE:
<223> OTHER INFORMATION: Synthetic Construct

<400> SEQUENCE: 93

Arg Ile Asp Pro Ala Asn Gly Asn Thr Ile Tyr Ala Glu Arg Phe Lys
1               5                   10                  15

Asn

<210> SEQ ID NO 94
<211> LENGTH: 8
<212> TYPE: PRT
<213> ORGANISM: Artificial Sequence
<220> FEATURE:
<223> OTHER INFORMATION: Synthetic Construct

<400> SEQUENCE: 94

Glu Ile Leu Gly Ile Phe Asp Tyr
```

<210> SEQ ID NO 95
<211> LENGTH: 117
<212> TYPE: PRT
<213> ORGANISM: Artificial Sequence
<220> FEATURE:
<223> OTHER INFORMATION: Synthetic Construct

<400> SEQUENCE: 95

```
Gln Val Gln Leu Val Gln Ser Gly Ala Glu Val Lys Lys Pro Gly Ser
1               5                   10                  15

Ser Val Lys Val Ser Cys Lys Val Ser Gly Tyr Ser Ile Arg Ser Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Thr Ile Tyr Ala Glu Arg Phe
    50                  55                  60

Lys Asn Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Val Glu Ile Leu Gly Ile Phe Asp Tyr Trp Gly Gln Gly Thr Leu
            100                 105                 110

Val Thr Val Ser Ser
        115
```

<210> SEQ ID NO 96
<211> LENGTH: 213
<212> TYPE: PRT
<213> ORGANISM: Artificial Sequence
<220> FEATURE:
<223> OTHER INFORMATION: Synthetic Construct

<400> SEQUENCE: 96

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asp Trp Tyr Gln Gln Lys Pro Gly Lys Ala Pro Lys Leu Leu Met
        35                  40                  45

Tyr Asn Thr Asn Ser Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Leu Gln His Asn Ser Gly Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175
```

```
Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 97
<211> LENGTH: 11
<212> TYPE: PRT
<213> ORGANISM: Artificial Sequence
<220> FEATURE:
<223> OTHER INFORMATION: Synthetic Construct

<400> SEQUENCE: 97

```
Lys Ala Ser Gln Asn Ile Asp Lys Tyr Leu Asp
1               5                   10
```

<210> SEQ ID NO 98
<211> LENGTH: 7
<212> TYPE: PRT
<213> ORGANISM: Artificial Sequence
<220> FEATURE:
<223> OTHER INFORMATION: Synthetic Construct

<400> SEQUENCE: 98

```
Asn Thr Asn Ser Leu His Thr
1               5
```

<210> SEQ ID NO 99
<211> LENGTH: 8
<212> TYPE: PRT
<213> ORGANISM: Artificial Sequence
<220> FEATURE:
<223> OTHER INFORMATION: Synthetic Construct

<400> SEQUENCE: 99

```
Leu Gln His Asn Ser Gly Tyr Thr
1               5
```

<210> SEQ ID NO 100
<211> LENGTH: 106
<212> TYPE: PRT
<213> ORGANISM: Artificial Sequence
<220> FEATURE:
<223> OTHER INFORMATION: Synthetic Construct

<400> SEQUENCE: 100

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asp Trp Tyr Gln Gln Lys Pro Gly Lys Ala Pro Lys Leu Leu Met
        35                  40                  45

Tyr Asn Thr Asn Ser Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Leu Gln His Asn Ser Gly Tyr Thr
                85                  90                  95

Phe Gly Gln Gly Thr Lys Val Glu Ile Lys
            100                 105
```

<210> SEQ ID NO 101
<211> LENGTH: 213
<212> TYPE: PRT
<213> ORGANISM: Artificial Sequence
<220> FEATURE:
<223> OTHER INFORMATION: Synthetic Construct

<400> SEQUENCE: 101

```
Asp Ile Gln Met Thr Gln Ser Pro Ser Phe Leu Ser Ala Ser Val Gly
1               5                   10                  15

Asp Arg Val Thr Ile Asn Cys Lys Ala Ser Gln Asn Ile Asp Lys Tyr
            20                  25                  30

Leu Asp Trp Tyr Gln Gln Lys Leu Gly Glu Ala Pro Lys Leu Leu Met
        35                  40                  45

Tyr Asn Thr Asn Ser Leu His Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Leu Gln His Asn Ser Gly Tyr Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 102
<211> LENGTH: 106
<212> TYPE: PRT
<213> ORGANISM: Artificial Sequence
<220> FEATURE:
<223> OTHER INFORMATION: Synthetic Construct

<400> SEQUENCE: 102

```
Asp Ile Gln Met Thr Gln Ser Pro Ser Phe Leu Ser Ala Ser Val Gly
1               5                   10                  15

Asp Arg Val Thr Ile Asn Cys Lys Ala Ser Gln Asn Ile Asp Lys Tyr
            20                  25                  30

Leu Asp Trp Tyr Gln Gln Lys Leu Gly Glu Ala Pro Lys Leu Leu Met
        35                  40                  45

Tyr Asn Thr Asn Ser Leu His Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Leu Gln His Asn Ser Gly Tyr Thr
                85                  90                  95
```

Phe Gly Ala Gly Thr Lys Leu Glu Leu Lys
                100                 105

<210> SEQ ID NO 103
<211> LENGTH: 447
<212> TYPE: PRT
<213> ORGANISM: Artificial Sequence
<220> FEATURE:
<223> OTHER INFORMATION: Synthetic Construct

<400> SEQUENCE: 103

Glu Val Gln Leu Gln Gln Ser Gly Ala Glu Leu Gly Lys Pro Gly Thr
1               5                   10                  15

Ser Val Lys Leu Ser Cys Lys Val Ser Gly Tyr Ser Ile Arg Ser Thr
            20                  25                  30

Tyr Met His Trp Val Asn Gln Arg Pro Gly Lys Gly Leu Glu Trp Val
        35                  40                  45

Gly Arg Ile Asp Pro Ala Asn Gly Asn Thr Ile Tyr Ala Glu Arg Phe
    50                  55                  60

Lys Asn Lys Ala Thr Leu Thr Ala Asp Thr Ser Ser Asn Thr Ala Tyr
65                  70                  75                  80

Met Gln Leu Ser Gln Leu Lys Ser Asp Asp Thr Ala Ile Tyr Phe Cys
                85                  90                  95

Ala Val Glu Ile Leu Gly Ile Phe Asp Tyr Trp Gly Gln Gly Val Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

```
Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 104
<211> LENGTH: 117
<212> TYPE: PRT
<213> ORGANISM: Artificial Sequence
<220> FEATURE:
<223> OTHER INFORMATION: Synthetic Construct

<400> SEQUENCE: 104

Glu Val Gln Leu Gln Gln Ser Gly Ala Glu Leu Gly Lys Pro Gly Thr
1               5                   10                  15

Ser Val Lys Leu Ser Cys Lys Val Ser Gly Tyr Ser Ile Arg Ser Thr
            20                  25                  30

Tyr Met His Trp Val Asn Gln Arg Pro Gly Lys Gly Leu Glu Trp Val
        35                  40                  45

Gly Arg Ile Asp Pro Ala Asn Gly Asn Thr Ile Tyr Ala Glu Arg Phe
    50                  55                  60

Lys Asn Lys Ala Thr Leu Thr Ala Asp Thr Ser Ser Asn Thr Ala Tyr
65                  70                  75                  80

Met Gln Leu Ser Gln Leu Lys Ser Asp Asp Thr Ala Ile Tyr Phe Cys
                85                  90                  95

Ala Val Glu Ile Leu Gly Ile Phe Asp Tyr Trp Gly Gln Gly Val Met
            100                 105                 110

Val Thr Val Ser Ser
        115

<210> SEQ ID NO 105
<211> LENGTH: 214
<212> TYPE: PRT
<213> ORGANISM: Artificial Sequence
<220> FEATURE:
<223> OTHER INFORMATION: Synthetic Construct

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln His Ile Asn Arg Tyr
            20                  25                  30

Leu Asn Trp Tyr Gln Gln Lys Pro Gly Lys Ala Pro Lys Leu Leu Ile
        35                  40                  45

Tyr Asp Ala Asn Asn Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Leu Gln His Asn Ser Trp Pro Asn
```

```
                    85                  90                  95
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 106
<211> LENGTH: 11
<212> TYPE: PRT
<213> ORGANISM: Artificial Sequence
<220> FEATURE:
<223> OTHER INFORMATION: Synthetic Construct

<400> SEQUENCE: 106

```
Lys Ala Ser Gln His Ile Asn Arg Tyr Leu Asn
1               5                   10
```

<210> SEQ ID NO 107
<211> LENGTH: 7
<212> TYPE: PRT
<213> ORGANISM: Artificial Sequence
<220> FEATURE:
<223> OTHER INFORMATION: Synthetic Construct

<400> SEQUENCE: 107

```
Asp Ala Asn Asn Leu Gln Thr
1               5
```

<210> SEQ ID NO 108
<211> LENGTH: 9
<212> TYPE: PRT
<213> ORGANISM: Artificial Sequence
<220> FEATURE:
<223> OTHER INFORMATION: Synthetic Construct

<400> SEQUENCE: 108

```
Leu Gln His Asn Ser Trp Pro Asn Thr
1               5
```

<210> SEQ ID NO 109
<211> LENGTH: 107
<212> TYPE: PRT
<213> ORGANISM: Artificial Sequence
<220> FEATURE:
<223> OTHER INFORMATION: Synthetic Construct

<400> SEQUENCE: 109

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln His Ile Asn Arg Tyr
```

```
            20                  25                  30
Leu Asn Trp Tyr Gln Gln Lys Pro Gly Lys Ala Pro Lys Leu Leu Ile
        35                  40                  45

Tyr Asp Ala Asn Asn Leu Gln Thr Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Leu Gln His Asn Ser Trp Pro Asn
                85                  90                  95

Thr Phe Gly Gln Gly Thr Lys Val Glu Ile Lys
            100                 105

<210> SEQ ID NO 110
<211> LENGTH: 446
<212> TYPE: PRT
<213> ORGANISM: Artificial Sequence
<220> FEATURE:
<223> OTHER INFORMATION: Synthetic Construct

<400> SEQUENCE: 110

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Lys Ile Arg Ser Ser
            20                  25                  30

Tyr Met His Trp Val Arg Gln Ala Pro Gly Lys Gly Leu Glu Trp Ile
        35                  40                  45

Gly Arg Ile Asp Pro Ala Asn Gly Asn Thr Ile Tyr Gly Asp Lys Phe
 50                  55                  60

Lys Ser Arg Phe Thr Leu Ser Ser Asp Thr Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Ile Asp Ile Gly Thr Thr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
```

```
            275                 280                 285
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 111
<211> LENGTH: 10
<212> TYPE: PRT
<213> ORGANISM: Artificial Sequence
<220> FEATURE:
<223> OTHER INFORMATION: Synthetic Construct

<400> SEQUENCE: 111

Gly Tyr Lys Ile Arg Ser Ser Tyr Met His
1               5                   10

<210> SEQ ID NO 112
<211> LENGTH: 17
<212> TYPE: PRT
<213> ORGANISM: Artificial Sequence
<220> FEATURE:
<223> OTHER INFORMATION: Synthetic Construct

<400> SEQUENCE: 112

Arg Ile Asp Pro Ala Asn Gly Asn Thr Ile Tyr Gly Asp Lys Phe Lys
1               5                   10                  15

Ser

<210> SEQ ID NO 113
<211> LENGTH: 8
<212> TYPE: PRT
<213> ORGANISM: Artificial Sequence
<220> FEATURE:
<223> OTHER INFORMATION: Synthetic Construct

<400> SEQUENCE: 113

Asp Ile Gly Thr Thr Phe Asp Tyr
1               5

<210> SEQ ID NO 114
<211> LENGTH: 117
<212> TYPE: PRT
<213> ORGANISM: Artificial Sequence
<220> FEATURE:
```

<223> OTHER INFORMATION: Synthetic Construct

<400> SEQUENCE: 114

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Lys Ile Arg Ser Ser
            20                  25                  30

Tyr Met His Trp Val Arg Gln Ala Pro Gly Lys Gly Leu Glu Trp Ile
        35                  40                  45

Gly Arg Ile Asp Pro Ala Asn Gly Asn Thr Ile Tyr Gly Asp Lys Phe
    50                  55                  60

Lys Ser Arg Phe Thr Leu Ser Ser Asp Thr Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Ile Asp Ile Gly Thr Thr Phe Asp Tyr Trp Gly Gln Gly Thr Leu
            100                 105                 110

Val Thr Val Ser Ser
            115
```

<210> SEQ ID NO 115
<211> LENGTH: 214
<212> TYPE: PRT
<213> ORGANISM: Artificial Sequence
<220> FEATURE:
<223> OTHER INFORMATION: Synthetic Construct

<400> SEQUENCE: 115

```
Asp Ile Gln Met Thr Gln Ser Pro Ser Phe Leu Ser Ala Ser Val Gly
1               5                   10                  15

Asp Arg Val Thr Ile Asn Cys Lys Ala Ser Gln His Ile Asn Arg Tyr
            20                  25                  30

Leu Asn Trp Tyr Gln Gln Lys Leu Gly Glu Ala Pro Lys Leu Leu Ile
        35                  40                  45

Tyr Asp Ala Asn Asn Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Leu Gln His Asn Ser Trp Pro Asn
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 116
<211> LENGTH: 107
<212> TYPE: PRT
<213> ORGANISM: Artificial Sequence
<220> FEATURE:
<223> OTHER INFORMATION: Synthetic Construct

<400> SEQUENCE: 116

```
Asp Ile Gln Met Thr Gln Ser Pro Ser Phe Leu Ser Ala Ser Val Gly
1               5                   10                  15

Asp Arg Val Thr Ile Asn Cys Lys Ala Ser Gln His Ile Asn Arg Tyr
            20                  25                  30

Leu Asn Trp Tyr Gln Gln Lys Leu Gly Glu Ala Pro Lys Leu Leu Ile
        35                  40                  45

Tyr Asp Ala Asn Asn Leu Gln Thr Gly Ile Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Leu Gln His Asn Ser Trp Pro Asn
                85                  90                  95

Thr Phe Gly Ala Gly Thr Lys Leu Glu Leu Lys
            100                 105
```

<210> SEQ ID NO 117
<211> LENGTH: 447
<212> TYPE: PRT
<213> ORGANISM: Artificial Sequence
<220> FEATURE:
<223> OTHER INFORMATION: Synthetic Construct

<400> SEQUENCE: 117

```
Glu Val Gln Leu Gln Gln Ser Gly Ala Glu Leu Gly Lys Pro Gly Thr
1               5                   10                  15

Ser Val Lys Leu Ser Cys Lys Val Ser Gly Tyr Lys Ile Arg Ser Ser
            20                  25                  30

Tyr Met His Trp Val Asn Gln Arg Pro Gly Lys Gly Leu Glu Trp Ile
        35                  40                  45

Gly Arg Ile Asp Pro Ala Asn Gly Asn Thr Ile Tyr Gly Asp Lys Phe
50                  55                  60

Lys Ser Lys Ala Thr Leu Thr Ser Asp Thr Ser Ser Asn Thr Ala Tyr
65                  70                  75                  80

Ile Gln Leu Ser Gln Leu Lys Ser Asp Asp Thr Ala Ile Tyr Phe Cys
                85                  90                  95

Ala Ile Asp Ile Gly Thr Thr Phe Asp Tyr Trp Gly Gln Gly Val Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
```

```
            195                 200                 205
Thr Lys Val Asp Lys Val Glu Pro Lys Ser Cys Asp Lys Thr His
    210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 118
<211> LENGTH: 117
<212> TYPE: PRT
<213> ORGANISM: Artificial Sequence
<220> FEATURE:
<223> OTHER INFORMATION: Synthetic Construct

<400> SEQUENCE: 118

Glu Val Gln Leu Gln Gln Ser Gly Ala Glu Leu Gly Lys Pro Gly Thr
1               5                   10                  15

Ser Val Lys Leu Ser Cys Lys Val Ser Gly Tyr Lys Ile Arg Ser Ser
            20                  25                  30

Tyr Met His Trp Val Asn Gln Arg Pro Gly Lys Gly Leu Glu Trp Ile
        35                  40                  45

Gly Arg Ile Asp Pro Ala Asn Gly Asn Thr Ile Tyr Gly Asp Lys Phe
    50                  55                  60

Lys Ser Lys Ala Thr Leu Thr Ser Asp Thr Ser Asn Thr Ala Tyr
65                  70                  75                  80

Ile Gln Leu Ser Gln Leu Lys Ser Asp Asp Thr Ala Ile Tyr Phe Cys
                85                  90                  95

Ala Ile Asp Ile Gly Thr Thr Phe Asp Tyr Trp Gly Gln Gly Val Met
            100                 105                 110

Val Thr Val Ser Ser
115
```

```
<210> SEQ ID NO 119
<211> LENGTH: 214
<212> TYPE: PRT
<213> ORGANISM: Artificial Sequence
<220> FEATURE:
<223> OTHER INFORMATION: Synthetic Construct

<400> SEQUENCE: 119

Asp Ile Gln Met Thr Gln Ser Pro Ser Phe Leu Ser Ala Ser Val Gly
1               5                   10                  15

Asp Arg Ile Thr Ile Asn Cys Lys Thr Ser Gln Asn Ile Asn Arg Tyr
            20                  25                  30

Leu Asn Trp Phe Gln Gln Lys Leu Gly Glu Pro Pro Lys Leu Leu Ile
        35                  40                  45

Tyr Asn Ala Asn Ser Leu Gln Ala Asp Ile Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Val Ala Thr Tyr Phe Cys Leu Gln His His Phe Trp Pro Tyr
                85                  90                  95

Thr Phe Gly Ala Gly Thr Lys Leu Glu Leu Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 120
<211> LENGTH: 7
<212> TYPE: PRT
<213> ORGANISM: Artificial Sequence
<220> FEATURE:
<223> OTHER INFORMATION: Synthetic Construct

<400> SEQUENCE: 120

Asn Ala Asn Ser Leu Gln Ala
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic Construct

<400> SEQUENCE: 121

Leu Gln His His Phe Trp Pro Tyr Thr
1               5
```

```
<210> SEQ ID NO 122
<211> LENGTH: 107
<212> TYPE: PRT
<213> ORGANISM: Artificial Sequence
<220> FEATURE:
<223> OTHER INFORMATION: Synthetic Construct

<400> SEQUENCE: 122
```

Asp Ile Gln Met Thr Gln Ser Pro Ser Phe Leu Ser Ala Ser Val Gly
1               5                   10                  15

Asp Arg Ile Thr Ile Asn Cys Lys Thr Ser Gln Asn Ile Asn Arg Tyr
            20                  25                  30

Leu Asn Trp Phe Gln Gln Lys Leu Gly Glu Pro Pro Lys Leu Leu Ile
        35                  40                  45

Tyr Asn Ala Asn Ser Leu Gln Ala Asp Ile Pro Ser Arg Phe Ser Gly
50                  55                  60

Ser Gly Ser Gly Thr Asp Phe Thr Leu Thr Ile Thr Ser Leu Gln Pro
65                  70                  75                  80

Glu Asp Val Ala Thr Tyr Phe Cys Leu Gln His His Phe Trp Pro Tyr
                85                  90                  95

Thr Phe Gly Ala Gly Thr Lys Leu Glu Leu Arg
            100                 105

```
<210> SEQ ID NO 123
<211> LENGTH: 10
<212> TYPE: PRT
<213> ORGANISM: Artificial Sequence
<220> FEATURE:
<223> OTHER INFORMATION: Synthetic Construct

<400> SEQUENCE: 123
```

Phe Gly Ala Gly Thr Lys Leu Glu Leu Arg
1               5                   10

```
<210> SEQ ID NO 124
<211> LENGTH: 449
<212> TYPE: PRT
<213> ORGANISM: Artificial Sequence
<220> FEATURE:
<223> OTHER INFORMATION: Synthetic Construct

<400> SEQUENCE: 124
```

Glu Val His Leu His Gln Ser Gly Pro Glu Leu Gly Arg Pro Gly Ser
1               5                   10                  15

Ser Val Lys Ile Ser Cys Lys Ala Ser Gly Tyr Thr Phe Thr Asp Tyr
            20                  25                  30

Val Met Asn Trp Val Arg Gln Ser Pro Gly Gln Gly Leu Glu Trp Ile
        35                  40                  45

Gly Trp Ile Asn Pro Glu Asp Tyr Ser Phe Asp Ser Gly Glu Lys Phe
    50                  55                  60

Leu Glu Arg Ala Thr Leu Thr Ala Ala Thr Ser Ser Asn Thr Val Tyr
65                  70                  75                  80

Ile Gln Leu Ser Gly Leu Thr Ser Asp Asp Thr Ala Thr Tyr Phe Cys
                85                  90                  95

Val Arg Gly Gly Leu Pro Gly Asp Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 125
<211> LENGTH: 10
<212> TYPE: PRT
<213> ORGANISM: Artificial Sequence
<220> FEATURE:
<223> OTHER INFORMATION: Synthetic Construct

<400> SEQUENCE: 125

Gly Tyr Thr Phe Thr Asp Tyr Val Met Asn
1               5                   10

<210> SEQ ID NO 126
<211> LENGTH: 17
<212> TYPE: PRT
```

<213> ORGANISM: Artificial Sequence
<220> FEATURE:
<223> OTHER INFORMATION: Synthetic Construct

<400> SEQUENCE: 126

Trp Ile Asn Pro Glu Asp Tyr Ser Phe Asp Ser Gly Glu Lys Phe Leu
1               5                   10                  15
Glu

<210> SEQ ID NO 127
<211> LENGTH: 10
<212> TYPE: PRT
<213> ORGANISM: Artificial Sequence
<220> FEATURE:
<223> OTHER INFORMATION: Synthetic Construct

<400> SEQUENCE: 127

Gly Gly Leu Pro Gly Asp Trp Phe Ala Tyr
1               5                   10

<210> SEQ ID NO 128
<211> LENGTH: 119
<212> TYPE: PRT
<213> ORGANISM: Artificial Sequence
<220> FEATURE:
<223> OTHER INFORMATION: Synthetic Construct

<400> SEQUENCE: 128

Glu Val His Leu His Gln Ser Gly Pro Glu Leu Gly Arg Pro Gly Ser
1               5                   10                  15

Ser Val Lys Ile Ser Cys Lys Ala Ser Gly Tyr Thr Phe Thr Asp Tyr
            20                  25                  30

Val Met Asn Trp Val Arg Gln Ser Pro Gly Gln Gly Leu Glu Trp Ile
        35                  40                  45

Gly Trp Ile Asn Pro Glu Asp Tyr Ser Phe Asp Ser Gly Glu Lys Phe
    50                  55                  60

Leu Glu Arg Ala Thr Leu Thr Ala Ala Thr Ser Ser Asn Thr Val Tyr
65                  70                  75                  80

Ile Gln Leu Ser Gly Leu Thr Ser Asp Asp Thr Ala Thr Tyr Phe Cys
                85                  90                  95

Val Arg Gly Gly Leu Pro Gly Asp Trp Phe Ala Tyr Trp Gly Gln Gly
            100                 105                 110

Thr Leu Val Thr Val Ser Ser
        115

<210> SEQ ID NO 129
<211> LENGTH: 19
<212> TYPE: PRT
<213> ORGANISM: Artificial Sequence
<220> FEATURE:
<223> OTHER INFORMATION: Synthetic Construct

<400> SEQUENCE: 129

Met Gly Trp Ser Cys Ile Ile Leu Phe Leu Val Ala Thr Ala Thr Gly
1               5                   10                  15

Val His Ser

<210> SEQ ID NO 130
<211> LENGTH: 19
<212> TYPE: PRT
<213> ORGANISM: Artificial Sequence
<220> FEATURE:

<223> OTHER INFORMATION: Synthetic Construct

<400> SEQUENCE: 130

```
Met Glu Trp Ser Trp Val Phe Leu Phe Phe Leu Ser Val Thr Thr Gly
1               5                   10                  15

Val His Ser
```

<210> SEQ ID NO 131
<211> LENGTH: 19
<212> TYPE: PRT
<213> ORGANISM: Artificial Sequence
<220> FEATURE:
<223> OTHER INFORMATION: Synthetic Construct

<400> SEQUENCE: 131

```
Met Gly Trp Ser Cys Ile Ile Leu Phe Leu Val Ala Thr Ala Thr Gly
1               5                   10                  15

Ala His Ser
```

<210> SEQ ID NO 132
<211> LENGTH: 589
<212> TYPE: PRT
<213> ORGANISM: Artificial Sequence
<220> FEATURE:
<223> OTHER INFORMATION: Synthetic Construct

<400> SEQUENCE: 132

```
Trp Ser Tyr Asn Thr Ser Thr Glu Ala Met Thr Tyr Asp Glu Ala Ser
1               5                   10                  15

Ala Tyr Cys Gln Gln Arg Tyr Thr His Leu Val Ala Ile Gln Asn Lys
                20                  25                  30

Glu Glu Ile Glu Tyr Leu Asn Ser Ile Leu Ser Tyr Ser Pro Ser Tyr
            35                  40                  45

Tyr Trp Ile Gly Ile Arg Lys Val Asn Asn Val Trp Val Trp Val Gly
        50                  55                  60

Thr Gln Lys Pro Leu Thr Glu Glu Ala Lys Asn Trp Ala Pro Gly Glu
65                  70                  75                  80

Pro Asn Asn Arg Gln Lys Asp Glu Asp Cys Val Glu Ile Tyr Ile Lys
                85                  90                  95

Arg Glu Lys Asp Val Gly Met Trp Asn Asp Glu Arg Cys Ser Lys Lys
            100                 105                 110

Lys Leu Ala Leu Cys Tyr Thr Ala Ala Cys Thr Asn Thr Ser Cys Ser
        115                 120                 125

Gly His Gly Glu Cys Val Glu Thr Ile Asn Asn Tyr Thr Cys Lys Cys
    130                 135                 140

Asp Pro Gly Phe Ser Gly Leu Lys Cys Glu Gln Ile Val Asn Cys Thr
145                 150                 155                 160

Ala Leu Glu Ser Pro Glu His Gly Ser Leu Val Cys Ser His Pro Leu
                165                 170                 175

Gly Asn Phe Ser Tyr Asn Ser Ser Cys Ser Ile Ser Cys Asp Arg Gly
            180                 185                 190

Tyr Leu Pro Ser Ser Met Glu Thr Met Gln Cys Met Ser Ser Gly Glu
        195                 200                 205

Trp Ser Ala Pro Ile Pro Ala Cys Asn Val Val Glu Cys Asp Ala Val
    210                 215                 220

Thr Asn Pro Ala Asn Gly Phe Val Glu Cys Phe Gln Asn Pro Gly Ser
225                 230                 235                 240
```

Phe Pro Trp Asn Thr Thr Cys Thr Phe Asp Cys Glu Glu Gly Phe Glu
                245                 250                 255

Leu Met Gly Ala Gln Ser Leu Gln Cys Thr Ser Ser Gly Asn Trp Asp
            260                 265                 270

Asn Glu Lys Pro Thr Cys Lys Ala Val Thr Cys Arg Ala Val Arg Gln
        275                 280                 285

Pro Gln Asn Gly Ser Val Arg Cys Ser His Ser Pro Ala Gly Glu Phe
    290                 295                 300

Thr Phe Lys Ser Ser Cys Asn Phe Thr Cys Glu Glu Gly Phe Met Leu
305                 310                 315                 320

Gln Gly Pro Ala Gln Val Glu Cys Thr Thr Gln Gly Gln Trp Thr Gln
                325                 330                 335

Gln Ile Pro Val Cys Glu Ala Phe Gln Cys Thr Ala Leu Ser Asn Pro
            340                 345                 350

Glu Arg Gly Tyr Met Asn Cys Leu Pro Ser Ala Ser Gly Ser Phe Arg
        355                 360                 365

Tyr Gly Ser Ser Cys Glu Phe Ser Cys Glu Gln Gly Phe Val Leu Lys
    370                 375                 380

Gly Ser Lys Arg Leu Gln Cys Gly Pro Thr Gly Glu Trp Asp Asn Glu
385                 390                 395                 400

Lys Pro Thr Cys Glu Ala Val Arg Cys Asp Ala Val His Gln Pro Pro
                405                 410                 415

Lys Gly Leu Val Arg Cys Ala His Ser Pro Ile Gly Glu Phe Thr Tyr
            420                 425                 430

Lys Ser Ser Cys Ala Phe Ser Cys Glu Glu Gly Phe Glu Leu His Gly
        435                 440                 445

Ser Thr Gln Leu Glu Cys Thr Ser Gln Gly Gln Trp Thr Glu Glu Val
    450                 455                 460

Pro Ser Cys Gln Val Val Lys Cys Ser Ser Leu Ala Val Pro Gly Lys
465                 470                 475                 480

Ile Asn Met Ser Cys Ser Gly Glu Pro Val Phe Gly Thr Val Cys Lys
                485                 490                 495

Phe Ala Cys Pro Glu Gly Trp Thr Leu Asn Gly Ser Ala Ala Arg Thr
            500                 505                 510

Cys Gly Ala Thr Gly His Trp Ser Gly Leu Leu Pro Thr Cys Glu Ala
        515                 520                 525

Pro Thr Glu Ser Asn Ile Pro Leu Val Ala Gly Leu Ser Ala Ala Gly
    530                 535                 540

Leu Ser Leu Leu Thr Leu Ala Pro Phe Leu Leu Trp Leu Arg Lys Cys
545                 550                 555                 560

Leu Arg Lys Ala Lys Lys Phe Val Pro Ala Ser Ser Cys Gln Ser Leu
                565                 570                 575

Glu Ser Asp Gly Ser Tyr Gln Lys Pro Ser Tyr Ile Leu
            580                 585

<210> SEQ ID NO 133
<211> LENGTH: 535
<212> TYPE: PRT
<213> ORGANISM: Artificial Sequence
<220> FEATURE:
<223> OTHER INFORMATION: Synthetic Construct

<400> SEQUENCE: 133

Trp Ser Tyr Asn Thr Ser Thr Glu Ala Met Thr Tyr Asp Glu Ala Ser
1               5                   10                  15

-continued

```
Ala Tyr Cys Gln Gln Arg Tyr Thr His Leu Val Ala Ile Gln Asn Lys
             20                  25                  30

Glu Glu Ile Glu Tyr Leu Asn Ser Ile Leu Ser Tyr Ser Pro Ser Tyr
         35                  40                  45

Tyr Trp Ile Gly Ile Arg Lys Val Asn Asn Val Trp Val Trp Val Gly
 50                  55                  60

Thr Gln Lys Pro Leu Thr Glu Glu Ala Lys Asn Trp Ala Pro Gly Glu
65                  70                  75                  80

Pro Asn Asn Arg Gln Lys Asp Glu Asp Cys Val Glu Ile Tyr Ile Lys
                 85                  90                  95

Arg Glu Lys Asp Val Gly Met Trp Asn Asp Glu Arg Cys Ser Lys Lys
                100                 105                 110

Lys Leu Ala Leu Cys Tyr Thr Ala Ala Cys Thr Asn Thr Ser Cys Ser
            115                 120                 125

Gly His Gly Glu Cys Val Glu Thr Ile Asn Asn Tyr Thr Cys Lys Cys
        130                 135                 140

Asp Pro Gly Phe Ser Gly Leu Lys Cys Glu Gln Ile Val Asn Cys Thr
145                 150                 155                 160

Ala Leu Glu Ser Pro Glu His Gly Ser Leu Val Cys Ser His Pro Leu
                165                 170                 175

Gly Asn Phe Ser Tyr Asn Ser Ser Cys Ser Ile Ser Cys Asp Arg Gly
                180                 185                 190

Tyr Leu Pro Ser Ser Met Glu Thr Met Gln Cys Met Ser Ser Gly Glu
            195                 200                 205

Trp Ser Ala Pro Ile Pro Ala Cys Asn Val Val Glu Cys Asp Ala Val
    210                 215                 220

Thr Asn Pro Ala Asn Gly Phe Val Glu Cys Phe Gln Asn Pro Gly Ser
225                 230                 235                 240

Phe Pro Trp Asn Thr Thr Cys Thr Phe Asp Cys Glu Glu Gly Phe Glu
                245                 250                 255

Leu Met Gly Ala Gln Ser Leu Gln Cys Thr Ser Ser Gly Asn Trp Asp
            260                 265                 270

Asn Glu Lys Pro Thr Cys Lys Ala Val Thr Cys Arg Ala Val Arg Gln
        275                 280                 285

Pro Gln Asn Gly Ser Val Arg Cys Ser His Ser Pro Ala Gly Glu Phe
    290                 295                 300

Thr Phe Lys Ser Ser Cys Asn Phe Thr Cys Glu Glu Gly Phe Met Leu
305                 310                 315                 320

Gln Gly Pro Ala Gln Val Glu Cys Thr Thr Gln Gly Gln Trp Thr Gln
                325                 330                 335

Gln Ile Pro Val Cys Glu Ala Phe Gln Cys Thr Ala Leu Ser Asn Pro
            340                 345                 350

Glu Arg Gly Tyr Met Asn Cys Leu Pro Ser Ala Ser Gly Ser Phe Arg
        355                 360                 365

Tyr Gly Ser Ser Cys Glu Phe Ser Cys Glu Gln Gly Phe Val Leu Lys
    370                 375                 380

Gly Ser Lys Arg Leu Gln Cys Gly Pro Thr Gly Glu Trp Asp Asn Glu
385                 390                 395                 400

Lys Pro Thr Cys Glu Ala Val Arg Cys Asp Ala Val His Gln Pro Pro
                405                 410                 415

Lys Gly Leu Val Arg Cys Ala His Ser Pro Ile Gly Glu Phe Thr Tyr
            420                 425                 430

Lys Ser Ser Cys Ala Phe Ser Cys Glu Glu Gly Phe Glu Leu His Gly
```

```
                     435                 440                 445
Ser Thr Gln Leu Glu Cys Thr Ser Gln Gly Gln Trp Thr Glu Glu Val
    450                 455                 460

Pro Ser Cys Gln Val Val Lys Cys Ser Ser Leu Ala Val Pro Gly Lys
465                 470                 475                 480

Ile Asn Met Ser Cys Ser Gly Glu Pro Val Phe Gly Thr Val Cys Lys
                485                 490                 495

Phe Ala Cys Pro Glu Gly Trp Thr Leu Asn Gly Ser Ala Ala Arg Thr
            500                 505                 510

Cys Gly Ala Thr Gly His Trp Ser Gly Leu Leu Pro Thr Cys Glu Ala
        515                 520                 525

Pro Thr Glu Ser Asn Ile Pro
530                 535
```

<210> SEQ ID NO 134
<211> LENGTH: 591
<212> TYPE: PRT
<213> ORGANISM: Artificial Sequence
<220> FEATURE:
<223> OTHER INFORMATION: Synthetic Construct

<400> SEQUENCE: 134

```
Trp Tyr Tyr Asn Ala Ser Ser Glu Leu Met Thr Tyr Asp Glu Ala Ser
1               5                   10                  15

Ala Tyr Cys Gln Arg Asp Tyr Thr His Leu Val Ala Ile Gln Asn Lys
            20                  25                  30

Glu Glu Ile Asn Tyr Leu Asn Ser Asn Leu Lys His Ser Pro Ser Tyr
        35                  40                  45

Tyr Trp Ile Gly Ile Arg Lys Val Asn Asn Val Trp Ile Trp Val Gly
    50                  55                  60

Thr Gly Lys Pro Leu Thr Glu Glu Ala Gln Asn Trp Ala Pro Gly Glu
65                  70                  75                  80

Pro Asn Asn Lys Gln Arg Asn Glu Asp Cys Val Glu Ile Tyr Ile Gln
                85                  90                  95

Arg Thr Lys Asp Ser Gly Met Trp Asn Asp Glu Arg Cys Asn Lys Lys
            100                 105                 110

Lys Leu Ala Leu Cys Tyr Thr Ala Ser Cys Thr Asn Ala Ser Cys Ser
        115                 120                 125

Gly His Gly Glu Cys Ile Glu Thr Ile Asn Ser Tyr Thr Cys Lys Cys
    130                 135                 140

His Pro Gly Phe Leu Gly Pro Asn Cys Glu Gln Ala Val Thr Cys Lys
145                 150                 155                 160

Pro Gln Glu His Pro Asp Tyr Gly Ser Leu Asn Cys Ser His Pro Phe
                165                 170                 175

Gly Pro Phe Ser Tyr Asn Ser Ser Cys Ser Phe Gly Cys Lys Arg Gly
            180                 185                 190

Tyr Leu Pro Ser Ser Met Glu Thr Thr Val Arg Cys Thr Ser Ser Gly
        195                 200                 205

Glu Trp Ser Ala Pro Ala Pro Ala Cys His Val Val Glu Cys Glu Ala
    210                 215                 220

Leu Thr His Pro Ala His Gly Ile Arg Lys Cys Ser Ser Asn Pro Gly
225                 230                 235                 240

Ser Tyr Pro Trp Asn Thr Thr Cys Thr Phe Asp Cys Val Glu Gly Tyr
                245                 250                 255

Arg Arg Val Gly Ala Gln Asn Leu Gln Cys Thr Ser Ser Gly Ile Trp
```

-continued

```
                260                 265                 270
Asp Asn Glu Thr Pro Ser Cys Lys Ala Val Thr Cys Asp Ala Ile Pro
            275                 280                 285

Gln Pro Gln Asn Gly Phe Val Ser Cys Ser His Ser Thr Ala Gly Glu
        290                 295                 300

Leu Ala Phe Lys Ser Ser Cys Asn Phe Thr Cys Glu Gln Ser Phe Thr
305                 310                 315                 320

Leu Gln Gly Pro Ala Gln Val Glu Cys Ser Ala Gln Gly Gln Trp Thr
                325                 330                 335

Pro Gln Ile Pro Val Cys Lys Ala Val Gln Cys Glu Ala Leu Ser Ala
            340                 345                 350

Pro Gln Gln Gly Asn Met Lys Cys Leu Pro Ser Ala Ser Gly Pro Phe
        355                 360                 365

Gln Asn Gly Ser Ser Cys Glu Phe Ser Cys Glu Glu Gly Phe Glu Leu
    370                 375                 380

Lys Gly Ser Arg Arg Leu Gln Cys Gly Pro Arg Gly Glu Trp Asp Ser
385                 390                 395                 400

Lys Lys Pro Thr Cys Ser Ala Val Lys Cys Asp Asp Val Pro Arg Pro
                405                 410                 415

Gln Asn Gly Val Met Glu Cys Ala His Ala Thr Thr Gly Glu Phe Thr
            420                 425                 430

Tyr Lys Ser Ser Cys Ala Phe Gln Cys Asn Glu Gly Phe Ser Leu His
        435                 440                 445

Gly Ser Ala Gln Leu Glu Cys Thr Ser Gln Gly Lys Trp Thr Gln Glu
    450                 455                 460

Val Pro Ser Cys Gln Val Val Gln Cys Pro Ser Leu Asp Val Pro Gly
465                 470                 475                 480

Lys Met Asn Met Ser Cys Ser Gly Thr Ala Val Phe Gly Thr Val Cys
                485                 490                 495

Glu Phe Thr Cys Pro Asp Asp Trp Thr Leu Asn Gly Ser Ala Val Leu
            500                 505                 510

Thr Cys Gly Ala Thr Gly Arg Trp Ser Gly Met Pro Pro Thr Cys Glu
        515                 520                 525

Ala Pro Val Ser Pro Thr Arg Pro Leu Val Val Ala Leu Ser Ala Ala
    530                 535                 540

Gly Thr Ser Leu Leu Thr Ser Ser Leu Leu Tyr Leu Leu Met Arg
545                 550                 555                 560

Tyr Phe Arg Lys Lys Ala Lys Lys Phe Val Pro Ala Ser Ser Cys Gln
                565                 570                 575

Ser Leu Gln Ser Phe Glu Asn Tyr His Val Pro Ser Tyr Asn Val
            580                 585                 590

<210> SEQ ID NO 135
<211> LENGTH: 536
<212> TYPE: PRT
<213> ORGANISM: Artificial Sequence
<220> FEATURE:
<223> OTHER INFORMATION: Synthetic Construct

<400> SEQUENCE: 135

Trp Tyr Tyr Asn Ala Ser Ser Glu Leu Met Thr Tyr Asp Glu Ala Ser
1               5                   10                  15

Ala Tyr Cys Gln Arg Asp Tyr Thr His Leu Val Ala Ile Gln Asn Lys
            20                  25                  30

Glu Glu Ile Asn Tyr Leu Asn Ser Asn Leu Lys His Ser Pro Ser Tyr
```

```
                35                  40                  45
Tyr Trp Ile Gly Ile Arg Lys Val Asn Asn Val Trp Ile Trp Val Gly
 50                  55                  60
Thr Gly Lys Pro Leu Thr Glu Glu Ala Gln Asn Trp Ala Pro Gly Glu
 65                  70                  75                  80
Pro Asn Asn Lys Gln Arg Asn Glu Asp Cys Val Glu Ile Tyr Ile Gln
                 85                  90                  95
Arg Thr Lys Asp Ser Gly Met Trp Asn Asp Glu Arg Cys Asn Lys Lys
                100                 105                 110
Lys Leu Ala Leu Cys Tyr Thr Ala Ser Cys Thr Asn Ala Ser Cys Ser
            115                 120                 125
Gly His Gly Glu Cys Ile Glu Thr Ile Asn Ser Tyr Thr Cys Lys Cys
            130                 135                 140
His Pro Gly Phe Leu Gly Pro Asn Cys Glu Gln Ala Val Thr Cys Lys
145                 150                 155                 160
Pro Gln Glu His Pro Asp Tyr Gly Ser Leu Asn Cys Ser His Pro Phe
                165                 170                 175
Gly Pro Phe Ser Tyr Asn Ser Ser Cys Ser Phe Gly Cys Lys Arg Gly
                180                 185                 190
Tyr Leu Pro Ser Ser Met Glu Thr Thr Val Arg Cys Thr Ser Ser Gly
            195                 200                 205
Glu Trp Ser Ala Pro Ala Pro Ala Cys His Val Val Glu Cys Glu Ala
            210                 215                 220
Leu Thr His Pro Ala His Gly Ile Arg Lys Cys Ser Ser Asn Pro Gly
225                 230                 235                 240
Ser Tyr Pro Trp Asn Thr Thr Cys Thr Phe Asp Cys Val Glu Gly Tyr
                245                 250                 255
Arg Arg Val Gly Ala Gln Asn Leu Gln Cys Thr Ser Ser Gly Ile Trp
            260                 265                 270
Asp Asn Glu Thr Pro Ser Cys Lys Ala Val Thr Cys Asp Ala Ile Pro
            275                 280                 285
Gln Pro Gln Asn Gly Phe Val Ser Cys Ser His Ser Thr Ala Gly Glu
            290                 295                 300
Leu Ala Phe Lys Ser Ser Cys Asn Phe Thr Cys Glu Gln Ser Phe Thr
305                 310                 315                 320
Leu Gln Gly Pro Ala Gln Val Glu Cys Ser Ala Gln Gly Gln Trp Thr
                325                 330                 335
Pro Gln Ile Pro Val Cys Lys Ala Val Gln Cys Glu Ala Leu Ser Ala
            340                 345                 350
Pro Gln Gln Gly Asn Met Lys Cys Leu Pro Ser Ala Ser Gly Pro Phe
            355                 360                 365
Gln Asn Gly Ser Ser Cys Glu Phe Ser Cys Glu Gly Phe Glu Leu
            370                 375                 380
Lys Gly Ser Arg Arg Leu Gln Cys Gly Pro Arg Gly Glu Trp Asp Ser
385                 390                 395                 400
Lys Lys Pro Thr Cys Ser Ala Val Lys Cys Asp Asp Val Pro Arg Pro
                405                 410                 415
Gln Asn Gly Val Met Glu Cys Ala His Ala Thr Thr Gly Glu Phe Thr
            420                 425                 430
Tyr Lys Ser Ser Cys Ala Phe Gln Cys Asn Glu Gly Phe Ser Leu His
            435                 440                 445
Gly Ser Ala Gln Leu Glu Cys Thr Ser Gln Gly Lys Trp Thr Gln Glu
450                 455                 460
```

```
Val Pro Ser Cys Gln Val Gln Cys Pro Ser Leu Asp Val Pro Gly
465                 470                 475                 480

Lys Met Asn Met Ser Cys Ser Gly Thr Ala Val Phe Gly Thr Val Cys
                485                 490                 495

Glu Phe Thr Cys Pro Asp Asp Trp Thr Leu Asn Gly Ser Ala Val Leu
                500                 505                 510

Thr Cys Gly Ala Thr Gly Arg Trp Ser Gly Met Pro Pro Thr Cys Glu
            515                 520                 525

Ala Pro Val Ser Pro Thr Arg Pro
            530                 535

<210> SEQ ID NO 136
<211> LENGTH: 351
<212> TYPE: DNA
<213> ORGANISM: Artificial Sequence
<220> FEATURE:
<223> OTHER INFORMATION: Synthetic Construct

<400> SEQUENCE: 136
gaagtgcagc ttgtggaatc cggggcggc ttggtccaac cgggtggcag cctccgtctg      60
tcgtgcgcgg cttcgggcta tgccatccgt tctgcctaca tgcactgggt tcgccaggcg    120
cctgggaagg gcctggaatg ggtggccagg attgatcctg caaacggaaa tactatatat    180
gtggactccg tgaccggccg ctttacaatc agcgccgaca cgctaagaa ttccgcctac     240 ctgcaaatga atagcctgcg ggcagaggat accgcggtgt actattgtgc catggattta    300
tattccacgt ctgaatattg gggccaagga accctggtaa cggtgtcgtc g             351

<210> SEQ ID NO 137
<211> LENGTH: 321
<212> TYPE: DNA
<213> ORGANISM: Artificial Sequence
<220> FEATURE:
<223> OTHER INFORMATION: Synthetic Construct

<400> SEQUENCE: 137
gatattcaga tgacgcagtc cccatcttcc ctttcagcat ctgtgggtga ccgggttaca     60
atcacttgta aacatcccca gaacattgag cgttatttaa attggtatca gcagaaaccg    120
ggtaaagccc cgaaactatt gatttatgcc gcgtcctcgc tgcaatccgg cgtgccgagt    180
cgttttagcg gctccgggag cggcaccgat tttactctta ccatttcgag tctgcagccg    240
gaagactttg ccacttattt ctgtctccag gataacgcct ggccattaac cttcggtcag    300
ggtaccaaag ttgaaattaa a                                              321

<210> SEQ ID NO 138
<211> LENGTH: 1341
<212> TYPE: DNA
<213> ORGANISM: Artificial Sequence
<220> FEATURE:
<223> OTHER INFORMATION: Synthetic Construct

<400> SEQUENCE: 138
gaagtgcagc ttgtggaatc cggggcggc ttggtccaac cgggtggcag cctccgtctg      60
tcgtgcgcgg cttcgggcta tgccatccgt tctgcctaca tgcactgggt tcgccaggcg    120
cctgggaagg gcctggaatg ggtggccagg attgatcctg caaacggaaa tactatatat    180
gtggactccg tgaccggccg ctttacaatc agcgccgaca cgctaagaa ttccgcctac     240 ctgcaaatga atagcctgcg ggcagaggat accgcggtgt actattgtgc catggattta    300
```

```
tattccacgt ctgaatattg gggccaagga accctggtaa cggtgtcgtc ggcgtcgacc      360
aagggcccat cggtcttccc cctggcaccc tcctccaaga gcacctctgg ggcacagcg       420 gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga agttgagcc caaatcttgt       660 gacaaaactc acacatgccc accgtgccca gcacctgaag ccgctggggc accgtcagtc      720
ttcctcttcc cccaaaacc caaggacacc ctcatgatct cccggacccc tgaggtcaca       780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc ccatcgaga aaaccatctc caaagccaaa      1020
gggcagcccc gagaaccaca ggtgtacacc ctgcccccat cccgggagga tgaccaag      1080 aaccaggtca gcctgacctg cctggtcaaa ggcttctatc ccagcgacat cgccgtggag     1140
tgggagagca atgggcagcc ggagaacaac tacaagacca cgcctcccgt gctggactcc    1200
gacggctcct tcttcctcta tagcaagctc accgtggaca agagcaggtg gcagcagggg    1260
aacgtcttct catgctccgt gatgcatgag gctctgcaca accactacac gcagaagagc    1320
ctctccctgt ccccgggaaa a                                              1341

<210> SEQ ID NO 139
<211> LENGTH: 642
<212> TYPE: DNA
<213> ORGANISM: Artificial Sequence
<220> FEATURE:
<223> OTHER INFORMATION: Synthetic Construct

<400> SEQUENCE: 139
gatattcaga tgacgcagtc cccatcttcc ctttcagcat ctgtgggtga ccgggttaca       60
atcacttgta aacatcccca gaacattgag cgttatttaa attggtatca gcagaaaccg      120
ggtaaagccc cgaaactatt gatttatgcc gcgtcctcgc tgcaatccgg cgtgccgagt      180
cgttttagcg gctccgggag cggcaccgat tttactctta ccatttcgag tctgcagccg      240
gaagactttg ccacttattt ctgtctccag gataacgcct ggccattaac cttcggtcag      300
ggtaccaaag ttgaaattaa acgtacggtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                        642

<210> SEQ ID NO 140
<211> LENGTH: 57
<212> TYPE: DNA
<213> ORGANISM: Artificial Sequence
<220> FEATURE:
<223> OTHER INFORMATION: Synthetic Construct

<400> SEQUENCE: 140
```
atggaatgga gctgggtctt tctcttcttc ctgtcagtaa ctacaggtgt ccactcc    57

<210> SEQ ID NO 141
<211> LENGTH: 57
<212> TYPE: DNA
<213> ORGANISM: Artificial Sequence
<220> FEATURE:
<223> OTHER INFORMATION: Synthetic Construct

<400> SEQUENCE: 141
atgggatgga gctgtatcat cctcttcttg gtggcaacag ctacaggcgt gcactcc    57

<210> SEQ ID NO 142
<211> LENGTH: 990
<212> TYPE: DNA
<213> ORGANISM: Artificial Sequence
<220> FEATURE:
<223> OTHER INFORMATION: Synthetic Construct

<400> SEQUENCE: 142
gcgtcgacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagaa agttgagccc   300
aaatcttgtg acaaaactca cacatgccca ccgtgcccag cacctgaagc cgctggggca   360
ccgtcagtct tcctcttccc cccaaaaccc aaggacaccc tcatgatctc ccggaccccT   420
gaggtcacat gcgtggtggt ggacgtgagc cacgaagacc ctgaggtcaa gttcaactgg   480
tacgtggacg gcgtggaggt gcataatgcc aagacaaagc cgcggaggga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctat agcaagctca ccgtggacaa gagcaggtgg   900
cagcagggga acgtcttctc atgctccgtg atgcatgagg ctctgcacaa ccactacacg   960
cagaagagcc tctccctgtc cccgggaaaa                                   990

<210> SEQ ID NO 143
<211> LENGTH: 321
<212> TYPE: DNA
<213> ORGANISM: Artificial Sequence
<220> FEATURE:
<223> OTHER INFORMATION: Synthetic Construct

<400> SEQUENCE: 143
cgtacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca gggggagagtg t                                           321

<210> SEQ ID NO 144
<211> LENGTH: 351
<212> TYPE: DNA
<213> ORGANISM: Artificial Sequence
<220> FEATURE:
<223> OTHER INFORMATION: Synthetic Construct

<400> SEQUENCE: 144

```
gaagtgcagc ttgtggaatc cggggggcggc ttggtccaac cgggtggcag cctccgtctg    60
tcgtgcgcgg cttcgggcta taacatccgt tctagctaca tgcactgggt tcgccaggcg   120
cctgggaagg gcctggaatg ggtggccagg attgatcctg caaacggaaa tactatatat   180
gctgagaagt tcaaaatccg ctttacaatc agcgccgaca acgctaagaa ttccgcctac   240
ctgcaaatga atagcctgcg ggcagaggat accgcggtgt actattgtgc catggattta   300
tattccacgt ctgaatattg gggccaagga accctggtaa cggtgtcgtc g            351
```

<210> SEQ ID NO 145
<211> LENGTH: 321
<212> TYPE: DNA
<213> ORGANISM: Artificial Sequence
<220> FEATURE:
<223> OTHER INFORMATION: Synthetic Construct

<400> SEQUENCE: 145

```
gatattcaga tgacgcagtc cccatcttcc ctttcagcat ctgtgggtga ccgggttaca    60
atcacttgta aaacatccca gaacattaac cgttatttaa attggtatca gcagaaaccg   120
ggtaaagccc cgaaactatt gatttataac gcgaactcgc tgcaaactgg cgtgccgagt   180
cgttttagcg gctccgggag cggcaccgat tttactctta ccatttcgag tctgcagccg   240
gaagactttg ccacttattt ctgtctccag gataactcct ggccattaac cttcggtcag   300
ggtaccaaag ttgaaattaa a                                             321
```

<210> SEQ ID NO 146
<211> LENGTH: 351
<212> TYPE: DNA
<213> ORGANISM: Artificial Sequence
<220> FEATURE:
<223> OTHER INFORMATION: Synthetic Construct

<400> SEQUENCE: 146

```
gaagtgcagc ttgtggaatc cggggggcggc ttggtccaac cgggtggcag cctccgtctg    60
tcgtgcgcgg cttcgggcta taacatccgt tctagctaca tgcactgggt tcgccaggcg   120
cctgggaagg gcctggaatg ggtggccagg attgatcctg caaacggaaa tactatatat   180
gtggactccg tgaaaggccg ctttacaatc agcgccgaca acgctaagaa ttccgcctac   240
ctgcaaatga atagcctgcg ggcagaggat accgcggtgt actattgtgc catggattta   300
tattccacgt ctgaatattg gggccaagga accctggtaa cggtgtcgtc g            351
```

<210> SEQ ID NO 147
<211> LENGTH: 321
<212> TYPE: DNA
<213> ORGANISM: Artificial Sequence
<220> FEATURE:
<223> OTHER INFORMATION: Synthetic Construct

<400> SEQUENCE: 147

```
gatattcaga tgacgcagtc cccatcttcc ctttcagcat ctgtgggtga ccgggttaca    60
```

```
atcacttgta aaacatccca gaacattaac cgttatttaa attggtatca gcagaaaccg    120
ggtaaagccc cgaaactatt gatttatgcc gcgtcctcgc tgcaatccgg cgtgccgagt    180
cgttttagcg gctccgggag cggcaccgat tttactctta ccatttcgag tctgcagccg    240
gaagactttg ccacttattt ctgtctccag gataactcct ggccattaac cttcggtcag    300
ggtaccaaag ttgaaattaa a                                              321
```

<210> SEQ ID NO 148
<211> LENGTH: 351
<212> TYPE: DNA
<213> ORGANISM: Artificial Sequence
<220> FEATURE:
<223> OTHER INFORMATION: Synthetic Construct

<400> SEQUENCE: 148

```
gaagtccagc tgcagcagtc tggggctgag tttgggaaac ctgggacctc agtcaagttg     60
tcttgcaagg tttctgggta taacattagg agttcataca tgcactgggt gaatcagagg    120
cctggaaagg gcctggaatg gataggaagg attgatcctg caaacggaaa tactatatat    180
gctgagaagt tcaaaatcaa ggccattctg actgcagatt catcgtccaa cacagcctac    240
atgcaactca gccaactgaa atctgacgac acagcaatct atttttgtgc tatggaccct    300
tacagtacct ctgaatactg gggccaagga gtcatggtca cagtctcctc a             351
```

<210> SEQ ID NO 149
<211> LENGTH: 321
<212> TYPE: DNA
<213> ORGANISM: Artificial Sequence
<220> FEATURE:
<223> OTHER INFORMATION: Synthetic Construct

<400> SEQUENCE: 149

```
gacatccaga tgacccagtc tccttcattc ctgtctgcat ctgtgggaga cagagtcact     60
atcaactgca aaacgagtca gaatattaac aggtacttaa actggtacca gcaaaagctt    120
ggagaagctc ccaaactcct gatatataat gcaaacagtt tgcaaacggg catcccatca    180
cggttcagtg ccagtggatc cggtactgat ttcacactca ccatcaacag cctgcagcct    240
gaagatgttg ccacatattt ttgcttgcag gataatagtt ggccgctcac gttcggttct    300
gggaccaagc tggagatcaa a                                              321
```

<210> SEQ ID NO 150
<211> LENGTH: 351
<212> TYPE: DNA
<213> ORGANISM: Artificial Sequence
<220> FEATURE:
<223> OTHER INFORMATION: Synthetic Construct

<400> SEQUENCE: 150

```
gaagtgcagc ttgtggaatc cggggggcggc ttggtccaac cgggtggcag cctccgtctg     60
tcgtgcgcgg cttcgggcta tgccatccgt tctgcctaca tgcactgggt tcgccaggcg    120
cctgggaagg gcctggaatg ggtggccagg attgatcctg caaacggaaa tactatatat    180
gtggactccg tgaaagagcg ctttacaatc agcgccgaca cgctaagaa ttccgcctac     240 ctgcaaatga atagcctgcg ggcagaggat accgcggtgt actattgtgc catggattta    300
tattccacgt ctgaatattg gggccaagga accctggtaa cggtgtcgtc g             351
```

<210> SEQ ID NO 151
<211> LENGTH: 351

-continued

<212> TYPE: DNA
<213> ORGANISM: Artificial Sequence
<220> FEATURE:
<223> OTHER INFORMATION: Synthetic Construct

<400> SEQUENCE: 151

| gaagtgcagc ttgtggaatc cgggggcggc ttggtccaac cgggtggcag cctccgtctg | 60 |
| tcgtgcgcgg cttcgggcta tgccatccgt tctgcctaca tgcactgggt tcgccaggcg | 120 |
| cctgggaagg gcctggaatg ggtggccagg attgatcctg caaacggaaa tactatatat | 180 |
| gtggagtccg tgagggccg ctttacaatc agcgccgaca acgctaagaa ttccgcctac | 240 |
| ctgcaaatga atagcctgcg ggcagaggat accgcggtgt actattgtgc catggattta | 300 |
| tattccacgt ctgaatattg gggccaagga accctggtaa cggtgtcgtc g | 351 |

<210> SEQ ID NO 152
<211> LENGTH: 351
<212> TYPE: DNA
<213> ORGANISM: Artificial Sequence
<220> FEATURE:
<223> OTHER INFORMATION: Synthetic Construct

<400> SEQUENCE: 152

| gaagtgcagc ttgtggaatc cgggggcggc ttggtccaac cgggtggcag cctccgtctg | 60 |
| tcgtgcgcgg cttcgggcta tgccatccgt tctgcctaca tgcactgggt tcgccaggcg | 120 |
| cctgggaagg gcctggaatg ggtggccagg attgatcctg caaacggaaa tactatatat | 180 |
| gtggactccg tgagggccg ctttacaatc agcgccgaca acgctaagaa ttccgcctac | 240 |
| ctgcaaatga atagcctgcg ggcagaggat accgcggtgt actattgtgc catggattta | 300 |
| tattccacgt ctgaatattg gggccaagga accctggtaa cggtgtcgtc g | 351 |

<210> SEQ ID NO 153
<211> LENGTH: 372
<212> TYPE: DNA
<213> ORGANISM: Artificial Sequence
<220> FEATURE:
<223> OTHER INFORMATION: Synthetic Construct

<400> SEQUENCE: 153

| gaggtacagt tggtggaatc tggcggcggc ctggtccagc cgggcgggtc tttgcgcctg | 60 |
| agttgtgcag cgagtgggtt tagcctgacg ggctactaca tgcaatgggt ccgtcaggcg | 120 |
| ccgggcaaag gtctggaatg gatgggtttt atacggagta gtggaagcac agagtataat | 180 |
| tcagagttca atcccgtttt taccatctct cgcgataacg cgaaaaacag cgtgtatctg | 240 |
| cagatgaata gcctgcgcgc cgaagatacc gccgtgtact actgcgcgcg ttgcccgtat | 300 |
| aaatatagtt catttgtata tgtgggtgtc atggatgcgt ggggccaggg tacactggtt | 360 |
| accgtgagct cg | 372 |

<210> SEQ ID NO 154
<211> LENGTH: 321
<212> TYPE: DNA
<213> ORGANISM: Artificial Sequence
<220> FEATURE:
<223> OTHER INFORMATION: Synthetic Construct

<400> SEQUENCE: 154

| gatatccaaa tgacgcaatc gcctagcagc ttatccgcgt cagttggcga tcgcgtgacc | 60 |
| atcacttgca aagcgtcgca aaccgtcgga atcaacgtgg attggtacca acagaaaccg | 120 |

| | |
|---|---|
| ggcaaggcgc cgaaactgct gatctatgga gccagcaatc gccacacagg agtgccgtcc | 180 |
| cgttttagcg gcagcgggag cggtacggat tttaccctga cgatttcttc actccaaccc | 240 |
| gaagactttg caacctattg ctgcttgcaa tatggttcaa tcccgcatac tttcggccag | 300 |
| ggtacaaaag tggaaattaa a | 321 |

<210> SEQ ID NO 155
<211> LENGTH: 372
<212> TYPE: DNA
<213> ORGANISM: Artificial Sequence
<220> FEATURE:
<223> OTHER INFORMATION: Synthetic Construct

<400> SEQUENCE: 155

| | |
|---|---|
| caggtgcagc tgaaggagac aggacctggc ctggtgcaac caacacagac cctgtccatc | 60 |
| acatgtactg tttctgggtt ctcattaacc ggctattata tgcagtgggt tcgccagact | 120 |
| ccaggaaagg ggctagaatg gatgggattt atacggagta gtggaagcac agagtataat | 180 |
| tcagagttca atcccgact tagcatcagc aggacacct ccaagaacca gttttctta | 240 |
| aaaatgaaca gtctgaaaac agaagataca ggcgtgtatt actgtgccag atgcccttat | 300 |
| aagtatagca gctttgtcta cgtaggggtt atggatgcct ggggtcaagg agctccagtc | 360 |
| actgtctcct ca | 372 |

<210> SEQ ID NO 156
<211> LENGTH: 321
<212> TYPE: DNA
<213> ORGANISM: Artificial Sequence
<220> FEATURE:
<223> OTHER INFORMATION: Synthetic Construct

<400> SEQUENCE: 156

| | |
|---|---|
| gaaattgtga tgacccagtc tcccacatcc atgtccacat caataggaga gagggtcacc | 60 |
| ctgaactgca aggccagtca gactgtgggt attaatgttg actggtacca acagacacca | 120 |
| gggcagcctc ctaaactact gatatatggg gcatccaacc gacacactgg ggtccctgat | 180 |
| cgcttcacag gcagtggatt tgggagagat ttcactctca ccatcagcaa cgtggaggct | 240 |
| gaagacctag ctgtttattg ctgtctgcaa tatggctcca ttcctcacac gtttggacct | 300 |
| gggaccaagc tggagctgaa a | 321 |

<210> SEQ ID NO 157
<211> LENGTH: 345
<212> TYPE: DNA
<213> ORGANISM: Artificial Sequence
<220> FEATURE:
<223> OTHER INFORMATION: Synthetic Construct

<400> SEQUENCE: 157

| | |
|---|---|
| gaagtgcagt tagtggaaag tggcggtggc ctggtgcaac cgggaggatc cttacgtttta | 60 |
| agctgcgccg tgtccgggtt tagtatcagc acctataatg tacactggct gcgtcaagcc | 120 |
| ccgggcaaag ggttagaatg gatgggaatg atgtggagtg gtggaagccc agattataat | 180 |
| tcagctctca aatcccgatt cactattagt cgcgataccg caaaaaactc cgtgtaccttt | 240 |
| cagatgaact ctcttcgcgc agaggatacg gcggtttact actgtgctcg ctggggcggc | 300 |
| gggtttgatt actggggcca gggaacgctg gtaacggttt ccagt | 345 |

<210> SEQ ID NO 158
<211> LENGTH: 321

```
<212> TYPE: DNA
<213> ORGANISM: Artificial Sequence
<220> FEATURE:
<223> OTHER INFORMATION: Synthetic Construct

<400> SEQUENCE: 158
gacattcaac tgacccagag cccgtccagc ttatctgcga gtgttgggga ccgggtcacg    60
attacctgcc gggctagtca cagcattggg acgaacttgc attggtacca gcagaaacct   120
ggcaaagctc cgaaactgct gatttatttt acatcccaaa gcatcagcgg tgtcccctcc   180
cgattttccg gtccggatc cggtaccgat tttactttaa cgatcagcag tctgcagcca    240
gaggatttcg ccacctacta ttgtcagcaa actcagtctt ggcccctgac ctttggccaa   300
gggaccaagg tagaaatcaa g                                             321

<210> SEQ ID NO 159
<211> LENGTH: 345
<212> TYPE: DNA
<213> ORGANISM: Artificial Sequence
<220> FEATURE:
<223> OTHER INFORMATION: Synthetic Construct

<400> SEQUENCE: 159
caggtgcagc tgaaggagtc aggacctggc ctggtgcagc cctcagagac cctgtccctc    60
acctgcactg tctctgggtt ctcaataagc acctataacg tacactggct tcgacagcct   120
ccaggaaaag gtctggagtg gatgggaatg atgtggagtg gtggaagccc agattataat   180
tcagctctca atcccgact gagcatcagc agggacacct ccaagaacca gttttcttta   240
aaaatgaaca gtctgcaaag tgaagacaca accacttact actgtgccag atggggggg    300 ggctttgatt actggggcca aggagtcatg gtcacagtct cctca                   345

<210> SEQ ID NO 160
<211> LENGTH: 321
<212> TYPE: DNA
<213> ORGANISM: Artificial Sequence
<220> FEATURE:
<223> OTHER INFORMATION: Synthetic Construct

<400> SEQUENCE: 160
gacatcgtgc tgactcagtc tccaaccacc ctgtctgtga ctccaggaga gacagtcagt    60
ctctcctgca gggctagcca tagtattggc acaaatctac actggtatca acaaaaaaca   120
aatgagtctc caaggcttct catcaagttt acttcccagt ccatctctgg gatccccctcc  180 aggttcagtg ccagtggatc aggacagat tttactctca acatcaacaa tgtggagttt    240
gatgatgtct caagttattt ttgtcaacag actcaaagct ggcccctcac gttcggttct   300
gggaccaagc tggagatcaa a                                             321

<210> SEQ ID NO 161
<211> LENGTH: 351
<212> TYPE: DNA
<213> ORGANISM: Artificial Sequence
<220> FEATURE:
<223> OTHER INFORMATION: Synthetic Construct

<400> SEQUENCE: 161
caagtacaac tggtgcagag tggggccgaa gtgaaaaaac ccggcgctag cgtgaaagtc    60
agctgtaaag tgtccggtta taatattaga agcacctata tgcattgggt gcgtcaagcg   120
ccgggccagg gcttagagtg gatgggtagg attgatcctg caaatggaaa tactatttat   180
```

```
gctgagaagt tcaaaaggag agttacgctg acccgcgaca cgtccacctc gacggcctat      240
atggagctgt cttctttacg ctcagaggac actgcagttt actattgtgc catggaagtt      300
agagttagct tcgaatattg gggtcaaggc acattggtca cggtcagcag t               351

<210> SEQ ID NO 162
<211> LENGTH: 318
<212> TYPE: DNA
<213> ORGANISM: Artificial Sequence
<220> FEATURE:
<223> OTHER INFORMATION: Synthetic Construct

<400> SEQUENCE: 162
gatatccaga tgactcaatc tccatcgagc ctttcggcgt cagtgggtga tcgtgttacc       60
atcacttgta aggcctccca aaacattaat aaatatctgg actggtacca gcagaaaccg      120
ggcaaagccc caaagttact gatctactat acaaataacc tacacacagg tgttccatca      180
cgcttttcag gtagcggaag cgggaccgac tttacgttta cgatctccag cttgcaacca      240
gaagacattg ccacttatta ttgtctccag catgacagtg ctataccttt ggacagggt       300 actaaggtgg aaatcaag                                                   318

<210> SEQ ID NO 163
<211> LENGTH: 351
<212> TYPE: DNA
<213> ORGANISM: Artificial Sequence
<220> FEATURE:
<223> OTHER INFORMATION: Synthetic Construct

<400> SEQUENCE: 163
gaagtccagc tgcagcagtc tggggctgag ctagggaaac ctgggacctc agtcaagttg       60
tcttgcaagg tttctggcta taacattagg agtacctaca tgcactgggt gagtcagagg      120
cctggaaagg gcctggaatg gataggaagg attgatcctg caaatggaaa tactatttat      180
gctgagaagt tcaaaaggaa ggccacactg actgcagata catcgtccaa cacagcctac      240
atgcaactca gccaactgaa atctgacgac agagcaatct atttttgtgc tatggaagta      300
cgggtgtcct ttgagtactg gggccaggga gtcatggtca ccgtctcctc a               351

<210> SEQ ID NO 164
<211> LENGTH: 318
<212> TYPE: DNA
<213> ORGANISM: Artificial Sequence
<220> FEATURE:
<223> OTHER INFORMATION: Synthetic Construct

<400> SEQUENCE: 164
gacatccaga tgacccagtc tccttcattc ctgtctgcat ctgtgggaga cagagtcact       60
atcaactgca aagcaagtca gaatattaac aagtacttag actggtatca gcaaaagctt      120
ggtgaaggtc ccaaactcct gatatattat acaaacaatt acatacagg aatcccatca      180 aggttcagtg gcagtgggtc tggtactgat ttcacactta ccatcagcag cctgcagcct      240
gaagatgttg ccacatattt ctgccttcag catgacagtg ggtacacgtt tggagctggg      300
accaagctgg aactgaaa                                                   318

<210> SEQ ID NO 165
<211> LENGTH: 351
<212> TYPE: DNA
<213> ORGANISM: Artificial Sequence
<220> FEATURE:
<223> OTHER INFORMATION: Synthetic Construct
```

<400> SEQUENCE: 165

| caagtgcagc tggtacagtc tggtgccgag gttaaaaagc cgggtagtag cgtgaaagta | 60 |
| agctgcaaag tgagtggtta tagcattcgt tcaacctata tgcactgggt tcgtcaggcg | 120 |
| ccaggccaag gtctcgagtg gatgggaagg attgatcctg caaatggaaa tacaatatat | 180 |
| gctgagaggt tcaaaaaccg cgtgacgctg accgcagata ccagcacttc cacggcgtac | 240 |
| atggaactgt cctccctgcg gtccgaagat accgcagtat attattgcgc cgtagaaatc | 300 |
| ctaggcattt ttgattattg ggggcagggc acactggtca ccgtatcgag c | 351 |

<210> SEQ ID NO 166
<211> LENGTH: 318
<212> TYPE: DNA
<213> ORGANISM: Artificial Sequence
<220> FEATURE:
<223> OTHER INFORMATION: Synthetic Construct

<400> SEQUENCE: 166

| gatatacaaa tgacacagag tccgagttcc ctatcagcga gcgtgggaga cagggttacc | 60 |
| ataacgtgta agcatcgca gaatattgac aaatatctcg actggtatca acagaagccg | 120 |
| ggcaaagcac caaaactcct tatgtataac accaactctt tacatactgg cgtcccaagt | 180 |
| cgttttttcgg ggtctggcag cggcacagat tttacgctca ccattagttc gctgcagcca | 240 |
| gaagactttg ctacctactt ctgtctgcaa cataatagcg gctacacctt cggtcagggg | 300 |
| actaaagttg aaataaaa | 318 |

<210> SEQ ID NO 167
<211> LENGTH: 351
<212> TYPE: DNA
<213> ORGANISM: Artificial Sequence
<220> FEATURE:
<223> OTHER INFORMATION: Synthetic Construct

<400> SEQUENCE: 167

| gaagtccagc tgcagcagtc cggggctgag cttgggaaac ctgggacctc agtcaagttg | 60 |
| tcttgcaagg tttctggcta tagtattagg agtacctaca tgcactgggt gaatcagagg | 120 |
| cctggaaagg gcctggaatg ggtaggaagg attgatcctg caaatggaaa tacaatatat | 180 |
| gctgagaggt tcaaaaacaa ggccacactg actgcagata catcgtccaa cacagcctac | 240 |
| atgcaactca gccaactgaa atctgacgac acagcaatct attttgtgc tgtggagatc | 300 |
| cttgggatct ttgattactg gggccaagga gtcatggtca cagtctcctc a | 351 |

<210> SEQ ID NO 168
<211> LENGTH: 318
<212> TYPE: DNA
<213> ORGANISM: Artificial Sequence
<220> FEATURE:
<223> OTHER INFORMATION: Synthetic Construct

<400> SEQUENCE: 168

| gacatccaga tgacccagtc tccttcattc ctgtctgcat ctgtgggaga cagagtcact | 60 |
| atcaactgca aagcaagtca gaatattgac aagtacttag actggtatca gcaaaagctt | 120 |
| ggtgaagctc ccaaactcct gatgtataat acaaacagtt tgcatacagg aattccatca | 180 |
| aggttcagtg gcagtggatc tggtactgat ttcacactta ccatcagcag cctgcagcct | 240 |
| gaagatgttg ccacatattt ctgccttcag cataacagtg ggtacacgtt tggagctggg | 300 |

```
<210> SEQ ID NO 169
<211> LENGTH: 351
<212> TYPE: DNA
<213> ORGANISM: Artificial Sequence
<220> FEATURE:
<223> OTHER INFORMATION: Synthetic Construct

<400> SEQUENCE: 169
gaggtacagc tggttgaatc gggtggtggt ctggttcagc cgggtggctc attaagactg      60
tcatgcgccg tgtctggtta taaaatccgc agcagttata tgcattgggt tcgtcaagct     120
ccgggtaaag gtttagaatg gatcgggagg attgatcctg caaatggaaa tactatatac     180
ggtgacaagt tcaaaagtcg gtttactctg tcatccgata ccgcgaaaaa ctcagcctat     240
ctgcaaatga attccctgcg cgcggaagac actgctgtct attattgcgc aattgatatc     300
ggtaccacgt ttgattattg gggccagggt acgttggtga cggttagctc c             351

<210> SEQ ID NO 170
<211> LENGTH: 321
<212> TYPE: DNA
<213> ORGANISM: Artificial Sequence
<220> FEATURE:
<223> OTHER INFORMATION: Synthetic Construct

<400> SEQUENCE: 170
gacatccaaa tgacccaatc tccgagttct ctgtctgctt ccgtgggcga ccgagtcacc      60
ataacctgta aggcttcgca acacatcaac cgttatttga actggtatca acagaaaccg     120
gggaaagcgc cgaaattgct gatttatgat gctaacaacc tgcagacagg cgtaccatcg     180
cgatttagcg gctccggaag cgggacggat tttactctca ccatcagctc tctgcagccg     240
gaagactttg caacctattt ctgtttacag cataattcct ggccgaatac ctttggccag     300
gggacaaagg tggaaatcaa a                                               321

<210> SEQ ID NO 171
<211> LENGTH: 351
<212> TYPE: DNA
<213> ORGANISM: Artificial Sequence
<220> FEATURE:
<223> OTHER INFORMATION: Synthetic Construct

<400> SEQUENCE: 171
gaggtccagc tgcagcagtc tggggctgag cttgggaaac ctgggacctc agtcaagttg      60
tcttgcaagg tttctggcta taagattagg agttcctaca tgcactgggt gaatcagagg     120
cctggaaagg gcctggaatg gataggaagg attgatcctg caaatggaaa tactatatac     180
ggtgacaagt tcaaaagtaa ggccacactg acttcagata tcatcgtcca cacagcctac     240
atccaactca gccaactgaa atctgacgac acagcaatct attttgtgc tatagatata     300 ggtacaacct ttgattattg gggccaagga gtcatggtca cagtctcctc a              351

<210> SEQ ID NO 172
<211> LENGTH: 321
<212> TYPE: DNA
<213> ORGANISM: Artificial Sequence
<220> FEATURE:
<223> OTHER INFORMATION: Synthetic Construct

<400> SEQUENCE: 172
gacatccaga tgacccagtc tccttcattc ctgtctgcat ctgtgggaga cagagtcact      60
```

```
atcaactgca aagcaagtca gcatattaat aggtacttaa actggtacca gcaaaagctt      120
ggagaagctc ccaaactcct gatatatgat gcaaacaatt tgcaaacggg catcccatca      180
cggttcagtg gcagtggatc tggtactgat ttcacactca ccatcagcag cctgcagcct      240
gaagatgttg ccacatattt ctgcttgcag cataatagtt ggccgaacac gtttgggct       300 gggaccaagc tggaattgaa a                                                 321

<210> SEQ ID NO 173
<211> LENGTH: 357
<212> TYPE: DNA
<213> ORGANISM: Artificial Sequence
<220> FEATURE:
<223> OTHER INFORMATION: Synthetic Construct

<400> SEQUENCE: 173
gaagtccacc tgcaccagtc tgggcctgag cttgggaggc ctgggtcctc agtcaagatt      60
tcttgcaagg cttctggcta cacctttaca gattacgtta tgaactgggt gaggcagagt      120
cctggacagg gctggaatg ataggatgg atcaatcctg aagattatag ttttgattct        180
ggtgagaagt tcctagagag ggccacactg actgcagcta cgtcctccaa cacagtctac      240
atccagctta gcggcctgac atctgacgac acagccacct atttttgtgt tagagggga      300 ctacccgggg attggtttgc ttactggggc caaggcactc tggtcactgt ctcttca        357

<210> SEQ ID NO 174
<211> LENGTH: 321
<212> TYPE: DNA
<213> ORGANISM: Artificial Sequence
<220> FEATURE:
<223> OTHER INFORMATION: Synthetic Construct

<400> SEQUENCE: 174
gacatccaga tgacccagtc tccttcattc ctgtctgcat ctgtgggaga cagaatcact      60
atcaactgca agacaagtca gaatattaac aggtacttaa actggttcca gcaaaagctt      120
ggagaacctc ccaaactcct gatatataat gcaaacagtt tgcaagcgga cattccatca      180
cggttcagtg gcagtggatc tggtactgat ttcacactca ccatcaccag cctgcagcct      240
gaagatgttg ccacatattt ctgcttgcag catcatttct ggccgtacac gtttggagct      300
gggaccaagc tggaactgag a                                                 321

<210> SEQ ID NO 175
<211> LENGTH: 535
<212> TYPE: PRT
<213> ORGANISM: Artificial Sequence
<220> FEATURE:
<223> OTHER INFORMATION: Synthetic Construct

<400> SEQUENCE: 175

Trp Ser Tyr Asn Thr Ser Thr Glu Ala Met Thr Tyr Asp Glu Ala Ser
1               5                   10                  15

Ala Tyr Cys Gln Gln Arg Tyr Thr His Leu Val Ala Ile Gln Asn Lys
                20                  25                  30

Glu Glu Ile Glu Tyr Leu Asn Ser Ile Leu Ser Tyr Ser Pro Ser Tyr
            35                  40                  45

Tyr Trp Ile Gly Ile Arg Lys Val Asn Asn Val Trp Val Trp Val Gly
        50                  55                  60

Thr Gln Lys Pro Leu Thr Glu Glu Ala Lys Asn Trp Ala Pro Gly Glu
65                  70                  75                  80
```

```
Pro Asn Asn Arg Gln Lys Asp Glu Asp Cys Val Glu Ile Tyr Ile Lys
            85                  90                  95

Arg Asp Lys Asp Val Gly Met Trp Asn Asp Glu Arg Cys Ser Lys Lys
            100                 105                 110

Lys Leu Ala Leu Cys Tyr Thr Ala Ala Cys Thr Asn Thr Ser Cys Ser
            115                 120                 125

Gly His Gly Glu Cys Val Glu Thr Ile Asn Asn Tyr Thr Cys Lys Cys
            130                 135                 140

Asp Pro Gly Phe Ser Gly Leu Glu Cys Glu Gln Ile Val Asn Cys Thr
145                 150                 155                 160

Ala Leu Glu Ser Pro Glu His Gly Ser Leu Val Cys Ser His Pro Leu
            165                 170                 175

Gly Asn Phe Ser Tyr Ser Ser Cys Ser Val Ser Cys Asp Arg Gly
            180                 185                 190

Tyr Leu Pro Ser Ser Val Glu Thr Thr Gln Cys Met Ser Ser Gly Glu
            195                 200                 205

Trp Ser Val Pro Ile Pro Ala Cys Lys Val Val Glu Cys Asp Ala Val
            210                 215                 220

Thr Asn Pro Ala Asn Gly Phe Val Glu Cys Phe Gln Asn Pro Gly Ser
225                 230                 235                 240

Phe Pro Trp Asn Thr Thr Cys Thr Phe Asp Cys Glu Glu Gly Phe Glu
            245                 250                 255

Leu Met Gly Ala Gln Ser Leu Gln Cys Thr Ser Ser Gly Asn Trp Asp
            260                 265                 270

Asn Glu Lys Pro Thr Cys Lys Ala Val Thr Cys Arg Ala Ile Arg Gln
            275                 280                 285

Pro Gln Asn Gly Ser Val Arg Cys Ser His Ser Pro Ala Gly Glu Phe
            290                 295                 300

Thr Phe Lys Ser Ser Cys Asn Phe Thr Cys Glu Glu Gly Phe Met Leu
305                 310                 315                 320

Gln Gly Ala Ala Gln Val Glu Cys Thr Thr Gln Gly Gln Trp Thr Gln
            325                 330                 335

Gln Val Pro Val Cys Glu Ala Phe Gln Cys Thr Ala Leu Ser Asn Pro
            340                 345                 350

Glu Arg Gly Tyr Met Asn Cys Leu Pro Ser Ala Ser Gly Ser Phe Arg
            355                 360                 365

Asn Gly Ser Ser Cys Glu Phe Ser Cys Glu Gln Gly Phe Val Leu Lys
            370                 375                 380

Gly Ser Lys Arg Leu Gln Cys Gly Pro Thr Gly Glu Trp Asp Asn Glu
385                 390                 395                 400

Lys Pro Thr Cys Glu Ala Val Arg Cys Asp Ala Val His Gln Pro Gln
            405                 410                 415

Arg Gly Leu Val Arg Cys Ala His Ser Pro Ile Gly Glu Phe Thr Tyr
            420                 425                 430

Lys Ser Ser Cys Ala Phe Ser Cys Glu Glu Gly Phe Glu Leu His Gly
            435                 440                 445

Ser Thr Gln Leu Glu Cys Thr Ser Gln Gly Gln Trp Thr Glu Glu Val
            450                 455                 460

Pro Ser Cys Gln Val Val Lys Cys Ser Ser Leu Ala Val Leu Glu Lys
465                 470                 475                 480

Ile Asn Met Ser Cys Ser Gly Glu Pro Val Phe Gly Thr Val Cys Asn
            485                 490                 495
```

```
Phe Ala Cys Pro Glu Gly Trp Arg Leu Asn Gly Ser Ala Ala Met Thr
                500                 505                 510

Cys Gly Ala Thr Gly His Trp Ser Gly Met Leu Pro Thr Cys Glu Ala
        515                 520                 525

Pro Thr Glu Ser Asn Thr Pro
    530                 535

<210> SEQ ID NO 176
<211> LENGTH: 13
<212> TYPE: PRT
<213> ORGANISM: Artificial Sequence
<220> FEATURE:
<223> OTHER INFORMATION: Synthetic Construct

<400> SEQUENCE: 176

Ile Asp Pro Ala Asn Gly Asn Thr Ile Tyr Ala Glu Lys
1               5                   10

<210> SEQ ID NO 177
<211> LENGTH: 18
<212> TYPE: PRT
<213> ORGANISM: Artificial Sequence
<220> FEATURE:
<223> OTHER INFORMATION: Synthetic Construct

<400> SEQUENCE: 177

Thr Ser Gln Asn Ile Asn Arg Tyr Leu Asn Trp Tyr Gln Gln Lys Pro
1               5                   10                  15

Gly Lys

<210> SEQ ID NO 178
<211> LENGTH: 9
<212> TYPE: PRT
<213> ORGANISM: Artificial Sequence
<220> FEATURE:
<223> OTHER INFORMATION: Synthetic Construct

<400> SEQUENCE: 178

Tyr Asn Ile Arg Ser Ser Tyr Met His
1               5

<210> SEQ ID NO 179
<211> LENGTH: 9
<212> TYPE: PRT
<213> ORGANISM: Artificial Sequence
<220> FEATURE:
<223> OTHER INFORMATION: Synthetic Construct

<400> SEQUENCE: 179

Phe Lys Ile Arg Phe Thr Ile Ser Ala
1               5

<210> SEQ ID NO 180
<211> LENGTH: 9
<212> TYPE: PRT
<213> ORGANISM: Artificial Sequence
<220> FEATURE:
<223> OTHER INFORMATION: Synthetic Construct

<400> SEQUENCE: 180

Ile Arg Phe Thr Ile Ser Ala Asp Asn
1               5

<210> SEQ ID NO 181
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 181

Ile Asn Arg Tyr Leu Asn Trp Tyr Gln
1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic Construct

<400> SEQUENCE: 182

Leu Leu Ile Tyr Asn Ala Asn Ser Leu
1               5

<210> SEQ ID NO 183
<211> LENGTH: 9
<212> TYPE: PRT
<213> ORGANISM: Artificial Sequence
<220> FEATURE:
<223> OTHER INFORMATION: Synthetic Construct

<400> SEQUENCE: 183

Leu Ile Tyr Asn Ala Asn Ser Leu Gln
1               5

<210> SEQ ID NO 184
<211> LENGTH: 9
<212> TYPE: PRT
<213> ORGANISM: Artificial Sequence
<220> FEATURE:
<223> OTHER INFORMATION: Synthetic Construct

<400> SEQUENCE: 184

Ile Tyr Asn Ala Asn Ser Leu Gln Thr
1               5

<210> SEQ ID NO 185
<211> LENGTH: 9
<212> TYPE: PRT
<213> ORGANISM: Artificial Sequence
<220> FEATURE:
<223> OTHER INFORMATION: Synthetic Construct

<400> SEQUENCE: 185

Tyr Asn Ala Asn Ser Leu Gln Thr Gly
1               5

<210> SEQ ID NO 186
<211> LENGTH: 7
<212> TYPE: PRT
<213> ORGANISM: Artificial Sequence
<220> FEATURE:
<223> OTHER INFORMATION: Synthetic Construct

<400> SEQUENCE: 186

Tyr Val Asp Ser Val Lys Gly
1               5

<210> SEQ ID NO 187
<211> LENGTH: 9
<212> TYPE: PRT
```

```
<213> ORGANISM: Artificial Sequence
<220> FEATURE:
<223> OTHER INFORMATION: Synthetic Construct

<400> SEQUENCE: 187

Val Lys Gly Arg Phe Thr Ile Ser Ala
1               5

<210> SEQ ID NO 188
<211> LENGTH: 9
<212> TYPE: PRT
<213> ORGANISM: Artificial Sequence
<220> FEATURE:
<223> OTHER INFORMATION: Synthetic Construct

<400> SEQUENCE: 188

Tyr Ala Ile Arg Ser Ala Tyr Met His
1               5

<210> SEQ ID NO 189
<211> LENGTH: 9
<212> TYPE: PRT
<213> ORGANISM: Artificial Sequence
<220> FEATURE:
<223> OTHER INFORMATION: Synthetic Construct

<400> SEQUENCE: 189

Val Glu Gly Arg Phe Thr Ile Ser Ala
1               5

<210> SEQ ID NO 190
<211> LENGTH: 9
<212> TYPE: PRT
<213> ORGANISM: Artificial Sequence
<220> FEATURE:
<223> OTHER INFORMATION: Synthetic Construct

<400> SEQUENCE: 190

Val Thr Gly Arg Phe Thr Ile Ser Ala
1               5

<210> SEQ ID NO 191
<211> LENGTH: 9
<212> TYPE: PRT
<213> ORGANISM: Artificial Sequence
<220> FEATURE:
<223> OTHER INFORMATION: Synthetic Construct

<400> SEQUENCE: 191

Val Lys Glu Arg Phe Thr Ile Ser Ala
1               5

<210> SEQ ID NO 192
<211> LENGTH: 9
<212> TYPE: PRT
<213> ORGANISM: Artificial Sequence
<220> FEATURE:
<223> OTHER INFORMATION: Synthetic Construct

<400> SEQUENCE: 192

Ile Glu Arg Tyr Leu Asn Trp Tyr Gln
1               5

<210> SEQ ID NO 193
<211> LENGTH: 9
<212> TYPE: PRT
<213> ORGANISM: Artificial Sequence
```

```
<220> FEATURE:
<223> OTHER INFORMATION: Synthetic Construct

<400> SEQUENCE: 193

Cys Ser Ser Leu Ala Val Leu Glu Lys
1               5

<210> SEQ ID NO 194
<211> LENGTH: 17
<212> TYPE: PRT
<213> ORGANISM: Artificial Sequence
<220> FEATURE:
<223> OTHER INFORMATION: Synthetic Construct

<400> SEQUENCE: 194

Ile Asp Pro Ala Asn Gly Asn Thr Ile Tyr Val Asp Ser Val Thr Gly
1               5                   10                  15

Arg

<210> SEQ ID NO 195
<211> LENGTH: 18
<212> TYPE: PRT
<213> ORGANISM: Artificial Sequence
<220> FEATURE:
<223> OTHER INFORMATION: Synthetic Construct

<400> SEQUENCE: 195

Thr Ser Gln Asn Ile Glu Arg Tyr Leu Asn Trp Tyr Gln Gln Lys Pro
1               5                   10                  15

Gly Lys

<210> SEQ ID NO 196
<211> LENGTH: 610
<212> TYPE: PRT
<213> ORGANISM: Artificial Sequence
<220> FEATURE:
<223> OTHER INFORMATION: Synthetic Construct

<400> SEQUENCE: 196

Met Ile Ala Ser Gln Phe Leu Ser Ala Leu Thr Leu Val Leu Leu Ile
1               5                   10                  15

Lys Glu Ser Gly Ala Trp Ser Tyr Asn Thr Ser Thr Glu Ala Met Thr
                20                  25                  30

Tyr Asp Glu Ala Ser Ala Tyr Cys Gln Gln Arg Tyr Thr His Leu Val
            35                  40                  45

Ala Ile Gln Asn Lys Glu Glu Ile Glu Tyr Leu Asn Ser Ile Leu Ser
        50                  55                  60

Tyr Ser Pro Ser Tyr Tyr Trp Ile Gly Ile Arg Lys Val Asn Asn Val
65                  70                  75                  80

Trp Val Trp Val Gly Thr Gln Lys Pro Leu Thr Glu Glu Ala Lys Asn
                85                  90                  95

Trp Ala Pro Gly Glu Pro Asn Asn Arg Gln Lys Asp Glu Asp Cys Val
            100                 105                 110

Glu Ile Tyr Ile Lys Arg Glu Lys Asp Val Gly Met Trp Asn Asp Glu
        115                 120                 125

Arg Cys Ser Lys Lys Leu Ala Leu Cys Tyr Thr Ala Ala Cys Thr
            130                 135                 140

Asn Thr Ser Cys Ser Gly His Gly Glu Cys Val Glu Thr Ile Asn Asn
145                 150                 155                 160

Tyr Thr Cys Lys Cys Asp Pro Gly Phe Ser Gly Leu Lys Cys Glu Gln
```

```
                    165                 170                 175
Ile Val Asn Cys Thr Ala Leu Glu Ser Pro Glu His Gly Ser Leu Val
                180                 185                 190
Cys Ser His Pro Leu Gly Asn Phe Ser Tyr Asn Ser Ser Cys Ser Ile
            195                 200                 205
Ser Cys Asp Arg Gly Tyr Leu Pro Ser Ser Met Glu Thr Met Gln Cys
        210                 215                 220
Met Ser Ser Gly Glu Trp Ser Ala Pro Ile Pro Ala Cys Asn Val Val
225                 230                 235                 240
Glu Cys Asp Ala Val Thr Asn Pro Ala Asn Gly Phe Val Glu Cys Phe
                245                 250                 255
Gln Asn Pro Gly Ser Phe Pro Trp Asn Thr Thr Cys Thr Phe Asp Cys
            260                 265                 270
Glu Glu Gly Phe Glu Leu Met Gly Ala Gln Ser Leu Gln Cys Thr Ser
        275                 280                 285
Ser Gly Asn Trp Asp Asn Glu Lys Pro Thr Cys Lys Ala Val Thr Cys
    290                 295                 300
Arg Ala Val Arg Gln Pro Gln Asn Gly Ser Val Arg Cys Ser His Ser
305                 310                 315                 320
Pro Ala Gly Glu Phe Thr Phe Lys Ser Ser Cys Asn Phe Thr Cys Glu
                325                 330                 335
Glu Gly Phe Met Leu Gln Gly Pro Ala Gln Val Glu Cys Thr Thr Gln
            340                 345                 350
Gly Gln Trp Thr Gln Gln Ile Pro Val Cys Glu Ala Phe Gln Cys Thr
        355                 360                 365
Ala Leu Ser Asn Pro Glu Arg Gly Tyr Met Asn Cys Leu Pro Ser Ala
    370                 375                 380
Ser Gly Ser Phe Arg Tyr Gly Ser Ser Cys Glu Phe Ser Cys Glu Gln
385                 390                 395                 400
Gly Phe Val Leu Lys Gly Ser Lys Arg Leu Gln Cys Gly Pro Thr Gly
                405                 410                 415
Glu Trp Asp Asn Glu Lys Pro Thr Cys Glu Ala Val Arg Cys Asp Ala
            420                 425                 430
Val His Gln Pro Pro Lys Gly Leu Val Arg Cys Ala His Ser Pro Ile
        435                 440                 445
Gly Glu Phe Thr Tyr Lys Ser Ser Cys Ala Phe Ser Cys Glu Glu Gly
    450                 455                 460
Phe Glu Leu His Gly Ser Thr Gln Leu Glu Cys Thr Ser Gln Gly Gln
465                 470                 475                 480
Trp Thr Glu Glu Val Pro Ser Cys Gln Val Val Lys Cys Ser Ser Leu
                485                 490                 495
Ala Val Pro Gly Lys Ile Asn Met Ser Cys Ser Gly Glu Pro Val Phe
            500                 505                 510
Gly Thr Val Cys Lys Phe Ala Cys Pro Glu Gly Trp Thr Leu Asn Gly
        515                 520                 525
Ser Ala Ala Arg Thr Cys Gly Ala Thr Gly His Trp Ser Gly Leu Leu
    530                 535                 540
Pro Thr Cys Glu Ala Pro Thr Glu Ser Asn Ile Pro Leu Val Ala Gly
545                 550                 555                 560
Leu Ser Ala Ala Gly Leu Ser Leu Leu Thr Leu Ala Pro Phe Leu Leu
                565                 570                 575
Trp Leu Arg Lys Cys Leu Arg Lys Ala Lys Lys Phe Val Pro Ala Ser
            580                 585                 590
```

```
Ser Cys Gln Ser Leu Glu Ser Asp Gly Ser Tyr Gln Lys Pro Ser Tyr
        595                 600                 605

Ile Leu
    610

<210> SEQ ID NO 197
<211> LENGTH: 157
<212> TYPE: PRT
<213> ORGANISM: Artificial Sequence
<220> FEATURE:
<223> OTHER INFORMATION: Synthetic Construct

<400> SEQUENCE: 197

Trp Ser Tyr Asn Thr Ser Thr Glu Ala Met Thr Tyr Asp Glu Ala Ser
1               5                   10                  15

Ala Tyr Cys Gln Gln Arg Tyr Thr His Leu Val Ala Ile Gln Asn Lys
            20                  25                  30

Glu Glu Ile Glu Tyr Leu Asn Ser Ile Leu Ser Tyr Ser Pro Ser Tyr
        35                  40                  45

Tyr Trp Ile Gly Ile Arg Lys Val Asn Asn Val Trp Val Trp Val Gly
    50                  55                  60

Thr Gln Lys Pro Leu Thr Glu Glu Ala Lys Asn Trp Ala Pro Gly Glu
65                  70                  75                  80

Pro Asn Asn Arg Gln Lys Asp Glu Asp Cys Val Glu Ile Tyr Ile Lys
                85                  90                  95

Arg Glu Lys Asp Val Gly Met Trp Asn Asp Glu Arg Cys Ser Lys Lys
            100                 105                 110

Lys Leu Ala Leu Cys Tyr Thr Ala Ala Cys Thr Asn Thr Ser Cys Ser
        115                 120                 125

Gly His Gly Glu Cys Val Glu Thr Ile Asn Asn Tyr Thr Cys Lys Cys
    130                 135                 140

Asp Pro Gly Phe Ser Gly Leu Lys Cys Glu Gln Ile Val
145                 150                 155

<210> SEQ ID NO 198
<211> LENGTH: 612
<212> TYPE: PRT
<213> ORGANISM: Artificial Sequence
<220> FEATURE:
<223> OTHER INFORMATION: Synthetic Construct

<400> SEQUENCE: 198

Met Asn Ala Ser Arg Phe Leu Ser Ala Leu Val Phe Val Leu Leu Ala
1               5                   10                  15

Gly Glu Ser Thr Ala Trp Tyr Tyr Asn Ala Ser Ser Glu Leu Met Thr
            20                  25                  30

Tyr Asp Glu Ala Ser Ala Tyr Cys Gln Arg Asp Tyr Thr His Leu Val
        35                  40                  45

Ala Ile Gln Asn Lys Glu Glu Ile Asn Tyr Leu Asn Ser Asn Leu Lys
    50                  55                  60

His Ser Pro Ser Tyr Tyr Trp Ile Gly Ile Arg Lys Val Asn Asn Val
65                  70                  75                  80

Trp Ile Trp Val Gly Thr Gly Lys Pro Leu Thr Glu Glu Ala Gln Asn
                85                  90                  95

Trp Ala Pro Gly Glu Pro Asn Asn Lys Gln Arg Asn Glu Asp Cys Val
            100                 105                 110

Glu Ile Tyr Ile Gln Arg Thr Lys Asp Ser Gly Met Trp Asn Asp Glu
```

```
            115                 120                 125
Arg Cys Asn Lys Lys Leu Ala Leu Cys Tyr Thr Ala Ser Cys Thr
130                 135                 140

Asn Ala Ser Cys Ser Gly His Gly Glu Cys Ile Glu Thr Ile Asn Ser
145                 150                 155                 160

Tyr Thr Cys Lys Cys His Pro Gly Phe Leu Gly Pro Asn Cys Glu Gln
                165                 170                 175

Ala Val Thr Cys Lys Pro Gln Glu His Pro Asp Tyr Gly Ser Leu Asn
                180                 185                 190

Cys Ser His Pro Phe Gly Pro Phe Ser Tyr Asn Ser Ser Cys Ser Phe
                195                 200                 205

Gly Cys Lys Arg Gly Tyr Leu Pro Ser Ser Met Glu Thr Thr Val Arg
            210                 215                 220

Cys Thr Ser Ser Gly Glu Trp Ser Ala Pro Ala Pro Ala Cys His Val
225                 230                 235                 240

Val Glu Cys Glu Ala Leu Thr His Pro Ala His Gly Ile Arg Lys Cys
                245                 250                 255

Ser Ser Asn Pro Gly Ser Tyr Pro Trp Asn Thr Thr Cys Thr Phe Asp
            260                 265                 270

Cys Val Glu Gly Tyr Arg Arg Val Gly Ala Gln Asn Leu Gln Cys Thr
            275                 280                 285

Ser Ser Gly Ile Trp Asp Asn Glu Thr Pro Ser Cys Lys Ala Val Thr
290                 295                 300

Cys Asp Ala Ile Pro Gln Pro Gln Asn Gly Phe Val Ser Cys Ser His
305                 310                 315                 320

Ser Thr Ala Gly Glu Leu Ala Phe Lys Ser Ser Cys Asn Phe Thr Cys
                325                 330                 335

Glu Gln Ser Phe Thr Leu Gln Gly Pro Ala Gln Val Glu Cys Ser Ala
            340                 345                 350

Gln Gly Gln Trp Thr Pro Gln Ile Pro Val Cys Lys Ala Val Gln Cys
            355                 360                 365

Glu Ala Leu Ser Ala Pro Gln Gln Gly Asn Met Lys Cys Leu Pro Ser
370                 375                 380

Ala Ser Gly Pro Phe Gln Asn Gly Ser Ser Cys Glu Phe Ser Cys Glu
385                 390                 395                 400

Glu Gly Phe Glu Leu Lys Gly Ser Arg Arg Leu Gln Cys Gly Pro Arg
                405                 410                 415

Gly Glu Trp Asp Ser Lys Lys Pro Thr Cys Ser Ala Val Lys Cys Asp
                420                 425                 430

Asp Val Pro Arg Pro Gln Asn Gly Val Met Glu Cys Ala His Ala Thr
            435                 440                 445

Thr Gly Glu Phe Thr Tyr Lys Ser Ser Cys Ala Phe Gln Cys Asn Glu
            450                 455                 460

Gly Phe Ser Leu His Gly Ser Ala Gln Leu Glu Cys Thr Ser Gln Gly
465                 470                 475                 480

Lys Trp Thr Gln Glu Val Pro Ser Cys Gln Val Val Gln Cys Pro Ser
                485                 490                 495

Leu Asp Val Pro Gly Lys Met Asn Met Ser Cys Ser Gly Thr Ala Val
                500                 505                 510

Phe Gly Thr Val Cys Glu Phe Thr Cys Pro Asp Asp Trp Thr Leu Asn
                515                 520                 525

Gly Ser Ala Val Leu Thr Cys Gly Ala Thr Gly Arg Trp Ser Gly Met
530                 535                 540
```

```
Pro Pro Thr Cys Glu Ala Pro Val Ser Pro Thr Arg Pro Leu Val Val
545                 550                 555                 560

Ala Leu Ser Ala Ala Gly Thr Ser Leu Leu Thr Ser Ser Ser Leu Leu
                565                 570                 575

Tyr Leu Leu Met Arg Tyr Phe Arg Lys Lys Ala Lys Lys Phe Val Pro
            580                 585                 590

Ala Ser Ser Cys Gln Ser Leu Gln Ser Phe Glu Asn Tyr His Val Pro
        595                 600                 605

Ser Tyr Asn Val
    610

<210> SEQ ID NO 199
<211> LENGTH: 157
<212> TYPE: PRT
<213> ORGANISM: Artificial Sequence
<220> FEATURE:
<223> OTHER INFORMATION: Synthetic Construct

<400> SEQUENCE: 199

Trp Tyr Tyr Asn Ala Ser Ser Glu Leu Met Thr Tyr Asp Glu Ala Ser
1               5                   10                  15

Ala Tyr Cys Gln Arg Asp Tyr Thr His Leu Val Ala Ile Gln Asn Lys
            20                  25                  30

Glu Glu Ile Asn Tyr Leu Asn Ser Asn Leu Lys His Ser Pro Ser Tyr
        35                  40                  45

Tyr Trp Ile Gly Ile Arg Lys Val Asn Asn Val Trp Ile Trp Val Gly
    50                  55                  60

Thr Gly Lys Pro Leu Thr Glu Glu Ala Gln Asn Trp Ala Pro Gly Glu
65                  70                  75                  80

Pro Asn Asn Lys Gln Arg Asn Glu Asp Cys Val Glu Ile Tyr Ile Gln
                85                  90                  95

Arg Thr Lys Asp Ser Gly Met Trp Asn Asp Glu Arg Cys Asn Lys Lys
            100                 105                 110

Lys Leu Ala Leu Cys Tyr Thr Ala Ser Cys Thr Asn Ala Ser Cys Ser
        115                 120                 125

Gly His Gly Glu Cys Ile Glu Thr Ile Asn Ser Tyr Thr Cys Lys Cys
    130                 135                 140

His Pro Gly Phe Leu Gly Pro Asn Cys Glu Gln Ala Val
145                 150                 155

<210> SEQ ID NO 200
<211> LENGTH: 610
<212> TYPE: PRT
<213> ORGANISM: Artificial Sequence
<220> FEATURE:
<223> OTHER INFORMATION: Synthetic Construct

<400> SEQUENCE: 200

Met Ile Ala Ser Gln Phe Leu Ser Ala Leu Thr Leu Val Leu Leu Ile
1               5                   10                  15

Lys Glu Ser Gly Ala Trp Ser Tyr Asn Thr Ser Thr Glu Ala Met Thr
            20                  25                  30

Tyr Asp Glu Ala Ser Ala Tyr Cys Gln Gln Arg Tyr Thr His Leu Val
        35                  40                  45

Ala Ile Gln Asn Lys Glu Glu Ile Glu Tyr Leu Asn Ser Ile Leu Ser
    50                  55                  60

Tyr Ser Pro Ser Tyr Tyr Trp Ile Gly Ile Arg Lys Val Asn Asn Val
```

-continued

```
               65                  70                  75                  80
        Trp Val Trp Val Gly Thr Gln Lys Pro Leu Thr Glu Glu Ala Lys Asn
                            85                  90                  95

Trp Ala Pro Gly Glu Pro Asn Asn Arg Gln Lys Asp Glu Asp Cys Val
                        100                 105                 110

Glu Ile Tyr Ile Lys Arg Asp Lys Asp Val Gly Met Trp Asn Asp Glu
                    115                 120                 125

Arg Cys Ser Lys Lys Leu Ala Leu Cys Tyr Thr Ala Ala Cys Thr
                130                 135                 140

Asn Thr Ser Cys Ser Gly His Gly Glu Cys Val Glu Thr Ile Asn Asn
        145                 150                 155                 160

Tyr Thr Cys Lys Cys Asp Pro Gly Phe Ser Gly Leu Glu Cys Glu Gln
                        165                 170                 175

Ile Val Asn Cys Thr Ala Leu Glu Ser Pro Glu His Gly Ser Leu Val
                    180                 185                 190

Cys Ser His Pro Leu Gly Asn Phe Ser Tyr Ser Ser Cys Ser Val
                195                 200                 205

Ser Cys Asp Arg Gly Tyr Leu Pro Ser Ser Val Glu Thr Thr Gln Cys
            210                 215                 220

Met Ser Ser Gly Glu Trp Ser Val Pro Ile Pro Ala Cys Lys Val Val
        225                 230                 235                 240

Glu Cys Asp Ala Val Thr Asn Pro Ala Asn Gly Phe Val Glu Cys Phe
                        245                 250                 255

Gln Asn Pro Gly Ser Phe Pro Trp Asn Thr Thr Cys Thr Phe Asp Cys
                    260                 265                 270

Glu Glu Gly Phe Glu Leu Met Gly Ala Gln Ser Leu Gln Cys Thr Ser
                275                 280                 285

Ser Gly Asn Trp Asp Asn Glu Lys Pro Thr Cys Lys Ala Val Thr Cys
            290                 295                 300

Arg Ala Ile Arg Gln Pro Gln Asn Gly Ser Val Arg Cys Ser His Ser
        305                 310                 315                 320

Pro Ala Gly Glu Phe Thr Phe Lys Ser Ser Cys Asn Phe Thr Cys Glu
                        325                 330                 335

Glu Gly Phe Met Leu Gln Gly Ala Ala Gln Val Glu Cys Thr Thr Gln
                    340                 345                 350

Gly Gln Trp Thr Gln Gln Val Pro Val Cys Glu Ala Phe Gln Cys Thr
                355                 360                 365

Ala Leu Ser Asn Pro Glu Arg Gly Tyr Met Asn Cys Leu Pro Ser Ala
            370                 375                 380

Ser Gly Ser Phe Arg Asn Gly Ser Ser Cys Glu Phe Ser Cys Glu Gln
        385                 390                 395                 400

Gly Phe Val Leu Lys Gly Ser Lys Arg Leu Gln Cys Gly Pro Thr Gly
                        405                 410                 415

Glu Trp Asp Asn Glu Lys Pro Thr Cys Glu Ala Val Arg Cys Asp Ala
                    420                 425                 430

Val His Gln Pro Gln Arg Gly Leu Val Arg Cys Ala His Ser Pro Ile
                435                 440                 445

Gly Glu Phe Thr Tyr Lys Ser Ser Cys Ala Phe Ser Cys Glu Glu Gly
            450                 455                 460

Phe Glu Leu His Gly Ser Thr Gln Leu Glu Cys Thr Ser Gln Gly Gln
        465                 470                 475                 480

Trp Thr Glu Glu Val Pro Ser Cys Gln Val Val Lys Cys Ser Ser Leu
                        485                 490                 495
```

```
Ala Val Leu Glu Lys Ile Asn Met Ser Cys Ser Gly Glu Pro Val Phe
            500                 505                 510

Gly Thr Val Cys Asn Phe Ala Cys Pro Glu Gly Trp Arg Leu Asn Gly
            515                 520                 525

Ser Ala Ala Met Thr Cys Gly Ala Thr Gly His Trp Ser Gly Met Leu
530                 535                 540

Pro Thr Cys Glu Ala Pro Thr Glu Ser Asn Thr Pro Leu Val Ala Gly
545                 550                 555                 560

Leu Ser Ala Ala Gly Leu Ser Leu Leu Thr Leu Ala Pro Phe Leu Leu
                565                 570                 575

Trp Leu Arg Lys Cys Phe Arg Lys Ala Lys Lys Phe Val Pro Ala Ser
            580                 585                 590

Ser Cys Gln Ser Leu Glu Ser Asp Gly Ser Tyr Gln Lys Pro Ser Tyr
            595                 600                 605

Ile Leu
    610

<210> SEQ ID NO 201
<211> LENGTH: 589
<212> TYPE: PRT
<213> ORGANISM: Artificial Sequence
<220> FEATURE:
<223> OTHER INFORMATION: Synthetic Construct

<400> SEQUENCE: 201

Trp Ser Tyr Asn Thr Ser Thr Glu Ala Met Thr Tyr Asp Glu Ala Ser
1               5                   10                  15

Ala Tyr Cys Gln Gln Arg Tyr Thr His Leu Val Ala Ile Gln Asn Lys
            20                  25                  30

Glu Glu Ile Glu Tyr Leu Asn Ser Ile Leu Ser Tyr Ser Pro Ser Tyr
        35                  40                  45

Tyr Trp Ile Gly Ile Arg Lys Val Asn Asn Val Trp Val Trp Val Gly
    50                  55                  60

Thr Gln Lys Pro Leu Thr Glu Glu Ala Lys Asn Trp Ala Pro Gly Glu
65                  70                  75                  80

Pro Asn Asn Arg Gln Lys Asp Glu Asp Cys Val Glu Ile Tyr Ile Lys
                85                  90                  95

Arg Asp Lys Asp Val Gly Met Trp Asn Asp Glu Arg Cys Ser Lys Lys
            100                 105                 110

Lys Leu Ala Leu Cys Tyr Thr Ala Ala Cys Thr Asn Thr Ser Cys Ser
        115                 120                 125

Gly His Gly Glu Cys Val Glu Thr Ile Asn Asn Tyr Thr Cys Lys Cys
    130                 135                 140

Asp Pro Gly Phe Ser Gly Leu Glu Cys Glu Gln Ile Val Asn Cys Thr
145                 150                 155                 160

Ala Leu Glu Ser Pro Glu His Gly Ser Leu Val Cys Ser His Pro Leu
                165                 170                 175

Gly Asn Phe Ser Tyr Ser Ser Cys Ser Val Ser Cys Asp Arg Gly
            180                 185                 190

Tyr Leu Pro Ser Ser Val Glu Thr Thr Gln Cys Met Ser Ser Gly Glu
        195                 200                 205

Trp Ser Val Pro Ile Pro Ala Cys Lys Val Val Glu Cys Asp Ala Val
    210                 215                 220

Thr Asn Pro Ala Asn Gly Phe Val Glu Cys Phe Gln Asn Pro Gly Ser
225                 230                 235                 240
```

Phe Pro Trp Asn Thr Thr Cys Thr Phe Asp Cys Glu Glu Gly Phe Glu
                245                 250                 255

Leu Met Gly Ala Gln Ser Leu Gln Cys Thr Ser Ser Gly Asn Trp Asp
            260                 265                 270

Asn Glu Lys Pro Thr Cys Lys Ala Val Thr Cys Arg Ala Ile Arg Gln
        275                 280                 285

Pro Gln Asn Gly Ser Val Arg Cys Ser His Ser Pro Ala Gly Glu Phe
    290                 295                 300

Thr Phe Lys Ser Ser Cys Asn Phe Thr Cys Glu Glu Gly Phe Met Leu
305                 310                 315                 320

Gln Gly Ala Ala Gln Val Glu Cys Thr Thr Gln Gly Gln Trp Thr Gln
                325                 330                 335

Gln Val Pro Val Cys Glu Ala Phe Gln Cys Thr Ala Leu Ser Asn Pro
            340                 345                 350

Glu Arg Gly Tyr Met Asn Cys Leu Pro Ser Ala Ser Gly Ser Phe Arg
        355                 360                 365

Asn Gly Ser Ser Cys Glu Phe Ser Cys Glu Gln Gly Phe Val Leu Lys
    370                 375                 380

Gly Ser Lys Arg Leu Gln Cys Gly Pro Thr Gly Glu Trp Asp Asn Glu
385                 390                 395                 400

Lys Pro Thr Cys Glu Ala Val Arg Cys Asp Ala Val His Gln Pro Gln
                405                 410                 415

Arg Gly Leu Val Arg Cys Ala His Ser Pro Ile Gly Glu Phe Thr Tyr
            420                 425                 430

Lys Ser Ser Cys Ala Phe Ser Cys Glu Glu Gly Phe Glu Leu His Gly
        435                 440                 445

Ser Thr Gln Leu Glu Cys Thr Ser Gln Gly Gln Trp Thr Glu Glu Val
    450                 455                 460

Pro Ser Cys Gln Val Val Lys Cys Ser Ser Leu Ala Val Leu Glu Lys
465                 470                 475                 480

Ile Asn Met Ser Cys Ser Gly Glu Pro Val Phe Gly Thr Val Cys Asn
                485                 490                 495

Phe Ala Cys Pro Glu Gly Trp Arg Leu Asn Gly Ser Ala Ala Met Thr
            500                 505                 510

Cys Gly Ala Thr Gly His Trp Ser Gly Met Leu Pro Thr Cys Glu Ala
        515                 520                 525

Pro Thr Glu Ser Asn Thr Pro Leu Val Ala Gly Leu Ser Ala Ala Gly
    530                 535                 540

Leu Ser Leu Leu Thr Leu Ala Pro Phe Leu Leu Trp Leu Arg Lys Cys
545                 550                 555                 560

Phe Arg Lys Ala Lys Lys Phe Val Pro Ala Ser Ser Cys Gln Ser Leu
                565                 570                 575

Glu Ser Asp Gly Ser Tyr Gln Lys Pro Ser Tyr Ile Leu
            580                 585

<210> SEQ ID NO 202
<211> LENGTH: 98
<212> TYPE: PRT
<213> ORGANISM: Artificial Sequence
<220> FEATURE:
<223> OTHER INFORMATION: Synthetic Construct

<400> SEQUENCE: 202

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
65                   70                  75                  80

Leu Gln Met Asn Ser Leu Arg Ala Glu Asp Thr Ala Val Tyr Tyr Cys
                85                  90                  95

Ala Arg

<210> SEQ ID NO 203
<211> LENGTH: 15
<212> TYPE: PRT
<213> ORGANISM: Artificial Sequence
<220> FEATURE:
<223> OTHER INFORMATION: Synthetic Construct

<400> SEQUENCE: 203

Tyr Phe Asp Tyr Trp Gly Gln Gly Thr Leu Val Thr Val Ser Ser
1               5                   10                  15

<210> SEQ ID NO 204
<211> LENGTH: 95
<212> TYPE: PRT
<213> ORGANISM: Artificial Sequence
<220> FEATURE:
<223> OTHER INFORMATION: Synthetic Construct

<400> SEQUENCE: 204

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                   70                  75                  80

Glu Asp Phe Ala Thr Tyr Tyr Cys Gln Gln Ser Tyr Ser Thr Pro
                85                  90                  95

<210> SEQ ID NO 205
<211> LENGTH: 12
<212> TYPE: PRT
<213> ORGANISM: Artificial Sequence
<220> FEATURE:
<223> OTHER INFORMATION: Synthetic Construct

<400> SEQUENCE: 205

Trp Thr Phe Gly Gln Gly Thr Lys Val Glu Ile Lys
1               5                   10

<210> SEQ ID NO 206
<211> LENGTH: 1338
<212> TYPE: DNA
<213> ORGANISM: Artificial Sequence
<220> FEATURE:
<223> OTHER INFORMATION: Synthetic Construct

```
<400> SEQUENCE: 206
gaagtgcagc ttgtggaatc cggggggcggc ttggtccaac cgggtggcag cctccgtctg      60
tcgtgcgcgg cttcgggcta tgccatccgt tctgcctaca tgcactgggt tcgccaggcg     120
cctgggaagg gcctggaatg ggtggccagg attgatcctg caaacggaaa tactatatat     180
gtggactccg tgaccggccg ctttacaatc agcgccgaca acgctaagaa ttccgcctac     240
ctgcaaatga atagcctgcg ggcagaggat accgcggtgt actattgtgc catggatttta    300 tattccacgt ctgaatattg gggccaagga accctggtaa cggtgtcgtc ggcgtcgacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga aagttgagcc caaatcttgt     660
gacaaaactc acacatgccc accgtgccca gcacctgaag ccgctggggc accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga tgatgaccaag   1080 aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta tagcaagctc accgtggaca gagcaggtg gcagcagggg     1260 aacgtcttct catgctccgt gatgcatgag gctctgcaca accactacac gcagaagagc    1320
ctctccctgt ccccggga                                                   1338
```